United States Patent
Kapiloff et al.

(10) Patent No.: US 11,938,198 B2
(45) Date of Patent: Mar. 26, 2024

(54) TREATMENT OF HEART DISEASE BY DISRUPTION OF THE ANCHORING OF PP2A

(71) Applicants: University of Miami, Miami, FL (US); The Board of Trustees of the Leland Stanford Junior University, Stanford, CA (US)

(72) Inventors: Michael S. Kapiloff, Los Altos, CA (US); Jinliang Li, Palo Alto, CA (US)

(73) Assignees: University of Miami, Miami, FL (US); The Board of Trustees of the Leland Stanford Junior University, Stanford, CA (US)

( * ) Notice: Subject to any disclaimer, the term of this patent is extended or adjusted under 35 U.S.C. 154(b) by 284 days.

(21) Appl. No.: 16/818,771

(22) Filed: Mar. 13, 2020

(65) Prior Publication Data

US 2020/0360536 A1 Nov. 19, 2020
US 2022/0008560 A2 Jan. 13, 2022

Related U.S. Application Data

(60) Provisional application No. 62/848,156, filed on May 15, 2019.

(51) Int. Cl.
*A61K 48/00* (2006.01)
*A61K 35/761* (2015.01)
*A61P 9/04* (2006.01)

(52) U.S. Cl.
CPC ........ *A61K 48/0066* (2013.01); *A61K 35/761* (2013.01); *A61P 9/04* (2018.01)

(58) Field of Classification Search
CPC .............. A61K 48/0066; A61K 35/761; A61K 38/465; A61K 38/1719; A61P 9/04; C12Y 301/03016
See application file for complete search history.

(56) References Cited

U.S. PATENT DOCUMENTS

| | | |
|---|---|---|
| 7,691,997 B2 | 4/2010 | Khvorova et al. |
| 7,745,391 B2 | 6/2010 | Mintz et al. |
| 9,132,174 B2 | 9/2015 | Kapiloff et al. |
| 9,217,155 B2 | 12/2015 | Gao et al. |
| 9,937,228 B2 | 4/2018 | Kapiloff et al. |
| 10,029,386 B2 | 7/2018 | Chung et al. |
| 10,109,346 B2 | 10/2018 | Cho et al. |
| 10,617,737 B2 | 4/2020 | Kapiloff et al. |
| 10,907,153 B2 | 2/2021 | Kapiloff |
| 11,229,679 B2 | 1/2022 | Kapiloff et al. |
| 2003/0134331 A1 | 7/2003 | Marks et al. |
| 2003/0194704 A1 | 10/2003 | Penn et al. |
| 2005/0112128 A1 | 5/2005 | McKinsey et al. |
| 2005/0255487 A1 | 11/2005 | Khvorova |
| 2007/0083334 A1 | 4/2007 | Mintz et al. |
| 2013/0136729 A1 | 5/2013 | French et al. |
| 2014/0286928 A1* | 9/2014 | Kapiloff ............... A61K 38/45 514/249 |
| 2014/0296486 A1 | 10/2014 | Gao et al. |
| 2016/0038568 A1 | 2/2016 | Kapiloff et al. |
| 2019/0010493 A1 | 1/2019 | Kapiloff |

FOREIGN PATENT DOCUMENTS

WO 2012061548 A1 5/2012

OTHER PUBLICATIONS

Shirley McCartney, Cloning and Characterization of A-kinase Anchor Protein 100 (AKAPI00), The Journal of Biological Chemistry vol. 270, No. 16, Issue of Apr. 21, pp. 9327-9333, 1995.*
Abeer Rababa'h, Protein Kinase A and Phosphodiesterase-4D3 Binding to Coding Polymorphisms of Cardiac Muscle Anchoring Protein (mAKAP), J Mol Biol. Sep. 23, 2013; 425(18).*
Cell Biolabs Inc (https://www.cellbiolabs.com/adenoviral-expression, published online 2010).*
Anna Marabotti, The misuse of terms in scientific literature, Bioinformatics, vol. 26 No. 19, 2010, p. 2498.*
International Search Report and Written Opinion in PCT/US2020/022721 dated Oct. 7, 2020, 12 pages.
Abrenica et al., "The A-kinase anchor protein AKAP121 is a negative regulator of cardiomyocyte hypertrophy," J Mol Cell Cardiol, vol. 46, pp. 674-681 (2009).
Anjum et al., "The RSK family of kinases: emerging roles in cellular signalling," Nat Rev Mol Cell Biol, vol. 9, pp. 747-758 (Oct. 2008).
Amirak et al., "p90 Ribosomal S6 kinases play a significant role in early gene regulation in the cardiomyocyte response to Gq-protein-coupled receptor stimuli, endothelin-1 and α1-adrenergic receptor agonists," Biochemical Journal, vol. 456, pp. 351-363 (2013).
Appert-Collin et al., "The A-kinase anchoring protein (AKAP)-Lbc-signaling complex mediates α1 adrenergic receptor-induced cardiomyocyte hypertrophy," Proc Natl Acad Sci USA, vol. 104, pp. 10140-10145 (Jun. 12, 2007).
Avkiran et al., "Targeting Na+/H+ exchanger regulation for cardiac protection: a RSKy approach?" Curr Opin Pharmacol, vol. 8, pp. 133-140 (2008).
Bain et al., "The selectivity of protein kinase inhibitors: a further update," Biochem J, vol. 408, pp. 297-315 (2007).

(Continued)

*Primary Examiner* — Julie Ha
*Assistant Examiner* — Erinne R Dabkowski
(74) *Attorney, Agent, or Firm* — Sharon E. Crane

(57) ABSTRACT

The present invention provides a method of treating heart failure with reduced ejection fraction, by administering to a patient at risk of such damage, a pharmaceutically effective amount of a composition which inhibits the anchoring of PP2A to mAKAPβ. This composition is preferably in the form of a viral based gene therapy vector that encodes a fragment of mAKAPβ to which PP2A binds.

10 Claims, 49 Drawing Sheets
(33 of 49 Drawing Sheet(s) Filed in Color)
Specification includes a Sequence Listing.

(56) References Cited

OTHER PUBLICATIONS

Bauman et al., "The mAKAP Signalosome and Cardiac Myocyte Hypertrophy," IUBMB Life, vol. 59, No. 3, pp. 163-169, (Mar. 2007).
Beene et al., "A-kinase anchoring proteins take shape," Curr Opin Cell Biol, vol. 19, pp. 192-198 (2007).
Bers, "Calcium Cycling and Signaling in Cardiac Myocytes," Annu Rev Physiol, vol. 70, pp. 23-49 (2008).
Brown et al., "The Rac and Rho Hall of Fame: A Decade of Hypertrophic Signaling Hits," Circ Res, vol. 98, pp. 730-742 (2006).
Buck et al., "C/EBPβ-Thr217 Phosphorylation Signaling Contributes to the Development of Lung Injury and Fibrosis in Mice," PLoS One, vol. 6, Issue 10, e25497 (Oct. 2011).
Burns-Hamuro et al., "Designing isoform-specific peptide disruptors of protein kinase A localization," Proceedings of the National Academy of Sciences, vol. 100, No. 7, pp. 4072-4077 (Apr. 1, 2003).
Cappola, "Molecular Remodeling in Human Heart Failure," J Am Coll Cardiol, vol. 51, No. 2, pp. 137-138 (2008).
Cariolato et al., "A-Kinase Anchoring Protein (AKAP)-Lbc Anchors a PKN-based Signaling Complex Involved in α1-Adrenergic Receptor-induced p38 Activation," J Biol Chem, vol. 286, No. 10, pp. 7925-7937 (Mar. 11, 2011).
Carlucci et al., "Control of mitochondria dynamics and oxidative metabolism by cAMP, AKAPs and the proteasome," Trends in Cell Biol, vol. 18, No. 12, pp. 604-613 (Oct. 24, 2008).
Carnegie et al., "AKAP-Lbc Nucleates a Protein Kinase D Activation Scaffold," Mol Cell, vol. 15, pp. 889-899 (Sep. 24, 2004).
Chaturvedi et al., "Subcellular Localization and Biological Actions of Activated RSK1 Are Determined by Its Interactions with Subunits of Cyclic AMP-dependent Protein Kinase," Mol Cell Biol, vol. 26, No. 12, pp. 4586-4600 (Jun. 2006).
Chen et al., "Phosphorylation of the A-kinase anchoring Protein Yotiao Contributes to Protein Kinase A Regulation of a Heart Potassium Channel," J. Biol. Chem., vol. 280, pp. 31347-31352 (2005).
Chen et al., "Mutation of an A-kinase-anchoring protein causes long-QT syndrome," Proc Natl Acad Sci USA, vol. 104, No. 52, pp. 20990-20995 (Dec. 26, 2007).
Chen et al., "Protein kinase A-induced myofilament desensitization to Ca2+ as a result of phosphorylation of cardiac myosin-binding protein C," J. Gen. Physiol., vol. 136, No. 6, pp. 615-627 (Nov. 29, 2010).
Christian et al., "Small Molecule AKAP-Protein Kinase A (PKA) Interaction Disruptors That Activate PKA Interfere with Compartmentalized cAMP Signaling in Cardiac Myocytes," J Biol Chem, No. 286, pp. 9079-9096 (Mar. 18, 2011).
Cuello et al., "Evidence for Direct Regulation of Myocardial Na+/H+ Exchanger Isoform 1 Phosphorylation and Activity by 90-kDa Ribosomal S6 Kinase (RSK): Effects of the Novel and Specific RSK Inhibitor fmk on Responses to α1-Adrenergic Stimulation," Molecular Pharmacology, vol. 71, No. 3, pp. 799-806 (2007).
Diviani et al., "Anchoring of both PKA and 14-3-3 inhibits the Rho-GEF activity of the AKAP-Lbc signaling complex," EMBO J, vol. 23, No. 14, pp. 2811-2820 (2004).
Diviani et al., "AKAP-Lbc Anchors Protein Kinase A and Nucleates G α12-selective Rho-mediated Stress Fiber Formation," J Biol Chem, vol. 276, pp. 44247-44257 (2001).
Dodge et al., "mAKAP assembles a protein kinase A/PDE4 phosphodiesterase cAMP signaling module," EMBO J, vol. 20, No. 8, pp. 1921-1930 (2001).
Dodge-Kafka et al., "A-Kinase Anchoring Proteins as the Basis for cAMP Signaling," Handb Exp Pharmacol, vol. 186, pp. 3-14 (2008).
Dodge-Kafka et al., "The mAKAP signaling complex: Integration of cAMP, calcium, and MAP kinase signaling pathways," Eur J Cell Biol, vol. 85, pp. 593-602 (2006).

Dodge-Kafka et al., "The protein kinase A anchoring protein mAKAP coordinates two integrated cAMP effector pathways," Nature, vol. 437, pp. 574-578 (Sep. 22, 2005).
Dummler et al., "Functional Characterization of Human RSK4, a New 90-kDa Ribosomal S6 Kinase, Reveals Constitutive Activation in Most Cell Types," J Biol Chem, vol. 280, No. 14, pp. 13304-13314 (2005).
Edgley et al., "Targeting Fibrosis for the Treatment of Heart Failure: A Role for Transforming Growth Factor-β," Cardiovasc Ther, vol. 30, pp. e30-e40 (2012).
Eide et al., "Molecular Cloning, Chromosomal Localization, and Cell Cycle-Dependent Subcellular Distribution of the A-Kinase Anchoring Protein, AKAP95," Exp Cell Res, vol. 238, pp. 305-316 (1998).
Escobar et al., "Structural evidence for perinuclear calcium microdomains in cardiac myocytes," J Mol Cell Cardiol, vol. 50, pp. 451-459 (2011).
Fabiato, "Calcium-induced release of calcium from the cardiac sarcoplasmic reticulum," American Physiological Society, pp. C1-C14 (1983).
Farah et al., "The troponin complex and regulation of muscle contraction," FASEB J, vol. 9, pp. 755-767 (Jun. 1995).
Faul et al., "Protein Kinase A, Ca2+/Calmodulin-Dependent Kinase II, and Calcineurin egulate the Intracellular Trafficking of Myopodin between the Z-Disc and the Nucleus of Cardiac Myocytes," Mol Cell Biol, vol. 27, No. 23, pp. 8215-8227 (Dec. 2007).
Fink et al., "AKAP-Mediated Targeting of Protein Kinase A Regulates Contractility in Cardiac Myocytes," Circ Res, pp. 291-297 (Feb. 16, 2001).
Fisher et al., "Evidence for Two Catalytically Active Kinase Domains in pp90rsk," Molecular and Cellular Biology, vol. 16, No. 3, pp. 1212-1219 (Mar. 1996).
Fodstad et al., "Four potassium channel mutations account for 73% of the genetic spectrum underlying long-QT syndrome (LQTS) and provide evidence for a strong founder effect in Finland," Ann Med, vol. 36 (Suppl 1), pp. 53-63, (2004).
Francis et al., "Structure and function of cyclic nucleotide-dependent protein kinases," Annu. Rev. Physiol., vol. 56, pp. 237-272 (1994).
Fraser et al., "A novel lipid-anchored A-kinase Anchoring Protein facilitates cAMP-responsive membrane events," EMBO J, vol. 17, No. 8, pp. 2261-2272 (1998).
Frey et al., "Hypertrophy of the Heart: A New Therapeutic Target?" Circulation, vol. 109, pp. 1580-1589 (2004).
Fuller et al., "Molecular Mechanism of Calcium Channel Regulation in the Fight-or-Flight Response," Sci Signal, vol. 3, Issue 141 ra70 (Sep. 28, 2010).
Gaffin et al., "Long-term rescue of a familial hypertrophic cardiomyopathy caused by a mutation in the thin filament protein, tropomyosin, via modulation of a calcium cycling protein," J. Mol. Cell. Cardiol., vol. 51, pp. 812-820 (2011).
Gao et al., "cAMP-Dependent Regulation of Cardiac L-type Ca2+ Channels Requires Membrane Targeting of PKA and Phosphorylation of Channel Subunits," Neuron, vol. 19, pp. 185-196 (Jul. 1997).
Gao et al., "Rational design and characterization of a Rac GTPase-specific small molecule inhibitor," Proc Natl Acad Sci USA, vol. 101, No. 20, pp. 7618-7623 (May 18, 2004).
Gelb et al., "RAS signaling pathway mutations and hypertrophic cardiomyopathy: getting into and out of the thick of it," J Clin Invest, vol. 121, No. 3, pp. 844-847 (Mar. 2011).
Gentilucci et al., "Peptides and Peptidomimetics in Medicine, Surgery and Biotechnology," Curr Med Chem, vol. 13, pp. 2449-2466 (2006).
Gold et al., "Molecular Basis of AKAP Specificity for PKA Regulatory Subunits," Mol Cell, vol. 24. pp. 383-395 (Nov. 3, 2006).
Goldschmidt-Clermont et al., "Inflammation, stem cells and atherosclerosis genetics," Curr Opin Mol Ther, vol. 12, No. 6, pp. 712-723 (2010).
Good et al., "Scaffold Proteins: Hubs for Controlling the Flow of Cellular Information," Science, vol. 332, pp. 680-686 (May 6, 2011).
Gould et al., "cDNA cloning and sequencing of the protein-tyrosine kinase substrate, ezrin, reveals homology to band 4.1.," EMBO J, vol. 8, No. 13, pp. 4133-4142 (1989).

(56) References Cited

OTHER PUBLICATIONS

Gray et al., "Regulation of ion channels by cAMP-dependent protein kinase and A-kinase anchoring proteins," Curr Opin Neurobiol, vol. 8, pp. 330-334 (1998).
Guo et al., "Kinetics of FKBP12.6 Binding to Ryanodine Receptors in Permeabilized Cardiac Myocytes and Effects on Ca Sparks," Circ Res, vol. 106, pp. 1743-1752 (Jun. 11, 2010).
Hagemann et al., "Dual Site Phospholamban Phosphorylation and Its Physiological Relevance in the Heart," Trends Cardiovasc Med, vol. 12, No. 2, pp. 51-56 (2002).
Hanks et al., "The Protein Kinase Family: Conserved Features and Deduced Phylogeny of the Catalytic Domains," Science, vol. 241, pp. 42-52 (Jul. 1, 1988).
Harada et al., "Phosphorylation and Inactivation of BAD by Mitochondria-Anchored Protein Kinase A," Mol Cell, vol. 3, pp. 413-422 (Apr. 1999).
Hell, "β-Adrenergic Regulation of the L-Type Ca2+ Channel CaV1.2 by PKA Rekindles Excitement," Sci Signal, vol. 3, Issue 141 pe33, pp. 1-4 (Sep. 28, 2010).
Henn et al., "Identification of a Novel A-kinase Anchoring Protein 18 Isoform and Evidence for Its Role in the Vasopressin-induced Aquaporin-2 Shuttle in Renal Principal Cells," J Biol Chem, vol. 279, No. 25, pp. 26654-26665, (2004).
Hill et al., "Cardiac Plasticity," N Engl J Med, vol. 358, No. 13, pp. 1370-1380 (Mar. 27, 2008).
Huang et al., "D-AKAP2, a novel protein kinase A anchoring protein with a putative RGS domain," Proc Natl Acad Sci USA, vol. 94, pp. 11184-11189 (Oct. 1997).
Huang et al., "Identification of a Novel Protein Kinase A Anchoring Protein That Binds Both Type I and Type II Regulatory Subunits," J. Biol. Chem., vol. 272, pp. 8057-8064 (1997).
Hulme et al., "A Novel Leucine Zipper Targets AKAP15 and Cyclic AMP-dependent Protein Kinase to the C Terminus of the Skeletal Muscle Ca2+ Channel and Modulates Its Function," J Biol Chem, vol. 277, No. 6, pp. 4079-4087 (2002).
Hulme et al., "β-Adrenergic regulation requires direct anchoring of PKA to cardiac CaV1.2 channels via a leucine zipper interaction with A kinase-anchoring protein 15," Proc Natl Acad Sci USA, vol. 100, No. 22, pp. 13093-13098 (Oct. 28, 2003).
Hulme et al., "Phosphorylation of serine 1928 in the distal C-terminal domain of cardiac CaV1.2 channels during β1-adrenergic regulation," Proc Natl Acad Sci USA, vol. 103, No. 44, pp. 16574-16579 (Oct. 31, 2006).
Hundsrucker et al., "Direct AKAP-Mediated Protein-Protein Interactions as Potential Drug Targets," Hand Exp Pharmacol, vol. 186, pp. 483-503 (2008).
Hundsrucker et al., "High-affinity AKAP7δ-protein kinase A interaction yields novel protein kinase A-anchoring disruptor peptides," Biochem. J., vol. 396, pp. 297-306 (2006).
Itoh et al., "Role of p90 Ribosomal S6 Kinase-Mediated Prorenin-Converting Enzyme in Ischemic and Diabetic Myocardium," Circulation, vol. 113, pp. 1787-1798 (Apr. 11, 2006).
Jaakkola et al., "Targeting of HIF-α to the von Hippel-Lindau Ubiquitylation Complex by O2-Regulated Prolyl Hydroxylation," Science, vol. 292, pp. 468-472 (Apr. 20, 2001).
Kamisago et al., "Mutations in sarcomere protein genes as a cause of dilated cardiomyopathy," N Engl J Med, vol. 343, No. 23, pp. 1688-1696 (Dec. 7, 2000).
Kammerer et al., "Amino acid variant in the kinase binding domain of dual-specific A kinase-anchoring protein 2: A disease susceptibility polymorphism," Proc Natl Acad Sci USA, vol. 100, No. 7, pp. 4066-4071 (Apr. 1, 2003).
Kapiloff et al., "mAKAP and the ryanodine receptor are part of a multi-component signaling complex on the cardiomyocyte nuclear envelope," J Cell Sci, vol. 114, No. 17, pp. 3167-3176 (2001).
Kapiloff et al., "Calcium/calmodulin-dependent protein kinase mediates a pathway for transcriptional regulation," Proc. Natl. Acad. Sci. USA, vol. 88, pp. 3710-3714 (May 1991).
Kapiloff et al., "Variable Effects of Phosphorylation of Pit-1 Dictated by the DNA Response Elements," Science, vol. 253, pp. 786-789 (Aug. 16, 1991).
Kapiloff, "Contributions of Protein Kinase A Anchoring Proteins to Compartmentation of cAMP Signaling in the Heart," Molecular Pharmacology, vol. 62, No. 2, pp. 193-199 (2002).
Kehat et al., "Molecular Pathways Underlying Cardiac Remodeling During Pathophysiological Stimulation," Circulation, vol. 122, pp. 2727-2735 (2010).
Kehat et al., "Extracellular Signal-Regulated Kinases 1 and 2 Regulate the Balance Between Eccentric and Concentric Cardiac Growth," Circ Res, vol. 108, pp. 176-183 (2011).
Kentish et al., "Phosphorylation of Troponin I by Protein Kinase A Accelerates Relaxation and Crossbridge Cycle Kinetics in Mouse Ventricular Muscle," Circ Res, vol. 88, pp. 1059-1065 (May 25, 2001).
Kido et al., "Hypoxia-Inducible Factor 1-Alpha Reduces Infarction and Attenuates Progression of Cardiac Dysfunction After Myocardial Infarction in the Mouse," J Am Coll Cardiol, vol. 46, No. 11, pp. 2116-2124 (Dec. 6, 2005).
Kimura et al., "Targeted Deletion of the Extracellular Signal-Regulated Protein Kinase 5 Attenuates Hypertrophic Response and Promotes Pressure Overload-Induced Apoptosis in the Heart," Circ Res, vol. 106, pp. 961-970 (Mar. 19, 2010).
Kinderman et al., "A Novel and Dynamic Mechanism for AKAP Binding to RII Isoforms of cAMP-dependent Protein Kinase," Mol Cell., vol. 24, No. 3, pp. 397-408 (Nov. 3, 2006).
Klussmann et al., "Ht31: the first protein kinase A anchoring protein to integrate protein kinase A and Rho signaling," FEBS Lett, vol. 507, pp. 264-268 (2001).
Kodama et al., "Significance of ERK cascade compared with JAK/STAT and PI3-K pathway in gp130-mediated cardiac hypertrophy," Am J Physiol Heart Circ Physiol, vol. 279, pp. H1635-H1644 (2000).
Kontaridis et al., "Deletion of Ptpn11 (Shp2) in Cardiomyocytes Causes Dilated Cardiomyopathy via Effects on the Extracellular Signal-Regulated Kinase/Mitogen-Activated Protein Kinase and RhoA Signaling Pathways," Circulation, vol. 117, pp. 1423-1435 (2008).
Kritzer et al., "The Scaffold Protein Muscle A-Kinase Anchoring Protein β Orchestrates Cardiac Myocyte Hypertrophic Signaling Required for the Development of Heart Failure," Circulation Heart Failure, vol. 7, pp. 663-672 (Jul. 2014).
Lacana et al., "Cloning and Characterization of a Protein Kinase A Anchoring Protein (AKAP)-related Protein That Interacts with and Regulates Sphingosine Kinase 1 Activity," J Biol Chem, vol. 277, No. 36, pp. 32947-32953 (2002).
Layland et al., "Regulation of cardiac contractile function by troponin I phosphorylation," Cardiovasc Res, vol. 66, pp. 12-21 (2005).
Lester et al., "Anchoring of protein kinase A facilitates hormone-mediated insulin secretion," Proc Natl Acad Sci USA, vol. 94, pp. 14942-14947 (Dec. 1997).
Li et al., "Protein kinase A-anchoring (AKAP) domains in brefeldin A-inhibited guanine nucleotide-exchange protein 2 (BIG2)," Proc Natl Acad Sci USA, vol. 100, No. 4, pp. 1627-1632 (Feb. 18, 2003).
Li et al., "Regulation of MEF2 transcriptional activity by calcineurin/mAKAP complexes," Exp Cell Res, vol. 319, pp. 447-454 (2013).
Lohse et al., "What Is the Role of β-Adrenergic Signaling in Heart Failure?" Circ Res, vol. 93, pp. 896-906 (Nov. 14, 2003).
Lu et al., "Recent progress in congenital long QT syndrome," Curr Opin Cardiol., vol. 25, No. 3, pp. 216-221 (May 2010).
Lygren et al., "Akap-complex regulates the Ca2+ re-uptake into heart sarcoplasmic reticulum," EMBO Rep, vol. 8, No. 11, pp. 1061-1067 (2007).
Search Report and Written Opinion in Singapore Apln. No. 11202112499V dated Jun. 1, 2023, 7 pages.
Dodge-Kafka, K. L., et al., "cAMP-stimulated Protein Phosphatase 2A Activity Associated with Muscle A Kinase-anchoring Protein (mAKAP) Signaling Complexes Inhibits the Phosphorylation and Activity of the cAMP-specific Phosphodiesterase PDE4D3," The Journal of Biological Chemistry, Apr. 9, 2010, vol. 285, No. 15, pp. 11078-11086.

(56) References Cited

OTHER PUBLICATIONS

Diviani D, Dodge-Kafka KL, Li J, Kapiloff MS. A-kinase anchoring proteins: scaffolding proteins in the heart, Am J Physiol Heart Circ Physiol. 2011;301(5):H1742-53.
Kapiloff MS, Chandrasekhar KD, "AKAPs: temporal and spatial regulation of intracellular signal transduction in the cardiovascular system," Journal Cardiovasc Pharmacol. Oct. 2011;58(4):337-8.
Kapiloff MS, Piggott LA, Sadana R, Li J, Heredia LA, Henson E, Efendiev R, Dessauer CW, "An adenylyl cyclase-mAKAPbeta signaling complex regulates cAMP levels in cardiac myocytes," J Biol Chem. Aug. 28, 2009;284(35):23540-6.
Kapiloff MS, Schillace RV, Westphal AM, Scott JD. mAKAP: an A-kinase anchoring protein targeted to the nuclear membrane of differentiated myocytes. J Cell Sci 112: 2725-2736, 1999.
Kritzer MD, Li J, Dodge-Kafka K, Kapiloff MS, "AKAPs: the architectural underpinnings of local cAMP signaling," J Mol Cell Cardiol. Feb. 2012;52(2):351-8.
Li J, Kritzer MD, Michel JJ, Le A, Thakur H, Gayanilo M, Passariello CL, Negro A, Danial JB, Oskouei B, Sanders M, Hare JM, Hanauer A, Dodge-Kafka K, Kapiloff MS, "Anchored p90 ribosomal S6 kinase 3 is required for cardiac myocyte hypertrophy," Circ Res. Jan. 4, 2013;112(1):128-39.
Li J, Negro A, Lopez J, Bauman AL, Henson E, Dodge-Kafka K, Kapiloff MS. The mAKAPbeta scaffold regulates cardiac myocyte hypertrophy via recruitment of activated calcineurin. J Mol Cell Cardiol 48: 387-394, 2010.
Marx SO, Reiken S, Hisamatsu Y, Gaburjakova M, Gaburjakova J, Yang YM, Rosemblit N, Marks AR. Phosphorylation-dependent regulation of ryanodine receptors: a novel role for leucine/isoleucine zippers. J Cell Biol. 2001;153:699-708.
Pare GC, Easlick JL, Mislow JM, McNally EM, Kapiloff MS. Nesprin-1alpha contributes to the targeting of mAKAP to the cardiac myocyte nuclear envelope. Exp Cell Res 303: 388-399, 2005.
Passariello CL, Gayanilo M, Kritzer MD, Thakur H, Cozacov Z, Rusconi F, Wieczorek D, Sanders M, Li J, Kapiloff MS (2013) p90 ribosomal S6 kinase 3 contributes to cardiac insufficiency in alpha-tropomyosin Glu180Gly transgenic mice. Am J Physiol Heart Circ Physiol 305:H1010-1019.
Singh A, Redden JM, Kapiloff MS, Dodge-Kafka KL, "The large isoforms of A-kinase anchoring protein 18 mediate the phosphorylation of inhibitor-1 by protein kinase A and the inhibition of protein phosphatase 1 activity," Mol Pharmacol. Mar. 2011;79(3):533-40.
Zhang L, Malik S, Kelley GG, Kapiloff MS, Smrcka AV, "Phospholipase Cepsilon scaffolds to muscle-specific A kinase anchoring protein (mAKAPbeta) and integrates multiple hypertrophic stimuli in cardiac myocytes," J Biol Chem. Jul. 1, 2011;286(26):23012-21.
Lygren B et al., "The potential use of AKAP18δ as a drug target in heart failure patients," Expert Opin. Biol. Ther., vol. 8, pp. 1099-1108 (2008).
Maekawa et al., "Inhibiting p90 Ribosomal S6 Kinase Prevents Na+-H+ Exchanger-Mediated Cardiac Ischemia-Reperfusion Injury," Circulation, vol. 113, pp. 2516-2523 (2006).
Maloney et al., "Synthesis of a Potent and Selective Inhibitor of p90 Rsk," Org. Lett., vol. 7, No. 6, pp. 1097-1099 (2005).
Maron et al., "Hypertrophic cardiomyopathy," Lancet, vol. 381, pp. 242-255 (Jan. 19, 2013).
Maruyama et al., "Gα12/13 Mediates α1-Adrenergic Receptor-Induced Cardiac Hypertrophy," Circ Res, vol. 91, pp. 961-969 (Nov. 15, 2002).
Marx et al., "PKA Phosphorylation Dissociates FKBP12.6 from the Calcium Release Channel (Ryanodine Receptor): Defective Regulation in Failing Hearts," Cell, vol. 101, pp. 365-376 (May 12, 2000).
Marx et al., "Requirement of a Macromolecular Signaling Complex for β Adrenergic Receptor Modulation of the KCNQ1-KCNE1 Potassium Channel," Science, vol. 295, pp. 496-499 (Jan. 18, 2002).
Maxwell et al., "The tumour suppressor protein VHL targets hypoxia-inducible factors for oxygen-dependent proteolysis," Nature, vol. 399, pp. 271-275 (May 20, 1999).
Mayers et al., "The Rho Guanine Nucleotide Exchange Factor AKAP13 (BRX) Is Essential for Cardiac Development in Mice," J Biol Chem, vol. 285, No. 16, pp. 12344-12354 (Apr. 16, 2010).
McConnell et al., "Disruption of Protein Kinase A Interaction with A-kinase-anchoring Proteins in the Heart in vivo: effects on cardiac contractility, protein kinase A phosphorylation, and troponin I proteolysis," J Biol Chem, vol. 284, No. 3, pp. 1583-1592 (Jan. 16, 2009).
McKinsey et al., "Small-molecule therapies for cardiac hypertrophy: moving beneath the cell surface," Nat Rev Drug Discov, vol. 6, pp. 617-635 (Aug. 2007).
Michel et al., "Spatial Restriction of PDK1 Activation Cascades by Anchoring to mAKAPα," Molecular Cell, vol. 20, pp. 661-672 (Dec. 9, 2005).
Michele et al., "Cardiac Dysfunction in Hypertrophic Cardiomyopathy Mutant Tropomyosin Mice is Transgene-Dependent, Hypertrophy-Independent, and Improved by β-blockade," Circ. Res, vol. 91, pp. 255-262 (Aug. 9, 2002).
Morissette et al., "The Rho effector, PKN, regulates ANF gene transcription in cardiomyocytes through a serum response element," Am J Physiol Heart Circ Physiol, vol. 278, pp. H1769-H1774 (2000).
Naga Prasad et al., "Agonist-dependent Recruitment of Phosphoinositide 3-Kinase to the Membrane by β-Adrenergic Receptor Kinase 1: A role in receptor sequestration," J Biol Chem, vol. 276, No. 22, pp. 18953-18959 (2001).
Naga Prasad et al., "Phosphoinositide 3-kinase regulates β2-adrenergic receptor endocytosis by AP-2 recruitment to the receptor/β-arrestin complex," J Cell Biol, vol. 158, No. 3, pp. 563-575 (Nov. 3, 2002).
Nakagami et al., "Gene Polymorphism of Myospryn (Cardiomyopathy-Associated 5) Is Associated with Left Ventricular Wall Thickness in Patients with Hypertension," Hypertens Res, vol. 30, No. 12, pp. 1239-1246 (2007).
Nakamura et al., "LV systolic performance improves with development of hypertrophy after transverse aortic constriction in mice," Am J Physiol Heart Circ Physiol, vol. 281, pp. H1104-H1112 (Sep. 2001).
Nakayama et al., "Siah2 Regulates Stability of Prolyl-Hydroxylases, Controls HIF1α Abundance, and Modulates Physiological Responses to Hypoxia," Cell, vol. 117, pp. 941-952 (Jun. 25, 2004).
Nauert et al., "Gravin, an autoantigen recognized by serum from myasthenia gravis patients, is a kinase scaffold protein," Curr Biol, vol. 7, No. 1, pp. 52-62 (1996).
Nerbonne et al., "Molecular Physiology of Cardiac Repolarization," Physiol Rev, vol. 85, pp. 1205-1253 (Oct. 2005).
Pawson et al., "Signal integration through blending, bolstering and bifurcating of intracellular information," Nat Struct Mol Biol, vol. 17, No. 6, pp. 653-658 (Jun. 6, 2010).
Perino et al., "Integrating Cardiac PIP3 and cAMP Signaling through a PKA Anchoring Function of p110γ," Mol Cell., vol. 42, No. 1, pp. 84-95 (Apr. 8, 2011).
Perrino et al., "Intermittent pressure overload triggers hypertrophy-independent cardiac dysfunction and vascular rarefaction," J Clin Invest, vol. 116, No. 6, pp. 1547-1560 (Jun. 2006).
Perrino et al., "AKAP121 downregulation impairs protective cAMP signals, promotes mitochon-drial dysfunction, and increases oxidative stress," Cardiovasc Res, vol. 88, pp. 101-110 (2010).
Prabhakar et al., "A Familial Hypertrophic Cardiomyopathy α-Tropomyosin Mutation Causes Severe Cardiac Hypertrophy and Death in Mice," J Mol Cell Cardiol, vol. 33 pp. 1815-1828 (2001).
Reynolds et al., "Identification and mapping of protein kinase A binding sites in the costameric protein myospryn," Biochim Biophys Acta, vol. 1773, No. 6, pp. 891-902 (Jun. 2007).
Richards et al., "Characterization of Regulatory Events Associated with Membrane Targeting of p90 Ribosomal S6 Kinase 1," Mol Cell Biol, vol. 21, No. 21, pp. 7470-7480 (2001).
Rockman et al., "Segregation of atrial-specific and inducible expression of an atrial natriuretic factor transgene in an in vivo murine model of cardiac hypertrophy," Proc Natl Acad Sci USA, vol. 88, pp. 8277-8281 (Sep. 1991).
Rockman et al., "Seven-transmembrane-spanning receptors and heart function," Nature, vol. 415, pp. 206-212 (Jan. 10, 2002).

(56) References Cited

OTHER PUBLICATIONS

Roger et al., "Heart Disease and Stroke Statistics—2011 Update: A Report From the American Heart Association," Circulation, vol. 123, pp. e18-e209 (Feb. 1, 2011).
Rose et al., "Mitogen-Activated Protein Kinase Signaling in the Heart: Angels Versus Demons in a Heart-Breaking Tale," Physiol Rev., vol. 90, No. 4, pp. 1507-1546 (Oct. 2010).
Negro et al., "Signalosomes as therapeutic targets," Prog Pediatr Cardiol, vol. 25, pp. 51-56 (2008).
Nichols et al., "Sympathetic Stimulation of Adult Cardiomyocytes Requires Association of AKAP5 With a Subpopulation of L-Type Calcium Channels," Circ Res, vol. 107, pp. 747-756 (Sep. 17, 2010).
Nicol et al., "Activated MEK5 induces serial assembly of sarcomeres and eccentric cardiac hypertrophy," EMBO J., vol. 20, No. 11, pp. 2757-2767 (2001).
Niggli et al., "Voltage-Independent Calcium Release in Heart Muscle," Science, vol. 250, No. 4980, pp. 565-568 (Oct. 26, 1990).
Oka et al., "Genetic Nanipulation of Periostin Expression Reveals a Role in Cardiac Hypertrophy and Ventricular Remodeling," Circ. Res, vol. 101, pp. 313-321 (Aug. 3, 2007).
Papa et al., "The NADH: Ubiquinone Oxidoreductase (Complex I) of the Mammalian Respiratory Chain and the cAMP Cascade," Journal of Bioenergetics and Biomembranes, vol. 34, No. 1, pp. 1-10 (Feb. 2002).
Pare et al., "The mAKAP complex participates in the induction of cardiac myocyte hypertrophy by adrenergic receptor signaling," Journal of Cell Science, vol. 118, pp. 5637-5646 (2005).
Passariello et al., "Disruption of RSK3 binding to muscle A-kinase anchoring protein in vivo via adeno-associated virus expression of a competing peptide attenuates pressure overload-inducted cardiac hypertrophy," Journal of Molecular and Cellular Cardiology, Abstracts from the 2014 ISHR-NAS Annual Meeting, Miami, Florida, USA, vol. 74, p. S5 (2014).
Patel et al., "Disruption of Protein Kinase A Localization Using a Trans-activator of Transcription (TAT)-conjugated A-kinase-anchoring Peptide Reduces Cardiac Function," J Biol Chem, vol. 285, No. 36, pp. 27632-27640 (Sep. 3, 2010).
Rusconi et al., "CIP4 is required for the hypertrophic growth of neonatal cardiac myocytes," Journal of Biomedical Science, vol. 20, No. 56, pp. 1-7 (2013).
Russell et al., "The intermediate filament protein, synemin, is an AKAP in the heart," Arch Biochem Biophys, vol. 456, pp. 204-215 (2006).
Sadoshima et al., "Angiotensin II and Other Hypertrophic Stimuli Mediated by G Protein-Coupled Receptors Activate Tyrosine Kinase, Mitogen-Activated Protein Kinase, and 90-KD S6 Kinase in Cardiac Myocytes. The Critical Role of Ca(2+)-Dependent Signaling," Circ. Res, vol. 76, pp. 1-15 (1995).
Sapkota et al., "BI-D1870 is a specific inhibitor of the p90 RSK (ribosomal S6 kinase) isoforms in vitro and in vivo," Biochem J., vol. 401, pp. 29-38 (2007).
Scholten et al., "Analysis of the cGMP/cAMP Interactome Using a Chemical Proteomics Approach in Mammalian Heart Tissue Validates Sphingosine Kinase Type 1-interacting Protein as a Genuine and Highly Abundant AKAP," J Proteome Res, vol. 5, pp. 1435-1447 (2006).
Scholten et al., "Diversity of cAMP-Dependent Protein Kinase Isoforms and Their Anchoring Proteins in Mouse Ventricular Tissue," J Proteome Res, vol. 6, pp. 1705-1717 (2007).
Schulze et al., "Sodium/Calcium Exchanger (NCX1) Macromolecular Complex," J Biol Chem, vol. 278, No. 31, pp. 28849-28855 (2003).
Semenza, "Hypoxia-Inducible Factor 1 (HIF-1) Pathway," Science Signaling, vol. 407 cm8 (2007).
Semenza, "Regulation of Oxygen Homeostasis by Hypoxia-Inducible Factor 1," Physiology, vol. 24, pp. 97-106 (2009).
Sfichi-Duke et al., "Cardiomyopathy-causing deletion K210 in cardiac troponin T alters phosphorylation propensity of sarcomeric proteins," J Mol Cell Cardiol, vol. 48, pp. 934-942 (2010).

Shan et al., "Role of chronic ryanodine receptor phosphorylation in heart failure and β-adrenergic receptor blockade in mice," J Clin Invest, vol. 120, No. 12, pp. 4375-4387 (Dec. 2010).
Shan et al., "Phosphorylation of the ryanodine receptor mediates the cardiac fight or flight response in mice," J Clin Invest, vol. 120, No. 12, pp. 4388-4398 (Dec. 2010).
Shyu et al., "Intramyocardial injection of naked DNA encoding HIF-1α/VP16 hybrid to enhance angiogenesis in an acute myocardial infarction model in the rat," Cardiovasc Res, vol. 54, pp. 576-583 (2002).
Skroblin et al., "Mechanisms of Protein Kinase A Anchoring," Int Rev Cell Mol Biol, vol. 283, pp. 235-330 (2010).
Smith et al., "Identification of the First Specific Inhibitor of p90 Ribosomal S6 Kinase (Rsk) Reveals an Unexpected Role for RSK in Cancer Cell Proliferation," Cancer Res, vol. 65, No. 3, pp. 1027-1034 (Feb. 1, 2005).
Smith et al., "AKAP-Lbc enhances cyclic AMP control of the ERK1/2 cascade," Nat Cell Biol, vol. 12, No. 12, pp. 1242-1249 (Dec. 2010).
Spinale et al., "Membrane-Associated Matrix Proteolysis and Heart Failure," Circ. Res., vol. 112, pp. 195-208 (Jan. 4, 2013).
Stelzer et al., "Differential Roles of Cardiac Myosin-Binding Protein C and Cardiac Troponin I in the Myofibrillar Force Responses to Protein Kinase A Phosphorylation," Circ Res, vol. 101, pp. 503-511 (Aug. 31, 2007).
Stiles et al., "The role of soluble adenylyl cyclase in neurite outgrowth," Biochimica et Biophysica Acta, vol. 1842, pp. 2561-2568 (2014).
Sumandea et al., "Cardiac Troponin T, a Sarcomeric AKAP, Tethers Protein Kinase A at the Myofilaments," J Biol Chem, vol. 286, No. 1, pp. 530-541 (Jan. 7, 2011).
Takeishi et al., "Activation of mitogen-activated protein kinases and p90 ribosomal S6 kinase in failing human hearts with dilated cardiomyopathy," Cardiovascular Research, vol. 53, pp. 131-137 (2002).
Terrenoire et al., "The Cardiac IKs Potassium Channel Macromolecular Complex Includes the Phosphodiesterase PDE4D3," J Biol Chem, vol. 284, No. 14, pp. 9140-9146 (Apr. 3, 2009).
Thomas et al., "Ribosomal S6 kinase 2 interacts with and phosphorylates PDZ domain-containing proteins and regulates AMPA receptor transmission," Proc Natl Acad Sci USA, vol. 102, No. 42, pp. 15006-15011 (Oct. 18, 2005).
Tingley et al., "Gene-trapped mouse embryonic stem cell-derived cardiac myocytes and human genetics implicate AKAP10 in heart rhythm regulation," Proc Natl Acad Sci USA, vol. 104, No. 20, pp. 8461-8466 (May 15, 2007).
Uys et al., "Myomegalin is a novel A-kinase anchoring protein involved in the phosphorylation of cardiac myosin binding protein C," BMC Cell Biol, vol. 12, No. 18 (2011).
Vargas et al., "Myocyte enhancer factor 2 (MEF2) tethering to muscle selective A-kinase anchoring protein (mAKAP) is necessary for myogenic differentiation," Cellular Signalling, vol. 24, pp. 1496-1503 (2012).
Welch et al., "Networking with AKAPs: Context-dependent Regulation of Anchored Enzymes," Mol Interv, vol. 10, Issue 2, pp. 86-97 (Apr. 2010).
Wollert et al., "Cardiotrophin-1 Activates a Distinct Form of Cardiac Muscle Cell Hypertrophy. Assembly of sarcomeric units in series VIA gp130/leukemia inhibitory factor receptor-dependent pathways," J Biol Chem, vol. 271, No. 16, pp. 9535-9545 (1996).
Wong et al., "mAKAP Compartmentalizes Oxygen-Dependent Control of HIF-1α," Sci Signal, vol. 1, Issue 51, pp. 1-9 (Dec. 23, 2008).
Wu et al., "MEK-ERK pathway modulation ameliorates disease phenotypes in a mouse model of Noonan syndrome associated with the Raf1(L613V) mutation," J Clin Invest\, vol. 121, pp. 1009-1025 (Mar. 2011).
Xu et al., "Cardiomyocyte-Specific Loss of Neurofibromin Promotes Cardiac Hypertrophy and Dysfunction," Circ Res, vol. 105, pp. 304-311 (Jul. 31, 2009).
Yang et al., "Enhanced cardiac PI3Kα signalling mitigates arrhythmogenic electrical remodelling in pathological hypertrophy and heart failure," Cardiovasc Res, vol. 93, pp. 252-262 (2012).

(56) References Cited

OTHER PUBLICATIONS

Zhao et al., "Regulation and Interaction of pp90(rsk) Isoforms with Mitogen-activated Protein Kinases," J Biol Chem, vol. 271, No. 47, pp. 29773-29779 (1996).
Lin et al., "Molecular cloning of a brain-specific calcium/calmodulin-dependent protein kinase," Proc. Natl. Acad. Sci. USA, vol. 84, pp. 5962-5966 (Aug. 1987).
Graeme K Carnegie et al., "AKAP-Lbc mobilizes a cardiac hypertrophy signaling pathway," Mol Cell. 32(2): pp. 169-179 (Oct. 24, 2008).
Yi Zhao et al., "RSK3 Encodes a Novel pp90rsk Isoform with a Unique N-Terminal Sequence: Growth Factor-Stimulated Kinase Function and Nuclear Translocation," Molecular and Cellular Biology, vol. 15, No. 8, pp. 4353-4363 (Aug. 1995).
"Genome sequence of the Brown Norway rat yields insight into mammalian evolution," Nature, vol. 428, pp. 493-521 (Apr. 2004).
Lundby, A., et al., "Quantitative maps of protein phosphorylation sites across 14 different rat organs and tissues," Nature Communications, 3:876, 10 pages, Jun. 6, 2012.
Daya et al., 2008, Gene Therapy Using Adeno-Associated Virus Vectors, Clinical Microbiology Reviews, 21 (4):583-593.
International Preliminary Report issued in PCT/US2018/040913 dated Nov. 15, 2019, 23 pages.
Lee, S. et al., "AKAP6 inhibition impairs myoblast differentiation and muscle regeneration: Positive loop between AKAP6 and myogenin," Scientific Reports 5, doi: 10.1038/srep16523, Nov. 13, 2015, pp. 1-14.
Kapiloff, M. S. et al., "Disruption of RSK3 binding to muscle A-kinase anchoring protein in vivo via adeno-associated virus expression of a competing peptide attenuates pressure overload-induced cardiac hypertrophy," J Clin Exp Cardiolog, vol. 6, Issue 4, 2015, 8 pages.
International Search Report and Written Opinion, PCT/US2018/040913, dated Nov. 6, 2018, 19 pages.
Kapiloff, M. S., "mAKAP: A Scaffold that Coordinates Stress-Related Cardiac Signal Transduction," American Heart Association Council on Basic Cardiovascular Sciences, 2011 Scientific Sessions, New Orleans, Louisiana, 21 pages.
Using siRNA for gene silencing is a rapidly evolving tool in molecular biology, ThermoFisher Scientific, retrieved Jun. 16, 2017 <https://http://www.thermofisher.com/us/en/home/references/ambion-tech-support/rnai-sirna/general-articles/-sirna-design-guidelines.html>.
Ahn JH, McAvoy T, Rakhilin SV, Nishi A, Greengard P, Nairn AC (2007) Protein kinase A activates protein phosphatase 2A by phosphorylation of the B56delta subunit. Proc Natl Acad Sci USA 104:2979-2984.
Ai X, Pogwizd SM (2005) Connexin 43 downregulation and dephosphorylation in nonischemic heart failure is associated with enhanced colocalized protein phosphatase type 2A. Circ Res 96:54-63.
Andino LM, Conlon TJ, Porvasnik SL, Boye SL, Hauswirth WW, Lewin AS (2007) Rapid, widespread transduction of the murine myocardium using self-complementary Adeno-associated virus. Genetic vaccines and therapy 5:13.
Backs J, Worst BC, Lehmann LH, Patrick DM, Jebessa Z, Kreusser MM, Sun Q, Chen L, Heft C, Katus HA, Olson EN (2011) Selective repression of MEF2 activity by PKA-dependent proteolysis of HDAC4. J Cell Biol 195:403-415.
Bauman AL, Scott JD (2002) Kinase- and phosphatase-anchoring proteins: harnessing the dynamic duo. Nat Cell Biol 4:E203-206.
Beavo JA, Bechtel PJ, Krebs EG (1974) Preparation of homogeneous cyclic AMP-dependent protein kinase(s) and its subunits from rabbit skeletal muscle. Methods Enzymol 38:299-308.
Benjamin EJ et al. (2017) Heart Disease and Stroke Statistics—2017 Update: A Report From the American Heart Association. Circulation 135:e146-e603.
Benjamin EJ et al. (2019) Heart Disease and Stroke Statistics—2019 Update: A Report From the American Heart Association. Circulation 139: e56-e528.
Bers DM (2006) Cardiac ryanodine-receptor phosphorylation: target sites and functional consequences. Biochem J 396:e1-3.
Bione S, Maestrini E, Rivella S, Mancini M, Regis S, Romeo G, Toniolo D (1994) Identification of a novel X-linked gene responsible for Emery-Dreifuss muscular dystrophy. Nat Genet 8:323-327.
Black BL, Olson EN (1998) Transcriptional control of muscle development by myocyte enhancer factor-2 (MEF2) proteins. Annu Rev Cell Dev Biol 14:167-196.
Bonne G, Di Barletta MR, Varnous S, Becane HM, Hammouda EH, Merlini L, Muntoni F, Greenberg CR, Gary F, Urtizberea JA, Duboc D, Fardeau M, Toniolo D, Schwartz K (1999) Mutations in the gene encoding lamin NC cause autosomal dominant Emery-Dreifuss muscular dystrophy. Nat Genet 21:285-288.
Bourajjaj M, Armand AS, da Costa Martins PA, Weijts B, van der Nagel R, Heeneman S, Wehrens XH, De Windt LJ (2008) NFATc2 is a necessary mediator of calcineurin-dependent cardiac hypertrophy and heart failure. J Biol Chem 283:22295-22303.
Burns-Hamuro LL, Ma Y, Kammerer S, Reineke U, Self C, Cook C, Designing isoform-specific peptide disruptors of protein kinase A localization. Proc Natl Acad Sci U S A. Apr. 1, 2003;100(7):4072-7.
Brunton LL, Hayes JS, Mayer SE (1979) Hormonally specific phosphorylation of cardiac troponin I and activation of glycogen phosphorylase. Nature 280:78-80.
Bueno OF, Wilkins BJ, Tymitz KM, Glascock BJ, Kimball TF, Lorenz JN, Molkentin JD (2002) Impaired cardiac hypertrophic response in Calcineurin Abeta-deficient mice. Proc Natl Acad Sci U S A 99:4586-4591.
Bueno OF, Lips DJ, Kaiser RA Wilkins BJ, Dai YS, Glascock BJ, Klevitsky R, Hewett TE, Kimball TR, Aronow BJ, Doevendans PA, Molkentin JD (2004) Calcineurin Abeta gene targeting predisposes the myocardium to acute ischemia-induced apoptosis and dysfunction. Circ Res 94:91-99.
Burchfield JS, Xie M, Hill JA (2013) Pathological ventricular remodeling: mechanisms: part 1 of 2. Circulation 128:388-400.
Carlisle Michel JJ, Dodge KL, Wong W, Mayer NC, Langeberg LK, Scott JD (2004) PKA-phosphorylation of PDE4D3 facilitates recruitment of the mAKAP signalling complex. Biochem J 381:587-592.
Carnegie GK, Soughayer J, Smith FD, Pedroja BS, Zhang F, Diviani D, Bristow MR, Kunkel MT, Newton AC, Langeberg LK, Scott JD. AKAP-Lbc mobilizes a cardiac hypertrophy signaling pathway. Mol Cell 32: 169-179, 2008.
Chen L, Kurokawa J, Kass RS. Phosphorylation of the A-kinase-anchoring protein Yotiao contributes to protein kinase A regulation of a heart potassium channel. J Biol Chem 280: 31347-31352, 2005.
Clerk A, Cullingford TE, Fuller SJ, Giraldo A, Markou T, Pikkarainen S, Sugden PH (2007) Signaling pathways mediating cardiac myocyte gene expression in physiological and stress responses. J Cell Physiol 212:311-322.
Consensus (1987). "Effects of enalapril on mortality in severe congestive heart failure. Results of the Cooperative North Scandinavian Enalapril Survival Study (CONSENSUS)." N Engl J Med 316(23): 1429-1435.
De Arcangelis V, Soto D, Xiang Y (2008) Phosphodiesterase 4 and phosphatase 2A differentially regulate cAMP/protein kinase a signaling for cardiac myocyte contraction under stimulation ofbeta1 adrenergicreceptor. Mol Pharmacol 74:1453-1462.
Dobrev D, Wehrens XH (2014) Role of RyR2 phosphorylation in heart failure and arrhythmias: Controversies around ryanodine receptor phosphorylation in cardiac disease. Circ Res 114:1311-1319; discussion 1319.
Dodge-Kafka, K. L., M. Gildart, J. Li, H. Thakur, and M. S. Kapiloff. 2018. 'Bidirectional regulation of HDAC5 by mAKAPbeta signalosomes in cardiac myocytes', Journal of Molecular and Cellular Cardiology, 118: 13-25.
Diviani D, Soderling J, Scott JD. AKAP-Lbc anchors protein kinase A and nucleates Galpha 12-selective Rho-mediated stress fiber formation. J Biol Chem 276: 44247-44257, 2001.
Dodge KL, Khouangsathiene S, Kapiloff MS, Mouton R, Hill EV, Houslay MD, Langeberg LK, Scott JD. mAKAP assembles a protein kinase A/PDE4 phosphodiesterase cAMP signaling module. EMBO J 20: 1921-1930, 2001.

(56) References Cited

OTHER PUBLICATIONS

Dodge-Kafka KL, Kapiloff MS, "The mAKAP signaling complex: integration of cAMP, calcium, and MAP kinase signaling pathways," Eur J Cell Biol. Jul. 2006;85(7):593-602. Epub Feb. 7, 2006. Review.

Dodge-Kafka KL, Langeberg L, Scott JD (2006) Compartmentation of cyclic nucleotide signaling in the heart: the role of A-kinase anchoring proteins. Circ Res 98:993-1001.

DuBell WH, Lederer WJ, Rogers TB (1996) Dynamic modulation of excitation-contraction coupling by protein phosphatases in rat ventricular myocytes. J Physiol 493 (Pt 3):793-800.

DuBell WH, Gigena MS, Guatimosim S, Long X, Lederer WJ, Rogers TB (2002) Effects of PP1/PP2A inhibitor calyculin A on the E-C coupling cascade in murine ventricular myocytes. Am J Physiol Heart Circ Physiol 282:H38-48.

Dulhunty AF, Beard NA, Pouliquin P, Casarotto MG (2007) Agonists and antagonists of the cardiac ryanodine receptor: potential therapeutic agents? Pharmacol Ther 113:247-263.

Elbashir SM, Martinez J, Patkaniowska A, Lendeckel W, Tuschl T, Functional anatomy of SiRNAs for mediating efficient RNAi in Drosophila melanogaster embryo lysate, The EMBO Journal, vol. 20, No. 23, pp. 6877-6888, 2001.

Endo S, Zhou X, Connor J, Wang B, Shenolikar S (1996) Multiple structural elements define the specificity of recombinant human inhibitor-1 as a protein phosphatase-1 inhibitor. Biochemistry 35:5220-5228.

Fatkin D, MacRae C, Sasaki T, Wolff MR, Porcu M, Frenneaux M, Atherton J, Vidaillet HJ, Jr., Spudich S, De Girolami U, Seidman JG, Seidman C, Muntoni F, Muehle G, Johnson W, McDonough B (1999) Missense mutations in the rod domain of the lamin NC gene as causes of dilated cardiomyopathy and conduction-system disease. N Engl J Med 341:1715-1724.

Fischmeister R, Castro LR, Abi-Gerges A, Rochais F, Jurevicius J, Leroy J, Vandecasteele G (2006) Compartmentation of cyclic nucleotide signaling in the heart: the role of cyclic nucleotide phosphodiesterases. Circ Res 99:816-828.

Friday BB, Mitchell PO, Kegley KM, Pavlath GK (2003) Calcineurin initiates skeletal muscle differentiation by activating MEF2 and MyoD. Differentiation 71:217-227.

Gerber, Y., S. A. Weston, M. Enriquez-Sarano, C. Berardi, A. M. Chamberlain, S. M. Manemann, R. Jiang, S. M. Dunlay and V. L. Roger (2016). "Mortality Associated With Heart Failure After Myocardial Infarction: A Contemporary Community Perspective." Circ Heart Fail 9(1): e002460.

Gigena MS, Ito A, Nojima H, Rogers TB (2005) A B56 regulatory subunit of protein phosphatase 2A localizes to nuclear speckles in cardiomyocytes. Am J Physiol Heart Circ Physiol 289:H285-294.

Go AS et al. (2014) Heart disease and stroke statistics—2014 update: a report from the American Heart Association. Circulation 129:e28-e292.

Grossman W, Jones D, McLaurin LP (1975) Wall stress and patterns of hypertrophy in the human left ventricle. J Clin Invest 56:56-64.

Guo, H., B. Liu, L. Hou, E. The, G. Li, D. Wang, Q. Jie, W. Che and Y. Wei (2015). "The role of mAKAPbeta in the process of cardiomyocyte hypertrophy induced by angiotensin II." Int J Mol Med 35(5): 1159-1168.

Hanlon M, Sturgill TW, Sealy L (2001) ERK2- and p90(Rsk2)-dependent pathways regulate the CCAAT/enhancer-binding protein-beta interaction with serum response factor. J Biol Chem 276:38449-38456.

Hayes JS, Brunton LL, Mayer SE (1980) Selective activation of particulate cAMP-dependent protein kinase by isoproterenol and prostaglandin El. J Biol Chem 255:5113-5119.

Heidenreich, P. A., N. M. Albert, L. A. Allen, D. A. Bluemke, J. Butler, G. C. Fonarow, J. S. Ikonomidis, O. Khavjou, M. A. Konstam, T. M. Maddox, G. Nichol, M. Pham, I. L. Pina, J. G. Trogdon, C. American Heart Association Advocacy Coordinating, T. Council on Arteriosclerosis, B. Vascular, R. Council on Cardiovascular, Intervention, C. Council on Clinical, E. Council on, Prevention and C. Stroke (2013). "Forecasting the impact of heart failure in the United States: a policy statement from the American Heart Association." Circ Heart Fail 6(3): 606-619.

Heineke J, Molkentin JD (2006) Regulation of cardiac hypertrophy by intracellular signaling pathways. Nat Rev Mol Cell Biol 7:589-600.

Ho SN, Thomas DJ, Timmerman LA, Li X, Francke U, Crabtree GR (1995) NFATc3, a lymphoid-specific NFATc family member that is calcium-regulated and exhibits distinct DNA binding specificity. J Biol Chem 270:19898-19907.

Hoffmann R, Baillie GS, Mackenzie SJ, Yarwood SJ, Houslay MD (1999) The MAP kinase ERK2 inhibits the cyclic AMP-specific phosphodiesterase HSPDE4D3 by phosphorylating it at Ser579. EMBO J 18:893-903.

Houser SR (2014) Role of RyR2 phosphorylation in heart failure and arrhythmias: protein kinase A-mediated hyperphosphorylation of the ryanodine receptor at serine 2808 does not alter cardiac contractility or cause heart failure and arrhythmias. Circ Res 114:1320-1327; discussion 1327.

Huang LJ, Durick K, Weiner JA, Chun J, Taylor SS. Identification of a novel protein kinase A anchoring protein that binds both type I and type II regulatory subunits. J Biol Chem. 1997;272:8057-8064.

Janknecht R, Hipskind RA, Houthaeve T, Nordheim A, Stunnenberg HG (1992) Identification of multiple SRF N-terminal phosphorylation sites affecting DNA binding properties. EMBO J 11:1045-1054.

Jugdutt BI (2003) Remodeling of the myocardium and potential targets in the collagen degradation and synthesis pathways. Curr Drug Targets Cardiovasc Haematol Disord 3:1-30.

Kato Y, Zhao M, Morikawa A, Sugiyama T, Chakravortty D, Koide N, Yoshida T, Tapping RI, Yang Y, Yokochi T, Lee JD (2000) Big mitogen-activated kinase regulates multiple members of the MEF2 protein family. J Biol Chem 275:18534-18540.

Keely SL (1977) Activation of cAMP-dependent protein kinase without a corresponding increase in phosphorylase activity. Res Commun Chem Pathol Pharmacol 18:283-290.

Keely SL (1979) Prostaglandin El activation of heart cAMP-dependent protein kinase: apparent dissociation of protein kinase activation from increases in phosphorylase activity and contractile force. Mol Pharmacol 15:235-245.

Kim Y, Phan D, van Rooij E, Wang DZ, McAnally J, Qi X, Richardson JA, Hill JA, Bassel-Duby R, Olson EN (2008) The MEF2D transcription factor mediates stress-dependent cardiac remodeling in mice. J Clin Invest 118:124-132.

Kumar, D., T. A. Hacker, J. Buck, L. F. Whitesell, E. H. Kaji, P. S. Douglas and T. J. Kamp (2005). "Distinct mouse coronary anatomy and myocardial infarction consequent to ligation." Coron Artery Dis 16(1): 41-44.

Lechward K, Awotunde OS, Swiatek W, Muszynska G (2001) Protein phosphatase 2A: variety of forms and diversity of functions. Acta Biochim Pol 48:921-933.

Lehnart, S. E., X. H. Wehrens, S. Reiken, S. Warrier, A. E. Belevych, R. D. Harvey, W. Richter, S. L. Jin, M. Conti and A. R. Marks (2005). "Phosphodiesterase 4D deficiency in the ryanodine-receptor complex promotes heart failure and arrhythmias." Cell 123(1): 25-35.

Li CL, Sathyamurthy A, Oldenborg A, Tank D, Ramanan N (2014) SRF phosphorylation by glycogen synthase kinase-3 promotes axon growth in hippocampal neurons. J Neurosci 34:4027-4042.

Li J, Negro A, Lopez J, Bauman AL, Henson E, Dodge-Kafka K, Kapiloff MS, "The mAKAPbeta scaffold regulates cardiac myocyte hypertrophy via recruitment of activated calcineurin," J Mol Cell Cardiol. Feb. 2010;48(2):387-94.

Li, J., S. Aponte Paris, H. Thakur, M. S. Kapiloff, and K. L. Dodge-Kafka. 2019. 'Muscle A-kinase-anchoring protein-beta-bound calcineurin toggles active and repressive transcriptional complexes of myocyte enhancer factor 2D', Journal of Biological Chemistry, 294: 2543-54.

Li M, Makkinje A, Damuni Z (1996) Molecular identification of I1PP2A, a novel potent heat-stable inhibitor protein of protein phosphatase 2A. Biochemistry 35:6998-7002.

Liu Q, Hofmann PA (2004) Protein phosphatase 2A-mediated cross-talk between p38 MAPK and ERK in apopfosis of cardiac myocytes. Am J Physiol Heart Circ Physiol 286:H2204-2212.

(56) References Cited

OTHER PUBLICATIONS

Mack CP (2011) Signaling mechanisms that regulate smooth muscle cell differentiation. Arterioscler Thromb Vase Biol 31:1495-1505.

Mackenzie KF, Topping EC, Bugaj-Gaweda B, Deng C, Cheung YF, Olsen AE, Stockard CR, High Mitchell L, Baillie GS, Grizzle WE, De Vivo M, Houslay MD, Wang D, Bolger GB (2008) Human PDE4A8, a novel brain-expressed PDE4 cAMP-specific phosphodiesterase that has undergone rapid evolutionary change. Biochem J 411:361-369.

MacKenzie SJ, Baillie GS, McPhee I, Bolger GB, Houslay MD (2000) ERK2 mitogen-activated protein kinase binding, phosphorylation, and regulation of the PDE4D cAMP-specific phosphodiesterases. The involvement of COOH-terminal docking sites and NH2-terminal UCR regions. J Biol Chem 275:16609-16617.

Martinez, E. C., C. L. Passariello, J. Li, C. J. Matheson, K. Dodge-Kafka, P. Reigan and M. S. Kapiloff (2015). "RSK3: A regulator of pathological cardiac remodeling." IUBMB Life 67(5): 331-337.

McCright B, Rivers AM, Audlin S, Virshup DM (1996) The B56 family of protein phosphatase 2A (PP2A) regulatory subunits encodes differentiation-induced phosphoproteins that target PP2A to both nucleus and cytoplasm. J Biol Chem 271:22081-22089.

Miano JM (2010) Role of serum response factor in the pathogenesis of disease. Lab Invest 90:1274-1284.

Monovich L, Vega RB, Meredith E, Miranda K, Rao C, Capparelli M, Lemon DD, Phan D, Koch KA, Chapo JA, Hood DB, McKinsey TA (2010) A novel kinase inhibitor establishes a predominant role for protein kinase D as a cardiac class IIa histone deacetylase kinase. FEBS Lett 584:631-637.

Muchir A, Bonne G, van der Kooi AJ, van Meegen M, Baas F, Bolhuis PA, de Visser M, Schwartz K (2000) Identification of mutations in the gene encoding lamins A/C in autosomal dominant limb girdle muscular dystrophy with atrioventricular conduction disturbances (LGMDIB). Hum Mol Genet 9:1453-1459.

Naya FJ, Olson E (1999) MEF2: a transcriptional target for signaling pathways controlling skeletal muscle growth and differentiation. Curr Opin Cell Biol 11:683-688.

Naya FJ, Wu C, Richardson JA, Overbeek P, Olson EN (1999) Transcriptional activity of MEF2 during mouse embryogenesis monitored with a MEF2-dependent transgene. Development 126:2045-2052.

Newlon MG, Roy M, Morikis D, Hausken ZE, Coghlan V, Scott JD, Jennings PA (1999) The molecular basis for protein kinase A anchoring revealed by solution NMR. Nat Struct Biol 6:222-227.

Niggli E, Lederer WJ. Voltage-independent calcium release in heart muscle. Science 250: 565-568, 1990.

Ohh M, Park CW, Ivan M, Hoffman MA, Kim TY, Huang LE, Pavletich N, Chau V, Kaelin WG (2000) Ubiquitination of hypoxia-inducible factor requires direct binding to the beta-domain of the von Hippel-Lindau protein. Nat Cell Biol 2:423-427.

Okumura, S., G. Takagi, J. Kawabe, G. Yang, M. C. Lee, C. Hong, J. Liu, D. E. Vatner, J. Sadoshima, S. F. Vatner and Y. Ishikawa (2003). "Disruption of type 5 adenylyl cyclase gene preserves cardiac function against pressure overload." Proc Natl Acad Sci U S A 100(17): 9986-9990.

Passariello, C. L., J. Li, K. Dodge-Kafka and M. S. Kapiloff (2015). "mAKAP-a master scaffold for cardiac remodeling." J Cardiovasc Pharmacol 65(3): 218-225.

Passariello CL, Martinez EC, Thakur H, Cesareo M, Li J, Kapiloff MS (2016) RSK3 is required for concentric myocyte hypertrophy in an activated Raf1 model for Noonan syndrome. J Mol Cell Cardiol 93:98-105.

Pawson T, Nash P (2003) Assembly of cell regulatory systems through protein interaction domains. Science 300:445-452.

Peter AK, Bjerke MA, Leinwand LA (2016) Biology of the cardiac myocyte in heart disease. Mol Biol Cell 27:2149-2160.

Ponikowski, P., A. A. Voors, S. D. Anker, H. Bueno, J. G. Cleland, A. J. Coats, V. Falk, J. R. Gonzalez-Juanatey, V. P. Harjola, E. A. Jankowska, M. Jessup, C. Linde, P. Nihoyannopoulos, J. T. Parissis, B. Pieske, J. P. Riley, G. M. Rosano, L. M. Ruilope, F. Ruschitzka, F. H. Rutten, P. van der Meer and M. Authors/Task Force (2016). "2016 ESC Guidelines for the diagnosis and treatment of acute and chronic heart failure: The Task Force for the diagnosis and treatment of acute and chronic heart failure of the European Society of Cardiology (ESC) Developed with the special contribution of the Heart Failure Association (HFA) of the ESC." Eur Heart J 37(27): 2129-2200.

Potthoff MJ, Olson EN (2007) MEF2: a central regulator of diverse developmental programs. Development 134:4131-4140.

Prasad, K. M., Y. Xu, Z. Yang, S. T. Acton and B. A. French (2011). "Robust cardiomyocyte-specific gene expression following systemic injection of AAV: in vivo gene delivery follows a Poisson distribution." Gene Ther 18(1): 43-52.

Ranganathan A, Pearson GW, Chrestensen CA, Sturgill TW, Cobb MH (2006) The MAP kinase ERK5 binds to and phosphorylates p90 RSK. Arch Biochem Biophys 449:8-16.

Reiken S, Gaburjakova M, Gaburjakova J, He Kl KL, Prieto A, Becker E, Yi Gh GH, Wang J, Burkhoff D, Marks AR (2001) beta-adrenergic receptor blockers restore cardiac calcium release channel (ryanodine receptor) structure and function in heart failure. Circulation 104:2843-2848.

Resjo S, Oknianska A, Zolnierowicz S, Manganiello V, Degerman E (1999) Phosphorylation and activation of phosphodiesterase type 38 (PDE3B) in adipocytes in response to serine/threonine phosphatase inhibitors: deactivation of PDE3B in vitro by protein phosphatase type 2A. Biochem J 341 (Pt 3):839-845.

Rivera VM, Miranti CK, Misr;i RP, Ginty DD, Chen RH, Blenis J, Greenberg ME (1993) A growth factor-induced kinase phosphorylates the serum response factor at a site that regulates its DNA-binding activity. Mol Cell Biol 13:6260-6273.

Schiattarella GG, Hill JA (2015) Inhibition of hypertrophy is a good therapeutic strategy in ventricular pressure overload. Circulation 131:1435-1447.

Scott JD, Dessauer CW, Tasken K (2013) Creating order from chaos: cellular regulation by kinase anchoring. Annu Rev Pharmacol Toxicol 53:187-210.

Scott, J. D. and T. Pawson (2009). "Cell signaling in space and time: where proteins come together and when they're apart." Science 326(5957): 1220-1224.

Sette C, Conti M (1996) Phosphorylation and activation of a cAMP-specific phosphodiesterase by the cAMP-dependent protein kinase. Involvement of serine 54 in the enzyme activation. J Biol Chern 271:16526-16534.

Sharma K, Kass DA (2014) Heart failure with preserved ejection fraction: mechanisms, clinical features, and therapies. Circ Res 115:79-96.

Silva, J. M., M. Z. Li, K. Chang, W. Ge, M. C. Golding, R. J. Rickles, D. Siolas, G. Hu, P. J. Paddison, M. R. Schlabach, N. Sheth, J. Bradshaw, J. Burchard, A. Kulkarni, G. Cavet, R. Sachidanandam, W. R. McCombie, M. A. Cleary, S. J. Elledge and G. J. Hannon (2005). "Second-generation shRNA libraries covering the mouse and human genomes." Nat Genet 37(11): 1281-1288.

Steinberg SF, Brunton LL (2001) Compartmentation of G protein-coupled signaling pathways in cardiac myocytes. Annu Rev Pharmacol Toxicol 41:751-773.

Treisman R (1985) Transient accumulation of c-fos RNA following serum stimulation requires a conserved 5' element and c-fos 3' sequences. Cell 42:889-902.

Valdivia HH, Kaplan JH, Ellis-Davies GC, Lederer WJ (1995) Rapid adaptation of cardiac ryanodine receptors: modulation by Mg2+ and phosphorylation. Science 267:1997-2000.

Virshup DM (2000) Protein phosphatase 2A: a panoply of enzymes. Curr Opin Cell Biol 12:180-185.

Wang X, Tang X, Li M, Marshall J, Mao Z (2005) Regulation of neuroprotective activity of myocyte-enhancer factor 2 by cAMP-protein kinase A signaling pathway in neuronal survival. J Biol Chem 280:16705-16713.

Wang, Y., E. G. Cameron, J. Li, T. L. Stiles, M. D. Kritzer, R. Lodhavia, J. Hertz, T. Nguyen, M. S. Kapiloff and J. L. Goldberg (2015). "Muscle A-Kinase Anchoring Protein-alpha is an Injury-Specific Signaling Scaffold Required for Neurotrophic- and Cyclic Adenosine Monophosphate-Mediated Survival." EBioMedicine 2(12): 1880-1887.

(56) References Cited

OTHER PUBLICATIONS

Wang, Z., H. I. Ma, J. Li, L. Sun, J. Zhang and X. Xiao (2003). "Rapid and highly efficient transduction by double-stranded adeno-associated virus vectors in vitro and in vivo." Gene Ther 10(26): 2105-2111.

Wera S, Hemmings BA (1995) Serine/threonine protein phosphatases. Biochem J 311 ( Pt 1):17-29.

Wilkins BJ, De Windt LJ, Bueno OF, Braz JC, Glascock BJ, Kimball TF, Molkentin JD (2002) Targeted disruption of NFATc3, but not NFATc4, reveals an intrinsic defect m calcineurin-mediated cardiac hypertrophic growth. Mol Cell Biol 22:7603-7613.

Wilkins BJ, Dai YS, Bueno OF, Parsons SA, Xu J, Plank DM, Jones F, Kimball TR, Molkentin JD (2004) Calcineurin/NFAT coupling participates in pathological, but not physiological, cardiac hypertrophy. Circ Res 94:110-118.

Wu X, Simpson J, Hong JH, Kim KH, Thavarajah NK, Backx PH, Neel BG, Araki T. MEK-ERK pathway modulation ameliorates disease phe-notypes in a mouse model of Noonan syndrome associated with the Raf1(L613V) mutation. J Clin Invest. 2011;121:1009-1025.

Writing Group, M., D. Mozaffarian, E. J. Benjamin, A. S. Go, D. K. Arnett, M. J. Blaha, M. Cushman, S. R. Das, S. de Ferranti, J. P. Despres, H. J. Fullerton, V. J. Howard, M. D. Huffman, C. R. Isasi, M. C. Jimenez, S. E. Judd, B. M. Kissela, J. H. Lichtman, L. D. Lisabeth, S. Liu, R. H. Mackey, D. J. Magid, D. K. McGuire, E. R. Mohler, 3rd, C. S. Moy, P. Muntner, M. E. Mussolino, K. Nasir, R. W. Neumar, G. Nichol, L. Palaniappan, D. K. Pandey, M. J. Reeves, C. J. Rodriguez, W. Rosamond, P. D. Sorlie, J. Stein, A. Towfighi, T. N. Turan, S. S. Virani, D. Woo, R. W. Yeh, M. B. Turner, C. American Heart Association Statistics and S. Stroke Statistics (2016). "Heart Disease and Stroke Statistics—2016 Update: A Report From the American Heart Association." Circulation 133(4): e38-360.

Wu H, Rothermel B, Kanatous S, Rosenberg P, Naya FJ, Shelton JM, Hutcheson KA, DiMaio JM, Olson EN, Bassel-Duby R, Williams RS (2001) Activation of MEF2 by muscle activity is mediated through a calcineurin-dependent pathway. EMBO J 20:6414-6423.

Xie M, Hill JA (2013) HDAC-dependent ventricular remodeling. Trends Cardiovasc Med 23:229-235.

Yang J, Drazba JA, Ferguson DG, Bond M (1998) A-kinase anchoring protein 100 (AKAPlOO) is localized in multiple subcellular compartments in the adult rat heart. J Cell Biol 142:511-522.

Zakhary DR, Fink MA, Ruehr ML, Bond M (2000) Selectivity and regulation of A-kinase anchoring proteins in the heart. The role of autophosphorylation of the type II regulatory subunit of cAMP-dependent protein kinase. J Biol Chem 275:41389-41395.

Zhang, L., S. Malik, J. Pang, H. Wang, K. M. Park, D. I. Yule, B. C. Blaxall and A. V. Smrcka (2013). "Phospholipase Cepsilon hydrolyzes perinuclear phosphatidylinositol 4-phosphate to regulate cardiac hypertrophy." Cell 153(1): 216-227.

Zhang Q, Bethmann C, Worth NF, Davies JD, Wasner C, Feuer A, Ragnauth CD, Yi Q, Mellad JA, Warren DT, Wheeler MA, Ellis JA, Skepper JN, Vorgerd M, Schlotter-Weigel B, Weissberg PL, Roberts RG, Wehnert M, Shanahan CM (2007) Nesprin-1 and -2 are involved in the pathogenesis of Emery Dreifuss muscular dystrophy and are critical for nuclear envelope integrity. Hum Mol Genet 16:2816-2833.

Notice of Reasons for Refusal in Japanese patent application No. 2021-568509 dated Nov. 14, 2023, 11 pages (with English translation).

\* cited by examiner

FIGURE 2

```
>h-RSK3 1-12 A yellow
MECHMSELVSSINRSEPVKLRRGHPSSLGRLDRGHVPR IDISHHVEEGFEKADPSQFELLKVLGQGSY
GKVFLVRKVKGSDAGQLYAMKVLKKATLKVRDFVRSKMERDILAEVNHPFIVKLHYAFQTEGKLYLILDF
LRGGDLFTRLSKEVMFTEEDVKFYLAELALALDHLHSLGIIYRDLKPENILLDEEGHIKITDFGLSKEAI
DHOKPAYSFCGTIEYMAPEVVNRRGHTQSADWWSFGVLMFEMLTGSLPFQGKDRKETMALILKARLGMPQ
FLSGEAQSLLRALFKRNPCNRLGAGIDGVEEIKRHPFFVTIDWNTLYRKEIKPPFKPAVGRPEDTFHFDP
EFTARTPTDSPGVPPSANAHHLPRGFSFVASSLIQEPSQQDLHKVPVEPIVQQLEGNNIHFTDGYEIKED
IGVGSYSVCKRCVHKATDTEYAVKIIDKSERDPSEEIEILLRYGQHPNIITLKDVYDDGKFVYLVMELMR
GGELLDRILRQKYFSEREASDVLCTITKTMDYLHSQGVVHRDLKPSNILYRDESGSPESIRVCDFGFAKQ
LRAGNGLLMTPCYTANFVAPEVLKRQGYDAACDIWSLGILLYTMLAGFTPFANGPDDTPEEILARIGSGK
YALSGGNWDSISDAAKDVVSRMLHVDFHQRLTAMQVLKHPWVVNREYLSPNQLSRQDVHLVKGAMAATYF
ALNRTPQAPRLEPVLSSNLAQRRGMKRLTSTFL
```

FIGURE 3 rat mAKAP sequence (PBD highlighted)

```
   1  MLTMSVTLSP  LRSQGPDPMA  TDASPMAINM  TPTVEQEEGE  GEEAVKAIDA
  51  EQQYGKPPPL  HTAADWKIVL  HLPEIETWLR  MTSERVRDLT  YSVQQDADSK
 101  HVDVHLVQLK  DICEDISDHV  EQIHALLETE  FSLKLLSYSV  NVIVDIHAVQ
 151  LLWHQLRVSV  LVLRERILQG  LQDANGNYTR  QTDILQAFSE  ETTEGRLDSL
 201  TEVDDSGQLT  IKCSQDYLSL  DCGITAFELS  DYSPSEDLLG  GLGDMTTSQA
 251  KTKSFDSWSY  SEMEKEFPEL  IRSVGLLTVA  TEPVPSSCGE  ANEDSSQASL
 301  SDDHKGEHGE  DGAPVPGQQL  DSTVGMSSLD  GTLANAAEHP  SETAKQDSTS
 351  SPQLGAKKTQ  PGPCEITTPK  RSIRDCFNYN  EDSPTQPTLP  KRGLFLKETQ
 401  KNERKGSDRK  GQVVDLKPEL  SRSTPSLVDP  PDRSKLCLVL  QSSYPSSPSA
 451  ASQSYECLHK  VGLGNLENIV  RSHIKEISSS  LGRLTDCHKE  KLRLKKPHKT
 501  LAEVSLCRIP  KQGGGSGKRS  ESTGSSAGPS  MVSPGAPKAT  MRPETDSAST
 551  ASGGLCHQRN  RSGQLPVQSK  ASSSPPCSHS  SESSLGSDSI  KSPVPLLSKN
 601  KSQKSSPPAP  CHATQNGQVV  EAWYGSDEYL  ALPSHLKQTE  VLALKLESLT
 651  KLLPQKPRGE  TIQDIDDWEL  SEMNSDSEIY  PTYHIKKKHT  RLGTVSPSSS
 701  SDIASSLGES  IESGPLSDIL  SDEDLCLPLS  SVKKFTDEKS  ERPSSSEKNE
 751  SHSATRSALI  QKLMHDIQHQ  ENYEAIWERI  EGFVNKLDEF  IQWLNEAMET
 801  TENWTPPKAE  TDSLRLYLET  HLSFKLNVDS  HCALKEAVEE  EGHQLLELVV
 851  SHKAGLKDTL  RMIASQWKEL  QRQIKRQHSW  ILRALDTIKA  EILATDVSVE
 901  DEEGTGSPKA  EVQLCHLETQ  RDAVEQMSLK  LYSEQYTSGS  KRKEEFANMS
 951  KAHAEGSNGL  LDFDSEYQEL  WDWLIDMESL  VMDSHDLMMS  EEQQQHLYKR
1001  YSVEMSIRHL  KKSELLSKVE  ALKKGGLSLP  DDILEKVDSI  NEKWELLGKT
1051  LREKIQDTIA  GHSGSGPRDL  LSPESGSLVR  QLEVRIKELK  RWLRDTELFI
1101  FNSCLRQEKE  GTSAEKQLQY  FKSLCREIKQ  RRRGVASILR  LCQHLLDDRD
1151  TCNLNADHQP  MQLIIVNLER  RWEAIVMQAV  QWQTRLQKKM  GKESETLNVI
1201  DPGLMDLNGM  SEDALEWDET  DISNKLISVH  EESNDLDQDP  EPMLPAVKLE
1251  ETHHKDSGYE  EEAGDCGGSP  YTSNITAPSS  PHIYQVYSLH  NVELHEDSHT
1301  PFLKSSPKFT  GTTQPTVLTK  SLSKDSSFSS  TKSLPDLLGG  SGLVRPYSCH
1351  SGDLSQNSGS  ESGIVSEGDN  EMPTNSDMSL  FSMVDGSPSN  PETEHPDPQM
1401  GDAANVLEQK  FKDNGESIKL  SSVSRASVSP  VGCVNGKAGD  LNSVTKHTAD
1451  CLGEELQGKH  DVFTFYDYSY  LQGSKLKLPM  IMKQPQSEKA  HVEDPLLGGF
1501  YFDKKSCKAK  HQASESQPDA  PPHERILASA  PHEMGRSAYK  SSDIEKTFTG
1551  IQSARQLSLL  SRSSSVESLS  PGGDLFGLGI  FKNGSDSLQR  STSLESWLTS
1601  YKSNEDLFSC  HSSGDISVSS  GSVGELSKRT  LDLLNRLENI  QSPSEQKIKR
1651  SVSDMTLQSS  SQKMPFAGQM  SLDVASSINE  DSPASLTELS  SSDELSLCSE
1701  DIVLHKNKIP  ESNASFRKRL  NRSVADESDV  NVSMIVNVSC  TSACTDDEDD
1751  SDLLSSSTLT  LTEEELCLKD  EDDDSSIATD  DEIYEESNLM  SGLDYIKNEL
1801  QTWIRPKLSL  TREKKRSGVT  DEIKVNKDGG  GNEKANPSDT  LDIEALLNGS
1851  IRCLSENNGN  GKTPPRTHGS  GTKGENKKST  YDVSKDPHVA  DMENGNIEST
1901  PEREREKPQG  LPEVSENLAS  NVKTISESEL  SEYEAVMDGS  EDSSVARKEF
1951  CPPNDRHPPQ  MGPKLQHPEN  QSGDCKPVQN  PCPGLLSEAG  VGSRQDSNGL
2001  KSLPNDAPSG  ARKPAGCCLL  EQNETEESAS  ISSNASCCNC  KPDVFHQKDD
```

FIGURE 3 (cont.)

```
2051  EDCSVHDFVK  EIIDMASTAL  KSKSQPESEV  AAPTSLTQIK  EKVLEHSHRP
2101  IHLRKGDFYS  YLSLSSHDSD  CGEVTNYIDE  KSSTPLPPDA  VDSGLDDKED
2151  MDCFFEACVE  DEPVNEEAGL  PGALPNESAI  EDGAEQKSEQ  KTASSPVLSD
2201  KTDLVPLSGL  SPQKGADDAK  EGDDVSHTSQ  GCAESTEPTT  PSGKANAEGR
2251  SRMQGVSATP  EENAASAKPK  IQAFSLNAKQ  PKGKVAMRYP  SPQTLTCKEK
2301  LVNFHEDRHS  NMHR
```

FIGURE 4

Sequence for myc-PBD:

```
  1 meqkliseed lspgmltmsv tlsplrsqtp lppdavdsgl ddkedmdcff eacvedenvn
 61 eeaglpgalp nesaiedgae qkseqktass pvlsdktdlv plsglspqkg addakegddv
121 shtsqgcaes tepttpsgka naegrsrnqg vsatpeenaa sakpkiqafs lnakqpkgkv
181 amrvpspqtl tckeklvnfh edrhsnmhr
```

FIGURE 5 pscA-TnT-myc-rat mAKAP PBD

```
   1  ACTCAACCAA GTCATTCTGA GAATAGTGTA TGCGGCGACC GAGTTGCTCT
  51  TGCCCGGCGT CAATACGGGA TAATACCGCG CCACATAGCA GAACTTTAAA
 101  AGTGCTCATC ATTGGAAAAC GTTCTTCGGG GCGAAAACTC TCAAGGATCT
 151  TACCGCTGTT GAGATCCAGT TCGATGTAAC CCACTCGTGC ACCCAACTGA
 201  TCTTCAGCAT CTTTTACTTT CACCAGCGTT TCTGGGTGAG CAAAAACAGG
 251  AAGGCAAAAT GCCGCAAAAA AGGGAATAAG GGCGACACGG AAATGTTGAA
 301  TACTCATACT CTTCCTTTTT CAATATTATT GAAGCATTTA TCAGGGTTAT
 351  TGTCTCATGA GCGGATACAT ATTTGAATGT ATTTAGAAAA ATAAACAAAT
 401  AGGGGTTCCG CGCACATTTC CCCGAAAAGT GCCACCTGAC GTCTAAGAAA
 451  CCATTATTAT CATGACATTA ACCTATAAAA ATAGGCGTAT CACGAGGCCC
 501  TTTCGTCTCG CGCGTTTCGG TGATGACGGT GAAAACCTCT GACACATGCA
 551  GCTCCCGGAG ACGGTCACAG CTTGTCTGTA AGCGGATGCC GGGAGCAGAC
 601  AAGCCCGTCA GGGCGCGTCA GCGGGTGTTG GCGGGTGTCG GGCTGGCTT
 651  AACTATGCGG CATCAGAGCA GATTGTACTG AGAGTGCACC ATATGGACAT
 701  ATTGTCGTTA GAACGCGGCT ACAATTAATA CATAACCTTA TGTATCATAC
 751  ACATACGATT TAGGTGACAC TATAGAACTC GAGCCTGCGC GCTCGCTCGC
 801  TCACTGAGGC CGCCCGGGCA AGCCCGGGC GTCGGCGAC CTTTGGTCGC
 851  CCGGCCTCAG TGAGCGAGCG AGCGCGCAGA GAGGGAGTGG CCAACTCCAT
 901  CACTAGGGGT TCCTTGTAGT TAATGATTAA CCCGCCATGC TACTTATCTA
 951  CGTAGCCATG CTCTAGAGCA GTCTGGGCTT TCACAAGACA GCATCTGGGG
1001  CTGCGGCAGA GGGTCGGGTC CGAAGCGCTG CCTTATCAGC GTCCCCAGCC
1051  CTGGGAGGTG ACAGCTGGCT GGCTTGTGTC AGCCCCTCGG CACTCACGT
1101  ATCTCCGTCC GACGGGTTTA AAATAGCAAA ACTCTGAGGC CACACAATAG
1151  CTTGGGCTTA TATGGGCTCC TGTGGGGGAA GGGGGAGCAC GGAGGGGGCC
1201  GGGGCCGCTG CTGCCAAAAT AGCAGCTCAC AAGTGTTGCA TTCCTCTCTG
1251  GGCGCCGGGC ACATTCCTGC TGGCTCTGCC CGCCCCGGGG TGGGCGCCGG
1301  GGGGACCTTA AAGCCTCTGC CCCCAAGGA GCCCTTCCCA GACAGCCGCC
1351  GGCACCCACC GCTCCGTGGG ACCTAAGCTT GCTAGCGCTA CCGGTCGCCA
              M   E   Q   K   L   I   S   E   E   D   L   S   P   G   M   L
1401  CCATGGAGCA GAAACTCATC TCTGAAGAGG ATCTGAGCCC GGGGATGTTA
       T   M   S   V   T   L   S   P   L   R   S   Q   T   P   L   P   P ·
1451  ACCATGAGCG TGACACTTTC CCCACTGAGG TCACAGACTC CATTGCCACC
      · D   A   V   D   S   G   L   D   D   K   E   D   M   D   C   F   F ·
1501  GGACGCTGTG GACTCTGGCT TAGATGACAA GGAAGACATG GACTGCTTCT
      · E   A   C   V   E   D   E   P   V   N   E   E   A   G   L   P
1551  TTGAAGCTTG TGTTGAGGAT GAGCCTGTCA ATGAGGAAGC TGGTCTCCCC
          G   A   L   P   N   E   S   A   I   E   D   G   A   E   Q   K   S ·
1601  GGTGCCCTTC CCAATGAATC AGCCATCGAG GATGGAGCAG AGCAAAAGTC
      · E   Q   K   T   A   S   S   P   V   L   S   D   K   T   D   L   V ·
1651  AGAACAAAAG ACAGCCAGCT CTCCTGTGCT CAGTGACAAG ACAGACCTGG
      ·   P   L   S   G   L   S   P   Q   K   G   A   D   D   A   K   E
```

FIGURE 5 (cont.)

```
1701  TGCCTCTTTC AGGACTTTCC CCTCAGAAGG GAGCTGATGA TGCAAAGGAA
        G   D   D   V   S   H   T   S   Q   G   C   A   E   S   T   E   P  ·
1751  GGAGATGATG TGTCTCACAC TTCCCAGGGC TGTGCAGAGA GCACAGAGCC
      ·  T   T   P   S   G   K   A   N   A   E   G   R   S   R   M   Q   G  ·
1801  TACCACCCCC TCAGGAAAGG CCAATGCAGA GGGGAGGTCA AGAATGCAAG
      ·  V   S   A   T   P   E   N   A   A   S   A   K   P   K   I
1851  GTGTATCAGC AACGCCAGAA GAAAACGCTG CTTCGGCCAA ACCGAAAATT
        Q   A   F   S   L   N   A   K   Q   P   K   G   K   V   A   M   R  ·
1901  CAAGCTTTCT CTTTGAATGC AAAACAGCCA AAAGGCAAGG TTGCCATGAG
      ·  Y   P   S   P   Q   T   L   T   C   K   E   K   L   V   N   F   H  ·
1951  GTATCCCAGC CCCCAAACTC TAACCTGTAA AGAGAAGCTC GTAAACTTTC
      ·  E   D   R   H   S   N   M   H   R
2001  ATGAAGATCG ACACAGTAAC ATGCATAGGT AGAGTGTAAT GCCCCACGC
2051  ATGGAAATCA TCTCATTGAA AGATAGCCTG GCTGAAGCTC AGGGCTAGTT
2101  AAGTTTGATC CAGACATGAT AAGATACATT GATGAGTTTG ACAAACCAC
2151  AACTAGAATG CAGTGAAAAA AATGCTTTAT TTGTGAAATT TGTGATGCTA
2201  TTGCTTTATT TGTAACCATT ATAAGCTGCA ATAAACAAGT TAACAACAAC
2251  AATTGCATTC ATTTTATGTT TCAGGTTCAG GGGGAGGTGT GGGAGGTTTT
2301  TTAAAGCAAG TAAAACCTCT ACAAATGTGG TATGGCTGAT TACCACTCCC
2351  TCTCTGCGCG CTCGCTCGCT CACTGAGGCC GGGCGACCAA AGGTCGCCCG
2401  ACGCCCGGGC TTTGCCCGGG CGGCCTCAGT GAGCGAGCGA GCGCGCCAGC
2451  TGAAGCTATC AGATCTGCCG GTCTCCCTAT AGTGAGTCGT ATTAATTTCG
2501  ATAAGCCAGG TTAACCTGCA TTAATGAATC GGCCAACGCG CGGGGAGAGG
2551  CGGTTTGCGT ATTGGGCGCT CTTCCGCTTC CTCGCTCACT GACTCGCTGC
2601  GCTCGGTCGT TCGGCTGCGG CGAGCGGTAT CAGCTCACTC AAAGGCGGTA
2651  ATACGGTTAT CCACAGAATC AGGGGATAAC GCAGGAAAGA ACATGTGAGC
2701  AAAAGGCCAG CAAAAGGCCA GGAACCGTAA AAAGGCCGCG TTGCTGGCGT
2751  TTTTCCATAG GCTCCGCCCC CCTGACGAGC ATCACAAAAA TCGACGCTCA
2801  AGTCAGAGGT GGCGAAACCC GACAGGACTA TAAAGATACC AGGCGTTTCC
2851  CCCTGGAAGC TCCCTCGTGC GCTCTCCTGT TCCGACCCTG CCGCTTACCG
2901  GATACCTGTC CGCCTTTCTC CCTTCGGGAA GCGTGGCGCT TTCTCATAGC
2951  TCACGCTGTA GGTATCTCAG TTCGGTGTAG GTCGTTCGCT CCAAGCTGGG
3001  CTGTGTGCAC GAACCCCCCG TTCAGCCCGA CCGCTGCGCC TTATCCGGTA
3051  ACTATCGTCT TGAGTCCAAC CCGGTAAGAC ACGACTTATC GCCACTGGCA
3101  GCAGCCACTG GTAACAGGAT TAGCAGAGCG AGGTATGTAG GCGGTGCTAC
3151  AGAGTTCTTG AAGTGGTGGC CTAACTACGG CTACACTAGA AGAACAGTAT
3201  TTGGTATCTG CGCTCTGCTG AAGCCAGTTA CCTTCGGAAA AGAGTTGGT
3251  AGCTCTTGAT CCGGCAAACA AACCACCGCT GGTAGCGGTG GTTTTTTTGT
3301  TTGCAAGCAG CAGATTACGC GCAGAAAAAA AGGATCTCAA GAAGATCCTT
3351  TGATCTTTTC TACGGGGTCT GACGCTCAGT GGAACGAAAA CTCACGTTAA
3401  GGGATTTTGG TCATGAGATT ATCAAAAAGG ATCTTCACCT AGATCCTTTT
3451  AAATTAAAAA TGAAGTTTTA AATCAATCTA AGTATATAT GAGTAAACTT
3501  GGTCTGACAG TTACCAATGC TTAATCAGTG AGGCACCTAT CTCAGCGATC
3551  TGTCTATTTC GTTCATCCAT AGTTGCCTGA CTCCCCGTCG TGTAGATAAC
3601  TACGATACGG GAGGGCTTAC CATCTGGCCC CAGTGCTGCA ATGATACCGC
```

FIGURE 5 (cont.)

```
3651 GAGACCCACG CTCACCGGCT CCAGATTTAT CAGCAATAAA CCAGCCAGCC
3701 GGAAGGGCCG AGCGCAGAAG TGGTCCTGCA ACTTTATCCG CCTCCATCCA
3751 GTCTATTAAT TGTTGCCGGG AAGCTAGAGT AAGTAGTTCG CCAGTTAATA
3801 GTTTGCGCAA CGTTGTTGCC ATTGCTACAG GCATCGTGGT GTCACGCTCG
3851 TCGTTTGGTA TGGCTTCATT CAGCTCCGGT TCCCAACGAT CAAGGCGAGT
3901 TACATGATCC CCATGTTGT GCAAAAAAGC GGTTAGCTCC TTCGGTCCTC
3951 CGATCGTTGT CAGAAGTAAG TTGGCCGCAG TGTTATCACT CATGGTTATG
4001 GCAGCACTGC ATAATTCTCT TACTGTCATG CCATCCGTAA GATGCTTTTC
4051 TGTGACTGGT GAGT
```

FIGURE 6
A
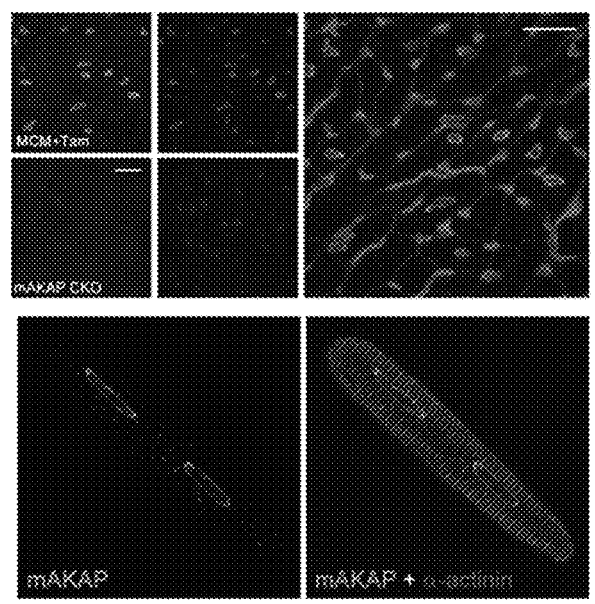
B
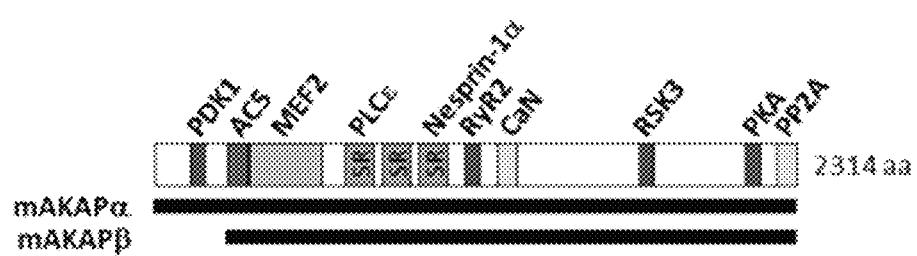

FIGURE 10
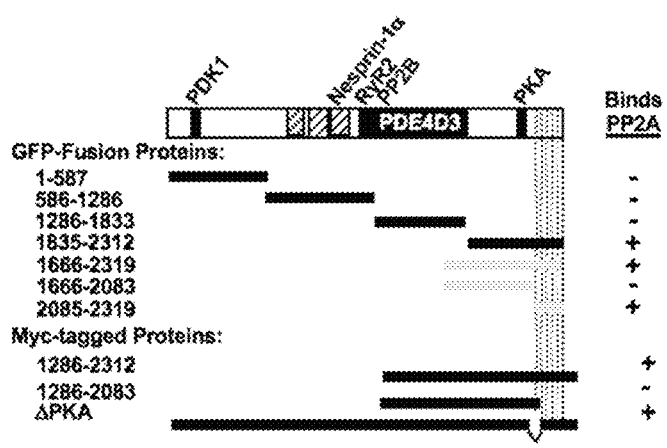
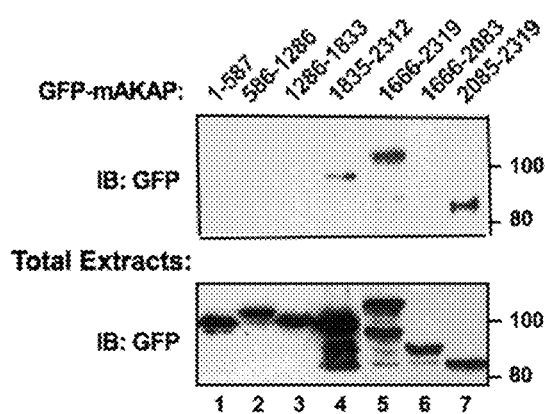
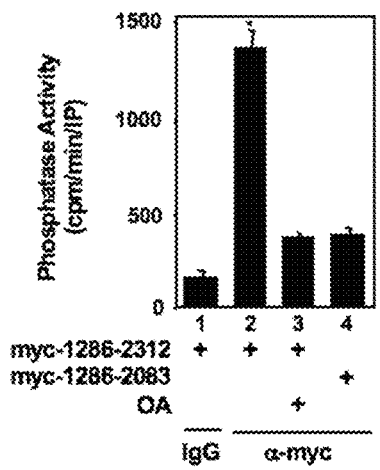

FIGURE 18
IP: PP1
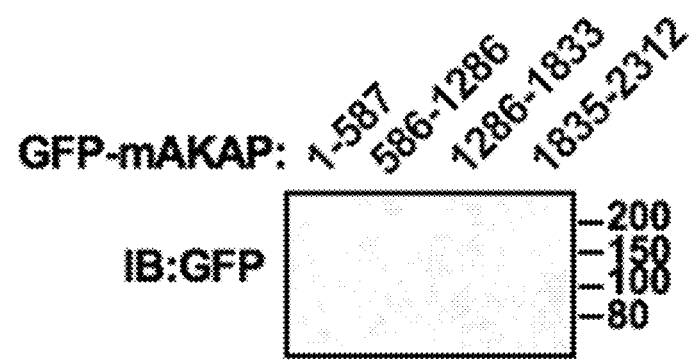
Total Extracts
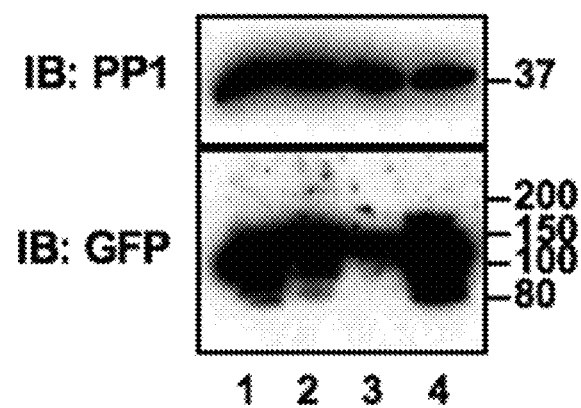

FIGURE 22
A
B
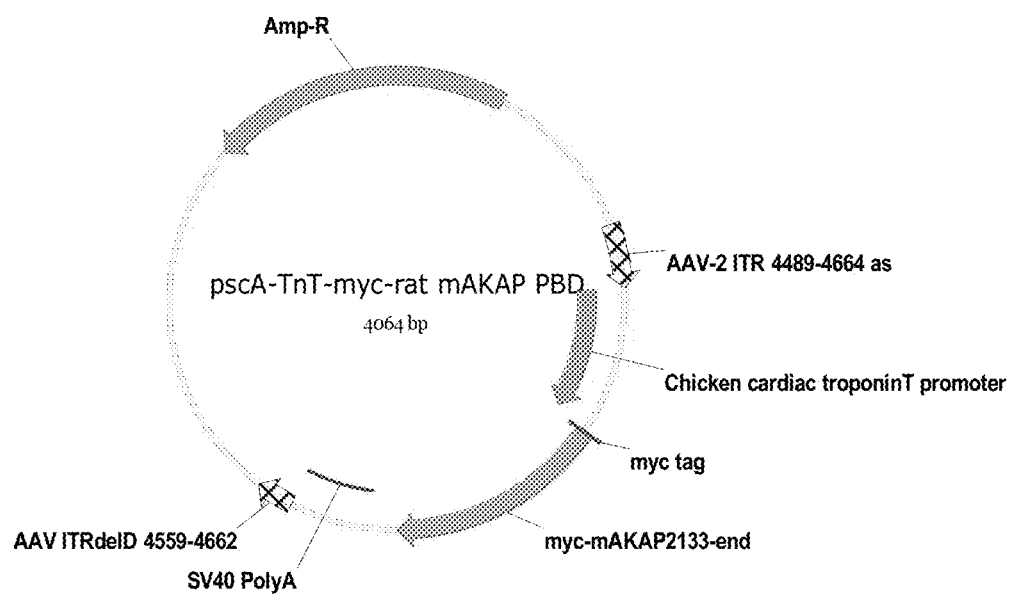

FIGURE 24

```
LOCUS       hRSK3                   5817 bp    DNA     linear   PRI 22-JAN-2009
DEFINITION  Homo sapiens ribosomal protein S6 kinase, 90kDa, polypeptide 2
(RPS6KA2), transcript variant 1, mRNA.
BASE COUNT     1285 a   1585 c   1591 g   1356 t
ORIGIN
        1 gcggagaagg aggcggaggg agcgattgtg gcccggccg cggtggcgg cgcggcctgc
       61 cctttgtgac cgcagctgc gcccacgcc ccgcgccat ggccgccgtg ccgggctccc
      121 tggccacgcg tgcccgccg cggacctgag ccccgcgcct gggatgccgg ggatgcgcgt
      181 cccccggccc tcggctgct ccgggctggg cgcggggcga tggacctgag catgaagaag
      241 ttcgccgtgc gcaggttctt ctctgtgtac ctgcgcagga agtcgcgctc caagagctcc
      301 agcctgagcc ggctcgagga agaaggcgtc gtgaaggaga tagacatcag ccatcatgtg
      361 aaggagggct ttgagaaggc agatccttcc cagtttgagc tgctgaaggt tttaggacaa
      421 ggatcctatg gaaaggtgtt cctggtgagg aaggtgaagg ggtcgacgc tgggcagctc
      481 tacgccatga aggtccttaa gaaagccacc ctaaaagttc gggaccgagt gagatcgaag
      541 atggagagag acatcttggc agaagtgaat cacccctca ttgtgaagct tcattatgcc
      601 tttcagacgg aaggaaagct ctacctgatc ctggacttcc tgcggggagg ggacctcttc
      661 acccggctct ccaaagaggt catgtccacg gaggaggatg tcaagttcta cctggctgag
      721 ctggccttgg ctttagacca tctccacagc ctggggatca tctacagaga tctgaagcct
      781 gagaacatcc tcctggatga agaggggcac attaagatca cagatttcgg cctgagtaag
      841 gaggccattg accacgacaa gagagcgtac tccttctgcg gacgatcga gtacatggcg
      901 ccggaggtgg tgaacggcg aggacacacg cagagtgccg actggtggtc cttcggcgtg
      961 ctcatgtttg agatgctcac gggtcctg ccgttccagg ggaaggacag gaaggagacc
     1021 atggctctca tcctcaagc caagctgggg atgcccagt tcctcagtgg ggaggcacag
     1081 agtttgctgc gagctctctt caaacggaac cctgcaacc ggctgggtgc tggcattgac
     1141 ggagtggagg aaattaagcg ccatccctc tttgtgacca tagactggaa cacgctgtac
     1201 cggaaggaga tcaagccacc gttcaaacca gcagtgggca ggcctgagga caccttccac
     1261 tttgacccg agttcacagc gcggacgcc acagactctc ctggctccc ccgagtgca
     1321 aacgctcatc acctgtttag aggattcagc tttgtggcct caagcctgat ccaggagcc
     1381 tcacagcaag atctgcacaa agtccagtt cacccaatcg tgcagcagtt acacgggaac
     1441 aacatccact tcaccgatgg ctacgagatc aaggaggaca tcgggtggg ctcctactca
     1501 gtgtgcaagc gatgtgtgca taaagccaca gacaccgagt atgccgtgaa gatcattgat
     1561 aagagcaaga gagacccctc ggaagagatt gagatcctcc tgcggtacgg ccagcaccg
     1621 aacatcatca ccctcaagga tgtctatgat gatggcaagt ttgtgacct ggtaatggag
     1681 ctgatgcgtg gtgggagct cctggaccgc atcctcggc agagatactt ctggagcgc
     1741 gaagccagtg acgtcctgtg caccatcacc aagaccatgg actacctcca ttccaggg
     1801 gttgttcatc gagacctgaa gccgagtaac atcctgtaca gggatgagtc gggagccca
     1861 gaatccatcc gagtctgcga cttcggcttt gccaagcagc tgcgcgcgg gaacgggctg
     1921 ctcatgacac cctgctacac ggccaattc gtggcccgg aggtcctgaa gcgtcaaggc
     1981 tatgatgcgg cgtgtgacac ctggagtttg gggatcctgt tgtacaccat gctggcagga
     2041 tttacccctt ttgcaaatgg gccagacgat accctgaagg agattctggc gggatcggc
     2101 agtgggaagt atgcccttc tgggggaaac tgggactcga tatctgacgc agctaaagac
     2161 gtcgtgtcca agatgctcca cgtggaccct catcagcgcc tgaccgcgat gcaagtgctc
     2221 aaacaccgt gggtggtcaa cagagagtac ctgtcccaa accagctcag cagacaggac
     2281 gtgcacctgg tgaagggcgc gatggccgcc acctactttg ctctaaacag aacacctcag
     2341 gcccgcggc tggagccgt gtgtcatcc aactggctc agcgcagagg catgaagaga
     2401 ctcacgtcca cgcggctgta gcgggtgga ccctggcccc agctccct gcagcatcc
     2461 tcgtgggctc acagaccccg gcctggagc ccgtctggca ccagagtga ccacaagtcc
     2521 agcagggagg cggcgccgc cctcgcgtg tccgtgtttt cttttcagc ccggagagg
     2581 gtcctgacct gggggcttct ccaagcctca ctgcgccagc ctcccgccc gctctcttt
     2641 ctcccaagcg aaaccaaatg cgcccttca cctcgcgtgc ccgtgcgagg cggggcctt
     2701 ctttcagagc ccgcgggtcc tctcatacat ggcttctgtt tctgccgaga gatctgtttt
     2761 ccaattatga agccggtcgg tttggtcaga ctcccgacac ccacgtccca ggtacccggt
```

FIGURE 24 (cont.)

```
2821 gggaaagtgg cagtgcgagg gcgcagccat tggtggttgc agggcccag  agggctgggg
2881 tgacctggca tcccggggct cccacgggc  tggatgacgg ggttggcact gtggcgtcca
2941 ggaggagatg cctggttctg cccaaaataa tccaagagc  cgtttcctcc tcgcccttca
3001 gttttgcct  gaggtgctgg gtagcccatc ctttcctctg tcccagattc aaatgaggag
3061 taagagccca gacgagagga aggcaggctg gatctttgcc ttgagagctc cgtgtcacca
3121 ggatggaagg gggtgcctct cggaggagcc tgtgtccacc tccagtctcg gcttcccg
3181 gggggccaag cgcactgggc tgccgtctgt cccagctcc  cgtggccaca cagctatctg
3241 gaggctttgc agggagtcgt gggttctgc  acctgctcag ccctgtgtcg gcttcctgtg
3301 tgctcaccta aagctgtggt tttgctgtgt tcacttcgat ttttctggtc tgtggagaaa
3361 ctgtgaattg gagaaatgga gctctgtggc tcccaccca  aaccttctca gtccagctgg
3421 aggctggagg gagacacagg cccacccag  cagactgagg ggcagaggca caggtgggag
3481 ggcagcggag atcagcgtgg acaggagcga tgcactttgt agatgctgtg gctttgtgtt
3541 gcgttttgtg tctctgttgc acagatctgt ttttcacac  tgatccgtat tccctgggt
3601 gtgcacacag ggcgggtgtg gggcatttag gccatgcgt  gctctactc  attgagtaaa
3661 atcgagtgag aggttccggg cagcaggatc gacgcccagt ccagccggca gagggaacac
3721 acgggtcctt cattgtcctg taagggtgtt gaagatgctc ctggcggcc  cccaagcaga
3781 ctagatggga ggaggcgccg ctcagcccct caccctgcat cactgaagag cggcgcctct
3841 gcagcaagca gggcttcagg aggtgccgc  tggccacagc caggttttcc ctaagaagat
3901 gttatttgt  tgggttttgt tccccctcca tctcgattct cgtacccaac taaaaaaaaa
3961 aaaataaaga aaaaatgtgc tgcgttctga aaaataactc cttagcttgg tctgattgtt
4021 ttcagacctt aaaatataaa cttgtttcac aagctttaat ccatgtggat ttttttttc
4081 ttagagaacc acaaaacata aaggagcaa  gtcggactga atacctgttt ccatagtgcc
4141 cacagggtat tcctcacatt ttctccatag aagatgcttt ttcccaaggc tagaacgact
4201 tccaccatga tgaatttgct ttttaggtct taattatttc acttcttttt agaaacttag
4261 gaagaagtgg ataatcctga ggtcacacaa tctgtcctcc cagaaatgaa caaagtcat
4321 cacctttct  gctgctaca  caggcaacga ttccccatc  agctgccgg  acctttggc
4381 ctggcttggt gtgcaggcct gtctgtttgc ttaaagtcag tgggttctgg tgcagggagt
4441 gagaagtggg ggaagtgaaa gggaaagcat ccgtgagaaa gcggccacgg ttttccctcc
4501 ttgtgtgccc atggggcacc agctcatggt cttttttcagt catcccagtt tgtacagact
4561 tagcttctga actctaagaa tgccaaaggg accgacgaga ctccccatca cagcgagctc
4621 tgtccttaca tgtatttgat gtgcatcagc ggaggagaac actggcttgg ccctgctccg
4681 ctgagtgtct gtgaaatacc tctactttcc ctcccatatc cagaacaaaa tgatacttga
4741 catccttcca caaaagtcag cctaaagaag ttatggtatc atatgttaaa ctaagcttc
4801 aaaaacctta gtgaaatagc aagtgactgc tttcaagcag cagtcgacat gtaaatgaag
4861 gtgttcttag aattcgcatt ttgccagctc agcgcacctc cacaacgaat gaaatgctcc
4921 gtatgatttg cacaaatgac atagacctcc ccaaaagtta actggctctc cttcctcaca
4981 cagttcatca taaccaacc  ccccacccc  gggtcatgaa aatcacagaa cttataaaca
5041 cattgaaccc tagatctcag gcttcctgac ctaccgcag  tgcccttg  ctggccacc
5101 tatagggtcc tccttccctg gcagccccc  atgtgggaga aataccgat  tctcccaatc
5161 tgcagtggga gagctttgct gaattccatc ccaagtcaa  acatgggcaa gaggtgagga
5221 tttcactttt accctcaagt ccgatttgtc tgtgatttta aactaactgt gtatgtattg
5281 atgtttggaa gattgtttga attttaaagt gataatagta cttaatgcta tccagtattg
5341 ttcattaaat ggtgttatcc taaagctgca cttgggattt ttacctaacg ctttactgat
5401 tctctcaagc acatggcaaa gtttgatttg cactccgttc atttctgaca cgtttgctg
5461 cctcctacct ttctaagcgt catgcaaatt cgagaatgga gaaggacgct gccggtcct
5521 cagcggtgtg gagagggcgg aaggtggact ccagcgcagc ttgagggct  gaggacgag
5581 gctgcagcat ctgtgtcgtt ctactgagca cgttctctg  cctcgctcct gactcagcac
5641 tttgttcact ggctcagcag ttatgtttac acatcatttt tatgttcctg ctttgtaatt
5701 catgtttgag atgggtggcc actgtacaga tatttattac gctttccaga ctttctgaat
5761 agattttttt gaataaacat ggttttatga agtgtaatct ttttctagcc taacaat
```

FIGURE 25 rat mAKAPα mRNA with open reading frame translated:

```
   1 GCATCATGCA GCAGGTCAAA CAAGGCATCT CCTAGTATTG CATCCTCCAG ATGTGCTGTA AACATCAAAA
                                                                       M  L  T  M  S
  71 GGAGACGCTG GGAGCAGGAG ATGCTGTTTT GGAAAGAAGT AAGGCTTAGA TTTCTCCATG TTAACCATGA
      · V  T  L  S  P  L  R  S  Q  G  P  D  P  M  A  T  D  A  S  P  M  A  I ·
 141 GCGTGACACT TTCCCCACTG AGGTCACAGG GCCCAGATCC CATGGCGACG GATGCTTCAC CCATGGCCAT
      · N  M  T  P  T  V  E  Q  E  E  G  E  G  E  E  A  V  K  A  I  D  A  E
 211 CAACATGACA CCCACTGTGG AGCAGGAGGA AGGAGAGGGA GAGGAAGCCG TGAAGGCCAT AGACGCTGAG
         Q  Q  Y  G  K  P  P  L  H  T  A  A  D  W  K  I  V  L  H  L  P  E  I ·
 281 CAGCAGTATG GAAAGCCACC TCCGCTCCAC ACAGCAGCCG ACTGGAAGAT TGTCCTGCAC TTACCTGAGA
      · E  T  W  L  R  M  T  S  E  R  V  R  D  L  T  Y  S  V  Q  Q  D  A  D ·
 351 TTGAGACCTG GCTCCGGATG ACCTCAGAGA GGGTCCGTGA CCTGACCTAC TCAGTCCAGC AGGATGCAGA
      · S  K  H  V  D  V  H  L  V  Q  L  K  D  I  C  E  D  I  S  D  H  V  E
 421 CAGCAAGCAT GTGGATGTGC ATCTAGTTCA GCTGAAGGAC ATTTGTGAGG ATATTTCTGA CCATGTGGAG
         Q  I  H  A  L  L  E  T  E  F  S  L  K  L  L  S  Y  S  V  N  V  I  V  D ·
 491 CAGATCCATG CCCTCCTTGA GACGGAGTTT TCCCTAAAGC TGCTGTCCTA CTCGGTCAAC GTCATCGTAG
      · I  H  A  V  Q  L  L  W  H  Q  L  R  V  S  V  L  V  L  R  E  R  I  L ·
 561 ACATCCACGC AGTACAGCTG CTCTGGCACC AGCTCCGCGT ATCCGTGCTG GTCCTCCGGG AGCGCATCCT
      · Q  G  L  Q  D  A  N  G  N  Y  T  R  Q  T  D  I  L  Q  A  F  S  E  E
 631 ACAAGGTCTG CAGGACGCCA ATGGCAACTA CACCAGGCAG ACTGACATTC TGCAAGCGTT CTCTGAAGAA
         T  T  E  G  R  L  D  S  L  T  E  V  D  D  S  G  Q  L  T  I  K  C  S  Q ·
 701 ACAACGGAGG GCCGGCTTGA TTCCCTTACA GAAGTGGACG ACTCAGGGCA GTTAACTATC AAATGTTCAC
      · D  Y  L  S  L  D  C  G  I  T  A  F  E  L  S  D  Y  S  P  S  E  D  L ·
 771 AGGATTACTT GTCTCTGGAT TGTGGCATTA CCGCATTTGA ACTCTCCGAC TACAGTCCAA GTGAGGATCT
      · L  G  G  L  G  D  M  T  T  S  Q  A  K  T  K  S  F  D  S  W  S  Y  S
 841 GCTTGGTGGC CTGGGCGACA TGACCACCAG CCAGGCCAAA ACTAAATCTT TTGACTCTTG GAGCTACAGT
         E  M  E  K  E  F  P  E  L  I  R  S  V  G  L  L  T  V  A  T  E  P  V  P ·
 911 GAGATGGAGA AAGAGTTCCC TGAGCTTATC CGAAGCGTTG GGCTGCTTAC AGTGGCCACC GAGCCTGTCC
      · S  S  C  G  E  A  N  E  D  S  S  Q  A  S  L  S  D  D  H  K  G  E  H ·
 981 CTTCCAGCTG TGGAGAAGCC AATGAGGATT CATCTCAAGC GTCCCTTTCA GATGATCACA AAGGTGAACA
      · G  E  D  G  A  P  V  P  G  Q  Q  L  D  S  T  V  G  M  S  S  L  D  G
1051 CGGGGAAGAC GGTGCTCCCG TACCTGGACA GCAGCTGGAC TCAACGGTGG GAATGTCTTC CTTAGACGGC
         T  L  A  N  A  A  E  H  P  S  E  T  A  K  Q  D  S  T  S  S  P  Q  L  G ·
1121 ACGCTGGCAA ATGCTGCCGA ACACCCTTCG GAGACAGCAA AACAAGACTC TACTTCCTCC CCACAGCTTG
      · A  K  K  T  Q  P  G  P  C  E  I  T  T  P  K  R  S  I  R  D  C  F  N ·
1191 GTGCGAAGAA AACCCAGCCT GGTCCTTGTG AAATTACGAC TCCCAAGAGA TCCATCCGCG ATTGCTTTAA
      · Y  N  E  D  S  P  T  Q  P  T  L  P  K  R  G  L  F  L  K  E  T  Q  K
1261 TTATAACGAG GACTCCCCCA CACAGCCCAC ATTACCCAAA AGAGGGCTTT TTCTAAAAGA AACTCAAAAG
         N  E  R  K  G  S  D  R  K  G  Q  V  V  D  L  K  P  E  L  S  R  S  T  P ·
1331 AATGAGCGCA AAGGCAGTGA CAGGAAGGGG CAGGTGGTTG ATTTAAAGCC TGAACTGAGC AGAAGCACCC
      · S  L  V  D  P  P  D  R  S  K  L  C  L  V  L  Q  S  S  Y  P  S  S  P ·
1401 CTTCCCTGGT GGACCCCCCT GACAGATCGA AGCTCTGCCT AGTGTTGCAG TCCTCCTACC CCAGCAGCCC
      · S  A  A  S  Q  S  Y  E  C  L  H  K  V  G  L  G  N  L  E  N  I  V  R
1471 TTCTGCTGCC AGCCAGTCCT ATGAATGTTT GCACAAGGTG GGGCTCGGCA ATCTTGAAAA CATAGTCAGA
         S  H  I  K  E  I  S  S  L  G  R  L  T  D  C  H  E  K  L  R  L  K ·
1541 AGTCACATTA AGAAATTTC TTCCAGTCTG GAAGGCTTA CTGACTGCCA TAAAGAGAAA TTGCGACTGA
      · K  P  H  K  T  L  A  E  V  S  L  C  R  I  P  K  Q  G  G  G  S  G  K ·
1611 AAAAGCCACA CAAGACCTTG GCCGAAGTGT CTCTGTGCAG AATCCCTAAA CAGGGAGGCG GTTCAGGAAA
      · R  S  E  S  T  G  S  S  A  G  P  S  M  V  S  P  G  A  P  K  A  T  M
1681 GCGATCTGAG AGCACCGGGA GCTCAGCAGG GCCAGCATG GTATCACCTG GAGCTCCCAA AGCCACGATG
         R  P  E  T  D  S  A  S  T  A  S  G  G  L  C  H  Q  R  N  R  S  G  Q  L ·
1751 AGACCAGAAA CAGATTCTGC GTCTACAGCC TCAGGTGGCC TGTGCCACCA GAGAAATCGC AGTGGACAAT
      · P  V  Q  S  K  A  S  S  S  P  P  C  S  H  S  S  E  S  S  L  G  S  D ·
1821 TGCCAGTGCA GTCGAAGGCC TCCAGTTCAC CCCCTTGCAG TCACAGCAGT GAATCTTCTC TTGGCTCAGA
      · S  I  K  S  P  V  P  L  L  S  K  N  K  S  Q  K  S  P  P  A  P  C
1891 TAGCATCAAA TCCCCGGTTC CTCTTCTTTC AAAAACAAA AGCCAAAAA GCTCCCACC TGCTCCATGT
         H  A  T  Q  N  G  Q  V  V  E  A  W  Y  G  S  D  E  Y  L  A  L  P  S  H ·
1961 CACGCCACAC AGAACGGTCA GGTGGTGGAG GCCTGGTACG GCTCTGATGA GTACCTAGCG CTGCCCTCTC
      · L  K  Q  T  E  V  L  A  L  K  L  E  S  L  T  K  L  L  P  Q  K  P  R ·
```

FIGURE 25 (cont.)

```
2031 ACCTGAAGCA GACGGAGGTG TTAGCTCTCA AGCTGGAGAG CCTAACCAAG CTCCTACCCC AGAAACCCAG
      · G  E  T   I  Q  D  I  D   D  W  E  L  S  E   M  N  S  D  S  E   I  Y  P
2101 AGGAGAGACC ATCCAGGATA TTGATGACTG GAACTGTCT GAAATGAATT CAGATTCCGA AATCTATCCA
      T  Y  H   I  K  K  K  H   T  R  L  G  T  V   S  P  S  S  S  S   D  I  A  S ·
2171 ACATACCACA TCAAGAAAAA ACACACGAGA CTGGGCACAG TGTCTCCAAG CTCATCCAGC GACATAGCCT
      · S  L  G   E  S  I  E  S   G  P  L  S  D   I  L  S  D  E  D   L  C  L  P ·
2241 CATCTCTCGG GGAGAGCATT GAATCCGGGC CCCTGAGTGA CATTCTTTCT GACGAGGACT TATGTCTGCC
      · L  S  S   V  K  K  F  T   D  E  K  S  E   R  P  S  S  S  E   K  N  E  S
2311 CCTCTCCAGC GTGAAAAAGT TCACTGACGA GAAATCAGAG AGACCTTCAT CCTCCGAGAA GAACGAGAGC
       H  S  A  T   R  S  A  L   I  Q  K  L  M  H   D  I  Q  H  Q  E   N  Y  E  A ·
2381 CATTCTGCAA CAAGATCAGC TTTGATTCAG AAACTAATGC ACGATATTCA GCACCAAGAG AACTATGAAG
      · I  W  E   R  I  E  G  F   V  N  K  L  D   E  F  I  Q  W  L   N  E  A  M ·
2451 CCATCTGGGA AAGAATTGAG GGGTTTGTGA ACAAGCTGGA TGAATCATT CAGTGGCTAA ACGAAGCCAT
      · E  T  T   E  N  W  T  P   P  K  A  E  T   D  S  L  R  L  Y   L  E  T  H
2521 GGACACCACC GAGAACTGGA CTCCTCCTAA AGCCGAGACC GACAGCCTCC GGCTGTACCT GGAGACACAC
       L  S  F  K   L  N  V  D   S  H  C  A  L  K   E  A  V  E  E  E   G  H  Q  L ·
2591 TTGAGTTTTA AGTTGAACGT AGACAGCCAC TGTGCCCTCA AGGAAGCCGT GGAGGAAGAA GGACACCAAC
      · L  E  L   V  V  S  H  K   A  G  L  K  D   T  L  R  M  I  A   S  Q  W  K ·
2661 TTCTTGAGCT CGTTGTATCT CACAAAGCAG GACTGAAGGA CACGCTGAGG ATGATTGCGA GTCAATGGAA
      · E  L  Q   R  Q  I  K  R   Q  H  S  W  I   L  R  A  L  D  T   I  K  A  E
2731 GGAGCTGCAG AGGCAAATCA AACGGCAACA CAGCTGGATT CTCAGAGCCC TGGACACCAT CAAAGCCGAG
       I  L  A  T   D  V  S  V   E  D  E  E  G  T   G  S  P  K  A  E   V  Q  L  C ·
2801 ATACTGGCTA CTGATGTGTC TGTGGAGGAC GAGGAGGGGA CGGGAAGCCC CAAGGCCGAG GTTCAGCTCT
      · H  L  E   T  Q  R  D  A   V  E  Q  M  S   L  K  L  Y  S  E   Q  Y  T  S ·
2871 GCCACCTGGA ACACAGAGA GACGCCGTGG AACAGATGTC CCTGAAGCTG TACAGCGAGC AGTACACCAG
       G  S  K  R   K  E  E  F   A  N  M  S  K  A   H  A  E  G  S  N   G  L  L
2941 CGGGAGCAAG AGGAAGGAAG AGTTTGCCAA CATGTCGAAA GCGCACGCGG AGGGAAGCAA TGGGCTTCTG
       D  F  D  S   E  Y  Q  E   L  W  D  W  L  I   D  M  E  S  L  V   M  D  S  H ·
3011 GACTTTGATT CAGAATATCA GGAGCTCTGG GATTGGCTGA TTGACATGGA GTCCCTCGTG ATGGACAGCC
      · D  L  M   M  S  E  E  Q   Q  Q  H  L  Y   K  R  Y  S  V  E   M  S  I  R ·
3081 ACGACCTGAT GATGTCAGAG GAGCAGCAGC AGCATCTTTA CAAGAGGTAC AGTGTGGAAA TGTCCATCAG
      · H  L  K   K  S  E  L  L   S  K  V  E  A   L  K  K  G  G  L   S  L  P  D
3151 GCATCTGAAA AAGTCAGAGC TACTCAGCAA GGTTGAAGCT TTGAAGAAAG GTGGCCTTTC ACTACCAGAC
       D  I  L  E   K  V  D  S   I  N  E  K  W  E   L  L  G  K  T  L   R  E  K  I ·
3221 GATATCCTGG AAAAAGTGGA TTCAATTAAT GAAAAATGGG AGCTGCTTGG GAAAACCCTA AGAGAGAAGA
      · Q  D  T   I  A  G  H  S   G  S  P  R  D   L  L  S  P  E  S   G  S  L ·
3291 TACAGGACAC AATAGCGGGG CACAGTGGGT CGGGCCCACG TGACCTGCTA TCTCCTGAAA GCGGAAGCCT
      · V  R  Q   L  E  V  R  I   K  E  L  K  R   W  L  R  D  T  E   L  F  I  F
3361 GGTAAGGCAG CTGGAGGTCA GGATCAAAGA GCTGAAAAGG TGGCTAAGAG ATACAGAGCT TTTCATCTTC
       N  S  C  L   R  Q  E  K   E  G  T  S  A  E   K  Q  L  Q  Y  F   K  S  L  C ·
3431 AATTCCTGTC TGAGACAAGA GAAGGAAGGA ACAAGCGCCG AGAAACAGCT CCAATACTTT AAGTCGCTCT
      · R  E  I   K  Q  R  R  R   G  V  A  S  I   L  R  L  C  Q  H   L  D  D ·
3501 GTCGTGAGAT CAAGCAGCGG CGTCGAGGAG TGGCCTCCAT TCTGAGGTTG TGCCAGCACC TTCTGGATGA
      · R  D  T   C  N  L  N  A   D  H  Q  P  M   Q  L  I  I  V  N   L  E  R  R
3571 CCGGGACACG TGCAACCTGA ACGCAGATCA CCAGCCCATG CAGCTGATCA TTGTAAACCT CGAGAGGCGG
       W  E  A  I   V  M  Q  A   V  Q  W  Q  T  R   L  Q  K  M  G  K   E  S  E ·
3641 TGGGAGGCCA TCGTCATGCA AGCTGTCCAG TGGCAAACAC GGTTACAAAA GAAGATGGGG AAGGAATCCG
      · T  L  N   V  I  D  P  G   L  M  D  L  N   G  M  S  E  D  A   L  E  W  D ·
3711 AGACTTTGAA TGTGATTGAT CCTGGCTTGA TGGACCTGAA TGGAATGAGT GAGGATGCCC TGGAATGGGA
      · E  T  D   I  S  N  K  L   I  S  V  H  E   E  S  N  D  L  D   Q  P  E
3781 TGAAACAGAC ATAAGTAACA AACTCATTAG TGTGCATGAA GAATCAAACG ACCTTGATCA AGACCCAGAG
       P  M  L  P   A  V  K  L   E  E  T  H  H  K   D  S  G  Y  E  E   A  G  D ·
3851 CCTATGCTAC CCGCAGTGAA GCTTGAAGAG ACACACCACA AGGACTCTGG TTATGAAGAG GAGGCAGGTG
      · C  G  G   S  P  Y  T  S   N  I  T  A  P   S  S  P  H  I  Y   Q  V  Y  S ·
3921 ACTGTGGAGG GTCTCCGTAT ACCTCAAATA TCACTGCACC TTCCAGCCCA CACATTTACC AAGTGTACAG
      · L  H  N   V  E  L  H  E   D  S  H  T  P   F  L  K  S  P  K   F  T  G
3991 TCTTCACAAT GTGGAGCTCC ACGAGGACAG CCACACTCCA TTTCTGAAAA GCAGCCCTAA GTTCACAGGC
       T  T  Q  P   T  V  L  T   K  S  L  S  K  D   S  S  F  S  S  T   K  S  L  P ·
4061 ACAACACAGC CTACTGTTTT AACTAAGAGC CTCAGCAAGG ACTCTTCCTT TTCATCTACA AAATCGTTAC
      · D  L  L   G  G  S  G  L   V  R  P  Y  S   C  H  S  G  D  L   S  Q  N  S ·
```

FIGURE 25 (cont.)

```
4131 CAGACCTTCT AGGGGGTTCC GGTTTGGTGA GGCCTTACTC GTGTCACAGT GGAGACTTGA GCCAGAATTC
      · G  S  E    S  G  I  V    S  E  G  D    N  E  M  P    T  N  S  D    M  S  L  F
4201 AGGCAGTGAG AGTGGAATTG TCAGCGAAGG AGACAACGAG ATGCCGACCA ACTCTGACAT GAGCTTGTTC
        S  M  V  D    G  S  P  S    N  P  E  T    E  H  P  D    P  Q  M  G    D  A  A  N  ·
4271 AGTATGGTAG ACGGGTCCCC AAGTAACCCT GAAACGGAGC ATCCGGACCC ACAAATGGGA GATGCAGCCA
      ·  V  L  E    Q  K  F    K  D  N  G    E  S  I  K    L  S  V  S    R  A  S  V  ·
4341 ATGTGCTAGA GCAAAAGTTT AAAGACAACG GGGAAAGCAT TAAGCTTTCA AGTGTCTCTC GGGCATCCGT
      ·  S  P  V    G  C  V  N    G  K  A    G  D  L  N    S  V  T    K  H  T    A  D  C
4411 CTCACCAGTG GGTTGTGTAA ATGGAAAAGC AGGGGATTTA ACAGTGTTA CCAAACACAC TGCTGATTGT
         L  G  E  E    L  Q  G    K  H  D    V  F  T  F    Y  D  Y    S  Y  L    Q  G  S  K  ·
4481 TTGGGAGAAG AACTACAAGG AAAACATGAC GTGTTTACAT TTTATGATTA CTCGTACCTC CAAGGCTCAA
      ·  L  K  L    P  M  I    M  K  Q  P    Q  S  E    K  A  H    V  E  D  P    L  L  G  ·
4551 AACTCAAATT ACCAATGATA ATGAAACAGC CACAGAGTGA AAAGGCACAC GTGGAGGATC CCCTTCTTGG
      ·  G  F  Y    F  D  K  K    S  C  K    A  K  H    Q  A  S  E    S  Q  P    D  A  P
4621 TGGTTTTTAT TTTGATAAAA AGTCCTGCAA AGCTAAACAT CAGGCTTCAG AGTCACAACC AGATGCGCCT
         P  H  E  R    I  L  A    S  A  P    H  E  M  G    R  S  A    Y  K  S    S  D  I  E  ·
4691 CCCCACGAAA GGATTCTGGC AAGCGCGCCC CACGAGATGG GACGCAGCGC ATACAAAGT AGCGACATAG
      ·  K  T  F    T  G  I    Q  S  A  R    Q  L  S    L  L  S  R    S  S  S    V  E  S  ·
4761 AGAAGACATT CACGGGCATT CAGAGTGCCA GACAGCTCTC CCTTCTATCT CGTAGCTCAT CTGTAGAGTC
      ·  L  S  P    G  G  D  L    F  G  L    G  I  F    K  N  G    S  D  L    Q  R  S
4831 CCTTTCTCCA GGGGGTGATT TGTTTGGATT GGGAATCTTT AAAAATGGCA GTGACAGCCT CCAGCGGAGC
         T  S  L  E    S  W  L    T  S  Y    K  S  N  E    D  L  F    S  C  H    S  S  G  D  ·
4901 ACTTCTTTAG AAAGTTGGTT GACATCCTAT AAGAGCAATG AGGATCTCTT TAGCTGTCAC AGCTCTGGGG
      ·  I  S  V    S  S  G    S  V  G  E    L  S  K    R  T  L    D  L  L  N    R  L  E  ·
4971 ACATAAGTGT GAGCAGTGGC TCAGTTGGTG AGCTGAGTAA GGACGTTA GACCTTCTGA ATCGCCTGGA
      ·  N  I  Q    S  P  S  E    Q  K  I    K  R  S    V  S  D  M    T  L  Q    S  S  S
5041 GAATATACAG AGCCCCTCGG AGCAAAAGAT CAAGCGGAGT GTTTCTGACA TGACTCTACA AAGCAGTTCC
         Q  K  M  P    F  A  G    Q  M  S    L  D  V  A    S  S  I    N  E  D    S  P  A  S  ·
5111 CAAAAGATGC CCTTCGCTGG CCAGATGTCA CTGGATGTCG CATCCTCCAT CAATGAAGAC TCTCCGGCAT
      ·  L  T  E    L  S  S    S  D  E  L    S  L  C    S  E  D    I  V  L    H  K  N  K  ·
5181 CTCTTACAGA ACTGAGTAGT AGCGATGAGC TCTCTCTTTG CTCGGAGGAC ATTGTGTTAC ACAAAACAA
      ·  I  P  E    S  N  A  S    F  R  K    R  L  N    R  S  V  A    D  E  S    D  V  N
5251 GATCCCAGAA TCCAACGCAT CATTCAGGAA GCGCCTGAAT CGCTCAGTGG CTGATGAGAG CGACGTCAAT
         V  S  M  I    V  N  V    S  C  T    S  A  C  T    D  D  E    D  D  S    D  L  L  S  ·
5321 GTTAGCATGA TTGTCAATGT GTCCTGCACC TCTGCTTGCA CTGATGATGA AGATGACAGC GACCTCCTCT
      ·  S  S  T    L  T  L    T  E  E  E    L  C  L    K  D  E    D  D  S    S  I  A  ·
5391 CCAGCTCCAC TCTCACCTTA ACTGAAGAAG AGCTGTGCCT CAAAGATGAG GATGACGACT CCAGTATTGC
      ·  T  D  D    E  I  Y  E    E  S  N    L  M  S    G  L  D  Y    I  K  N    E  L  Q
5461 AACAGATGAT GAAATTTATG AAGAGAGCAA CCTGATGTCT GGGCTGGACT ACATAAAGAA TGAACTGCAG
         T  W  I  R    P  K  L    S  L  T    R  E  K  K    R  S  G    V  T  D    E  I  K  V  ·
5531 ACTTGGATAA GACCAAAACT TTCCTTGACG AGAGAAAAGA AACGGTCCGG TGTCACTGAT GAAATAAAGG
      ·  N  K  D    G  G  G  N    E  K  A    N  P  S    D  T  L    D  I  E  A    L  L  N  ·
5601 TCAATAAAGA TGGGGGAGGC AATGAGAAGG CCAATCCCTC GGACACCCTG GACATCGAGG CCCTTCTCAA
         G  S  I  R    C  L  S    E  N  N    G  N  G    K  T  P  P    R  T  H    G  S  G
5671 TGGCTCCATA AGATGTCTTT CCGAAAACAA CGGGAATGGT AAGACTCCGC CAGAACTCA TGGCTCAGGA
         T  K  G  E    N  K  K    S  T  Y    D  V  S  K    D  P  H    V  A  D    M  E  N  G  ·
5741 ACCAAAGGTG AAAATAAGAA AAGTACGTAT GACGTTAGTA AGGATCCGCA CGTGGCTGAC ATGGAAAATG
      ·  N  I  E    S  T  P    E  R  E  R    E  K  P    Q  G  L    P  E  V    S  E  N  L  ·
5811 GCAATATTGA AAGTACCCCA GAAAGAGAAA GGGAGAAGCC ACAAGGGCTT CCAGAGGTGT CAGAGAACCT
      ·  A  S  N    V  K  T  I    S  E  S    E  L  S    E  Y  E  A    V  M  D    G  S  E
5881 TGCTTCAAAT GTGAAAACGA TTTCTGAATC TGAGCTCAGC GAGTATGAAG CAGTAATGGA TGGTTCTGAG
         D  S  S  V    A  R  K    E  F  C    P  P  N  D    R  H  P    P  Q  M    G  P  K  L  ·
5951 GATTCAAGTG TTGCCAGAAA GGAATTTTGT CCCCCAAATG ACAGACATCC TCCACAGATG GGTCCCAAAC
      ·  Q  H  P    E  N  Q    S  G  D  C    K  P  V    Q  N  P    C  P  G    L  L  S  E  ·
6021 TCCAGCATCC CGAAAATCAA AGTGGCGACT GCAAGCCAGT CCAGAACCCT TGCCCGGGGC TACTGTCGGA
      ·  A  G  V    G  S  R  Q    D  S  N    G  L  K    S  L  P    N  D  A  P    S  G  A
6091 AGCTGGCGTT GGAAGCAGGC AAGACAGCAA TGGACTAAAA TCTTTGCCTA ACGATGCACC AAGTGGGGCT
         R  K  P  A    G  C  C    L  L  E    Q  N  E  T    E  E  S    A  S  I    S  S  N  A  ·
6161 AGAAAACCTG CCGGTTGCTG CCTGCTGGAG CAGAATGAGA CAGAGGAAAG TGCTTCTATC AGCAGCAACG
      ·  S  C  C    N  C  K    P  D  V  F    H  Q  K    D  D  E    D  C  S    V  H  D  F  ·
```

FIGURE 25 (cont.)

```
6231 CTTCCTGTTG CAACTGCAAG CCAGATGTTT TCCATCAAAA AGATGATGAA GATTGTTCAG TACATGACTT
      · V  K  E    I  I  D  M    A  S  T    A  L  K    S  K  S  Q    P  E  S    E  V  A
6301 TGTTAAGGAA ATCATTGACA TGGCATCAAC AGCCCTAAAA AGTAAGTCAC AGCCTGAAAG TGAGGTGGCC
         A  P  T  S    L  T  Q    I  K  E    K  V  L  E    H  S  H  R    P  I    H  L  R  K ·
6371 GCACCCACAT CACTAACCCA AATTAAGGAG AAGGTGTTAG AGCATTCGCA CCGGCCCATA CACCTGAGAA
      · G  D  F    Y  S  Y    L  S  L  S    S  H  D    S  D  C    G  E  V    T  N  Y  I ·
6441 AGGGGGACTT TTACTCCTAC TTATCACTTT CGTCCCACGA CAGTGACTGT GGGGAGGTCA CCAATTACAT
      · D  E  K    S  S  T  P    L  P  P    D  A  V    D  S  G  L    D  D  K    E  D  M
6511 AGATGAGAAG AGCAGTACTC CATTGCCACC GGACGCTGTG GACTCTGGCT TAGATGACAA GGAAGACATG
         D  C  F  F    E  A  C    V  E  D    E  P  V  N    E  E  A    G  L  P    G  A  L  P ·
6581 GACTGCTTCT TTGAAGCTTG TGTTGAGGAT GAGCCTGTCA ATGAGGAAGC TGGTCTCCCC GGTGCCCTTC
      · N  E  S    A  I  E    D  G  A  E    Q  K  S    E  Q  K    T  A  S  S    F  V  L ·
6651 CCAATGAATC AGCCATCGAG GATGGAGCAG AGCAAAAGTC AGAACAAAAG ACAGCCAGCT CTCCTGTGCT
      · S  D  K    T  D  L  V    P  L  S    G  L  S    P  Q  K  G    A  D  D    A  K  E
6721 CAGTGACAAG ACAGACCTGG TGCCTCTTTC AGGACTTTCC CCTCAGAAGG GAGCTGATGA TGCAAAGGAA
         G  D  D  V    S  H  T    S  Q  G    C  A  E  S    T  E  P    T  T  P    S  G  K  A ·
6791 GGAGATGATG TGTCTCACAC TTCCCAGGGC TGTGCAGAGA GCACAGAGCC TACCACCCCC TCAGGAAAGG
      · N  A  E    G  R  S    R  M  Q  G    V  S  A    T  P  E    E  N  A  A    S  A  K ·
6861 CCAATGCAGA GGGGAGGTCA AGAATGCAAG GTGTATCAGC AACGCCAGAA GAAAACGCTG CTTCGGCCAA
      · P  K  I    Q  A  F  S    L  N  A    K  Q  P    K  G  K  V    A  M  R    Y  P  S
6931 ACCGAAAATT CAAGCTTTCT CTTTGAATGC AAAACAGCCA AAAGGCAAGG TTGCCATGAG GTATCCCAGC
         P  Q  T  L    T  C  K    E  K  L    V  N  F  H    E  D  R    H  S  N    M  H  R
7001 CCCCAAACTC TAACCTGTAA AGAGAAGCTC GTAAACTTTC ATGAAGATCG ACACAGTAAC ATGCATAGGT
7071 AGAGTGTAAT GCCCCACGC ATGGAAATCA TCTCATTGAA AGATAGCCTG GCTGAAGCTC AGGGCTAGCC
7141 CAATCCACCC TGGGCCGGTC TTGGGCTCCA TCCTGTTATC ACTGCCGCCT GTCACATTGA CTTTCTGAAG
7211 ACGAACCTTC CTTCCGAATG CAGTCTGTCC ACGTGGGCCT CTCGACCTGG ATGTGTGCAT TGCTTCTCTT
7281 AGGTGATCAT CCTAGTTCCA CAAAGCTGCT TGTTCTCCCG TGGATTCCTG TCCCAAGCTA CCTCTGGCAA
7351 CCCTGTCTCT CCAGCAAGAC TTCGGTTTTC CCTCCCCCTC CTCCCCCCCC TTAAAGTTCC GCGGCTCACC
7421 AAATTGATGG TCCATCAAAC CCACTGTCTG GAATGATACC CCTCCCATCA GTACTTGACC AATGTTATGT
7491 TTTGCTCTGA AAACTTTCGC TGTATTAGAC CAATGTTTAT TGAAAGAGAT TTACCTAAAA AGCCCGCCCT
7561 TGATTTGGTT GCAGTATAGA GGAGACACAT TGATCCTTCT AACAAAATTA AGTGATGTCT GAAAGCGCCA
7631 TTTTAATTAT TTCTTTTAA ATAATGATCT ATGCAGCACT TCAAGAAACA ACTATAACAG TGTTGTATCT
7701 TATAAACTGG TACATTCTAC TATTAAGTTT GTTTTGGTT TCTATGCTTC TTGAGGTGGT GATGAGAAAA
7771 ATGGTTTTTT TTTTAAAACG GTGTGCCTTG CTGTATTACT TATAGCATTT ATTAAAAAGC TGCTTTCATG
7841 GTAAGATTAC ACTGGTTTGA AAGGAGGAAA TAGCAAGGTT AAGATGCGTG CATAATTTCT GTATATATGT
7911 ATAAGCTAGT GCAAACACTG ATGTATGACA GTATAAAATG CTTTCATGTT TGTGATGTCC AGTGGTGTGG
7981 AATATAAGCC TTAAACCCGT TCGATTGCAT GGTAATTAAA ATTGGCATAA TAAAAATAGC TTATTGGGG
8051 AAAGGAAAAT TAATGATCTC TTCTACCTGT GTTTACCAAT TTCTTTCATG TGGTTCTGGG AAAGAAAAAG
8121 AAACAAACCC CATATATTAG CTTCCAAAAT ATCCATATTG CACAGAAGGC TTAAGTTGCT TAGACTACAG
8191 ACTGGGCCTG AAGACTTCAT GATTTTCCAA ATTTTTCTGT TTCACTATAA ACATCCGAAA TAGCAAAGAT
8261 TTCTTTCCCC TCCATCAACA GCATTTTATT CTGAATGTTT TTATTTCTAC TTGTTAATGG TTTAAAGTTG
8331 TATTTGGAGA TCTCTTACAT GCCCTAATTT ATTTTAAATA TTTGAATGGG TTTGGTGGAT GGTATAGAAA
8401 ATTTAATTAT TATTTTATTT AAACTACAGA TTTCAGGTGT ATTTATTTTG TTAAATATTC CATTTGGTCT
8471 TTTGGTCTTT TTATGACTTG AAAGTTTCAG CTTTTAATTT ATATCATAAC TCCTACTAAA GTGCCTGACA
8541 CACAGTAGGT ATTTCATAGA GTTTCCTGAA TTAGAGTATT GGGTGGTTTA TATATATATA TATATATATG
8611 AGATTCCTGC ATTAAAACTA GAAAAAGATG TGCAAAGTGA ACCAGACACA GCATATTATC AGATTTCAAA
8681 AAGGAAAGAG AACATAGCCA CAGAAATGAC AATCATTCAT TCAGTAGATT AGCATCTTTT GCCTGCAAGT
8751 CACCATTCTA GATTCAGGGA GAGCAGCTAT GACCGATGCA CTGCCTTTGG AGGCTTCTGT GTTAGAGACA
8821 GAGTGACCTC GTGCCGAATT C
```

FIGURE 26 human mAKAPβ mRNA with open reading frame translated:

```
   1 GAGTCTGGGA GCTGAGTGAC TGAGGATTTG AAACCTTGCT ATAGTTACAG TTCATAACAA GCGTCTAGGC
  71 AGTTAGACCT TAAGTGTTCA GGTATGGAAA GAAAGTCATA TGTTATGTTT TAGATTCTGT TTGTAAAGCT
 141 GGTTAACTAG AGACAGCTGA TGAAAAACCA AATCGACTTG AGTTACAAGA TCTGGGCTTT CTCTGCTCTG
 211 CTTTCAACCT GTTGGTTGGT GGTGGAGTAG CTGACAGAAG CGAATGGCTT GGCTGAGGGA CATGAAGTGA
 281 CAGCAGCCTG TTTAGGACCA CACCACATTT TGGACCTCTT GCTGTGCAGT TCAGGACATT TGTGAAGATA
 351 TTTCTGATCA TGTTGAGCAA ATCCATGCCC TCCTTGAAAC AGAGTTCTCC CTAAAGCTGC TGTCTTACTC
 421 TGTCAACGTG ATAGTGGACA TCCACGCAGT GCAGCTCCTC TGGCACCAGC TTCGAGTCTC AGTGCTGGTT
 491 CTGCGGGAGC GCATTCTGCA AGGTCTGCAG GACGCCAATG GCAACTACAC TAGGCAGACG GACATTCTGC
 561 AAGCTTTCTC TGAAGAGACA AAAGAGGGCC GGCTTGATTC TCTAACAGAA GTGGATGACT CAGGACAATT
 631 AACCATCAAA TGTTCTCAAA ATTACTTGTC TCTGGATTGT GGCATTACTG CATTCGAACT GTCTGACTAC
                                                                   M  T  S  S  Q  V  K  T  K  P  F  D
 701 AGTCCAAGTG AGGATTTGCT CAGTGGGCTA GGTGACAGAA CCTCTAGCCA AGTCAAAACC AAACCCTTTG
      ·  S  W  S  Y  S  E  M  E  K  E  F  P  E  L  I  R  S  V  G  L  L  T  V  ·
 771 ACTCTTGGAG CTACAGTGAG ATGGAAAAGG AGTTTCCTGA GCTTATCCGA AGTGTTGGTT TACTTACGGT
      ·  A  A  D  S  I  S  T  N  G  S  E  A  V  T  E  E  V  S  Q  V  S  L  S
 841 AGCTGCTGAC TCTATCTCTA CCAATGGCAG TGAAGCAGTT ACTGAGGAGG TATCTCAAGT ATCTCTCTCA
         V  D  D  K  G  G  C  E  E  D  N  A  S  A  V  E  E  Q  P  G  L  T  L  G  ·
 911 GTAGACGACA AAGGTGGATG TGAGGAAGAC AATGCTTCTG CAGTCGAAGA GCAACCAGGC TTAACACTGG
      ·  V  S  S  S  S  G  E  A  L  T  N  A  A  Q  P  S  E  T  V  Q  Q  E  ·
 981 GGGTGTCATC ATCTTCAGGA GAAGCTCTGA CAAATGCTGC TCAACCCTCC TCTGAGACTG TGCAGCAAGA
      ·  S  S  S  S  S  H  H  D  A  K  N  Q  Q  P  V  P  C  E  N  A  T  P  K
1051 ATCCAGTTCC TCCTCCCATC ATGATGCAAA GAATCAGCAG CCTGTTCCTT GTGAAAATGC AACCCCCAAA
         R  T  I  R  D  C  F  N  Y  N  E  D  S  P  T  Q  P  T  L  P  K  R  G  L  ·
1121 CGAACCATCA GAGATTGCTT TAATTATAAC GAGGACTCTC CCACGCAGCC TACATTGCCA AAAAGAGGAC
      ·  F  L  K  E  E  T  F  K  N  D  L  K  G  N  G  G  K  R  Q  M  V  D  L  ·
1191 TTTTTCTTAA AGAGGAAACT TTTAAGAATG ATCTGAAAGG CAATGGTGGA AAGAGGCAAA TGGTTGATCT
      ·  K  P  E  M  S  R  S  T  P  S  L  V  D  P  P  D  R  S  K  L  C  L  V
1261 AAAGCCTGAG ATGAGCAGAA GCACCCCTTC GCTAGTAGAT CCTCCTGACA GATCCAAACT TTGCCTGGTA
         L  Q  S  S  Y  P  N  S  P  S  A  A  S  Q  S  Y  E  C  L  H  K  V  G  N  ·
1331 TTGCAGTCTT CTTACCCCAA CAGCCCTTCT GCTGCCAGCC AGTCTTATGA GTGTTTACAC AAGGTGGGA
      ·  G  N  L  E  N  T  V  K  F  H  I  K  E  I  S  S  S  L  G  R  L  N  D  ·
1401 ATGGGAACCT TGAAAACACA GTCAAATTTC ACATTAAAGA AATTTCTTCC AGCCTGGGAA GGCTTAACGA
      ·  C  Y  K  E  K  S  R  L  K  K  P  H  K  T  S  E  E  V  P  P  C  R  T
1471 CTGCTATAAA GAGAAATCTC GACTTAAAAA GCCACACAAG ACCTCAGAAG AGGTGCCTCC ATGCCGAACA
         P  K  R  G  T  G  S  G  K  Q  A  K  N  T  K  S  S  A  V  P  N  G  E  L  ·
1541 CCTAAACGGG GGACTGGTTC AGGCAAACAA GCTAAAAATA CAAAGAGCTC AGCAGTGCCA ATGGAGAGC
      ·  S  Y  T  S  K  A  I  E  G  P  Q  T  N  S  A  S  T  S  S  L  E  P  C  ·
1611 TTTCTTATAC TTCCAAGGCC ATAGAGGGGC CACAAACAAA TTCTGCTTCC ACATCCTCAC TTGAGCCTTG
      ·  N  Q  R  S  W  N  A  K  L  Q  L  Q  S  E  T  S  S  S  P  A  F  T  Q
1681 TAATCAGAGA AGTTGGAATG CCAAATTGCA ATTGCAGTCA GAAACATCCA GTTCACCAGC TTTTACTCAG
         S  S  E  S  S  V  G  S  D  N  I  M  S  P  V  P  L  L  S  K  H  K  S  K  ·
1751 AGCAGTGAAT CCTCTGTTGG CTCAGACAAC ATCATGTCTC CGGTGCCACT TCTTTCAAAA CACAAAAGCA
      ·  K  G  Q  A  S  S  P  S  H  V  T  R  N  G  E  V  V  E  A  W  Y  G  S  ·
1821 AAAAAGGTCA AGCCTCCTCT CCAAGTCACG TCACTAGGAA TGGTGAGGTT GTGGAGGCCT GGTATGGCTC
      ·  D  E  Y  L  A  L  P  S  H  L  K  Q  T  E  V  L  A  L  K  L  E  N  L
1891 TGATGAATAC CTAGCACTGC CCTCTCACCT TAAGCAGACA GAAGTATTGG CTTTGAAGTT GGAAAACCTA
         T  K  L  L  P  Q  K  P  R  G  E  T  I  Q  N  I  D  D  W  E  L  S  E  M  ·
1961 ACAAAGCTTC TGCCTCAGAA ACCCAGAGGA GAAACCATCC AGAATATTGA TGACTGGGAA CTGTCTGAAA
      ·  N  S  D  S  E  I  Y  P  T  Y  H  V  K  K  K  H  T  R  L  G  R  V  S  ·
2031 TGAATTCAGA TTCTGAAATC TATCCAACCT ATCATGTCAA AAAGAAGCAT ACAAGGCTAG GCAGGGTGTC
      ·  P  S  S  S  S  D  I  A  S  S  L  G  E  S  I  E  S  G  P  L  S  D  I
2101 TCCAAGCTCA TCTAGTGACA TAGCCTCTTC ACTAGGGGAG AGCATTGAAT CTGGGCCCCT GAGTGACATT
         L  S  D  E  E  S  S  M  P  L  A  G  M  K  K  Y  A  D  E  K  S  E  R  A  ·
2171 CTTTCTGATG AGGAGTCCAG TATGCCTCTC GCTGGCATGA AAAAGTATGC TGATGAGAAG TCAGAAAGAG
      ·  S  S  S  E  K  N  E  S  H  S  A  T  K  S  A  L  I  Q  K  L  M  Q  D  ·
2241 CTTCATCCTC TGAGAAAAAT GAGAGCCATT CTGCCACTAA ATCAGCTTTA ATTCAGAAAC TGATGCAAGA
         I  Q  H  Q  D  N  Y  E  A  I  W  E  K  I  E  G  F  V  N  K  L  D  E
```

FIGURE 26 (cont.)

```
2311 TATTCAGCAC CAAGACAACT ATGAAGCCAT ATGGGAAAAA ATAGAGGGGT TTGTAAACAA ACTGGATGAA
       F  I  Q  W   L  N  E  A  M  E  T   T  E  N  W  T   P  P  K  A  E   M  D  D
2381 TTCATTCAAT GGTTAAATGA AGCCATGGAA ACTACAGAGA ATTGGACTCC CCCTAAAGCA GAGATGGATG
       L  K  L  Y  L  E   T  H  L  S  F  K   L  N  V  D  S  H   C  A  L  K  E
2451 ACCTTAAACT GTATCTGGAG ACACACTTGA GTTTTAAGTT GAATGTAGAC AGTCATTGTC CTCTCAAGGA
       A  V  E  E  E  G  H   Q  L  L  E  L  I   A  S  H  K  A  G   L  K  D  M
2521 AGCTGTGGAG GAGGAAGGAC ACCAACTTCT TGAGCTTATT GCATCTCACA AAGCAGGACT GAAGGACATG
       L  R  M  I  A  S  Q   W  K  E  L  Q  R  Q   I  K  R  Q  H  S   W  I  L  R
2591 CTGCGGATGA TTGCAAGTCA ATGGAAGGAG CTGCAGAGGC AAATCAAACG GCAGCACAGC TGGATTCTCA
       A  L  D  T  I  K   A  E  I  L  A  T  D   V  S  V  E  D  E  E   G  T  G
2661 GGGCTCTGGA TACCATCAAA GCCGAGATAC TGGCTACTGA TGTGTCTGTG GAGGATGAGG AAGGGACTGG
       S  P  K  A  E  V  Q   L  C  Y  L  E  A   Q  R  D  A  V  E  Q   M  S  L
2731 AAGCCCCAAG GCTGAGGTTC AACTATGCTA CCTGGAAGCA CAAAGAGATG CTGTTGAGCA GATGTCCCTC
       K  L  Y  S  E  Q  Y   T  S  S  S  K  R  K   E  E  F  A  D  M   S  K  V  H
2801 AAGCTGTACA GCGAGCAGTA TACCAGCAGC AGCAAGCGAA AGGAAGAGTT TGCTGATATG TCAAAAGTTC
       S  V  G  S  N  G   L  L  D  F  D  S  E   Y  Q  E  L  W  D  C   L  I  D
2871 ATTCAGTGGG AAGCAATGGG CTTCTGGACT TTGATTCAGA ATATCAGGAG CTCTGGGATT GCTTGATTGA
       M  E  S  L  V  M  D   S  H  D  L  M  M   S  E  E  Q  Q  H  L  Y  K
2941 CATGGAGTCC CTTGTGATGG ACAGCCACGA CCTGATGATG TCAGAGGAGC AGCAGCAGCA TCTTTACAAG
       R  Y  S  V  E  M  S   I  R  H  L  K  K  T   E  L  L  S  K  V  E  A  L  K
3011 CGATACAGTG TGGAAATGTC CATCAGACAC CTGAAAAAGA CGGAGCTGCT TAGTAAGGTT GAAGCTTTGA
       K  G  G  V  L  L   P  N  D  L  L  E  K   V  D  S  I  N  E  K   W  E  L
3081 AGAAAGGTGG CGTTTTACTA CCAAATGATC TCCTTGAAAA AGTGGATTCA ATTAATGAAA AATGGGAACT
       L  G  K  T  L  G  E  K  I  Q   D  T  M  A  G  H  S   G  S  S  P  R  D
3151 GCTTGGGAAA ACCCTAGGAG AGAAGATCCA GGACACAATG GCAGGGCACA GTGGGTCGAG TCCACGTGAC
       L  L  S  P  E  S  G   S  L  V  R  Q  L  E   V  R  I  K  E  L   K  G  W  L
3221 CTGCTCTCTC CTGAAAGTGG AAGCCTGGTA AGGCAGCTGG AGGTCAGGAT CAAAGAACTG AAAGGATGGC
       R  D  T  E  L  F   I  F  N  S  C  L  R   Q  E  K  E  G  T  M   N  T  E
3291 TAAGAGATAC AGAGCTTTTC ATCTTCAATT CCTGTCTGAG ACAAGAAAAG GAAGGAACAA TGAATACTGA
       K  Q  L  Q  Y  F  K   S  L  C  R  E  I   K  Q  R  R  R  G  V   A  S  I
3361 GAAACAACTG CAATACTTTA AGTCCCTCTG TCGTGAAATC AAGCAACGGC GAGGAGTGGC TTCCTCCATT
       L  R  L  C  Q  H  L   L  D  D  R  E  T  C   N  L  N  A  D  H   Q  P  M  Q
3431 CTGCGACTAT GCCAGCATCT TTTGGATGAC CGGGAGACTT GCAATCTGAA TGCAGACCAC CAGCCCATGC
       L  I  I  V  N  L   E  R  R  W  E  A  I   V  M  Q  A  V  Q  W   Q  T  R
3501 AGCTGATCAT TGTAAATCTT GAAAGAAGGT GGGAAGCCAT TGTCATGCAA GCCGTCCAGT GGCAAACACG
       L  Q  K  K  M  G  K  E  S  E   T  L  N  V  I  D  P   G  L  M  D  L  N
3571 TCTACAAAAG AAGATGGGAA AGGAATCTGA GACTTTGAAT GTGATTGATC CTGGCTTGAT GGACCTAAAT
       G  M  S  E  D  A  L   E  W  D  E  M  D  I   S  N  K  L  I  S   L  N  E  E
3641 GGGATGAGTG AGGATGCCCT GGAATGGGAT GAAATGGACA TAAGTAACAA GTTAATTAGT TTGAATGAGG
       S  N  D  L  D  Q   E  L  Q  P  V  I  P   S  L  K  L  G  E  T   S  N  E
3711 AATCAAATGA CCTTGATCAA GAACTCCAAC CTGTTATCCC TTCCTTGAAG CTTGGAGAGA CAAGTAATGA
       D  P  G  Y  D  E  E   A  D  N  H  G  G   S  Q  Y  A  S  N  I   T  A  P
3781 GGACCCTGGT TATGACGAGG AGGCTGATAA CCATGGGGGA TCTCAGTATG CCTCAAATAT TACTGCCCCC
       S  S  P  H  I  Y  Q   V  Y  S  L  H  N  V   E  L  Y  E  D  N   H  M  P  F
3851 TCTAGTCCAC ACATTTACCA GGTGTACAGC CTCCACAATG TTGAACTCTA TGAGGACAAC CACATGCCAT
       L  K  N  N  P  K   V  T  G  M  T  Q  P   N  V  L  T  K  S  L   S  K  D
3921 TTCTGAAAAA CAATCCAAAG GTCACTGGCA TGACACAGCC TAATGTTTTA ACTAAGAGTC TCAGTAAAGA
       S  S  F  S  S  T  K   S  L  P  D  L  L   G  G  S  N  L  V  K   P  C  A
3991 CTCTTCATTT TCATCATCCA AATCTTTGCC AGATCTTCTA GGTGGTTCCA ATTTGGTAAA GCCCTGCGCA
       C  H  G  G  D  M  S   Q  N  S  G  S  E  S   G  I  V  S  E  G   D  T  E  T
4061 TGTCATGGAG GAGACATGAG CCAGAATTCA GGCAGTGAGA GTGGAATTGT CAGTGAAGGA GACACAGAAA
       T  T  N  S  E  M   C  L  L  N  A  V  D   G  S  P  S  N  L  E   T  E  H
4131 CCACTACCAA CTCTGAAATG TGCTTGCTCA ATGCAGTGGA TGGGTCCCCA AGTAACCTTG AAACTGAACA
       L  D  P  Q  M  G  D   A  V  N  V  L  K   Q  K  F  T  D  E  G   E  S  I
4201 TCTGGACCCA CAAATGGGAG ATGCAGTTAA CGTGTTAAAG CAAAAATTTA CAGATGAGGG GGAAAGCATT
       K  L  P  N  S  S  Q   S  S  I  S  P  V  G   C  V  N  G  K  V   G  D  L  N
4271 AAGCTTCCAA ATAGCTCTCA GTCGTCCATT TCACCAGTGG GTTGTGTAAA TGGAAAAGTT GGAGATTTAA
       S  I  T  K  H  T   P  D  C  L  G  E  E   L  Q  G  K  H  D  V   F  T  F
4341 ACAGTATTAC CAAACATACC CCTGACTGTT TGGGAGAAGA ATTACAAGGA AAACATGATG TGTTTACATT
       Y  D  Y  S  Y  L  Q   G  S  K  L  K  L   P  M  I  M  K  Q  S   Q  S  E
```

FIGURE 26 (cont.)

```
4411 TTATGATTAC TCATACCTCC AAGGCTCAAA ACTCAAATTA CCAATGATAA TGAAACAGTC ACAAAGCGAA
      K  V  H  V  E  D  P  L  L  R  G  F  Y  F  D  K  K  S  C  K  S  K  H  Q
4481 AAAGTGCATG TGGAGGATCC CCTGCTTCGT GGTTTTTATT TTGATAAAAA ATCATGCAAA TCTAAACATC
       T  T  E  L  Q  P  D  V  P  P  H  E  R  I  L  A  S  A  S  H  E  M  D
4551 AGACTACAGA GTTACAACCA GATGTACCTC CCCATGAAAG GATTTGGCA AGTGCATCTC ATGAAATGGA
       R  I  S  Y  K  S  G  N  I  E  K  T  F  T  G  M  Q  N  A  K  Q  L  S
4621 TCGCATTTCA TATAAAAGTG GCAATATAGA AAAGACATTC ACTGGCATGC AGAATGCCAA ACAGCTCTCC
       L  L  S  H  S  S  S  I  E  S  L  S  P  G  G  D  L  F  G  L  G  I  F  K
4691 CTTTTATCTC ATAGTTCATC TATTGAGTCC CTTTCTCCAG GGGGTGATTT ATTTGGATTG GCATCTTTA
       N  G  S  D  L  Q  R  S  T  S  L  E  S  W  L  T  S  Y  K  S  N  E
4761 AAAATGGCAG TGACAGCCTC CAGCGAAGCA CTTCTTTAGA AAGTTGGTTG ACTTCCTATA AAGCAATGA
       D  L  F  S  C  H  S  S  G  D  I  S  V  S  S  G  S  V  G  E  L  S  K
4831 AGATCTCTTT AGCTGTCACA GCTCGGGGA TATAAGCGTG AGCAGTGGCT CAGTTGGTGA ACTAAGTAAA
       R  T  L  D  L  L  N  R  L  E  N  I  Q  S  P  S  E  Q  K  I  K  R  S  V
4901 AGAACATTAG ATCTCCTGAA TCGTTTGGAG AATATCCAGA GCCCCTCAGA GCAAAAGATA AACGAAGTG
       S  D  I  T  L  Q  S  S  S  Q  K  M  S  F  T  G  Q  M  S  L  D  I  A
4971 TTTCTGATAT CACTCTTCAA AGCAGTTCCC AAAAGATGTC CTTTACTGGC CAGATGTCAT TGGACATAGC
       S  S  I  N  E  D  S  A  A  S  L  T  E  L  S  S  S  D  E  L  S  L  C
5041 ATCTTCTATC AATGAAGACT CAGCGGCATC TCTAACAGAA CTTAGCAGCA GTGACGAGCT CTCTCTTTGC
       S  E  D  I  V  L  H  K  N  K  I  P  E  S  N  A  S  F  R  K  R  L  T  R
5111 TCAGAGGATA TTGTGTTACA CAAGAACAAG ATCCCGGAAT CGAATGCATC GTTCAGGAAG CGTCTGACTC
       S  V  A  D  E  S  D  V  N  V  S  M  I  V  N  V  S  C  T  S  A  C  T
5181 GTTCAGTGGC TGATGAAAGC GATGTCAATG TCAGCATGAT TGTTAATGTC TCTTGCACCT CTGCTTGCAC
       D  D  E  D  D  S  D  L  L  S  S  T  L  T  L  T  E  E  E  L  C  I
5251 TGATGATGAA GATGACAGCG ACCTGCTCTC CAGCTCTACC CTTACCTTGA CTGAAGAAGA GCTGTGCATC
       K  D  E  D  D  D  S  I  A  T  D  D  E  I  Y  E  D  C  T  L  M  S  G
5321 AAAGATGAGG ATGACGACTC CAGTATTGCA ACAGATGATG AAATTTATGA AGACTGCACC TTGATGTCAG
       L  D  Y  I  K  N  E  L  Q  T  W  I  R  P  K  L  S  L  T  R  D  K  K
5391 GGCTAGACTA CATAAAGAAT GAATTACAGA CCTGGATTAG GCCAAAATTG TCTTTGACAA GAGATAAGAA
       R  C  N  V  S  D  E  M  K  G  S  K  D  I  S  S  S  E  M  T  N  P  S
5461 AAGGTGCAAT GTCAGTGATG AGATGAAGGG CAGTAAGAT ATAAGTAGCA GTGAGATGAC CAATCCCTCT
       D  T  L  N  I  E  T  L  L  N  G  S  V  K  R  V  S  E  N  N  G  N  G  K
5531 GATACTCTGA ATATTGAGAC CCTTCTAAAT GGCTCTGTAA ACGTGTCTC TGAAAATAAT GGAAATGGTA
       N  S  S  H  T  H  E  L  G  T  K  R  E  N  K  K  T  I  F  K  V  N  K
5601 AGAATTCATC TCATACCCAT GAGTTAGGGA CAAAGCGTGA AAATAAGAAA ACTATTTTCA AGTTAATAA
       D  P  Y  V  A  D  M  E  N  G  N  I  E  G  I  P  E  R  Q  K  G  K  P
5671 AGATCCATAT GTGGCTGACA TGGAAAATGG CAATATTGAA GGTATTCCAG AAAGGCAAAA GGGCAAACCG
       N  V  T  S  K  V  S  E  N  L  G  S  H  G  K  E  I  S  E  S  E  H  C  K
5741 AATGTGACTT CAAAGGTATC AGAAAATCTT GGTTCACATG GAAAGAGAT TTCAGAGAGT GAGCATTGTA
       C  K  A  L  M  D  S  L  D  D  S  N  T  A  G  K  E  F  V  S  Q  D  V
5811 AGTGTAAAGC ACTTATGGAT AGTTTAGATG ATTCAAATAC TGCTGGCAAG GAATTTGTTT CCAAGATGT
       R  H  L  P  K  K  C  P  N  H  H  F  E  N  Q  S  T  A  S  T  P  T
5881 TAGACATCTT CCAAAGAAAT GTCCAAATCA CCACCATTTT GAAAATCAAA GCACTGCCTC TACTCCCACT
       E  K  S  F  S  E  L  A  L  E  T  R  F  N  N  R  Q  D  S  D  A  L  K  S
5951 GAGAAGTCTT TCTCAGAACT GGCTTTAGAA ACCAGGTTTA ACAACAGACA AGACTCTGAT GCACTGAAAT
       S  D  D  A  P  S  M  A  G  K  S  A  G  C  C  L  A  L  E  Q  N  G  T
6021 CATCTGATGA TGCACCGAGT ATGGCTGGAA AATCTGCTGG TTGTTGCCTA GCACTTGAAC AAAACGGAAC
       E  E  N  A  S  I  S  N  I  S  C  C  N  C  E  P  D  V  F  H  Q  K  D
6091 AGAGGAAAAT GCTTCATCA GCAACATTTC CTGTTGCCAG TGTGAGCCAG ATGTTTTCCA TCAAAAAGAT
       A  E  D  C  S  V  H  N  F  V  K  E  I  I  D  M  A  S  T  A  L  K  S  K
6161 GCCGAAGATT GTTCAGTCA CAACTTTGTT AAGGAAATCA TTGACATGGC TTCGACAGCC CTAAAAAGTA
       S  Q  P  E  N  E  V  A  A  P  T  S  L  T  Q  I  K  E  K  V  L  E  H
6231 AATCTCAACC TGAAAACGAG GTGGCTGCTC CTACTTCATT AACTCAAATC AAGGAGAAAG TGTTGGAGCA
       S  H  R  P  I  Q  L  R  K  G  D  F  Y  S  Y  L  S  L  S  S  H  D  S
6301 TTCTCACCGG CCCATCCAGC TGAGAAAAGG GGACTTTTAT TCGTACTTAT CTCTCTCATC TCATGACAGT
       D  C  G  E  V  T  N  Y  I  E  E  K  S  S  T  P  L  P  L  D  T  T  D  S
6371 GATTGTGGGG AGGTCACCAA TTACATAGAA GAGAAAAGCA GCACTCCATT GCCACTAGAC ACCACTGACT
       G  L  D  D  K  E  D  I  E  C  F  F  E  A  C  V  E  G  D  S  D  G  E
6441 CGGGCTTAGA TGACAAGGAA GATATTGAAT GCTTTTTTGA GGCCTGTGTT GAGGGTGACT CTGATGGAGA
       E  P  C  F  S  S  A  P  P  N  E  S  A  V  P  S  E  A  A  M  P  L  Q
```

FIGURE 26 (cont.)

```
6511 GGAGCCTTGT TTCTCTAGTG CTCCTCCAAA TGAATCTGCA GTTCCCAGCG AAGCTGCAAT GCCACTACAA
      A  T  A  C  S  S  E   F  S  D   S  S  L  S   A  D  D   A  D  T   V  A  L  S·
6581 GCAACAGCAT GTTCTTCTGA GTTCAGTGAT AGTTCTCTTT CAGCTGATGA TGCAGATACA GTGGCTCTTT
     ·S  P  S   S  Q  E   R  A  E  V   G  K  E   V  N  G   L  P  Q  T   S  S  G·
6651 CAAGTCCTTC CTCTCAGGAA AGAGCTGAGG TTGGAAAGGA AGTGAATGGT TTGCCCCAAA CTTCCAGTGG
     ·C  A  E   N  L  E  F   T  P  S   K  L  D   S  E  K  E   S  S  G   K  P  G·
6721 CTGTGCAGAA AACTTAGAGT TTACTCCTTC AAAGCTTGAC AGTGAAAAGG AAGTTCCGG  AAAACCAGGT
      E  S  C  M   P  E  E   H  N  A   A  S  A  K   S  K  V   Q  D  L   S  L  K  A·
6791 GAATCTGGAA TGCCAGAAGA ACATAATGCT GCTTCAGCCA AATCTAAAGT TCAAGACCTC TCCTTGAAGG
     ·N  Q  P   T  D  K   A  A  L  H   P  S  P   K  T  L   T  C  E  E   N  L  L·
6861 CAAATCAGCC AACAGACAAG GCCGCATTGC ATCCCAGCCC CAAAACTTTA ACCTGTGAAG AAAATCTTCT
     ·N  L  H   E  K  R  H   R  N  M   H  R
6931 AAACCTTCAT GAAAACGAC  ATAGAAATAT GCATAGGTAG AATGTACCCC CTCCCCAAGC ATGAAAATCA
7001 TCTCACTGAA AGATACGCCT GGCTGCAACT CAGGGGTGGC CTCATCCTCC CGCCCTGGGC TGGCCTCTGG
7071 TTCCATCACG TTTGTCACTG CCGTTTATTA CATTGACTTC TCCCAAGATG AATCTTCCTT CCAAATGTGT
7141 TTTCTCCACA CAAGCCTTGT GATCTGAATG TGTGCGCTGG TTCTCTTTAG GTGATCGTCT TTGAAGTTCA
7211 GCAAAGCTGC TTGTTCTCCC ATGGATTCCT GTCCCAAGCT ACCTCTACCA ACCCTCTCTC TCCAGCTAGA
7281 CTTTTCTCTT TGCCTCCTCC CTTCCCTTCC ACTCTTTAAA GTTCTGCAGT TCACCAACTG GTAGTCCATT
7351 AAATTCTCCT GTCTAGAATG ACCCCCCCAC CAGTACTTGA CCAATTTCAT GTATCAATCT GGATTTTTTT
7421 TTTAACGGTA TAATGACTGT GCTTATTGAA AGAGTTTTAC CTAAAAAGCC AACATTTGAA TTGGTTGCAG
7491 CATAGAGAAG AAACACTGGT CCTTCTTTCA AAATTAAGCA ACTATTAAAA GCGCCATTTT ATTTATTTCA
7561 TTTAAAAAAT AATCTATGCA GCATTTCAAG AAACAACCAT ATGGTGTTGT ATATTATAAA CTGGTGACAT
7631 TCTACTATTG AATTATGTAC AACATTTCA  TTTTTTATGC TTCTTGAGGT GGTAATGAGA AAAAGTTTT
7701 TTAAAAAAGT GTGCCTTGCT GTATTTCTTA TACCATTTAT TAAAAAGCTG CTTTCACGGT AAAATTATGT
7771 TGGTTTGAAA GGAGGAAATA GCAAGGTTAA GATGTGTGAA TAATTTCTGT ATATATGTAT AACCAAGTAC
7841 AAACATTGAT GTATAATGAC AGTATAAAAT GCTTTCATGT TTGTGATGTC TAGTGATGTG GAAAATATAA
7911 GCCTTAAATC CATTAGATTG CATGGTAATT AAAATTGGCA TAATAAACAC AGATTATTGG GGGAAAAGGA
7981 AAATTAGTGA TCTCTTCTAC TATGTTCTTT ACCAAATTGT TGCATCTGGT TCTGAAAAAG TATAGCATGT
8051 AGCAGCTTCC AAACATATTC ATATTGCTTA AGAGGCTTAA CATTACCTAA ACTAGAGACT AGACGTAAAG
8121 CCTTCAGTTT TCAAAATCTT TCTGGTCACT ATAAAGATCT TGGAACAGCA AATGATTAAA TGTCAGTTCC
8191 CCTAAACCAA TAAACATTTA TACTAGATTT TTTATTTCCA CTTATCATTA ATGATTTAAT GTTGGATTTC
8261 AGGTACCTTG TATGTCTTAA TTTATTTTAA ATATTTATTT TGAATGAGTT TGATAGAAAG CTAGTAGAAA
8331 AGTACAGAAA ATTTGACTAT TATTTATAGA TTTCAGGTAT ATTTATATGT GTAAAAGAAA TTGACAAAGA
8401 AATATTTCAT CTGGCCTTTA CTGACTCCTG TTAAATGCAG TTTTAAATTT ATATCGTAAC ACCTACTTAA
8471 GTGCCTGACA CAGTAGGTAT TCAATAAAAA TTTACTGAAT TAAAGGATTA AATTAGGTGA CATGGTGACA
8541 TCTATCCCTT TATTTTGACA CTAAAACATG GACACAACTA GAAAGAGGTA CAATGCAATA TAAAGTCACA
8611 ATAGATAATA TATATCAAAT TTCTAAAAGG TAAAGAATGT TGTGGGTTCA TGCAGTCACA GGAATGACAA
8681 TCATTCAACA GATAGTTCAG AAACACTTTT TATCTGCAAG GCACTATTCT AGATCCAGAA GATGCAATGT
8751 TGAACAAACA GACAAAGCCC TGCCCTCAGA AGGCTGTCCT GCATTAGGAA CAAGTGAACA CGCAAATGAC
8821 ATGAAGTATT TGTTGCAGAG CTGAGGAACA GAGCAAATGT AGTGATAGAA GCGCAATGAG AGAAGCAGCA
8891 GTGGGTACAA GGAGGAAGAA AAAGGGCTTG CAGAGAGTGG AAAGTTAGTG GAATATTCAT GAAACTTCAT
8961 TGCAGGGGTA ATAGAAGAAA AGTAAATTG  GGAGGACTTA ATGGAAGGTC TTTTAAAAAG TTAACTTGGA
9031 GCTTCTGTAT GTAAAATGCT AGGTAATAAG GACACTTTGT ACAGGCTGTT TTGCACCTGA TTTTATTTAT
9101 CATTAGTGCC ACGCCAAGAT CATTTAGACG ATGCTTATCT GTAATTCTAC CACTTTAATA ACTATTTGTA
9171 TTTTTATGCC CCTTCTGATC TTTTCCATAT GTATTCTAA  ATGGATAAAT TATTCTAGGC TTCTTAATAG
9241 GTAGTAATTT GTTCAAAAGC GGTTTTAGCC AGACATCTAG TTGCAGTGTT CAAGAGGATT ATGGGGGAAA
9311 GAGATTAGAG ATAATTGTAT AGTTAGGGGG CAGCTGGAGA AAATAAGCTA AGTTTGCAAT AACAGAGTAC
9381 ACAAGTATAG TGGCCCAGGA TGTAGTGAAA GAACAAATCC TAGAGTCTTT GAAATTTCTA AGGGCATTCT
9451 AGACCTCTGT TGGGATATGG TATTATTTTA CATACTGACA CAACCTAAAT TTTCTTTGGG TAGTAACTAA
9521 TGTCAAGTCT ACATCGACTG GTAAAACATT CAAAGAACAA ACTGACAATG ATGTTCTACC TACTTGTTAC
9591 ATGCTCATGG AAGACCGTGC AGTATTGAAA GTATTTGTTA ATTATCTGCT TAGTATTAAC ACTAAATTTG
9661 TAGAATGACT TTCAGGTTTG TTGAACAATG CCTTTTCAGG TTGGAAGAAG AAAAATAGCC TCAATCTCCC
9731 ACCCCATGTA GGCACTACCT CCCCAATTAC CCTTAGAAAA TGATCACACC AACTCTGCCT ACACACTTCC
9801 AGTGATAGTG GCTCATTGTC TGTTAAGCA  AACTGTTCCA CTGTTGGGCA TATCTCTTTG TTAGAAAGTT
9871 CTTTCTTAGG TTGCTAAAAT CTGCCTAGTA CCCCGCTACC CTGTTCTGTC TTATGGAGCA GCCAGATTA
9941 TCTTTACTCC CTCTTTCTCA TGGCAACCCT GAAGATAATC AAGGCCAGTT ACTCATCATC TCCCAACCAC
10011 TGTTTCCTCA ACTGCCCTTC ATATGTCATG GTTTTCAGAT CCATTCCAAC CTGACTGAAT GTTAACAGAC
10081 AGAATTCTTC ACATTAAGGA ACTGTCTTCA TCATCATACA TGTAGAAAAG AATCTGAACA TTTAAGTGCG
10151 AAGTTTCTC  TAGAAATATA TTCAAGATAT GTTTATTCTA TTATTGTAAA TTTCAAACAA TAAATAAATA
10221 AGAATCC
```

FIGURE 27 human mAKAPα mRNA with open reading frame translated:

```
   1 CATCATGCAG CAGGTCAAAC AAGGCATCTC CTAGTATTGC ATCCTACAGA TGTGCTGTAA ACATCAAAAG
                                                                    M  L  T  M  S
  71 AAGACGGTGG GATCAGGAGA TGCTGTTTTG GAAAGAAGTG AGGTTTAGAC TTCTCCATGT TAACCATGAG
      V  T  L  S  P  L  R  S  Q  D  L  D  P  M  A  T  D  A  S  P  M  A  I
 141 CGTGACACTT TCCCCCCTGA GGTCACAGGA CCTGGATCCC ATGGCTACTG ATGCTTCACC CATGGCCATC
        N  M  T  P  T  V  E  Q  G  E  G  E  E  A  M  K  D  M  D  S  D  Q  Q  Y
 211 AACATGACAC CCACTGTGGA GCAGGGTGAG GGAGAAGAGG CAATGAAGGA CATGGACTCT GACCAGCAGT
      E  K  P  P  P  L  H  T  G  A  D  W  K  I  V  L  H  L  P  E  I  E  T
 281 ATGAAAAGCC ACCCCCACTA CACACAGGGG CTGACTGGAA GATTGTCCTC CACTTACCTG AAATTGAGAC
      W  L  R  M  T  S  E  R  V  R  D  L  T  Y  S  V  Q  Q  D  S  D  S  K
 351 CTGGCTCCGG ATGACCTCAG AGAGGTCCGA GACCTAACC TATTCAGTCC AGCAGGATTC GGACAGCAAG
        H  V  D  V  H  L  V  Q  L  K  D  I  C  E  D  I  S  D  H  V  E  Q  I  H
 421 CATGTGGATG TACATCTAGT TCAACTAAAG GACATTTGTG AAGATATTTC TGATCATGTT GAGCAAATCC
      A  L  L  E  T  E  F  S  L  K  L  L  S  Y  S  V  N  V  I  V  D  I  H
 491 ATGCCCTCCT TGAAACAGAG TTCTCCCTAA AGCTGCTGTC TTACTCTGTC AACGTGATAG TGGACATCCA
      A  V  Q  L  L  W  H  Q  L  R  V  S  V  L  V  L  R  E  R  I  L  Q  G
 561 CGCAGTGCAG CTCCTCTGGC ACCAGCTTCG AGTCTCAGTG CTGGTTCTGC GGGAGCGCAT TCTGCAAGGT
        L  Q  D  A  N  G  N  Y  T  R  Q  T  D  I  L  Q  A  F  S  E  E  T  K  E
 631 CTGCAGGACG CCAATGGCAA CTACACTAGG CAGACGGACA TTCTGCAAGC TTTCTCTGAA GAGACAAAAG
        G  R  L  D  S  L  T  E  V  D  D  S  G  Q  L  T  I  K  C  S  Q  N  Y
 701 AGGGCCGGCT TGATTCTCTA ACAGAAGTGG ATGACTCAGG ACAATTAACC ATCAAATGTT CTCAAAATTA
      L  S  L  D  C  G  I  T  A  F  E  L  S  D  Y  S  P  S  E  D  L  L  S
 771 CTTGTCTCTG GATTGTGGCA TTACTGCATT CGAACTGTCT GACTACAGTC CAAGTGAGGA TTTGCTCAGT
        G  L  G  D  M  T  S  S  Q  V  K  T  K  P  F  D  S  W  S  Y  S  E  M  E
 841 GGGCTAGGTG ACATGACCTC TAGCCAAGTC AAAACCAAAC CCTTTGACTC TTGGAGCTAC AGTGAGATGG
      K  E  F  P  E  L  I  R  S  V  G  L  L  T  V  A  A  D  S  I  S  T  N
 911 AAAAGGAGTT TCCTGAGCTT ATCCGAAGTG TTGGTTTACT TACGGTAGCT GCTGACTCTA TCTCTACCAA
      G  S  E  A  V  T  E  E  V  S  Q  V  S  L  S  V  D  D  K  G  G  C  E
 981 TGGCAGTGAA GCAGTTACTG AGGAGGTATC TCAAGTATCT CTCTCAGTAG ACGACAAAGG TGGATGTGAA
      E  D  N  A  S  A  V  E  E  Q  P  G  L  T  L  G  V  S  S  S  G  E  A
1051 GAAGACAATG CTTCTGCAGT CGAAGAGCAA CCAGGCTTAA CACTGGGGGT GTCATCATCT TCAGGAGAAG
      L  T  N  A  A  Q  P  S  S  E  T  V  Q  Q  E  S  S  S  S  H  H  D
1121 CTCTGACAAA TGCTGCTCAA CCCTCCTCTG AGACTGTGCA GCAAGAATCC AGTTCCTCCT CCCATCATGA
      A  K  N  Q  Q  P  V  P  C  E  N  A  T  P  K  R  T  I  R  D  C  F  N
1191 TGCAAAGAAT CAGCAGCCTG TTCCTTGTGA AAATGCAACC CCCAAACGAA CCATCAGAGA TTGCTTTAAT
        Y  N  E  D  S  P  T  Q  P  T  L  P  K  R  G  L  F  L  K  E  E  T  F  K
1261 TATAACGAGG ACTCTCCCAC GCAGCCTACA TTGCCAAAAA GAGGACTTTT TCTTAAAGAG GAAACTTTTA
        N  D  L  K  G  N  G  G  K  R  Q  M  V  D  L  K  P  E  M  S  R  S  T
1331 AGAATGATCT GAAAGGCAAT GGTGGAAAGA GGCAAATGGT TGATCTAAAG CCTGAGATGA GCAGAAGCAC
      P  S  L  V  D  P  P  D  R  S  K  L  C  L  V  L  Q  S  S  Y  P  N  S
1401 CCCTTCGCTA GTAGATCCTC CTGACAGATC CAAACTTTGC CTGGTATTGC AGTCTTCTTA CCCCAACAGC
        P  S  A  A  S  Q  S  Y  E  C  L  H  K  V  G  N  G  N  L  E  N  T  V  K
1471 CCTTCTGCTG CCAGCCAGTC TTATGAGTGT TTACACAAGG TGGGGAATGG GAACCTTGAA AACACAGTCA
      F  H  I  K  E  I  S  S  S  L  G  R  L  N  D  C  Y  K  E  K  S  R  L
1541 AATTTCACAT TAAAGAAATT TCTTCCAGCC TGGGAAGGCT TAACGACTGC TATAAAGAGA AATCTCGACT
        K  K  P  H  K  T  S  E  E  V  P  P  C  R  T  P  K  R  G  T  G  S  G
1611 TAAAAAGCCA CACAAGACCT CAGAAGAGGT GCCTCCATGC CGAACACCTA AACGGGGAC TGGTTCAGGC
      K  Q  A  K  N  T  K  S  S  A  V  P  N  G  E  L  S  Y  T  S  K  A  I  E
1681 AAACAAGCTA AAAATACAAA GAGCTCAGCA GTGCCAAATG GAGAGCTTTC TTATACTTCC AAGGCCATAG
       G  P  Q  T  N  S  A  S  T  S  S  L  E  P  C  N  Q  R  S  W  N  A  K
1751 AGGGGCCACA AACAAATTCT GCTTCCACAT CCTCACTTGA GCCTTGTAAT CAGAGAAGTT GGAATGCCAA
      L  Q  L  Q  S  E  T  S  S  S  P  A  F  T  Q  S  S  E  S  S  V  G  S
1821 ATTGCAATTG CAGTCAGAAA CATCCAGTTC ACCAGCTTTT ACTCAGAGCA GTGAATCCTC TGTTGGCTCA
        D  N  I  M  S  P  V  P  L  L  S  K  H  K  S  K  K  G  Q  A  S  S  P  S
1891 GACAACATCA TGTCTCCGGT GCCACTTCTT TCAAAACACA AAGCAAAAA AGGTCAAGCC TCCTCTCCAA
      H  V  T  R  N  G  E  V  V  E  A  W  Y  G  S  D  E  Y  L  A  L  P  S
1961 GTCACGTCAC TAGGAATGGT GAGGTTGTGG AGGCCTGGTA TGGCTCTGAT GAATACCTAG CACTGCCCTC
      H  L  K  Q  T  E  V  L  A  L  K  L  E  N  L  T  K  L  L  P  Q  K  P
```

FIGURE 27 (cont.)

```
2031 TCACCTTAAG CAGACAGAAG TATTGGCTTT GAAGTTGGAA AACCTAACAA AGCTTCTGCC TCAGAAACCC
      R  G  E  T     I  Q  N     I  D  D     W  E  L  S     E  M  N     S  D  S     E  I  Y  P·
2101 AGAGGAGAAA CCATCCAGAA TATTGATGAC TGGGAACTGT CTGAAATGAA TTCAGATTCT GAAATCTATC
     ·T  Y  H     V  K  K     K  H  T  R     L  G  R     V  S  P     S  S  S  S     D  I  A·
2171 CAACCTATCA TGTCAAAAAG AAGCATACAA GGCTAGGCAG GGTGTCTCCA AGCTCATCTA GTGACATAGC
     ·S  S  L     G  E  S  I     E  S  G     P  L  S     D  I  L  S     D  E  E     S  S  M
2241 CTCTTCACTA GGGGAGAGCA TTGAATCTGG GCCCCTGAGT GACATTCTTT CTGATGAGGA GTCCAGTATG
      P  L  A  G     M  K  K     Y  A  D     E  K  S     E  R  A  S     S  S  E     K  N  E  S·
2311 CCTCTCGCTG GCATGAAAAA GTATGCTGAT GAGAAGTCAG AAAGAGCTTC ATCCTCTGAG AAAAATGAGA
     ·H  S  A     T  K  S     A  L  I  Q     K  L  M     Q  D  I     Q  H  Q  D     N  Y  E·
2381 GCCATTCTGC CACTAAATCA GCTTTAATTC AGAAACTGAT GCAAGATATT CAGCACCAAG ACAACTATGA
     ·A  I  W     E  K  I  E     G  F  V     N  K  L     D  E  F  I     Q  W  L     N  E  A
2451 AGCCATATGG GAAAAAATAG AGGGGTTTGT AAACAAACTG GATGAATTCA TTCAATGGTT AAATGAAGCC
      M  E  T  T     E  N  W     T  P  P     K  A  E  M     D  D  L     K  L  Y     L  E  T  H·
2521 ATGGAAACTA CAGAGAATTG GACTCCCCCT AAAGCAGAGA TGGATGACCT TAAACTGTAT CTGGAGACAC
     ·L  S  F     K  L  N     V  D  S  H     C  A  L     K  E  A     V  E  E  E     G  H  Q·
2591 ACTTGAGTTT TAAGTTGAAT GTAGACAGTC ATTGTGCTCT CAAGGAAGCT GTGGAGGAGG AAGGACACCA
     ·L  L  E     L  I  A  S     H  K  A     G  L  K     D  M  L  R     M  I  A     S  Q  W
2661 ACTTCTTGAG CTTATTGCAT CTCACAAAGC AGGACTGAAG GACATGCTGC GGATGATTGC AAGTCAATGG
      K  E  L  Q     R  Q  I     K  R  Q     H  S  W  I     L  R  A     L  D  T     I  K  A  E·
2731 AAGGAGCTGC AGAGGCAAAT CAAACGGCAG CACAGCTGGA TTCTCAGGGC TCTGGATACC ATCAAAGCCG
     ·I  L  A     T  D  V     S  V  E  D     E  E  G     T  G  S     P  K  A  E     V  Q  L·
2801 AGATACTGGC TACTGATGTG TCTGTGGAGG ATGAGGAAGG GACTGGAAGC CCCAAGGCTG AGGTTCAACT
     ·C  Y  L     E  A  Q  R     D  A  V     E  Q  M     S  L  K  L     Y  S  E     Q  Y  T
2871 ATGCTACCTG GAAGCACAAA GAGATGCTGT TGAGCAGATG TCCCTCAAGC TGTACAGCGA GCAGTATACC
      S  S  S  K     R  K  E     E  F  A     D  M  S  K     V  H  S     V  G  S     N  G  L  L·
2941 AGCAGCAGCA AGCGAAAGGA AGAGTTTGCT GATATGTCAA AAGTTCATTC AGTGGGAAGC AATGGGCTTC
     ·D  F  D     S  E  Y     Q  E  L  W     D  C  L     I  D  M     E  S  L  V     M  D  S·
3011 TGGACTTTGA TTCAGAATAT CAGGAGCTCT GGGATTGCTT GATTGACATG GAGTCCCTTG TGATGGACAG
     ·H  D  L     M  M  S  E     E  Q  Q     Q  H  L     Y  K  R  Y     S  V  E     M  S  I
3081 CCACGACCTG ATGATGTCAG AAGGAGCAGCA GCACATCTT TACAAGCGAT ACAGTGTGGA AATGTCCATC
      R  H  L  K     K  T  E     L  L  S     K  V  E  A     L  K  K     G  G  V     L  L  P  N·
3151 AGACACCTGA AAAAGACGGA GCTGCTTAGT AAGGTTGAAG CTTTGAAGAA AGGTGGCGTT TTACTACCAA
     ·D  L  L     E  K  V     D  S  I  N     E  K  W     E  L  L     G  K  T  L     G  E  K·
3221 ATGATCTCCT TGAAAAAGTG GATTCAATTA ATGAAAAATG GGAACTGCTT GGGAAAACCC TAGGAGAGAA
     ·I  Q  D     T  M  A  G     H  S  G     S  S  P     R  D  L  L     S  P  E     S  G  S
3291 GATCCAGGAC ACAATGGCAG GGCACAGTGG GTCGAGTCCA CGTGACCTGC TCTCTCCTGA AGTGGAAGC
      L  V  R  Q     L  E  V     R  I  K     E  L  K  G     W  L  R     D  T  E     L  F  I  F·
3361 CTGGTAAGGC AGCTGGAGGT CAGGATCAAA GAACTGAAAG GATGGCTAAG AGATACAGAG CTTTTCATCT
     ·N  S  C     L  R  Q     E  K  E  G     T  M  N     T  E  K     Q  L  Q  Y     F  K  S·
3431 TCAATTCCTG TCTGAGACAA GAAAAGGAAG GAACAATGAA TACTGAGAAA CAACTGCAAT ACTTTAAGTC
     ·L  C  R     E  I  K  Q     R  R  R     G  V  A     S  I  L  R     L  C  Q     H  L  L
3501 CCTCTGTCGT GAAATCAAGC AACGACGTCG AGGAGTTGCC TCCATTCTGC GACTATGCCA GCATCTTTTG
      D  D  R  E     T  C  N     L  N  A     D  H  Q  P     M  Q  L     I  I  V     N  L  E  R·
3571 GATGACCGGG AGACTTGCAA TCTGAATGCA GACCACCAGC CCATGCAGCT GATCATTGTA AATCTTGAAA
     ·R  W  E     A  I  V     M  Q  A  V     Q  W  Q     T  R  L     Q  K  K  M     G  K  E·
3641 GAAGGTGGGA AGCCATTGTC ATGCAAGCCG TCCAGTGGCA AACACGTCTA CAAAAGAAGA TGGGAAAGGA
     ·S  E  T     L  N  V  I     D  P  G     L  M  D     L  N  G  M     S  E  D     A  L  E
3711 ATCTGAGACT TTGAATGTGA TTGATCCTGG CTTGATGGAC CTAAATGGGA TGAGTGAGGA TGCCCTGGAA
      W  D  E  M     D  I  S     N  K  L     I  S  L  N     E  E  S     N  D  L     D  Q  E  L·
3781 TGGGATGAAA TGGACATAAG TAACAAGTTA ATTAGTTTGA ATGAGGAATC AAATGACCTT GATCAAGAAC
     ·Q  P  V     I  P  S     L  K  L  G     E  T  S     N  E  D     P  G  Y  D     E  E  A·
3851 TCCAACCTGT TATCCCTTCC TTGAAGCTTG GAGAGACAAG TAATGAGGAC CCTGGTTATG ACGAGGAGGC
     ·D  N  H     G  G  S  Q     Y  A  S     N  I  T     A  P  S  S     P  H  I     Y  Q  V
3921 TGATAACCAT GGGGGATCTC AGTATGCCTC AAATATTACT GCCCCCTCTA GTCCACACAT TTACCAGGTG
      Y  S  L  H     N  V  E     L  Y  E     D  N  H  M     P  F  L     K  N  N     P  K  V  T·
3991 TACAGCCTCC ACAATGTTGA ACTCTATGAG GACAACCACA TGCCATTTCT GAAAAACAAT CCAAAGGTCA
     ·G  M  T     Q  P  N     V  L  T  K     S  L  S     K  D  S     S  F  S  S     T  K  S·
4061 CTGGCATGAC ACAGCCTAAT GTTTTAACTA AGAGTCTCAG TAAAGACTCT TCATTTCAT CTACCAAATC
     ·L  P  D     L  L  G  G     S  N  L     V  K  P     C  A  C  H     G  G  D     M  S  Q
```

FIGURE 27 (cont.)

```
4131 TTTGCCAGAT CTTCTAGGTG GTTCCAATTT GGTAAAGCCC TGCGCATGTC ATGGAGGAGA CATGAGCCAG
      N  S  G  S  E  S  G   I  V  S  E  G  D  T   E  T  T   T  N  S   E  M  C  L
4201 AATTCAGGCA GTGAGAGTGG AATTGTCAGT GAAGGAGACA CAGAAACCAC TACCAACTCT GAAATGTGCT
      L  N  A   V  D  G   S  P  S  N   L  E  T   E  H  L   D  P  Q  M  G  D  A
4271 TGCTCAATGC AGTGGATGGG TCCCCAAGTA ACCTTGAAAC TGAACATCTG GACCCACAAA TGGGAGATGC
      V  N  V  L  K  Q  K   F  T  D   E  G  E   S  I  K  L   P  N  S   S  Q  S
4341 AGTTAACGTG TTAAAGCAAA AATTTACAGA TGAGGGGGAA AGCATTAAGC TTCCAAATAG CTCTCAGTCG
      S  I  S  P   V  G  C   V  N  G   K  V  G  D   L  N  S   I  T  K   H  T  P  D
4411 TCCATTTCAC CAGTGGGTTG TGTAAATGGA AAAGTTGGAG ATTTAAACAG TATTACCAAA CATACCCCTG
      C  L  G   E  E  L   Q  G  K  H   D  V  F   T  F  Y   D  Y  S  Y   L  Q  G
4481 ACTGTTTGGG AGAAGAATTA CAAGGAAAAC ATGATGTGTT TACATTTTAT GATTACTCAT ACCTCCAAGG
      S  K  L   K  L  P  M   I  M  K   Q  S  Q   S  E  K  V   H  V  E   D  P  L
4551 CTCAAAACTC AAATTACCAA TGATAATGAA ACAGTCACAA AGCGAAAAGC TGCATGTGGA GGATCCCCTG
      L  R  G  F   Y  F  D   K  K  S   C  K  S  K   H  Q  T   T  E  L   Q  P  D  V
4621 CTTCGTGGTT TTTATTTTGA TAAAAAATCA TGCAAATCTA AACATCAGAC TACAGAGTTA CAACCAGATG
      P  P  H   E  R  I   L  A  S  A   S  H  E  M   D  R  I   S  Y  K   S  G  N
4691 TACCTCCCCA TGAAAGGATT TTGGCAAGTG CATCTCATGA AATGGATCGC ATTTCATATA AAAGTGGCAA
      I  E  K   T  F  T  G   M  Q  N   A  K  Q   L  S  L  L   S  H  S   S  S  I
4761 TATAGAAAAG ACATTCACTG GCATGCAGAA TGCCAAACAG CTCTCCCTTT TATCTCATAG TTCATCTATT
      E  S  L   S  P  G  G   D  L  F   G  L  G  I   F  K  N   G  S  D   S  L  Q  R
4831 GAGTCCCTTT CTCCAGGGGG TGATTTATTT GGATTGGGCA TCTTTAAAAA TGGCAGTGAC AGCCTCCAGC
      S  T  S   L  E  S   W  L  T  S   Y  K  S   N  E  D   L  F  S  C   H  S  S
4901 GAAGCACTTC TTTAGAAAGT TGGTTGACTT CCTATAAAAG CAATGAAGAT CTCTTTAGCT GTCACAGCTC
      G  D  I   S  V  S  S   G  S  V   G  E  L   S  K  R  T   L  D  L   L  N  R
4971 TGGGGATATA AGCGTGAGCA GTGGCTCAGT TGGTGAACTA AGTAAAAGAA CATTAGATCT CCTGAATCGT
      L  E  N  I   Q  S  P   S  E  Q   K  I  K  R   S  V  S   D  I  T   L  Q  S  S
5041 TTGGAGAATA TCCAGAGCCC CTCAGAGCAA AAGATAAAAC GAAGTGTTTC TGATATCACT CTTCAAAGCA
      S  Q  K   M  S  F   T  G  Q  M   S  L  D   I  A  S   S  I  N  E   D  S  A
5111 GTTCCCAAAA GATGTCCTTT ACTGGCCAGA TGTCATTGGA CATAGCATCT TCTATCAATG AAGACTCAGC
      A  S  L   T  E  L  S   S  S  D   E  L  S   L  C  S  E   D  I  V   L  H  K
5181 GGCATCTCTA ACAGACTTA GCAGCAGTGA CGAGCTCTCT CTTTGCTCAG AGGATATTGT GTTACACAAG
      N  K  I  P   E  S  N   A  S  F   R  K  R  L   T  R  S   V  A  D   E  S  D  V
5251 AACAAGATCC CGGAATCGAA TGCATCGTTC AGGAAGCGTC TGACTCGTTC AGTGGCTGAT GAAAGCGATG
      N  V  S   M  I  V   N  V  S  C   T  S  A   C  T  D   D  E  D  D   S  D  L
5321 TCAATGTCAG CATGATTGTT AATGTCTCTT GCACCTCTGC TTGCACTGAT GATGAAGATG ACAGCGACCT
      L  S  S   S  T  L  T   L  T  E   E  E  L   C  I  K  D   E  D  D   D  S  S
5391 GCTCTCCAGC TCTACCCTTA CCTTGACTGA AGAAGAGCTG TGCATCAAAG ATGAGGATGA CGACTCCAGT
      I  A  T  D   D  E  I   Y  E  D   C  T  L  M   S  G  L   D  Y  I   K  N  E  L
5461 ATTGCAACAG ATGATGAAAT TTATGAAGAC TGCACCTTGA TGTCAGGGCT AGACTACATA AAGAATGAAT
      Q  T  W   I  R  P   K  L  S  L   T  R  D   K  K  R   C  N  V  S   D  E  M
5531 TACAGACCTG GATTAGGCCA AAATTGTCTT TGACAAGAGA TAAGAAAAGG TGCAATGTCA GTGATGAGAT
      K  G  S   K  D  I  S   S  S  E   M  T  N   P  S  D  T   L  N  I   E  T  L
5601 GAAGGGCAGT AAAGATATAA GTAGCAGTGA GATGACCAAT CCCTCTGATA CTCTGAATAT TGAGACCCTT
      L  N  G   S  V  K  R   V  S  E   N  N  G   N  G  K  N   S  S  H   T  H  E  L
5671 CTAAATGGCT CTGTAAAACG TGTCTCTGAA AATAATGGAA ATGGTAAGAA TTCATCTCAT ACCCATGAGT
      G  T  K   R  E  N   K  K  T  I   F  K  V   N  K  D   P  Y  V  A   D  M  E
5741 TAGGGACAAA GCGTGAAAAT AAGAAAACTA TTTTCAAAGT TAATAAAGAT CCATATGTGG CTGACATGGA
      N  G  N   I  E  G  I   P  E  R   Q  K  G   K  P  N  V   T  S  K   V  S  E
5811 AAATGGCAAT ATTGAAGGTA TTCCAGAAAG GCAAAAGGGC AAACCGAATG TGACTTCAAA GGTATCAGAA
      N  L  G   S  H  G  K   E  I  S   E  S  E  H   C  K  C   K  A  L   M  D  S  L
5881 AATCTTGGTT CACATGGGAA AGAGATTTCA GAGAGTGAGC ATTGTAAGTG TAAAGCACTT ATGGATAGTT
      D  D  S   N  T  A   G  K  E  F   V  S  Q   D  V  R   H  L  P  K   C  P
5951 TAGATGATTC AAATACTGCT GGCAAGGAAT TTGTTTCCCA AGATGTTAGA CATCTTCCAA AGAAATGTCC
      N  H  H   H  F  E  N   Q  S  T   A  S  T   P  T  E  K   S  F  S   E  L  A
6021 AAATCACCAC CATTTTGAAA ATCAAAGCAC TGCCTCTACT CCCACTGAGA AGTCTTTCTC AGAACTGGCT
      L  E  T  R   F  N  N   R  Q  D   S  D  A  L   K  S  S   D  D  A   P  S  M  A
6091 TTAGAAACCA GGTTTAACAA CAGACAAGAC TCTGATGCAC TGAAATCATC TGATGATGCA CCGAGTATGG
      G  K  S   A  G  C   C  L  A  L   E  Q  N   G  T  E   E  N  A  S   I  S  N
6161 CTGGAAAATC TGCTGGTTGT TGCCTAGCAC TTGAACAAAA CGGAACAGAG GAAAATGCTT CTATCAGCAA
      I  S  C   C  N  C  E   P  D  V   F  H  Q   K  D  A  E   D  C  S   V  H  N
```

FIGURE 27 (cont.)

```
6231 CATTTCCTGT TGCAACTGTG AGCCAGATGT TTTCCATCAA AAGATGCCG AAGATTGTTC AGTACACAAC
      F  V  K  E  I  I  D  M  A  S  T  A  L  K  S  K  S  Q  P  E  N  E  V  A
6301 TTTGTTAAGG AAATCATTGA CATGGCTTCG ACAGCCCTAA AAGTAAATC TCAACCTGAA AACGAGGTGG
      ·  A  P  T  S  L  T  Q  I  K  E  K  V  L  E  H  S  H  R  P  I  Q  L  R  ·
6371 CTGCTCCTAC TTCATTAACT CAAATCAAGG AGAAAGTGTT GGAGCATTCT CACCGGCCCA TCCAGCTGAG
      ·  K  G  D  F  Y  S  Y  L  S  L  S  S  H  D  S  D  C  G  E  V  T  N  Y
6441 AAAAGGGGAC TTTTATTCGT ACTTATCTCT CTCATCTCAT GACAGTGATT GTGGGGAGGT CACCAATTAC
      I  E  E  K  S  S  T  P  L  P  L  D  T  T  D  S  G  L  D  D  K  E  D  I  ·
6511 ATAGAAGAGA AAAGCAGCAC TCCATTGCCA CTAGACACCA CTGACTCGGG CTTAGATGAC AAGGAAGATA
      ·  E  C  F  F  E  A  C  V  E  G  D  S  D  G  E  E  P  C  F  S  S  A  P  ·
6581 TTGAATGCTT TTTTGAGGCC TGTGTTGAGG GTGACTCTGA TGGAGAGGAG CCTTGTTTCT CTAGTGCTCC
      ·  P  N  E  S  A  V  P  S  E  A  A  M  P  L  Q  A  T  A  C  S  S  E  F
6651 TCCAAATGCA TCTGCATTCC CCAGCAAGCA CTGACAAGCA CTACAAGCCA CAGCATGTTC TTCTGAGTTC
      S  D  S  S  L  S  A  D  D  A  D  T  V  A  L  S  S  P  S  S  Q  E  R  A  ·
6721 AGTGATAGTT CTCTTTCAGC TGATGATGCA GATACAGTGG CTCTTCAAG TCCTTCCTCT CAGGAAAGAG
      ·  E  V  G  K  E  V  N  G  L  P  Q  T  S  S  G  C  A  E  N  L  E  F  T  ·
6791 CTGAGGTTGG AAAGGAAGTG AATGGTTTGC CCCAAACTTC CAGTGGCTGT GCAGAAAACT TAGAGTTTAC
      ·  P  S  K  L  D  S  E  K  E  S  S  G  K  P  G  E  S  G  M  P  E  E  H
6861 TCCTTCAAAG CTTGACAGTG AAAAGGAAAG TTCCGGAAAA CCAGGTGAAT CTGGAATGCC AGAAGAACAT
      N  A  A  S  A  K  S  K  V  Q  D  L  S  L  K  A  N  Q  P  T  D  K  A  A  ·
6931 AATGCTGCTT CAGCCAAATC TAAAGTTCAA GACCTCTCCT TGAAGGCAAA TCAGCCAACA GACAAGGCCG
      ·  L  H  P  S  P  K  T  L  T  C  E  E  N  L  L  N  L  H  E  K  R  H  R  ·
7001 CATTGCATCC CAGCCCCAAA ACTTTAACCT GTGAAGAAAA TCTTCTAAAC CTTCATGAAA AACGACATAG
      ·  N  M  H  R
7071 AAATATGCAT AGGTAGAATG TACCCCCTCC CCAAGCATGA AAATCATCTC ACTGAAAGAT ACGCCTGGCT
7141 GCAACTCAGG GGTGGCCTCA TCCTCCCGCC CTGGGCTGGC CTCTGGTTCC ATCACGTTTG TCACTGCCGT
7211 TTATTACATT GACTTCTCCC AAGATGAATC TTCCTTCCAA ATGTGTTTTC TCCACACAAG CCTTGTGATC
7281 TGAATGTGTG CGCTGGTTCT CTTTAGGTGA TCGTCTTTGA AGTTCAGCAA AGCTGCTTGT TCTCCCATGG
7351 ATTCCTGTCC CAAGCTACCT CTACCAACCC TCTCTCTCCA GCTAGACTTT TCTCTTTGCC TCCTCCCTTC
7421 CCTTCCACTC TTTAAAGTTC TGCAGTTCAC CAACTGGTAG TCCATTAAAT TCTCCTGTCT AGAATGACCC
7491 CCCCACCAGT ACTTGACCAA TTTCATGTAT CAATCTGGAT TTTTTTTTA ACGGTATAAT GACTGTGCTT
7561 ATTGAAAGAG TTTTACCTAA AACCCAACA TTTGAATTGG TTGCAGCATA GAGAAGAAAC ACTGGTCCTT
7631 CTTTCAAAAT TAAGCAACTA TTAAAAGCGC CATTTTATTT ATTTCATTTA AAAAATAATC TATGCAGCAT
7701 TTCAAGAAAC AACCATATGG TGTTGTATAT TATAAACTGG TGACATTCTA CTATTGAATT ATGTACAACA
7771 TTTTCATTTT TTATGCTTCT TGAGGTGGTA ATGAGAAAAA AGTTTTTTAA AAAAGTGTGC CTTGCTGTAT
7841 TTCTTATACC ATTTATTAAA AAGCTGCTTT CACGGTAAAA TTATGTTGGT TTGAAAGGAG GAAATAGCAA
7911 GGTTAAGATG TGTGAATAAT TTCTGTATAT ATGTATAACC AAGTACAAAC ATTGATGTAT AATGACAGTA
7981 TAAAATGCTT TCATGTTTGT GATGTCTAGT GATGTGGAAA ATATAAGCCT TAAATCCATT AGATTGCATG
8051 GTAATTAAAA TTGGCATAAT AAACACAGAT TATTGGGGGA AAAGGAAAAT TAGTGATCTC TTCTACTATG
8121 TTCTTTACCA AATTGTTGCA TCTGGTTCTG AAAAAGTATA GCATGTAGCA GCTTCCAAAC ATATTCATAT
8191 TGCTTAAGAG GCTTAACATT ACCTAAACTA GAGACTAGAC GTAAAGCCTT CAGTTTTCAA AATCTTTCTG
8261 GTCACTATAA AGATCTTGGA ACAGCAAATG ATTAAATGTC AGTTCCCCTA AACCAATAAA CATTTATACT
8331 AGATTTTTTA TTTCCACTTA TCATTAATGA TTTAATGTTG GATTTCAGGT ACCTTGTATG TCTTAATTTA
8401 TTTTAAATAT TTATTTTGAA TGAGTTTGAT AGAAAGCTAG TAGAAAGTA CAGAAAATTT GACTATTATT
8471 TATAGATTTC AGGTATATTT ATATGTGTAA AAGAAATTGA CAAAGAAATA TTTCATCTGG CCTTTACTGA
8541 CTCCTGTTAA ATGCAGTTTT AAATTTATAT CGTAACACCT ACTTAAGTGC CTGACACAGT AGGTATTCAA
8611 TAAAAATTTA CTGAATTAAA GGATTAAATT AGGTGACATG GTGACATCTA TCCCTTTATT TTGACACTAA
8681 AACATGGACA CAACTAGAAA GAGGTACAAT GCAATATAAA GTCACAATAG ATAATATATA TCAAATTTCT
8751 AAAAGGTAAA GAATGTTGTG GGTTCATGCA GTCACAGGAA TGACAATCAT TCAACAGATA GTTCAGAAAC
8821 ACTTTTTATC TGCAAGGCAC TATTCTAGAT CCAGAAGATG CAATGTTGAA CAAACAGACA AAGCCCTGCC
8891 CTCAGAAGGC TGTCCTGCAT TAGGACAAG TGAACACGCA AATGACATGA AGTATTTGTT GCAGAGCTGA
8961 GGAACAGAGC AAATGTAGTG ATAGAAGCGC AATGAGAGAA GCAGCAGTGG GTACAAGGAG GAAGAAAAAG
9031 GGCTTGCAGA GAGTGGAAAG TTAGTGGAAT ATTCATGAAA CTTCATTGCA GGGGTAATAG AAGAAAAAGT
9101 AAATTGGGAG GACTTAATGG AAGGTCTTTT AAAAAGTTAA CTTGGAGCTT CTGTATGTAA AATGCTAGGT
9171 AATAAGGACA CTTTGTACAG GCTGTTTTGC ACCTGATTTT ATTTATCATT AGTGCCACGC CAAGATCATT
9241 TAGACGATGC TTATCTGTAA TTCTACCACT TTAATAACTA TTTGTATTTT TATGCCCCTT CTGATCTTTT
9311 CCATATGTAT TTCTAAATGG ATAAATTATT CTAGGCTTCT TAATAGGTAG TAATTTGTTC AAAAGCGGTT
9381 TTAGCCAGAC ATCTAGTTGC AGTGTTCAAG AGGATTATGG GGGAAAGAGA TTAGAGATAA TTGTCTAGTT
9451 AGGGGGCAGC TGGAGAAAAT AAGCTAAGTT TGCAATAACA GAGTCACAA GTATAGTGGC CCAGGATGTA
9521 GTGAAAGAAC AAATCCTAGA GTCTTTGAAA TTTCTAAGGG CATTCTAGAC CTCTGTTGGG ATATGGTATT
```

FIGURE 27 (cont.)

```
 9591 ATTTTACATA CTGACACAAC CTAAATTTTC TTTGGGTAGT AACTAATGTC AAGTCTACAT CGACTGGTAA
 9661 AACATTCAAA GAACAAACTG ACAATGATGT TCTACCTACT TGTTACATGC TCATGGAAGA CCGTGCAGTA
 9731 TTGAAAGTAT TTGTTAATTA TCTGCTTAGT ATTAACACTA AATTTGTAGA ATGACTTTCA GGTTTGTTGA
 9801 ACAATGCCTT TTCAGGTTGG AAGAAGAAAA ATAGCCTCAA TCTCCCACCC CATGTAGGCA CTACCTCCCC
 9871 AATTACCCTT AGAAAATGAT CACACCAACT CTGCCTACAC ACTTCCAGTG ATAGTGGCTC ATTGTCTGTT
 9941 AAGGCAAACT GTTCCACTGT TGGGCATATC TCTTTGTTAG AAAGTTCTTT CTTAGGTTGC TAAAATCTGC
10011 CTAGTACCCC GCTACCCTGT TCTGTCTTAT GGAGCAGCCC AGATTATCTT TACTCCCTCT TTCTCATGGC
10081 AACCCTGAAG ATAATCAAGG CCAGTTACTC ATCATCTCCC AACCACTGTT TCCTCAACTG CCCTTCATAT
10151 GTCATGGTTT TCAGATCCAT TCCAACCTGA CTGAATGTTA ACAGACAGAA TTCTTCACAT TAAGGAACTG
10221 TCTTCATCAT CATACATGTA GAAAAGAATC TGAACATTTA AGTGCGAAGT TTTCTCTAGA AATATATTCA
10291 AGATATGTTT ATTCTATTAT TGTAAATTTC AACAATAAA TAAATAAGAA TCC
```

FIGURE 28 human mAKAP sequence (PBD in bold)

```
   1  MLTMSVTLSP  LRSQDLDPMA  TDASPMAINM  TPTVEQGEGE  EAMKDMDSDQ
  51  QYEKPPPLHT  GADWKIVLHL  PEIETWLRMT  SERVRDLTYS  VQQDSDSKHV
 101  DVHLVQLKDI  CEDISDHVEQ  IHALLETEFS  LKLLSYSVNV  IVDIHAVQLL
 151  WHQLRVSVLV  LRERILQGLQ  DANGNYTRQT  DILQAFSEET  KEGRLDSLTE
 201  VDDSGQLTIK  CSQNYLSLDC  GITAFELSDY  SPSEDLLSGL  GDMTSSQVKT
 251  KPFDSWSYSE  MEKEFPELIR  SVGLLTVAAD  SISTNGSEAV  TEEVSQVSLS
 301  VDDKGGCEED  NASAVEEQPG  LTLGVSSSSG  EALTNAAQPS  SETVQQESSS
 351  SSHHDAKNQQ  PVPCENATPK  RTIRDCFNYN  EDSPTQPTLP  KRGLFLKEET
 401  FKNDLKGNGG  KRQMVDLKPE  MSRSTPSLVD  PPDRSKLCLV  LQSSYPNSPS
 451  AASQSYECLH  KVGNGNLENT  VKFHIKEISS  SLGRLNDCYK  EKSRLKKPHK
 501  TSEEVPPCRT  PKRGTGSGKQ  AKNTKSSAVP  NGELSYTSKA  IEGPQTNSAS
 551  TSSLEPCNQR  SWNAKLQLQS  ETSSSPAFTQ  SSESSVGSDN  IMSPVPLLSK
 601  HKSKKGQASS  PSHVTRNGEV  VEAWYGSDEY  LALPSHLKQT  EVLALKLENL
 651  TKLLPQKPRG  ETIQNIDDWE  LSEMNSDSEI  YPTYHVKKKH  TRLGRVSPSS
 701  SSDIASSLGE  SIESGPLSDI  LSDEESSMPL  AGMKKYADEK  SERASSSEKN
 751  ESHSATKSAL  IQKLMQDIQH  QDNYEAIWEK  IEGFVNKLDE  FIQWLNEAME
 801  TTENWTPPKA  EMDDLKLYLE  THLSFKLNVD  SHCALKEAVE  EEGHQLLELI
 851  ASHKAGLKDM  LRMIASQWKE  LQRQIKRQHS  WILRALDTIK  AEILATDVSV
 901  EDEEGTGSPK  AEVQLCYLEA  QRDAVEQMSL  KLYSEQYTSS  SKRKEEFADM
 951  SKVHSVGSNG  LLDFDSEYQE  LWDCLIDMES  LVMDSHDLMM  SEEQQQHLYK
1001  RYSVEMSIRH  LKKTELLSKV  EALKKGGVLL  PNDLLEKVDS  INEKWELLGK
1051  TLGEKIQDTM  AGHSGSSPRD  LLSPESGSLV  RQLEVRIKEL  KGWLRDTELF
1101  IFNSCLRQEK  EGTMNTEKQL  QYFKSLCREI  KQRRRGVASI  LRLCQHLLDD
1151  RETCNLNADH  QPMQLIIVNL  ERRWEAIVMQ  AVQWQTRLQK  KMGKESETLN
1201  VIDPGLMDLN  GMSEDALEWD  EMDISNKLIS  LNEESNDLDQ  ELQPVIPSLK
1251  LGETSNEDPG  YDEEADNHGG  SQYASNITAP  SSPHIYQVYS  LHNVELYEDN
1301  HMPFLKNNPK  VTGMTQPNVL  TKSLSKDSSF  SSTKSLPDLL  GGSNLVKPCA
1351  CHGGDMSQNS  GSESGIVSEG  DTETTTNSEM  CLLNAVDGSP  SNLETEHLDP
1401  QMGDAVNVLK  QKFTDEGESI  KLPNSSQSSI  SPVGCVNGKV  GDLNSITKHT
1451  PDCLGEELQG  KHDVFTFYDY  SYLQGSKLKL  PMIMKQSQSE  KVHVEDPLLR
1501  GFYFDKKSCK  SKHQTTELQP  DVPPHERILA  SASHEMDRIS  YKSGNIEKTF
1551  TGMQNAKQLS  LLSHSSSIES  LSPGGDLFGL  GIFKNGSDSL  QRSTSLESWL
1601  TSYKSNEDLF  SCHSSGDISV  SSGSVGELSK  RTLDLLNRLE  NIQSPSEQKI
1651  KRSVSDITLQ  SSSQKMSFTG  QMSLDIASSI  NEDSAASLTE  LSSSDELSLC
1701  SEDIVLHKNK  IPESNASFRK  RLTRSVADES  DVNVSMIVNV  SCTSACTDDE
1751  DDSDLLSSST  LTLTEEELCI  KDEDDDSSIA  TDDEIYEDCT  LMSGLDYIKN
1801  ELQTWIRPKL  SLTRDKKRCN  VSDEMKGSKD  ISSSEMTNPS  DTLNIETLLN
1851  GSVKRVSENN  GNGKNSSHTH  ELGTKRENKK  TIFKVNKDPY  VADMENGNIE
1901  GIPERQKGKP  NVTSKVSENL  GSHGKEISES  EHCKCKALMD  SLDDSNTAGK
1951  EFVSQDVRHL  PKKCPNHHHF  ENQSTASTPT  EKSFSELALE  TRFNNRQDSD
2001  ALKSSDDAPS  MAGKSAGCCL  ALEQNGTEEN  ASISNISCCN  CEPDVFHQKD
2051  AEDCSVHNFV  KEIIDMASTA  LKSKSQPENE  VAAPTSLTQI  KEKVLEHSHR
```

FIGURE 28 (cont.)

```
2101  PIQLRKGDFY  SYLSLSSHDS  DCGEVTNYIE  EKSSTPLPLD  TTDSGLDDKE
2151  DIECFFEACV  EGDSDGEEPC  FSSAPPNESA  VPSEAAMPLQ  ATACSSEFSD
2201  SSLSADDADT  VALSSPSSQE  RAEVGKEVNG  LPQTSSGCAE  NLEFTPSKLD
2251  SEKESSGKPG  ESGMPEEHNA  ASAKSKVQDL  SLKANQPTDK  AALHPSPKTL
2301  TCEENLLNLH  EKRHRNMHR
```

FIGURE 29

```
human PBD sequence:
  1 MGKSSTPLPL DTTDSGLDDK EDIECFFEAC VEGDSDGEEP CFSSAPPNES
 51 AVPSEAAMPL QATACSSEFS DSSLSADDAD TVALSSPSSQ ERAEVGKEVN
101 GLPQTSSGCA ENLEFTPSKL DSEKESSGKP GESGMPEEHN AASAKSKVQD
151 LSLKANQPTD KAALHPSPKT LTCEENLLNL HEKRHRNMHR
```

Alignment of human and rat PBD sequences

```
                            1                                                        50
human mAKAP PBD   (1)   ------------------------MG SSTPLPLDTT DSGLDDKEDI DCFF
rat   mAKAP PBD   (1)   MEQKLISEEDLSPGMLTMSVTLSPL SQTPLPDAV  DSGLDDKEDI DCFF
      Consensus   (1)                            KS TPLP D    DSGLDDKEDIDCFF 51                                                       100
human mAKAP PBD   (28)  EACVEG SDGEE PCFSSAP PNESAV PSEEAAMPLQ TACSSEF DSST SD
rat   mAKAP PBD   (51)  EACVED PVNEEAGLPGA GLPNESA EDGAEQ---K ---EQKT SSPL D
      Consensus   (51)  EACVE  D       EE    A PNESAI         A      A  S  L AD 101                                                      150
human mAKAP PBD   (78)  DADTVA SPSSQERA VKEVNGLPQTSS GCAENLFTPSKLD EKESS
rat   mAKAP PBD   (96)  KTDLNPLSGLSPQKGA DKEGDDVSHTSQCAESTEPTTPSGK NAEGR
      Consensus   (101)          D    VLS Q  AD  AKE L     TS GCAE  T   A  E 151                                                      200
human mAKAP PBD   (128) GPGESGMPEEHNAASAKSK QDLSLKANQPTDKAA HP-SPKTTTCEEN
rat   mAKAP PBD   (146) SMQGVSATPEENAASAKPK QAFSLNAKQPKGKVA RYPSPQTTCKEK
      Consensus   (151)       K        E NAASAK KIQ  A  QP  K AL      SP TLTC E 201    214
human mAKAP PBD   (177) LLNLHEKRHR NMHR
rat   mAKAP PBD   (196) LLNFHEDRHS NMHR
      Consensus   (201) LLN HE RH  NMHR
```

Sequence of pscAAV-hmAKAP PBD

```
   1 ACCGAGTTGC TCTCACCCGG CGTCAATACG GGATAATACC GCGCCACATA GCAGAACTTT AAAAGTGCTC ATCATTGGAA
  81 AACGTTCTTC GGGGCGAAAA CTCTCAAGGA TCTTACCGCT GTTGAGATCC AGTTCGATGT AACCCACTCG TGCACCCAAC
 161 TGATCTTCAG CATCTTTTAC TTTCACCAGC GTTTCTGGGT GAGCAAAAAC AGGAAGGCAA AATGCCGCAA AAAAGGGAAT
 241 AAGGGCGACA CGGAAATGTT CAATTCAACT ACTCTTCCTT TTTCAATATT ATTGAAGCAT TTATCAGGGT TATTGTCTCA
 321 TGAGCGGATA CATATTTGAA TGTATTTAGA AAAATAAACA AATAGGGGTT CCGCGCACAT TTCCCCGAAA AGTGCCACCT
 401 GACGTCTAAG AAACCATTAT TATCATGACA TTAACCTATA AAAATAGGCG TATCACGAGG CCCTTTCGTC TCGCGCGTTT
 481 CGGTGATGAC GGTGAAAACC TCTGACACAT GCAGCTCCCG GAGACGGTCA CAGCTTGTCT GTAAGCGGAT GCCGGGAGCA
 561 GACAAGCCCG TCAGGGCGCG TCAGCGGGTG TTGGCGGGTG TCGGGGCTGG CTTAACTATG CGGCATCAGA GCAGATTGTA
 641 CTGAGAGTGC ACCATATGGC CGTCCCGTCA AGTCAGCGTA ATGCTCTGCC AGTGTTACAA CCAATTAACC AATTCTGATT
 721 AGAAAAACTC ATCGAGCATC AAATGAAACT GCAATTTATT CATATCAGGA TTATCAATAC CATATTTTTG AAAAAGCCGT
 801 TTCTGTAATG AAGGAGAAAA CTCACCGAGG CAGTTCCATA GGATGGCAAG ATCCTGGTAT CGGTCTGCGA TTCCGACTCG
 881 TCCAACATCA ATACAACCTA TTAATTTCCC CTCGTCAAAA ATAAGGTTAT CAAGTGAGAA ATCACCATGA GTGACGACTG
 961 AATCCGGTGA GAATGGCAAA AGCTTATGCA TTTCTTTCCA GACTTGTTCA ACAGGCCAGC CATTACGCTC GTCATCAAAA
1041 TCACTCGCAT CAACCAAACC GTTATTCATT CGTGATTGCG CCTGAGCGAG AGGAAATACG CGATCGCTGT TAAAAGGACA
1121 ATTACAAACA GGAATCGAAT GCAACCGGCG CAGGAACACT GCCAGCGCAT CAACATATT TTCACCTGAA TCAGGATATT
1201 CTTCTAATAC CTGGAATGCT GTTTTCCCGG GGATCGCAGT GGTGAGTAAC CATGCATCAT CAGGAGTACG GATAAAATGC
1281 TTGATGGTCG GAAGAGGCAT AAATTCCGTC AGCCAGTTTA GTCTGACCAT CTCATCTGTA ACATCATTGG CAACGCTACC
1361 TTTGCCATGT TTCAGAAACA ACTCTGGCGC ATCGGGCTTC CCATACAATC GATAGATTGT CGCACCTGAT TGCCCGACAT
1441 TATCGCGAGC CCATTTATAC CCATATAAAT CAGCATCCAT GTTGGAATTT AATCGCGGCC TCGAGCAACA CGTTTCCCGT
1521 TGAATATGGC TCATAACACC CCTTGTATTA CTGTTTATGT AAGCAGACAG TTTTATTGTT CATGATGATA TATTTTTATC
1601 TTGTGCAATG TAACATCAGA GATTTTGAGA CACAACGTGG CTTTGTTGAA TAAATCGAAC TTTTGCTGAG TTGAAGGATC
1681 AGATCACGCA TCTTCCCGAC AACGCAGACC GTTCCGTGGC AAAGCAAAAG TTCAAAATCA CCAACTGGTC CACCTACAAC
1761 AAAGCTCTCA TCAACCGTGG CTCCCTCACT TTCTGGCTGG ATGATGGGGC GATTCAGGCC TGGTATGAGT CAGCAACACC
1841 TTCTTCACGA GGCAGACCTC AGCGCTACTC GAGCCTGCGC GCTCGCTCGC TCACTGAGGC CGCCCGGGCA AAGCCCGGGC
1921 GTCGGGCGAC CTTTGGTCGC CCGGCCTCAG TGAGCGAGCG AGCGCGCAGA GAGGGAGTGG CCAACTCCAT CACTAGGGGT
2001 TCCTTGTAGT TAATGATTAA CCCGCCATGC TACTTATCTA CGTAGCCATG CAGTAGAACA ACAGCCAAGC TAGGGAGGCT
2081 GGGAGGCCAA GCCCCAGATA CCTTACATAG CTCGCTCAG CCTCTGTCTC ATTAGGAACT CCATTTTTAG GATGCAGTTG
2161 TTTCAGGCTA AAAATAAATC ATGCAATGAA TAAAAAAGTT AGATACGACA CTGTAGAGGG ATTCGCTGAT ACAGTCTGTC
2241 CGATCTAGAG CAGTCTGGGC TTTCACAAGA CAGCATCTGG GGCTGCGGCA GAGGGTCGGG TCCGAAGCGC TGCCTTATCA
2321 GCGTCCCCAG CCCTGGGAGG TGACAGCTGG CTGGCTGTG TCAGCCCCTC GGGCACTCAC GTATCTCCGT CCGACGGGTT
2401 TAAAATAGCA AAACTCTGAG GCCACACAAT AGCTTGGGCT TATATGGGCT CCTGTGGGGG AAGGGGGAGC ACGGAGGGGG
2481 CCGGGGCCGC TGCTGCCAAA ATAGCAGCTC ACAAGTGTTG CATTCCTCTC TGGGCGCCGG GCACATTCCT GCTGGCTCTG
2561 CCCGCCCCGG GGTGGGCGCC GGGGGGGACCT TAAAGCCTCT GCCCCTTCCC CAGACAGCCG CCGGCACCCA
                                                          M  G  K  S  S  T  P  L  P  L  D  T
2641 CCGCTCCGTG GGACCTAAGC TTGCTAGCGC TACCGGTCGC CACCATGGGT AAAAGCAGCA CTCCATTGCC ACTAGACACC
        T  D  S  G  L  D  D  K  E  D  I  E  C  F  F  E  A  C  V  E  G  D  S  D  G  E  E
2721 ACTGACTCGG GCTTAGATGA CAAGGAAGAT ATTGAATGCT TTTTTGAGGC CTGTGTTGAG GGTGACTCTG ATGGAGAGGA
       P  C  F  S  S  A  P  P  N  E  S  A  V  P  S  E  A  A  M  P  L  Q  A  T  A  C  S
2801 GCCTTGTTTC TCTAGTGCTC CTCCAAATGA ATCTGCAGTT CCCAGCGAAG CTGCAATGCC ACTACAAGCA ACAGCCATGT
       S  E  F  S  D  S  S  L  S  A  D  D  A  D  T  V  A  L  S  S  P  S  S  Q  E  R
2881 CTTCTGAGTT CAGTGATAGT TCTCTTTCAG CTGATGATGC AGATACAGTG GCTCTTTCAA GTCCTTCCTC TCAGGAAAGA
       A  E  V  G  K  E  V  N  G  L  P  Q  T  S  G  C  A  E  N  L  E  F  T  P  S  K
2961 GCTGAGGTTG GAAAGGAAGT GAATGGTTTG CCCCAAACTT CCAGTGGCTG TGCAGAAAAC TTAGAGTTTA CTCCTTCAAA
       L  D  S  E  K  E  S  S  G  K  P  G  E  S  G  M  P  E  E  H  N  A  A  S  A  K  S
3041 GCTTGACAGT GAAAAGGAAA GTTCGGAAAA ACCAGGTGAA TCTGGAATGC CAGAAGAACA TAATGCTGCT TCAGCCAAAT
       K  V  Q  D  L  S  L  K  A  N  Q  P  T  D  K  A  A  L  H  P  S  P  K  T  L  T
3121 CTAAAGTTCA AGACCTCTCC TTGAAGGCAA ATCAGCCAAC AGACAAGGCC GCATTGCATC CCAGCCCCAA AACTTTAACC
       C  E  E  N  L  L  N  L  H  E  K  R  H  R  N  M  H  R
3201 TGTGAAGAAA ATCTTCTAAA CCTTCATGAA AAACGACATA GAAATATGCA TAGGTAGAGT GTAATGCCCC CACGCATGGA
3281 AATCATCTCA TTGAAAGATA GCCTGGCTGA AGCTCAGGGC TAGTTAAGTT TGATCCCGCG CCGCAATCAA CCTCTGGATT
3361 ACAAAATTTG TGAAAGATTG ACTGATATTC TTAACTATGT TGCTCCTTTT ACGCTGTGTG GATATGCTAC TTTAATACCT
3441 CTGTATCGTG CTATTGCTTC CCGTACGGCT TTCGTTTTCT CCTCCTTGTA TAAATCCTGG TTGCTGTCTC TTTATAAGGA
3521 GTTGTGGCCC GTTGTCCGTC AACGTGGCGT GGTGTGCTCT GTGTTTGCTG ACGCAACCCC CACTGGCTGG GGCATTGCCA
3601 CCACCTGTCA ACTCCTTTCT GGGACTTTCG CTTTCCCCCT CCCGATCGCC ACGGCAGAAC TCATCGCCGC TGCCTTGCC
3681 CGCTGCTGGA CAGGGGCTAG GTTGCTGGGC ACTGATAATT CCGTGGTGTT GTCGGGAAA TCATCGTCCT TTCCTTGGCT
3761 GCTCGCCTGT GTTGCCAACT GGATCCTGCG CGGGACGTCC TTCTGCTACG TCCCTTCGGC TCTCAATCCA GCGGACCTCC
3841 CTTCCCGCGG CCTTCTGCCG GTTCTGCGGC CTCTCCCGCG TCTTCGCTTT CGGCCTCCGA CGAGTCGGAT CTCCCTTTGG
```

FIGURE 32 (cont.)

```
3921 GCCGCCTCCC CGCCTGTAGG CCTCACCTGC GATCTCGATG CTTTATTTGT GAAATTTGTG ATGCTATTGC TTTATTTGTA
4001 ACCATTATAA GCTGCAATAA ACAAGTTAAC AACAACAATT GCATTCATTT TATGTTTCAG GTTCAGGGGG AGGTGTGGGA
4081 GGTTTTTTAA AGCAAGTAAA ACCTCTACAA ATGTGGTATG GCTGATTACC ACTCCCTCTC TGCGCGCTCG CTCGCTCACT
4161 CAGGCCGGCC GACCAAACGT CGCCCGACCC CCGGGCTTTG CCCGGGCGCC CTCAGTGAGC CACCCACCCC GCCAGCTGAA
4241 GCTATCAGAT CTGCCGGTCT CCCTATAGTG AGTCGTATTA ATTTCGATAA GCCAGGTTAA CCTGCATTAA TGAATCGGCC
4321 AACGCGCGGG GAGAGGCGGT TTGCGTATTG GGCGCTCTTC CGCTTCCTCG CTCACTGACT CGCTGCGCTC GGTCGTTCGG
4401 CTGCGGCGAG CGGTATCAGC TCACTCAAAG GCGGTAATAC GGTTATCCAC AGAATCAGGG GATAACGCAG GAAAGAACAT
4481 GTGAGCAAAA GGCCAGCAAA AGGCCAGGAA CCGTAAAAAG GCCGCGTTGC TGGCGTTTTT CCATAGGCTC CGCCCCCCTG
4561 ACGAGCATCA CAAAAATCGA CGCTCAAGTC AGAGGTGGCG AAACCCGACA GGACTATAAA GATACCAGGC GTTTCCCCCT
4641 GGAAGCTCCC TCGTGCGCTC TCCTGTTCCG ACCCTGCCGC TTACCGGATA CCTGTCCGCC TTTCTCCCTT CGGGAAGCGT
4721 GGCGCTTTCT CATAGCTCAC GCTGTAGGTA TCTCAGTTCG GTGTAGGTCG TTCGCTCCAA GCTGGGCTGT GTGCACGAAC
4801 CCCCCGTTCA GCCCGACCGC TGCGCCTTAT CCGGTAACTA TCGTCTTGAG TCCAACCCGG TAAGACACGA CTTATCGCCA
4881 CTGGCAGCAG CCACTGGTAA CAGGATTAGC AGAGCGAGGT ATGTAGGCGG TGCTACAGAG TTCTTGAAGT GGTGGCCTAA
4961 CTACGGCTAC ACTAGAAGAA CAGTATTTGG TATCTGCGCT CTGCTGAAGC CAGTTACCTT CGGAAAAAGA GTTGGTAGCT
5041 CTTGATCCGG CAAACAAACC ACCGCTGGTA GCGGTGGTTT TTTTGTTTGC AAGCAGCAGA TTACGCGCAG AAAAAAAGGA
5121 TCTCAAGAAG ATCCTTTGAT CTTTTCTACG GGGTCTGACG CTCAGTGGAA CGAAAACTCA CGTTAAGGGA TTTTGGTCAT
5201 GAGATTATCA AAAAGGATCT TCACCTAGAT CCTTTTAAAT TAAAAATGAA GTTTTAAATC AATCTAAAGT ATATATGAGT
5281 AAACTTGGTC TGACAGTTAC CAATGCTTAA TCAGTGAGGC ACCTATCTCA GCGATCTGTC TATTTCGTTC ATCCATAGTT
5361 GCCTGACTCC CCGTCGTGTA GATAACTACG ATACGGGAGG GCTTACCATC TGGCCCCAGT GCTGCAATGA TACCGCGAGA
5441 CCCACGCTCA CCGGCTCCAG ATTTATCAGC AATAAATCAG CCAGCCGGAA GGGCCGAGCG CAGAAGTGGT CCTGCAACTT
5521 TATCCGCCTC CATCCAGTCT ATTCATTGTT GCCGGGAAGC TAGAGTAAGT AGTTCGCCAG TTAATAGTTT TCACAACGTT
5601 GTTGCCATTG CTACAGGCAT CGTGGTGTCA CGCTCGTCGT TTGGTATGGC TTCATTCAGC TCCGGTTCCC AACGATCAAG
5681 GCGAGTTACA TGTCACCCCA TGTTGTGCAA AAAAGCGGTT AGCTCCTTCG GTCCTCCGAT CGTTGTCAGA AGTAAGTTGG
5761 CCGCAGTGTT ATCACTCATG GTTATGGCAG CACTGCATAA TTCTCTTACT GTCATGCCAT CCGTAAGATG CTTTTCTGTG
5841 ACTGGTGAGT ACTCAACCAA GTCATTCTGA GAATAGTGTA TGCGGCG
```

TREATMENT OF HEART DISEASE BY DISRUPTION OF THE ANCHORING OF PP2A

CROSS-REFERENCE TO RELATED APPLICATIONS

This application claims priority to U.S. Provisional Patent Application Ser. No. 62/848,156, filed May 15, 2019, which is hereby incorporated by reference in its entirety and this application incorporates by reference in their entireties U.S. patent application Ser. No. 14/821,082, filed Aug. 7, 2015, now U.S. Pat. No. 9,937,228, issued Apr. 10, 2018, U.S. patent application Ser. No. 14/213,583, filed on Mar. 14, 2014, now U.S. Pat. No. 9,132,174, issued on Sep. 15, 2015, U.S. patent application Ser. No. 16/028,004, filed Jul. 5, 2018, U.S. Provisional Application No. 61/798,268, filed Mar. 15, 2013, and U.S. Provisional Application 62/529,224, filed Jul. 6, 2017.

STATEMENT OF GOVERNMENTAL SUPPORT

This invention was made with Government support under contract RO1 HL 075398 and HL126825 awarded by the National Institutes of Health. The Government has certain rights in this invention.

The instant application contains a Sequence Listing which has been submitted electronically via EFS-Web in ASCII format and is hereby incorporated by reference in its entirety. Said ASCII copy, created on Feb. 21, 2023, is named 4175-105US2_ST25 and is 167,768 bytes in size.

BACKGROUND OF THE INVENTION

In response to chronic stress, the heart's main compensatory mechanism is myocyte hypertrophy, a non-mitotic increase in volume of the contractile cells (Hill and Olson 2008). The adult mammalian myocyte is roughly cylindrical and can grow either in width or length. Because myocytes contribute the vast majority of the myocardial mass of the heart (Jugdutt 2003), concentric and eccentric hypertrophy of the cardiac myocyte result in thickening of heart chamber walls and dilation of the chambers, respectively. In theory, "concentric" myocyte growth in width involving parallel assembly of sarcomeres reduces ventricular wall stress (Law of LaPlace), while "eccentric" lengthwise myocyte growth involving serial assembly of sarcomeres may accommodate greater ventricular volumes without stretching individual sarcomeres beyond the optimum length for contraction (length-tension relationship) (Grossman, Jones, and McLaurin 1975). While the left ventricle will undergo relatively symmetric hypertrophy in response to physiologic stress such as pregnancy or exercise training, concentric ventricular hypertrophy is the predominant initial response to the increased systolic wall stress present in pressure overload diseases such as hypertension or aortic stenosis. Eccentric ventricular hypertrophy predominates during states of volume overload such as occurs following myocardial infarction, as well as during the transition from concentric hypertrophy to the dilated heart in Heart Failure with Reduced Ejection Fraction (HFrEF) in some forms of cardiovascular disease, including diseases mainly characterized by pressure overload. Concentric and eccentric hypertrophy are also present in inherited hypertrophic and dilated cardiomyopathies, respectively.

At the cellular level, cardiac myocyte hypertrophy occurs as the result of an increase in protein synthesis and in the size and organization of sarcomeres within individual myocytes. For a more thorough review of cardiac remodeling and hypertrophy, see Kehat (2010) and Hill (2008), each herein incorporated by reference in their entirety. The prevailing view is that cardiac hypertrophy plays a major role in the development of heart failure. Traditional routes of treating heart failure include afterload reduction, blockage of beta-adrenergic receptors ($\beta$-ARs) and use of mechanical support devices in afflicted patients. However, the art is in need of additional mechanisms of preventing or treating pathological cardiac hypertrophy.

Research suggests that mechanisms that induce "compensatory" concentric hypertrophy early in pressure-overload related heart disease predispose the heart to later systolic dysfunction and eventual failure (Schiattarella and Hill 2015). In this regard, results show that targeting of RSK3-mAKAP$\beta$ complexes will attenuate cardiac remodeling due to pressure overload and prevent heart failure (Kritzer et al. 2014; Li, Kritzer, et al. 2013). Accordingly, inhibition of signaling pathways that induce remodeling, including concentric hypertrophy, may be desirable early in pressure overload disease. However, the question remained whether efforts to maintain signals that may promote concentric hypertrophy and oppose eccentric hypertrophy would preserve cardiac volumes and contractility when initiated when the heart is at a stage in the disease process characterized by the eccentric growth and ventricular dilatation leading to HFrEF, whether late in pressure overload-related disease or throughout the progression of volume overload-related disease. Further, it is unknown whether the enhancement of concentric myocyte hypertrophy and/or the inhibition of eccentric myocyte hypertrophy in familial dilated cardiomyopathy may be beneficial.

AKAPs and Cardiac Remodeling

Ventricular myocyte hypertrophy is the primary compensatory mechanism whereby the myocardium reduces ventricular wall tension when submitted to stress because of myocardial infarction, hypertension, and congenital heart disease or neurohumoral activation. It is associated with a nonmitotic growth of cardiomyocytes, increased myofibrillar organization, and upregulation of specific subsets of "fetal" genes that are normally expressed during embryonic life (Frey 2004, Hill 2008). The concomitant aberrant cardiac contractility, $Ca^{2+}$ handling, and myocardial energetics are associated with maladaptive changes that include interstitial fibrosis and cardiomyocyte death and increase the risk of developing heart failure and malignant arrhythmia (Cappola 2008, Hill 2008). Together, these adaptations contribute to both systolic and diastolic dysfunction that are present in different proportions depending upon the underlying disease (Sharma and Kass 2014). Pathological remodeling of the myocyte is regulated by a complex intracellular signaling network that includes mitogen-activated protein kinase (MAPK), cyclic nucleotide, $Ca^{2+}$, hypoxia, and phosphoinositide-dependent signaling pathways (Heineke and Molkentin 2006).

Increased in prevalence by risk factors such as smoking and obesity, in the United States, heart failure affects 6.2 million adults, and each year ~1,000,000 new adult cases are diagnosed (Benjamin et al. 2019). The prevalence and incidence of heart failure are increasing, mainly because of increasing life span, but also because of the increased prevalence of risk factors (hypertension, diabetes, dyslipidemia, and obesity) and improved survival rates from other types of cardiovascular disease (myocardial infarction [MI] and arrhythmias) (Heidenreich et al. 2013). First-line therapy for patients with heart failure includes angiotensin-converting enzyme (ACE) inhibitors and β-adrenergic receptor blockers (β-blockers) that can improve the survival and quality of life of such patients, as well as reduce mortality for those with left ventricular dysfunction (Group 1987). Subsequent or alternative therapies include aldosterone and angiotensin II receptor blockers, neprilysin inhibitors, loop and thiazide diuretics, vasodilators, and $I_f$ current blockers, as well as device-based therapies (Ponikowski et al. 2016). Nevertheless, the 5-year mortality for symptomatic heart failure remains ~50%, including >40% mortality for those post-MI (Heidenreich et al. 2013; Gerber et al. 2016).

Cardiac hypertrophy can be induced by a variety of neuro-humoral, paracrine, and autocrine stimuli, which activate several receptor families including G protein-coupled receptors, cytokine receptors, and growth factor tyrosine kinase receptors (Brown 2006, Frey 2004). In this context, it is becoming increasingly clear that A-kinase anchoring proteins (AKAPs) can assemble multiprotein complexes that integrate hypertrophic pathways emanating from these receptors. In particular, recent studies have now identified anchoring proteins including mAKAP, AKAP-Lbc, and D-AKAP1 that serve as scaffold proteins and play a central role in organizing and modulating hypertrophic pathways activated by stress signals.

As the organizers of "nodes" in the intracellular signaling network, scaffold proteins are of interest as potential therapeutic targets (Negro, Dodge-Kafka, and Kapiloff 2008). In cells, scaffold proteins can organize multimolecular complexes called "signalosomes," constituting an important mechanism responsible for specificity and efficacy in intracellular signal transduction (Scott and Pawson 2009). Firstly, many signaling enzymes have broad substrate specificity. Scaffold proteins can co-localize these pleiotropic enzymes with individual substrates, selectively enhancing the catalysis of substrates and providing a degree of specificity not intrinsic to the enzyme's active site (Scott and Pawson 2009). Secondly, some signaling enzymes are low in abundance. Scaffold proteins can co-localize a rare enzyme with its substrate, making signaling kinetically favorable. Thirdly, since many scaffolds are multivalent, scaffold binding can orchestrate the co-regulation by multiple enzymes of individual substrate effectors. Muscle A-kinase anchoring protein (mAKAP, a.k.a. AKAP6) is a large scaffold expressed in cardiac and skeletal myocytes and neurons that binds both signaling enzymes such as protein kinase A (PKA) and the $Ca^{2+}$/calmodulin-dependent phosphatase Calcineurin (CaN) that have broad substrate specificity and signaling enzymes such as p90 ribosomal S6 kinase 3 (RSK3) that is remarkably low in abundance (FIG. 1) (Wang et al. 2015; Pare, Easlick, et al. 2005; Michel et al. 2005a; Kapiloff et al. 1999b). mAKAPβ is the alternatively-spliced isoform expressed in myocytes, in which cells it is localized to the outer nuclear membrane by binding the integral membrane protein nesprin-1α (Pare, Easlick, et al. 2005).

Consistent with its role as a scaffold protein for stress-related signaling molecules in the cardiac myocyte, depletion of mAKAPβ in rat neonatal ventricular myocytes in vitro inhibited hypertrophy induced by α-adrenergic, β-adrenergic, endothelin-1, angiotensin II, and leucine inhibitor factor/gp130 receptor signaling (Zhang et al. 2011; Pare, Bauman, et al. 2005; Dodge-Kafka et al. 2005; Guo et al. 2015). In vivo, along with attenuating hypertrophy induced by short-term pressure overload and chronic β-adrenergic stimulation, mAKAP gene targeting in the mouse inhibited the development of heart failure following long-term pressure overload, conferring a survival benefit (Kritzer et al. 2014). Specifically, mAKAP gene deletion in the $mAKAP^{fl/fl}$;Tg(Myh6-cre/Esr1*), tamoxifen-inducible, conditional knock-out mouse reduced left ventricular hypertrophy, while greatly inhibiting myocyte apoptosis, and interstitial fibrosis, left atrial hypertrophy, and pulmonary edema (wet lung weight) due to transverse aortic constriction for 16 weeks (Kritzer et al. 2014).

mAKAP gene targeting is also beneficial following myocardial infarction (Kapiloff, unpublished observations). Permanent ligation of the left anterior descending coronary artery (LAD) in the mouse results in myocardial infarction, including extensive myocyte death, scar formation, and subsequent left ventricular (LV) remodeling. Four weeks following LAD ligation, mAKAP conditional knock-out mouse had preserved LV dimensions and function when compared to infarcted control cohorts. mAKAP conditional knock-out mice had preserved LV ejection fraction and indexed atrial weight compared to controls, while displaying a remarkable decrease in infarct size.

Introduction to mAKAP and Cardiac Remodeling mAKAP was originally identified in a cDNA library screen for new cAMP-dependent protein kinase (PKA) regulatory-subunit (R-subunit) binding proteins, i.e. A-kinase anchoring proteins or AKAPs (Mccartney et al. 1995). mAKAP was initially named "AKAP100" for the size of the protein encoded by the original cDNA fragment (Mccartney et al. 1995). Subsequently, the full-length mRNA sequence for mAKAPα, the alternatively-spliced isoform of mAKAP expressed in neurons, was defined, revealing that wildtype mAKAPα is a 255 kDA scaffold (Kapiloff et al. 1999b). The sequence for mAKAPβ, the 230 kDa alternatively-spliced isoform of mAKAP expressed in striated myocytes, was later obtained, showing that when expressed in heart or skeletal muscle, mAKAP is translated from an internal start site corresponding to mAKAPα residue Met-245 (Michel et al. 2005a).

mAKAP is localized to the nuclear envelope both in neurons and striated cardiac and skeletal myocytes (FIG. 6), the three cell types in which mAKAP is clearly expressed (Kapiloff et al. 1999b; Pare, Easlick, et al. 2005; Michel et al. 2005a). mAKAP is not a transmembrane domain protein and contains three spectrin-like repeat regions (residues 772-1187) that confer its localization (Kapiloff et al. 1999b). Binding of mAKAP's third spectrin repeat (residues 1074-1187) by the outer nuclear membrane protein nesprin-1α is both necessary and sufficient for mAKAP nuclear membrane localization, at least in myocytes and when expressed in heterologous cells (Pare, Easlick, et al. 2005). Nesprin-1a may also be present on the inner nuclear envelope where it might bind A-type lamins and emerin. Interestingly, mutations in lamin A/C, emerin, and nesprin-1α have been associated with Emery-Dreyfuss muscular dystrophy, as well as other forms of cardiomyopathy (Bonne et al. 1999; Fatkin et al. 1999; Muchir et al. 2000; Bione et al. 1994; Zhang et al. 2007). However, no disease-causing mutations have yet been identified in the human mAKAP gene, and mAKAPβ knock-out in the mouse heart early in development does not induce cardiomyopathy (Kritzer et al. 2014). Besides binding nesprin-1α, mAKAPβ also binds phospholipase Cε(PLCε) through mAKAP's first spectrin repeat, potentially strengthening its association with the nuclear envelope (Zhang et al. 2011). There were early reports of mAKAPβ being present on the sarcoplasmic reticulum (Mccartney et al. 1995; Marx et al. 2000; Yang et al. 1998), but these findings have been called into question due to technical issues including antibody specificity (Kapiloff, Jackson, and Airhart 2001; Kapiloff et al. 1999b).

Besides PKA, PLCε and nesprin-1α, mAKAPβ binds a wide variety of proteins important for myocyte stress responses: adenylyl cyclase type 5 (AC5), exchange protein activated by cAMP-1 (Epac1), cAMP-specific phosphodiesterase type 4D3 (PDE4D3), MEK5 and ERK5 MAP-kinases, 3-phosphoinositide-dependent protein kinase-1 (PDK1), p90 ribosomal S6 kinases 3 (RSK3), protein kinase Cε(PKCε), protein kinase D (PKD1, PKCμ), the protein phosphatases calcineurin (CaN) Aβ and PP2A, the type 2 ryanodine receptor (RyR2), the sodium/calcium exchanger NCX1, ubiquitin E3-ligases involved in HIF1α regulation, and myopodin (Pare, Bauman, et al. 2005; Pare, Easlick, et al. 2005; Dodge-Kafka et al. 2005; Marx et al. 2000; Kapiloff, Jackson, and Airhart 2001; Michel et al. 2005a; Li et al.; Wong et al. 2008; Zhang et al. 2011; Dodge-Kafka and Kapiloff 2006; Vargas et al. 2012; Faul et al. 2007; Schulze et al. 2003; Kapiloff et al. 2009; Zhang et al. 2013). Bound to mAKAPβ, these signaling molecules co-regulate the transcription factors hypoxia-inducible factor 1α (HIF1α), myocyte enhancer factor-2 (MEF2), and nuclear factor of activated T-cell (NFATc) transcription factors, as well as type II histone deacetylases (FIG. 7) (Kritzer et al. 2014; Li, Vargas, et al. 2013; Li et al. 2010; Wong et al. 2008; Li et al. 2019; Dodge-Kafka et al. 2018). Some of these molecules are bound directly and some indirectly, some constitutively and some in a regulated manner. Thus, it is likely that the composition of mAKAPβ signalosomes depends upon the underlying state of the myocyte. As research continues on mAKAPβ, the list of its binding partners grows, confirming its hypothesized role as an important orchestrator of signaling pathways required for remodeling. Most of what is known about mAKAPβ is based upon work using cultured neonatal rat ventricular myocytes, in which mAKAPβ was early on recognized to be required for the induction of hypertrophy by a variety of upstream receptors, including α- and β-adrenergic and cytokine receptors (Pare, Bauman, et al. 2005; Dodge-Kafka et al. 2005). However, recently, the phenotype of a conditional, cardiac-myocyte specific mAKAPβ knock-out mouse has been published confirming the centrality of mAKAPβ to remodeling (Kritzer et al. 2014). There are various upstream inputs, downstream effectors (outputs), and integrative circuitry within mAKAPβ signalosomes that impact pathological remodeling of the heart.

mAKAPβ—a Prototypical A-Kinase Anchoring Protein

Like most AKAPs, mAKAP contains an amphipathic helix (residues 2055-2072) responsible for binding PKA (Kapiloff et al. 1999b; Kritzer et al. 2012). PKA is a heterotetramer of two R-subunits and two catalytic C-subunits, in the configuration C—R—R—C. Within the holoenzyme, the N-terminal docking and dimerization domains of the PKA R-subunits form a X-type, antiparallel four-helix bundle (Newlon et al. 1999). This bundle contains a hydrophobic groove that accommodates the hydrophobic face of the AKAP amphipathic helix. mAKAPβ binds selectively type II PKA (that contains RII subunits) with high affinity ($K_D$=119 nM) (Zakhary et al. 2000). Interestingly, PKA-mAKAPβ binding is increased 16-fold following RIIα autophosphorylation (Zakhary et al. 2000), potentially affecting PKA-mAKAPβ binding in states of altered β-adrenergic signaling. Besides mAKAPβ, there are over a dozen other AKAPs expressed in the myocyte, each with its own distinct localization and sets of binding partners (Kritzer et al. 2014). Remarkably, mAKAP is one of the rarest AKAPs in the myocyte, such that loss of mAKAP does not even affect the localization of perinuclear PKA (Kapiloff, unpublished observations). Despite the low level of expression of the scaffold, replacement in myocytes of endogenous mAKAPβ with a full-length mAKAPβ mutant that cannot bind PKA is sufficient to inhibit the induction of myocyte hypertrophy (Pare, Bauman, et al. 2005). Thus, mAKAPβ signalosomes serve as an example of both how finely PKA signaling may be compartmentalized even on an individual organelle and how the level of expression of a protein or a protein complex is not necessarily indicative of the functional significance of that protein.

mAKAPβ is remarkable because it binds not only effectors for cAMP signaling, but also enzymes responsible for cAMP synthesis and degradation (Kapiloff et al. 2009; Dodge et al. 2001). The synthesis of cAMP from ATP is catalyzed by adenylyl cyclases (AC), while cAMP metabolism to 5'AMP is catalyzed by phosphodiesterases (PDE). The differential association of ACs and PDEs with AKAPs contributes to cAMP compartmentation in cells, providing both for local activation of cAMP effectors and regulation of local cAMP levels by unique regulatory feedback and feed-forward loops (Scott, Dessauer, and Tasken 2013). mAKAP is capable of binding both AC2 and AC5, but AC5 appears to be the relevant mAKAPβ-binding partner in the heart (Kapiloff et al. 2009). The N-terminal, C1 and C2 domains of AC5 bind directly to a unique N-terminal site on mAKAPβ (residues 275-340). AC5 activity is inhibited by PKA feedback phosphorylation that in cells is facilitated by mAKAPβ complex formation (Kapiloff et al. 2009). This negative feedback appears to be physiologically relevant to the maintenance of basal cAMP signaling. When the tethering of AC5 to mAKAPβ is inhibited by a competitive peptide comprising the mAKAP AC5-binding domain, both the cAMP content and size of myocytes were increased in the absence of hypertrophic stimulus (Kapiloff et al. 2009).

mAKAP was the first AKAP shown to bind a PDE (Dodge et al. 2001). A site within mAKAP 1286-1831 binds the unique N-terminal domain of PDE4D3. Phosphorylation of PDE4D3 serine residues 13 and 54 results in increased binding to the scaffold and increased PDE catalytic activity, respectively (Dodge et al. 2001; Sette and Conti 1996; Carlisle Michel et al. 2004). Because increased PDE4D3 activity accelerates cAMP degradation, PKA and PDE4D3 constitute a negative feedback loop that can modulate local cAMP levels and PKA activity (Dodge et al. 2001). PDE4D3 bound to mAKAP serves not only as a PDE, but also as an adapter protein recruiting the MAPKs MEK5 and ERK5 and the cAMP-dependent, Rap1-guanine nucleotide exchange factor Epac1 to the scaffold (Dodge-Kafka et al. 2005). Activation of MEK5 and ERK5 by upstream signals results in PDE4D3 phosphorylation on Ser-579, inhibiting the PDE and promoting cAMP accumulation and PKA activation (Dodge-Kafka et al. 2005; Hoffmann et al. 1999; Mackenzie et al. 2008). Epac1 is less sensitive to cAMP than PKA, such that very high cAMP levels results in the additional activation of mAKAP-associated Epac1. Through Rap1, Epac1 can inhibit ERK5 activity, thus preventing PDE4D3 inhibition by MAPK signaling, resulting presumably in maximal PDE4D3 activity due to concomitant PKA phosphorylation (Dodge-Kafka et al. 2005). As a result, Epac1, ERK5, and PDE4D3 constitute a third negative feedback loop that will attenuate cAMP levels in the vicinity of mAKAP complexes opposing cAMP elevation to extremely high levels.

Additional complexity is afforded by the binding of the serine-threonine phosphatase PP2A to the C-terminus of mAKAP (residues 2083-2319) (Dodge-Kafka et al. 2010). PP2A can catalyze the dephosphorylation of PDE4D3 Ser-54, thereby inhibiting the PDE in the absence of upstream stimulus. PP2A associated with mAKAP complexes contain B56δB subunits, which are PKA substrates. PKA phosphorylation enhances PP2A catalytic activity (Ahn et al. 2007), such that phosphorylation of B56δ by mAKAP-bound PKA increases PDE4D3 dephosphorylation, inhibiting the PDE. This presumably increases cAMP levels, constituting a positive feedforward loop for the initiation of cAMP signaling. Together with the negative feedback loops based upon AC5 phosphorylation and PDE4D3 regulation by PKA and ERK5, one would predict that cAMP levels at mAKAPβ signalosomes would be tightly controlled by upstream β-adrenergic and MAPK signaling. Signaling upstream of AC5 and ERK5 will promote cAMP signaling that will be initially promoted by PP2A feedfoward signaling, while PDE4D3 activation and AC5 inhibition by PKA and Epac1 negative feedback will constrain signaling. Interestingly, Rababa'h et al. demonstrated how mAKAP proteins containing non-synonymous polymorphisms differentially bound PKA and PDE4D3 (Rababa'h et al. 2013). The potential for cAMP signaling to be differentially modulated by crosstalk between upstream signaling pathways or by human polymorphisms makes compelling further work in myocytes to show the relevance of this complicated signaling network.

mAKAPβ and MAP-Kinase-RSK3 Signaling

The recruitment of ERK5 by PDE4D3 to mAKAPβ complexes was initially shown to be relevant to the local regulation of cAMP through the aforementioned feedback loops (Dodge-Kafka et al. 2005). However, ERK5 was also recognized to be an important inducer of myocyte hypertrophy, preferentially inducing the growth in length (eccentric hypertrophy) of cultured myocytes, while also being important for concentric hypertrophy in vivo due to pressure overload (transverse aortic constriction in the mouse) (Nicol et al. 2001; Kimura et al. 2010). Notably, inhibition by RNA interference (RNAi) of mAKAPβ expression in cultured myocytes inhibited the eccentric growth induced by the interleukin-6-type cytokine leukemia inhibitory factor (LIF) (Dodge-Kafka et al. 2005). A potential effector for mAKAPβ-bound ERK5 was MEF2 transcription factor, as discussed below. However, in both heart and brain, mAKAP bound PDK1, a kinase that together with ERKs (ERK1, 2 or 5) can activate the MAPK effector p90RSK, a kinase also associated with mAKAP (Ranganathan et al. 2006; Michel et al. 2005a). Importantly, binding of PDK1 to mAKAP obviated the requirement for membrane association in RSK activation (Michel et al. 2005a). Taken together, these data suggested that mAKAPβ could orchestrate RSK activation in myocytes in response to upstream MAPK signaling.

p90RSK is a pleiotropic ERK effector that regulates many cellular processes, including cell proliferation, survival, migration, and invasion. RSK activity is increased in myocytes by most hypertrophic stimuli (Anjum and Blenis 2008; Sadoshima et al. 1995). In addition, RSK activity was found to be increased in human end-stage dilated cardiomyopathy heart tissue (Takeishi et al. 2002). RSK family members contain 2 catalytic domains, an N-terminal kinase domain and a C-terminal kinase domain (Anjum and Blenis 2008). The N-terminal kinase domain phosphorylates RSK substrates and is activated by sequential phosphorylation of the C-terminal and N-terminal kinase domain activation loops by ERK and PDK1, respectively, such that PDK1 phosphorylation of the N-terminal domain on Ser-218 is indicative of full activation of the enzyme. There are 4 mammalian RSK family members that are ubiquitously expressed, but only RSK3 binds mAKAPβ (Li, Kritzer, et al. 2013). The unique N-terminal domain of RSK3 (1-30) binds directly mAKAPβ residues 1694-1833, explaining the selective association of that isoform with the scaffold (Li, Kritzer, et al. 2013). Despite the fact that RSK3 is expressed less in myocytes than other RSK family members, neonatal myocyte hypertrophy was found to be attenuated by RSK3 RNAi, inactivation of the RSK3 N-terminal kinase domain, and disruption of RSK3 binding to mAKAP using an anchoring disruptor peptide (Li, Kritzer, et al. 2013). Importantly, RSK3 expression in vivo was required for the induction of cardiac hypertrophy by both pressure overload and catecholamine infusion, as well as for the heart failure associated with a mouse model for familial hypertrophic cardiomyopathy (α-tropomyosin Glu180Gly) (Li, Kritzer, et al. 2013; Passariello et al. 2013). In addition, consistent with the reported role of ERK1/2 MAP-Kinase in selectively inducing concentric hypertrophy (Kehat et al. 2011), RSK3 gene deletion inhibited the concentric hypertrophy induced by Raf1$^{L613V}$ mutation in a mouse model for Noonan Syndrome (Passariello et al. 2016). The recognition that this specific RSK isoform is required for cardiac remodeling makes it a compelling candidate for therapeutic targeting.

mAKAPβ and Phosphatidylinositide Signaling

The cAMP effector Epac1 activates Rap1 at mAKAPβ complexes affecting ERK5 signaling (Dodge-Kafka et al. 2005). In addition, Epac1-Rap1 activates PLCε, a phospholipase whose Ras association domains directly bind the first spectrin repeat-like domain of mAKAPβ (Zhang et al. 2011). Like mAKAPβ, PLCε was required for neonatal myocyte hypertrophy, whether inhibited by RNAi or by displacement from mAKAPβ by expression of competitive binding peptides. In an elegant paper by the Smrcka laboratory, mAKAPβ-bound PLCε has been shown to regulate PKCε and PKD activation through a novel phosphatidylinositol-4-phosphate (PI4P) pathway in which PLCε selectively converts perinuclear PI4P to diacylglycerol and inositol-1,4-bisphosphate (Zhang et al. 2013). PKD1 phosphorylates type II histone deacetylases (HDACs 4/5/7/9) inducing their nuclear export and de-repressing hypertrophic gene expression (Monovich et al. 2010; Xie and Hill 2013). Smrcka and colleagues found that PLCε was required for pressure overload-induced PKD activation, type II HDAC phosphorylation and hypertrophy in vivo (Zhang et al. 2013). Subsequently, mAKAPβ was also found to be is required in vivo for PKD activation and HDAC4 phosphorylation in response to pressure overload (Kritzer et al. 2014). Remarkably, mAKAPβ can form a ternary complex with PKD and HDAC4. Together, these results show how local cAMP signaling can affect the regulation of cardiac gene expression.

Recently it was published that mAKAPβ is a scaffold for HDAC5 in cardiac myocytes, forming signalosomes containing HDAC5, PKD, and PKA (Dodge-Kafka et al. 2018). Inhibition of mAKAPβ expression attenuated the phosphorylation of HDAC5 by PKD and PKA in response to α- and β-adrenergic receptor stimulation, respectively. Importantly, disruption of mAKAPβ-HDAC5 anchoring prevented the induction of HDAC5 nuclear export by α-adrenergic receptor signaling and PKD phosphorylation. In addition, disruption of mAKAPβ-PKA anchoring prevented the inhibition by β-adrenergic receptor stimulation of α-adrenergic-induced HDAC5 nuclear export. Together, these data establish that mAKAPβ signalosomes serve to bidirectionally regulate the nuclear-cytoplasmic localization of class IIa HDACs. Thus, the mAKAPβ scaffold serves as a node in the myocyte regulatory network controlling both the repression and activation of pathological gene expression in health and disease, respectively.

mAKAPβ and Calcium signaling

Besides cAMP, phosphoinositide and MAP-kinase signaling, mAKAPβ contributes to the orchestration of $Ca^{2+}$-dependent signaling transduction. The second binding partner for mAKAPβ identified was the ryanodine receptor $Ca^{2+}$ release channel (RyR2) responsible for $Ca^{2+}$-induced $Ca^{2+}$ release from intracellular stores (Kapiloff, Jackson, and Airhart 2001; Marx et al. 2000). RyR2 is best known for its role in excitation-contraction coupling, in which bulk $Ca^{2+}$ is released to induce sarcomeric contraction. PKA phosphorylation can potentiate RyR2 currents (Valdivia et al. 1995; Dulhunty et al. 2007; Bers 2006), although the importance of PKA-catalyzed RyR2 phosphorylation to excitation-contraction coupling is highly controversial (Houser 2014; Dobrev and Wehrens 2014). A small fraction of RyR2, presumably located at perinuclear dyads (Escobar et al. 2011), can be immunoprecipitated with mAKAPβ and nesprin-1α antibodies (Pare, Easlick, et al. 2005; Kapiloff, Jackson, and Airhart 2001). mAKAPβ appears to bring together elements of the excitation-contraction coupling machinery and signaling molecules important for regulating nuclear events germane to pathological remodeling. Thus, mAKAPβ complexes may provide one mechanism for matching contractility to the induction of hypertrophy. β-adrenergic stimulation of primary myocyte cultures results in increased PKA phosphorylation of mAKAPβ-associated RyR2 (Pare, Bauman, et al. 2005). PKA-catalyzed RyR2 phosphorylation may potentiate local $Ca^{2+}$ release within the vicinity of mAKAPβ signalosomes during states of elevated sympathetic stimulation.

While it is unlikely that the few mAKAPβ-associated RyR2s could affect overall contractility, a potential target for increased perinuclear $Ca^{2+}$ may be the $Ca^{2+}$/calmodulin-dependent phosphatase calcineurin (CaN) that can bind the scaffold. There are three isoforms of the catalytic subunit for CaN (α,β,γ), but only CaNAβ-mAKAPβ complexes have been detected in myocytes (Li et al. 2010). Remarkably, CaNAβ is the CaNA isoform important for the induction of cardiac hypertrophy in vivo, as well as for myocyte survival after ischemia (Bueno et al. 2002; Bueno et al. 2004). CaNAβ binds directly to a unique site within mAKAPβ (residues 1286-1345) (Pare, Bauman, et al. 2005; Li et al. 2010). CaNAβ binding to mAKAPβ is enhanced in cells by adrenergic stimulation and directly by $Ca^{2+}$/calmodulin (Li et al. 2010). Notably, CaNAβ-mAKAPβ binding was required for α-adrenergic-induced neonatal myocyte hypertrophy in vitro (Li et al. 2010).

mAKAPβ and Gene Expression

Among its many substrates, CaN is responsible for the activation of NFATc and MEF2 transcription factors. The NFATc transcription factor family includes four CaN-dependent isoforms that are all expressed in myocytes and that can contribute to the induction of myocyte hypertrophy (Wilkins et al. 2004). In general, NFATc family members are retained in the cytoplasm when heavily phosphorylated on the multiple serine-rich motifs within the N-terminal regulatory domain. NFATc translocates into the nucleus when these motifs are dephosphorylated by CaN. Multiple NFATc family members can bind mAKAPβ, and binding to mAKAPβ was required for CaN-dependent dephosphorylation of NFATc3 in myocytes (Li et al. 2010). Accordingly, mAKAPβ expression was also required for NFAT nuclear translocation and transcriptional activity in vitro (Li et al. 2010; Pare, Bauman, et al. 2005). These results correlate with recent observations that NFAT-dependent gene expression in vivo was attenuated by mAKAPβ cardiac-myocyte specific knock-out following transverse aortic constriction (Kritzer et al. 2014).

Like NFATc2 and NFATc3, MEF2D is a transcription factor required for cardiac hypertrophy in vivo (Kim et al. 2008; Wilkins et al. 2002; Bourajjaj et al. 2008). MEF2 family members contain a conserved DNA binding domain that includes both a MADS box and a MEF2 homology domain (Potthoff and Olson 2007). The DNA-binding domain of MEF2D binds directly to an N-terminal domain of mAKAP (Vargas et al. 2012; Kim et al. 2008). CaN and MEF2D are important not only in the heart, but also in skeletal muscle (Naya et al. 1999; Naya and Olson 1999; Black and Olson 1998; Friday et al. 2003; Wu et al. 2001). Interference with MEF2-mAKAPβ binding blunted MEF2 transcriptional activity and the expression of endogenous MEF2 target genes in C2C12 skeletal myoblasts (Vargas et al. 2012). In addition, disruption of MEF2-mAKAP complexes attenuated the differentiation of C2C12 myoblasts into myotubes, as evidenced by decreased cell fusion and expression of differentiation markers (Vargas et al. 2012). Remarkably, CaN-MEF2 binding is mAKAPβ-dependent in cardiac myocytes (Li, Vargas, et al. 2013). Accordingly, disruption of CaN-mAKAPβ binding inhibited both MEF2 transcriptional activity in C2C12 cells and cardiac myocyte hypertrophy (Li, Vargas, et al. 2013). Like NFATc2, MEF2D de-phosphorylation in vivo in response to pressure overload was attenuated following mAKAPβ conditional knock-out, correlating with the decreased expression MEF2-target genes, including the expression of atrial natriuretic factor (Kritzer et al. 2014).

The regulation of NFATc, MEF2 and HDAC4 by mAKAPβ in vivo during pressure overload shows the importance of mAKAPβ to stress-regulated gene expression (Kritzer et al. 2014). Published reports show how, at mAKAPβ, NFATc and MEF2 are regulated by CaN, while HDAC4 and HDAC5 are regulated by PKD and PKA (Li, Vargas, et al. 2013; Zhang et al. 2013; Li et al. 2010; Dodge-Kafka et al. 2018). mAKAPβ appears to facilitate the modulation of these gene regulatory proteins by other signaling enzymes. For example, mAKAPβ-associated ERK5 may phosphorylate MEF2, activating the transcription factor (Kato et al. 2000). In addition, PKA can phosphorylate MEF2, affecting its DNA-binding affinity (Wang et al. 2005). On the other hand, the Olson group has proposed that PKA phosphorylation of HDAC4 can inhibit MEF2 activity through the generation of a novel HDAC4 proteolytic fragment (Backs et al. 2011). How the activities of the many mAKAPβ binding partners are ultimately integrated to control gene expression can be investigated both in vitro and in vivo.

Other mAKAPβ Binding Partners

There are other binding partners for mAKAPβ for whom the significance of docking to the scaffold remains poorly characterized, including myopodin and NCX1 (Faul et al. 2007; Schulze et al. 2003). HIF-1α, a transcription factor that regulates systemic responses to hypoxia, also binds mAKAPβ (Wong et al. 2008). Under normoxic conditions, the abundance of HIF-1a in the cell is kept low by ubiquitin-mediated proteasomal degradation. HIF-1α is hydroxylated by a family of oxygen-sensitive dioxygenases called prolyl hydroxylases (PHD1, PHD2, and PHD3) (Ohh et al. 2000). Hydroxylated HIF-1α is subsequently recognized by the von Hippel-Lindau protein (pVHL), which recruits the Elongin C ubiquitin ligase complex to ubiquitinate HIF-1α and to promote its proteasome-dependent degradation (Maxwell et al. 1999). Under hypoxic conditions, PHDs are inactivated, HIF-1α degradation is decreased and HIF-1α accumulates in the nucleus, where it can dimerize with HIF-1β to promote the transcription of target genes. mAKAPβ can assemble a signaling complex containing HIF-1α, PHD, pVHL and the E3 ligase Siah2 (seven in absentia homolog 2) in cultured neonatal myocytes (Wong et al. 2008). Under normoxic conditions, mAKAPβ-anchored PHD and pVHL favor HIF-1α ubiquitination and degradation (Wong et al. 2008). Under hypoxic conditions, however, Siah2 activation induces proteasomal degradation of bound PHD, favoring HIF-1α accumulation (Wong et al. 2008). An mAKAPβ knock-out may affect cardiac myocyte survival after ischemia-reperfusion.

mAKAPβ—a Conductor of the Remodeling Symphony

The above discussion shows how multiple signaling pathways known to be important for cardiac hypertrophy and pathological remodeling are modulated by the binding of key signaling intermediates to the mAKAPβ scaffold. Cardiac myocyte-specific, conditional mAKAP knock-out mouse has been characterized, showing the relevance of mAKAPβ signalosomes in vivo (Kritzer et al. 2014). mAKAPβ was required in cardiac myocytes for the induction of cardiac hypertrophy by transverse aortic constriction and isoproterenol infusion. Most remarkable, however, was the prevention of pathological remodeling, including myocardial apoptosis and interstitial fibrosis, and the preservation of cardiac function in the face of long-term pressure overload, together resulting in a significant increase in mouse survival (Kritzer et al. 2014). These results established mAKAPβ as the first scaffold whose ablation confers a survival benefit in heart disease. Importantly, mAKAPβ did not appear to be necessary for either the development or maintenance of normal adult cardiac function, as the use of a Nkx2-5-directed cre deleter line did not result in an overt phenotype by six months of age (Kritzer et al. 2014). Although mAKAPβ knock-out did attenuate the physiological hypertrophy induced by forced exercise (swimming), the targeting of mAKAPβ complexes in disease remains relevant.

Various strategies for targeting mAKAPβ complexes in humans may be envisioned, including siRNA knock-down of the scaffold. However, a relatively detailed understanding of the structure and function of mAKAPβ signalosomes provides us with additional approaches to targeting these pathways. For example, the expression of peptides targeting key protein-protein interactions involving mAKAPβ has already been shown to be effective in vitro, including anchoring disruptor peptides targeting mAKAPβ-CaNAβ, mAKAPβ-MEF2D, mAKAPβ-PLCε, and mAKAPβ-RSK3 binding (Li, Vargas, et al. 2013; Li, Kritzer, et al. 2013; Vargas et al. 2012; Zhang et al. 2011). A leading cause of death, heart failure is a disease that incurs 50% mortality within 5 years of diagnosis despite modern therapy, at a cost of over $30 billion/year in the USA alone (Go et al. 2014). Many candidates for potential targeting in cardiac disease are pleiotropic, complicating the development of drugs with sufficient specificity in vivo. The specific targeting of mAKAPβ signalosomes provides an opportunity to target relatively rare protein-protein interactions that appear to be dedicated to pathological cardiac remodeling and whose ablation may be promoted without significant side-effects. There is a clear need to develop new effective therapies to treat patients with heart failure, as well as to prevent its development in the context of other cardiovascular diseases such coronary artery disease, hypertension, and valvular disease.

SUMMARY OF THE INVENTION

The following brief summary is not intended to include all features and aspects of the present invention, nor does it imply that the invention must include all features and aspects discussed in this summary.

The present inventors have discovered methods of treating cardiac pathological processes by inhibiting the signaling properties of individual mAKAP signaling complexes using drugs that target unique protein-protein interactions. Such a therapeutic strategy offers an advantage over classical therapeutic approaches because it allows the selective inhibition of defined cellular responses.

In particular, the present inventors have found that disrupting mAKAP-mediated protein-protein interactions can be used to inhibit the ability of mAKAP to coordinate the activation of enzymes that play a central role in activating key transcription factors that initiate cellular processes leading to pathological cardiac remodeling.

Specifically, the inventors have discovered that inhibiting the binding interaction between PP2A and mAKAPβ can protect the heart from damage leading to heart failure, for example, following myocardial infarction.

Thus, the present invention comprises, in certain aspects a method for protecting the heart from damage, by administering to a patient at risk of such damage, a pharmaceutically effective amount of a composition which inhibits the interaction of PP2A and mAKAPβ.

The invention also relates to a method of treating heart disease, by administering to a patient a pharmaceutically effective amount of a composition which inhibits the interaction of PP2A and mAKAPβ.

The invention also relates to compositions which inhibit the interaction of PP2A and mAKAPβ.

In still other embodiments, the inhibitors include any molecule that inhibits the expression or activity of PP2A and mAKAPβ.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2. Shows the amino acid sequence of human RSK3 (SEQ ID NO: 1).

FIG. 3. Shows the amino acid sequence of rat mAKAP (SEQ ID NO: 2). —Note that within this document, references to mAKAP sequences, whether labelled "mAKAPβ" or "mAKAP" are according to the numbering for the mAKAPα alternatively-spliced form which contains within the entirety of mAKAPβ and is identical to the originally published mAKAP sequence as shown in this figure (Kapiloff 1999, Michel 2005). "mAKAP" is also referred to as "AKAP6" in reference databases and the literature. mAKAPβ starts at residue 245, while mAKAPα starts at residue 1. PP2A binding domain starts at residue 2134.

FIG. 4. Amino acid sequence of rat mAKAP PBD as expressed in AAV vector Includes N-terminal myc tag (SEO ID NO: 12).

FIG. 5. Sequence for pscA-TnT-myc-rat mAKAP PBD plasmid used to generate AAV9sc.rat PBD (SEO ID NOs: 13 and 14).

FIG. 6. mAKAPβ—A Perinuclear Scaffold. A. Top montage: Mouse heart sections (left ventricle) stained for with mAKAP antibody (gray scale panels and green), Hoechst nuclear stain (blue), and wheat germ agglutinin (red, shown in enlarged control image only). Lower left panels are from control, mAKAP knock-out mice. Bar=20 μm. Bottom montage: Adult rat myocyte stained with antibodies to mAKAP (green) and actinin (red). B. mAKAP domain structure. Direct binding partners whose sites have been finely mapped in mAKAPβ are shown. mAKAPβ starts at residue 245 of mAKAPα. Therefore, all binding sites are numbered per mAKAPα. Images are from Kritzer, et al. (Kritzer et al. 2014).

FIG. 10. PP2A binds a C-terminal mAKAP domain. A, schematic of mAKAP domains and GFP- and myc-tagged mAKAP proteins used in this paper. mAKAP fragments containing rat and human protein are drawn in black and grey, respectively. Hatched bars indicate the three spectrin repeat domains responsible for nuclear envelope targeting in myocytes (Kapiloff et al. 1999a). Binding sites are indicated for proteins known to bind mAKAP directly, including 3-phosphoinositide-dependent kinase-1 (PDK1, mAKAP residues 227-232) (Michel et al. 2005b), nesprin-1α (1074-1187) (Pare, Easlick, et al. 2005), ryanodine receptor (RyR2, 1217-1242) (Marx et al. 2000), PP2B (1286-1345) (Li et al. 2009), PDE4D3 (1285-1833) (Dodge et al. 2001), and PKA (2055-2072) (Kapiloff et al. 1999a). The stippled bar marks the PP2A binding site. The first and last residues of each fragment are indicated. B, purified GST-PP2A A subunit fusion protein was incubated with extracts prepared from HEK293 cells expressing the indicated GFP-mAKAP fusion protein and pulled down using glutathione resin. GFP-mAKAP fragments were detected in the pull-downs (25% loaded, top panel) and the extracts (5% loaded, bottom pane) using a GFP antibody. n=3. C, myc-tagged mAKAP fragments were expressed in HEK293 cells, and phosphatase binding was detected by immunoprecipitation using control (IgG) or myc-tag antibody followed by phosphatase assay using $^{32}$P-labelled histone substrate. n=3. *p<0.05 compared to the other samples. Note that the C-terminal homologous domain of both rat and human mAKAP binds PP2A.

FIG. 10A). After stimulation with 5 μM Fsk and 50 μM IBMX, protein complexes were immunoprecipitated with mAKAP antibody, and associated proteins were detected by immunoblotting with B56δ, mAKAP, and PP2A-C antibodies (lower three panels). PKA phosphorylation of B56δ was detected by immunoblotting with a B56δ phospho-Ser-566 specific antibody (P-B56δ, upper panel). n=3. B, Immunoprecipitates prepared as in B were assayed for associated phosphatase activity. n=3. *p<0.05.

FIG. 18. mAKAP Fragments do not bind PP1 in HEK293 cells. mAKAP-GFP fusion proteins were expressed in HEK293 cells and protein complexes were immunoprecipitated with PP1 antibody. Despite robust expression (bottom panels), no mAKAP fusion proteins were precipitated with the PP1 antibody. n=3.

FIG. 22. AAV9sc.myc-PBD. A. AAV9sc.myc-PBD includes a minigene that expresses the myc-tagged rat PDB peptide (rat mAKAP aa 2134-2314) and a defective right ITR, conferring self-complementarity and presumably decreasing the latency and increasing the efficacy of expression.(Andino et al., 2007). The AAV has the cardiotrophic serotype 9 capsid protein and directs expression of the encoded protein under the control of the cardiac myocyte-specific, chicken troponin T promoter (cTnT).(Prasad et al., 2011) B. Shuttle plasmid for AAV9sc.myc-PBD.

FIG. 24. Nucleotide sequence of human RSK3 (SEQ ID NO: 15).

FIG. 25. Nucleotide sequence of rat mAKAPα mRNA with open reading frame translated (SEO ID NOs: 2 and 16).

FIG. 26. Nucleotide sequence of human mAKAPβ mRNA with open reading frame translated (SEO ID NOs: 17 and 18).

FIG. 27. Nucleotide sequence of human mAKAPα mRNA with open reading frame translated (SEO ID NOs: 19 and 20).

FIG. 28. Amino acid sequence of human mAKAP. mAKAPα starts at residue 1, mAKAβ at residue 243. PBD in bold (SEQ ID NO: 8).

FIG. 29. Amino acid sequence of human PBD as expressed in AAV (SEO ID NO: 9).

FIG. 30. Alignment of human and rat PBD amino acid sequences as expressed by AAV species (SEQ ID NOs: 9 and 12). Rat PBD has an N-terminal Myc-tag [EQKLI-SEEDL (SEQ ID NO: 21), FIG. 4). The consensus sequence is represented by SEQ ID NO:22 or SEQ ID NO:23.

FIG. 32. Nucleotide sequence of pscAAV-hmAKAP PBD plasmid (SEO ID NOs: 10 and 11).

DETAILED DESCRIPTION OF THE INVENTION

Figure 1:
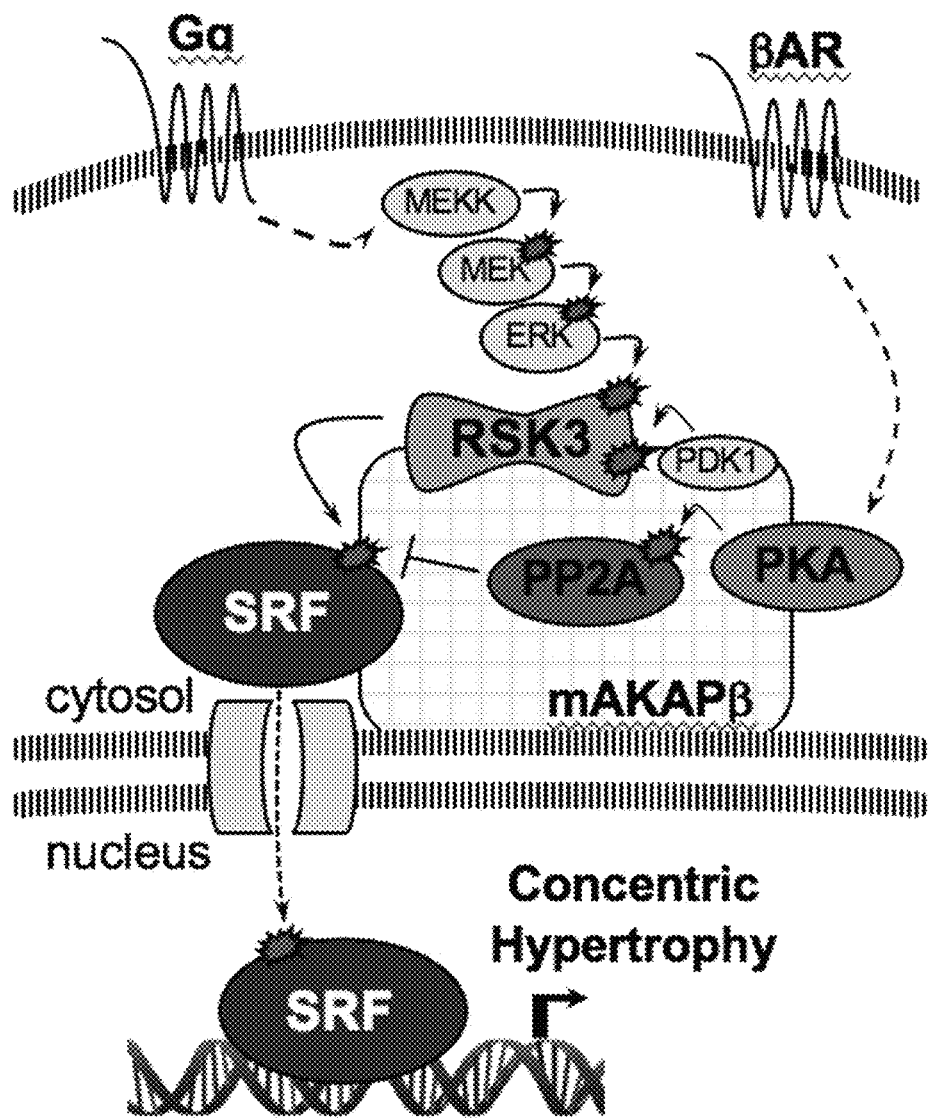
FIG. 1. Model for mAKAPβ-regulated, SRF-dependent gene expression. Anchored RSK3 is a Gq-protein coupled receptor-ERK effector that phosphorylates SRF associated with perinuclear mAKAPβ complexes. mAKAPβ-anchored PP2A that can be activated by cAMP-dependent protein kinase A (PKA) opposes SRF phosphorylation. Phosphorylated SRF induces gene expression that promotes concentric hypertrophy.
Figure 7:
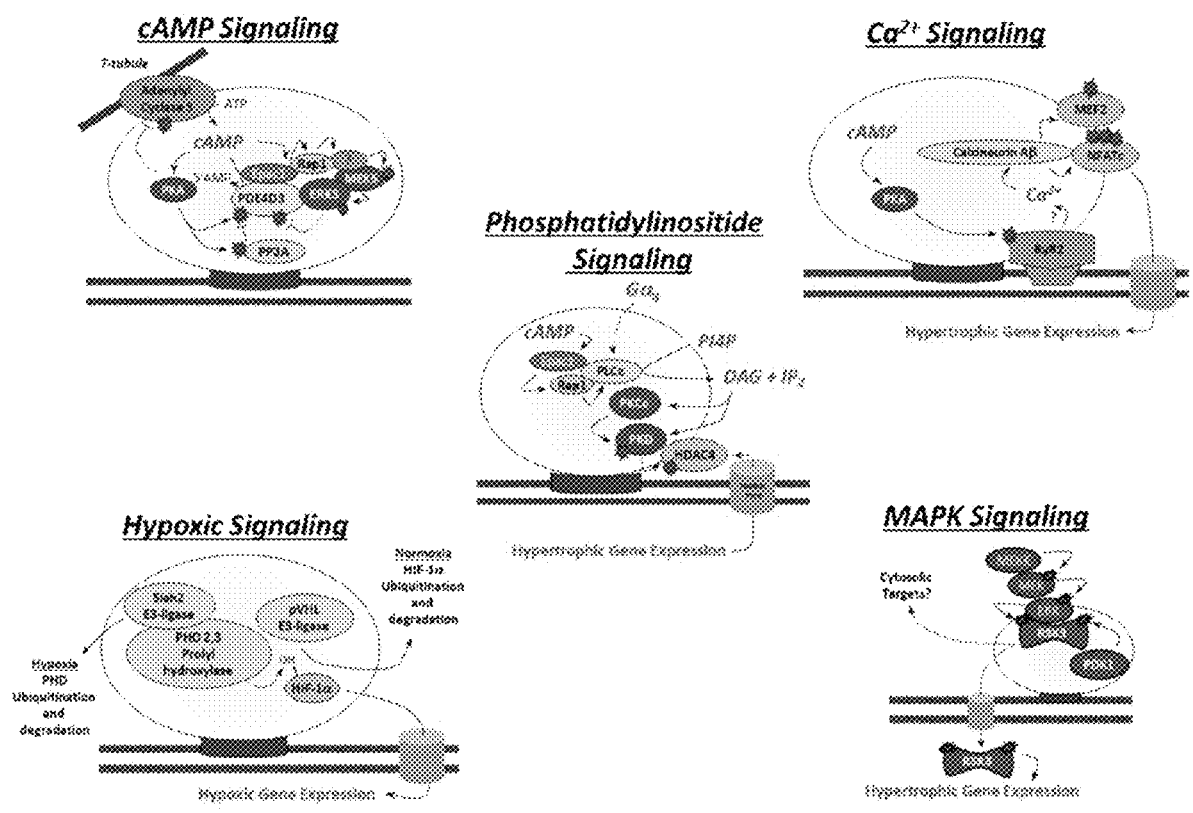
FIG. 7. mAKAPβ Signaling Modules. mAKAPβ binds multiple signaling enzymes and gene regulatory proteins. Modules may be defined that involve cAMP, $Ca^{2+}$, hypoxic, phosphatidylinositide and MAPK signaling. See above for details. In this figure, the mAKAPβ scaffold is presented as a yellow globe sitting on a grey base representing nesprin-1α, on which are assembled the various signaling molecules. Gold cylinders represent nuclear pore complexes inserted in the nuclear envelope.

As discussed above, AKAP-based signaling complexes play a central role in regulating physiological and pathological cardiac events. As such, the present inventors have examined inhibiting the signaling properties of individual AKAP signaling complexes using drugs that target unique protein-protein interactions as an approach for limiting cardiac pathological processes. Such a therapeutic strategy offers an advantage over classical therapeutic approaches since it allows the selective inhibition of defined cellular responses.

Anchoring proteins including mAKAP are therapeutic targets for the treatment of cardiac hypertrophy and heart failure. In particular, the present inventors have found that disrupting AKAP-mediated protein-protein interactions can be used to inhibit the ability of mAKAP to coordinate the activation of enzymes that play a central role in activating key transcription factors that initiate the remodeling process leading to cardiac hypertrophy.

One aspect of the current invention is that improved ventricular geometry, i.e. decreased LV internal diameters due to less elongated myocytes and/or increased LV wall thickness due to wider myocytes, will decrease wall stress (Law of LaPlace) and improve systolic function in the heart prone to HFrEF. Demonstration of the prevention of systolic dysfunction has been obtained for a new gene therapy vector based upon expression of a muscle A-kinase anchoring protein (mAKAP, a.k.a. AKAP6)-derived anchoring disruptor peptide for protein phosphatase 2A (PP2A).

As discussed below, the inventors have recently discovered that the transcription factor serum response factor (SRF) is Ser$^{103}$phosphorylated in the cardiac myocyte by RSK3 at mAKAPβ signalosomes where SRF may in turn be dephosphorylated by protein phosphatase 2A (PP2A) bound to the scaffold. Methods to block the eccentric changes in ventricular morphology that typify end-stage disease and HFrEF are the subject of this invention.

While previously thought to be a constitutive, housekeeping enzyme, it has become apparent that protein phosphatase 2A (PP2A) contributes to the regulation of many phosphorylation events. For example, in the cardiac myocyte, PP2A is involved in the modulation of calcium and MAPK signaling (duBell, Lederer, and Rogers 1996; duBell et al. 2002; Liu and Hofmann 2004). PP2A is a serine/threonine phosphatase that exists as a heterotrimeric complex consisting of a stable, ubiquitously expressed catalytic (PP2A-C) and scaffolding (PP2A-A) subunit heterodimer, and one of 21 known divergent B subunits (Lechward et al. 2001; Wera and Hemmings 1995). PP2A B subunits are grouped into three unrelated families termed B (or PR55), B' (or B56) and B" (or PR72) and are proposed to regulate both the catalytic activity and the intracellular targeting of the phosphatase (Virshup 2000). The present inventors have previously shown by reconstitution of mAKAP complexes in heterologous cells that protein phosphatase 2A (PP2A) associated with mAKAP complexes can reverse the activation of PDE4D3 by catalyzing the dephosphorylation of PDE4D3 serine residue 54 (Dodge-Kafka et al. 2010). Mapping studies revealed that a C-terminal mAKAP domain (residues 2085-2319) bound PP2A (Dodge-Kafka et al. 2010). Binding to mAKAP was required for PP2A function on PDE4D3, such that deletion of the C-terminal domain enhanced both baseline and forskolin-stimulated PDE4D3 activity. Interestingly, PP2A holoenzyme associated with mAKAP complexes in the heart contains the PP2A targeting subunit B56δ (Dodge-Kafka et al. 2010). Like PDE4D3, B56δ is a PKA substrate, and PKA phosphorylation of mAKAP-bound B56δ enhanced phosphatase activity 2-fold in the complex. Accordingly, expression of a B56δ mutant that could not be phosphorylated by PKA in heterologous cells with mAKAP resulted in increased PDE4D3 phosphorylation. Taken together, these findings demonstrated that PP2A associated with mAKAP complexes may promote PDE4D3 dephosphorylation, serving to both inhibit PDE4D3 in unstimulated cells and also to mediate a cAMP-induced positive feedback loop following adenylyl cyclase activation and B56δ phosphorylation. Thus PKA-PDE4D3-PP2A-mAKAP complexes exemplify how protein kinases and phosphatases may participate in molecular signaling complexes to dynamically regulate localized intracellular signaling. The relevance to cardiac myocyte function and any potential therapeutic significance were not defined in prior studies (Dodge-Kafka et al. 2010).

Figure 19:
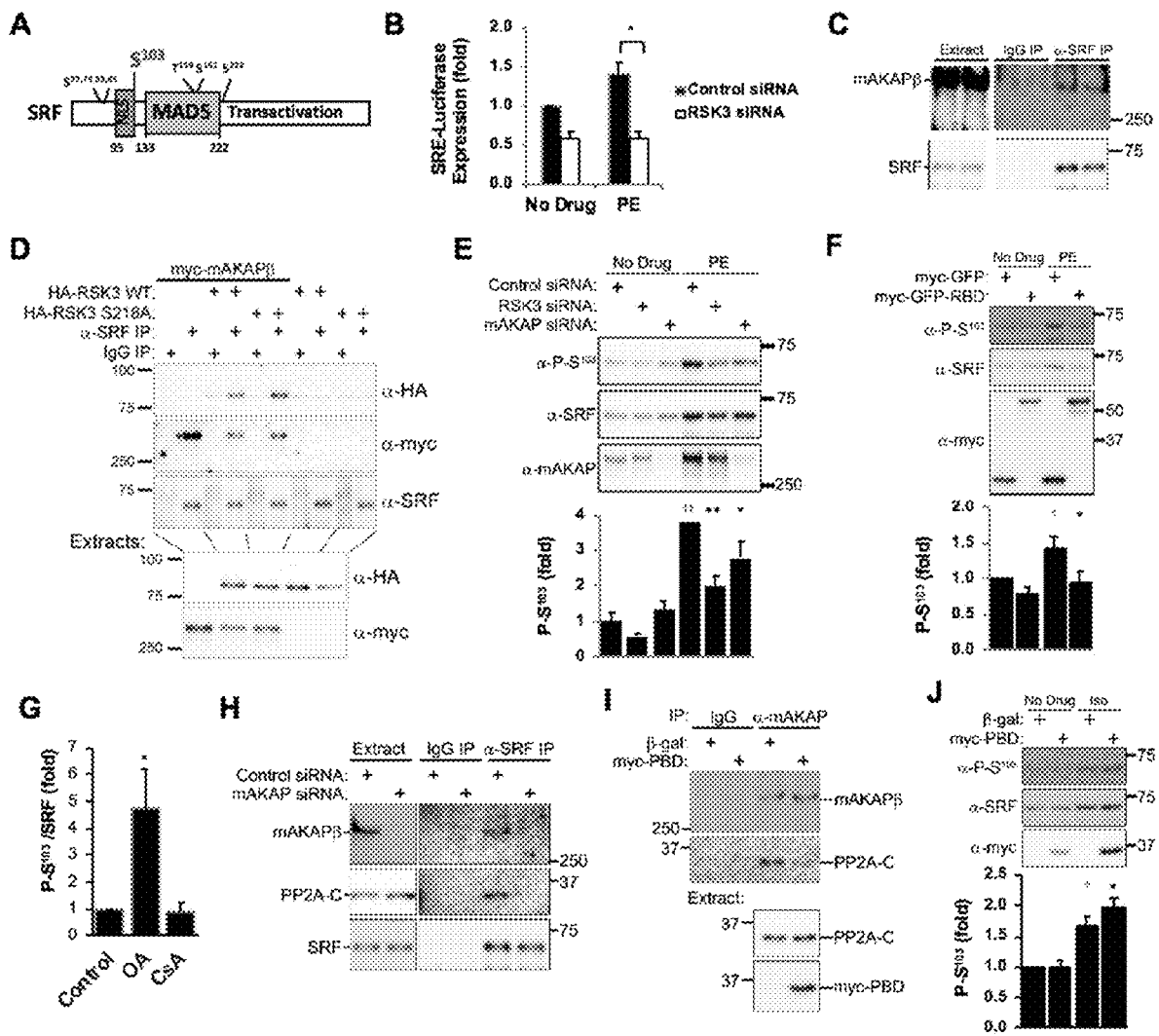
FIG. 19. SRF phosphorylation is regulated by mAKAPβ signalosomes in cardiac myocytes. (A) SRF Domain Structure. Known phosphorylated residues are indicated (Li et al. 2014; Mack 2011; Janknecht et al. 1992). (B) Neonatal rat ventricular myocytes (NRVM) transiently transfected with siRNA and SRE-luciferase and control renilla luciferase plasmids. Normalized luc:rluc ratios are shown. n=3. (C) Co-immunoprecipitation of endogenous complexes from mouse heart extracts. n=3. (D) HA-tagged RSK3 WT or S218A inactive mutant (Li, Kritzer, et al. 2013) and/or myc-mAKAPβ were expressed in COS-7 cells for co-immunoprecipitation assay. n=3. (E) NRVM extracts obtained 2 days after transfection with siRNA+/−10 μM PE. n=3. * vs. control siRNA+PE; † vs. control siRNA+no drug. (F) Adult rat ventricular myocytes (ARVM) infected with adenovirus expressing myc-GFP or myc-GFP-RBD and treated for 1 day with 20 μM PE. n=3. †vs. myc-GFP+PE; † vs. myc-GFP+no drug. (G) NRVM in minimal maintenance media were treated for 1 hour with 1 μM okadaic acid (OA) or 1 μg/ml cyclosporine A (CsA). n=4. * vs. no drug control. (H) NRVM transfected with control or mAKAP siRNA were used for co-immunoprecipitation assay. PP2A holoenzyme contains an A- and C-subunit homodimer core and a scaffolding B-subunit (Dodge-Kafka et al. 2010). PP2A C-subunit (PP2A-C) was detected by immunoblot. n=3. (I) NRVM infected with adenovirus expressing myc-PBD or β-gal before co-immunoprecipitation assay. n=3. (J) ARVM infected with myc-PBD or β-gal adenoviruses and treated for 1 day with 10 μM Iso. n=4. †vs. β-gal+Iso; † vs. β-gal+no drug.
Figure 20:
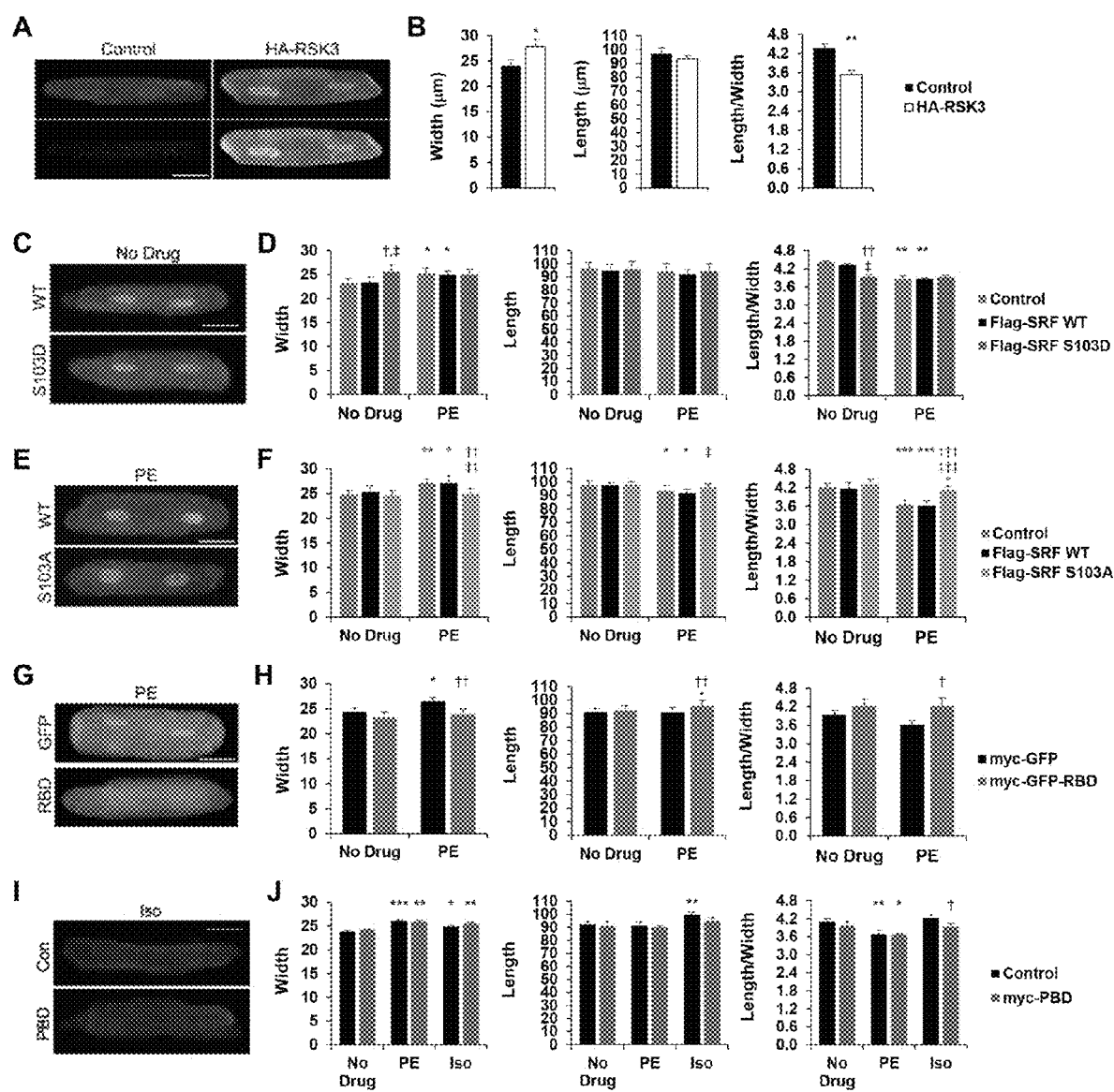
FIG. 20. SRF S$^{103}$ phosphorylation is a determinant of myocyte concentric growth. Adult rat ventricular myocytes (ARVM) were infected with adenovirus and cultured for 24 hours+/−20 μM PE or 10 μM Iso before immunocytochemistry and measurement of cell width and length (maximum dimension parallel or perpendicular to striations; bars=25 μm). (A,B) Myocytes were infected with adenovirus expressing either 3-gal (control) or HA-tagged RSK3 and maintained in minimal media. Top: α-actinin—red, nuclei—blue, HA-RSK3—green; bottom HA-RSK3—greyscale. n=4. (C-F). Myocytes were infected with adenovirus expressing SRF WT, S103D, S103A or control virus. Flag-SRF—green, α—actinin—red, nuclei—blue. ‡ vs. no drug for same virus; † vs. control under the same treatment condition; ‡ vs. SRF WT under the same treatment condition. D: n=3; F: n=5. (G,H) Myocytes were infected with adenovirus expressing myc-GFP or myc-GFP-RBD (green). (I,J) Myocytes were infected with adenovirus expressing myc-PBD or β-gal control. (G-J) α-actinin—red, nuclei—blue. * vs. no drug control for same protein; † vs. control protein with same treatment condition. n=4.
Figure 21:
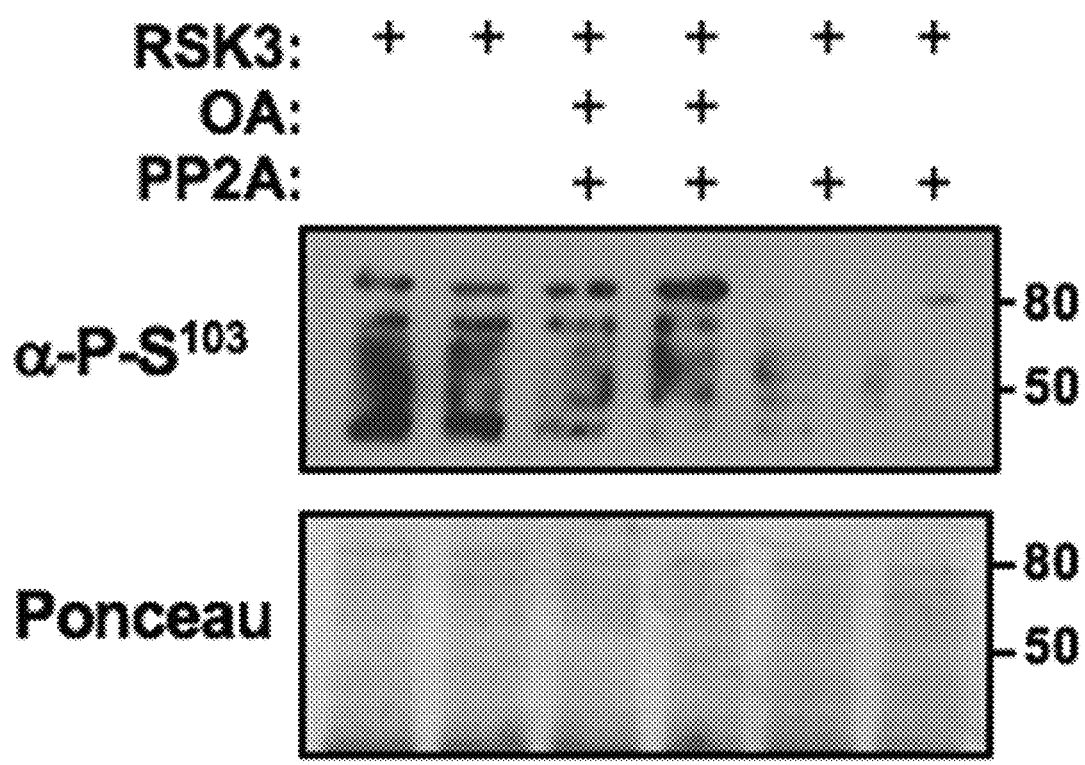
FIG. 21. PP2A dephosphorylates SRF $S^{103}$. GST-SRF fusion protein purified from bacterial extracts and on glutathione beads was incubated with purified 0.5 μg RSK3 (Millipore) for 30 minutes before washing twice with PP2A reaction buffer and then incubating for 30 min with 50 ng purified PP2A+/−10 nM okadaic acid.

The present inventors now disclose a new mechanism of action for mAKAPβ-bound PP2A in the cardiac myocyte and the therapeutic implications of this mechanism. The inventors show that the transcription factor SRF is phosphorylated at $Ser^{103}$ by mAKAPβ-bound RSK3 (FIG. 19) and that SRF phosphorylation at $Ser^{103}$ constitutes an epigenetic switch promoting concentric cardiac myocyte hypertrophy (FIG. 20). Importantly, it is disclosed that SRF $Ser^{103}$ can be dephosphorylated by PP2A bound to the mAKAPβ scaffold (FIGS. 19 and 21). SRF $Ser^{103}$ phosphorylation is shown to induce concentric myocyte hypertrophy (FIG. 20). These findings constitute the discovery of a novel mechanism for the regulation of cardiac myocyte morphology and an unexpected function for mAKAPβ-bound PP2A. In particular, the inventors disclose that consistent with the role of PP2A as a phosphatase for mAKAPβ-bound SRF, displacement of PP2A from mAKAPβ in vitro will promote SRF $Ser^{103}$ phosphorylation in cardiac mycoytes (FIG. 19) and concentric cardiac myocyte hypertrophy (FIG. 20) and in vivo will provide protection against the development of systolic dysfunction after myocardial infarction in mice (FIG. 23).

Inhibition of PP2A binding to mAKAPβ can be achieved by expression of a competing peptide comprising rat mAKAPβ 2134-2314 (FIG. 19) or 2132-2319 of human mAKAPβ, representing a new refinement in the mapping of the PP2A binding site on mAKAPβ and the first demonstration for heart disease in vivo of the inhibition of mAKAP-PP2A binding. Note that the C-terminal domain of human mAKAP homologous to that in rat mAKAP was also shown to bind PP2A (FIG. 10). Therefore the human sequence (human mAKAP amino acid residues homologous 2132-2319) to rat mAKAP 2134-2314 shown in FIGS. 28-30 is also expected to bind PP2A and constitute a PP2A-mAKAP binding competing peptide.

Figure 23:
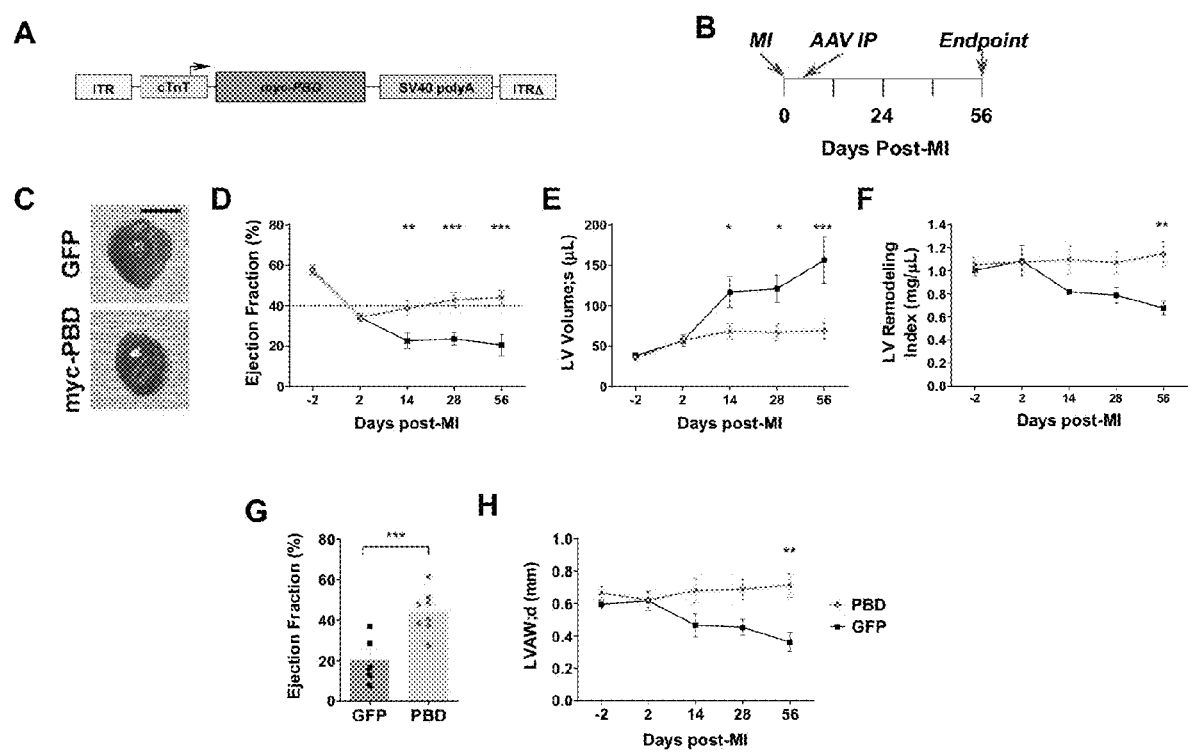
FIG. 23. PBD anchoring disruptor therapy. (A) myc-tagged rat mAKAP PBD (AAV9sc.myc-PBD) and myc-GFP (AAV9sc.GFP) were expressed in mice using a self-complementary AAV9 and the cardiac myocyte-specific chicken troponin T promoter.(Prasad et al., 2011) (B) Timeline for AAV9sc.myc-PBD treatment study shown in C-H. Mice were 8 weeks old at initation of study. (C) Representative whole heart pictures at endpoint. Bar=5 mm. (D-H) Serial M-mode echocardiography. n: AAV9sc.myc-PBD-8 (green); AAV9sc.GFP-5 (black). * p-value for difference in cohorts at given time point. LV Remodeling Index=Mass÷End-diastolic volume. LVAW; d—left ventricular anterior wall thickness in diastole.
Figure 31:
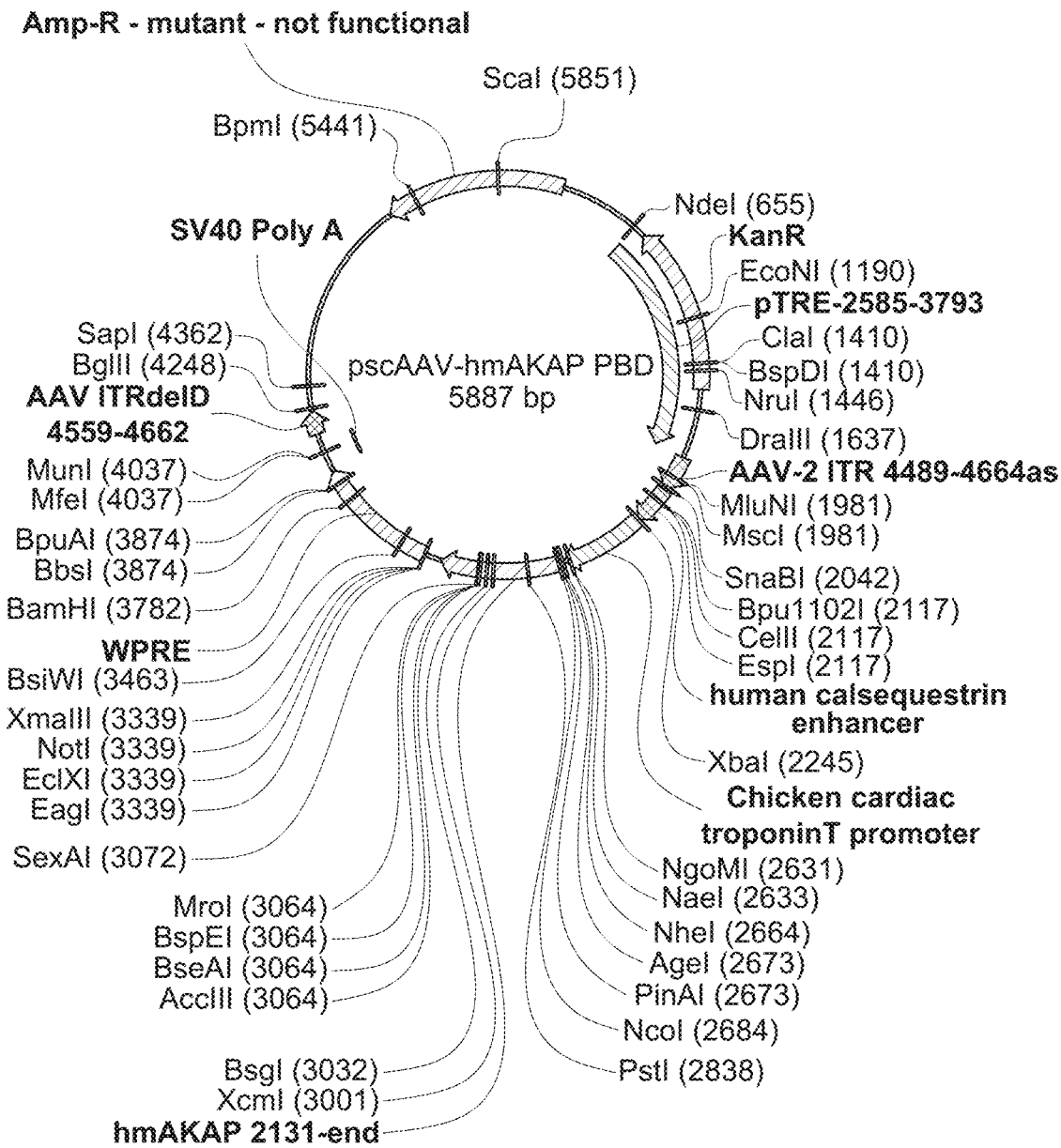
FIG. 31. Map of human PBD shuttle plasmid.

Effective delivery of PP2A anchoring disruptor peptides via viral-based gene therapy vectors are demonstrated by efficacy in the mouse infarction model (FIG. 23). Alternatively, delivery of such peptides that might inhibit PP2A-mAKAPβ interaction can be enhanced by the use of cell-penetrating sequences such as the transactivator of transcription peptide and polyarginine tails, or conjugation with lipid-derived groups such as stearate. Stability may also be enhanced by the use of peptidomimetics [i.e., peptides with structural modifications in the original sequence giving protection against exo- and endoproteases without affecting the structural and functional properties of the peptide.]

The inventors have also found that small molecule disruptors can be used to target specific interaction within AKAP-based complexes. Small molecule disruptors can be identified by combining rational design and screening approaches. Such compounds can be designed to target-specific binding surfaces on AKAPs, to disrupt the interaction between AKAPs and PP2A in cardiomyocytes and to enhance the contractility of intact hearts for the treatment of chronic heart failure.

The present invention relates to methods of treating any cardiac condition which is initiated through the interaction of PP2A and mAKAPβ. Such cardiac dysfunction can result in signs and symptoms such as shortness of breath and fatigue, and can have various causes, including, but not limited to hypertension, coronary artery disease, myocardial infarction, valvular disease, primary cardiomyopathy, congenital heart disease, arrhythmia, pulmonary disease, diabetes, anemia, hyperthyroidism and other systemic diseases.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (4th Ed., 2012); "Current Protocols in Molecular Biology" Volumes I-III [Ausubel, R. M., ed. (1994)]; "Cell Biology: A Laboratory Handbook" Volumes I-III [J. E. Celis, 3rd ed. (2005))]; "Current Protocols in Immunology" Volumes I-III [Coligan, J. E., ed. (2005)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984); C. Machida, "Viral Vectors for Gene Therapy: Methods and Protocols" (2010); J. Reidhaar-Olson and C. Rondinone, "Therapeutic Applications of RNAi: Methods and Protocols" (2009).

The following definitions and acronyms are used herein:
AC5—adenylyl cyclase type 5
ACE—angiotensin-converting enzyme
ANF atrial natriuretic factor ARVM—adult rat ventricular myocyte
CaN—calcineurin
CArG box—CC(A/T)$_6$GG
CPT-cAMP—8-(4-chlorophenylthio)adenosine 3',5'-cyclic monophosphate
CsA—cyclosporin A
CTKD—C-terminal kinase domain
ERK—extracellular signal-regulated kinase
FBS—fetal bovine serum
Fsk—forskolin
GFP—green fluorescent protein
GPCR—G-protein coupled receptor; HDAC—histone deacetylase
Gs—stimulatory G protein
GST—glutathione-S-transferase; HIF1α—hypoxia-inducible factor 1α
HFrEF—heart failure with reduced ejection fraction
IBMX—3-isobutyl-1-methylxanthine
Iso—isoproterenol
LIF—leukemia inhibitory factor
MADS—(MCM1, agamous, deficiens, SRF) domain—mediates DNA binding to CArG box CC(A/T)$_6$GG serum response elements (SRE); the MADS-box gene family got its name later as an acronym referring to the four founding members, ignoring ARG80:
  MCM1 from the budding yeast, *Saccharomyces cerevisiae*,
  AGAMOUS from the thale cress *Arabidopsis thaliana*,
  DEFICIENS from the snapdragon *Antirrhinum majus*,
  [10]
  SRF from the human *Homo sapiens*.
mAKAP—muscle A-kinase anchoring protein
mAKAPα—alternatively spliced isoform expressed in neurons; 255 kDa
mAKAPβ—alternatively spliced isoform expressed in striated myocytes; 230 kDa
MAPK—mitogen-activated protein kinase
MEF2—myocyte enhancer factor-2
MgAc—magnesium acetate
MI—myocardial infarction
NCX1—sodium/calcium exchanger
NFATc—nuclear factor of activate T-cell
NRVM—neonatal rat ventricular myocyte
NTKD—N-terminal kinase domain
OA—Okadaic acid
PBD—"PP2A binding domain" of mAKAP that binds PP2A and that when expressed attenuates eccentric hypertrophy
PDE4D3—cAMP-specific phosphodiesterase type 4D3
PDK1—3'phosphoinositide-dependent kinase 1
PE—phenylephrine
PHD—prolyl hydroxylase
PI4P—phosphatidylinositol-4-phosphate
PKA—protein kinase A
PKD—protein kinase D
PKI—protein kinase inhibitor
PLCε—phospholipase Cε
PKA—cAMP-dependent protein kinase
PP2A—protein (serine-threonine) phosphatase-dephosphorylates SRF Ser$^{103}$
PP2B—calcium/calmodulin-dependent protein phosphatase 2B
RBD—isoform-specific N-terminal RSK3 domain binds a discrete "RSK3-binding domain" within mAKAPβ at residues 1694-1833 (RBD)
RSK—p90 ribosomal S6 kinase
RyR2—type 2 ryanodine receptor
siRNA—small interfering RNA oligonucleotide
shRNA—short hairpin RNA
SRE—serum response elements
SRF—serum response factor—transcription factor (SRF Ser$^{103}$ phosphorylation induces concentric myocyte and cardiac hypertrophy)
siRNA—small interfering RNA
TAC transverse aortic constriction
TCA—trichloroacetic acid
VSV—vesicular stomatitis virus Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The present invention recognizes that the interaction of PP2A and mAKAPβ mediates various intracellular signals and pathways which lead to cardiac myocyte hypertrophy and/or dysfunction. As such, the present inventors have discovered various methods of inhibiting that interaction in order to prevent and/or treat cardiac myocyte hypertrophy and/or dysfunction.

Thus, the present invention includes a method for protecting the heart from damage, by administering to a patient at risk of such damage, a pharmaceutically effective amount of a composition, which inhibits the interaction of PP2A and mAKAPβ. It should be appreciated that "a pharmaceutically effective amount" can be empirically determined based upon the method of delivery, and will vary according to the method of delivery.

The invention also relates to a method of treating heart disease, by administering to a patient a pharmaceutically effective amount of a composition, which inhibits the interaction of PP2A and mAKAPβ.

The invention also relates to compositions which inhibit the interaction of PP2A and mAKAPβ. In particular embodiments, these inhibiting compositions or "inhibitors" include peptide inhibitors, which can be administered by any known method, including by gene therapy delivery. In other embodiments, the inhibitors can be small molecule inhibitors.

Specifically, the present invention is directed to methods and compositions for treating or protecting the heart from damage, by administering to a patient at risk of such damage, a pharmaceutically effective amount of a composition which (1) inhibits the interaction of PP2A and mAKAPβ; (2) inhibits the activity of PP2A and mAKAPβ; or (3) inhibits the expression of PP2A and mAKAPβ.

The invention also relates to methods of treating or protecting the heart from damage, by administering to a patient at risk of such damage, a pharmaceutically effective amount of a composition which inhibits a cellular process mediated by the anchoring of PP2A.

In one embodiment, the composition includes an mAKAPβ peptide. In a preferred embodiment, the mAKAPβ peptide is obtained from the carboxy terminus of the mAKAPβ amino acid sequence. In a particularly preferred embodiment, the mAKAPβ peptide is at least a fragment of amino acids 2083-2319 of the mAKAPβ amino acid sequence.

In one preferred embodiment, the mAKAPβ peptide is at least a fragment of amino acids 2132-2319 of the mAKAPβ amino acid sequence.

In another embodiment, the composition includes a small interfering RNA siRNA that inhibits the expression of either or both of PP2A and mAKAPβ. In a preferred embodiment, the siRNA that inhibits the expression of mAKAPβ is generated in vivo following administration of a short hairpin RNA expression vector or biologic agent (shRNA).

The composition of the invention can be administered directly or can be administered using a viral vector. In a preferred embodiment, the vector is adeno-associated virus (AAV).

In another embodiment, the composition includes a small molecule inhibitor. In preferred embodiments, the small molecule is a PP2A inhibitor.

In another embodiment, the composition includes a molecule that inhibits the binding, expression or activity of mAKAPβ. In a preferred embodiment, the molecule is a mAKAPβ peptide. The molecule may be expressed using a viral vector, including adeno-associated virus (AAV).

In yet another embodiment, the composition includes a molecule that interferes with mAKAPβ-mediated cellular processes. In preferred embodiments, the molecule interferes with the anchoring of PP2A.

The invention also relates to diagnostic assays for determining a propensity for heart disease, wherein the binding interaction of PP2A and mAKAPβ is measured, either directly, or by measuring a downstream effect of the binding of PP2A and mAKAPβ. The invention also provides a test kit for such an assay.

In still other embodiments, the inhibitors include any molecule that inhibits the expression of PP2A and mAKAPβ, including antisense RNA, ribozymes and small interfering RNA (siRNA), including shRNA.

The invention also includes an assay system for screening of potential drugs effective to inhibit the expression and/or binding of PP2A and mAKAPβ. In one instance, the test drug could be administered to a cellular sample with the PP2A and mAKAPβ, or an extract containing the PP2A and mAKAPβ, to determine its effect upon the binding activity of the PP2A and mAKAPβ, by comparison with a control. The invention also provides a test kit for such an assay.

In preparing the peptide compositions of the invention, all or part of the PP2A or mAKAP (FIG. 3 or FIG. 28) amino acid sequence may be used. In one embodiment, the carboxy-terminal region of the mAKAPβ protein is used as an inhibitor. Preferably, at least 10 amino acids of the mAKAP sequence are used. More preferably, at least 25 amino acids of the mAKAP sequence are used. Most preferably, peptide segments from amino acids 2132-2319 of mAKAP are used.

It should be appreciated that various amino acid substitutions, deletions or insertions may also enhance the ability of the inhibiting peptide to inhibit the interaction of PP2A and mAKAPβ. A substitution mutation of this sort can be made to change an amino acid in the resulting protein in a non-conservative manner (i.e., by changing an amino acid belonging to a grouping of amino acids having a particular size or characteristic to an amino acid belonging to another grouping) or in a conservative manner (i.e., by changing an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes, which do not significantly alter the activity, or binding characteristics of the resulting protein.

The following is one example of various groupings of amino acids:

Amino acids with nonpolar R groups: Alanine, Valine, Leucine, Isoleucine, Proline, Phenylalanine, Tryptophan, Methionine.

Amino acids with uncharged polar R groups: Glycine, Serine, Threonine, Cysteine, Tyrosine, Asparagine, Glutamine.

Amino acids with charged polar R groups (negatively charged at pH 6.0): Aspartic acid, Glutamic acid.

Basic amino acids (positively charged at pH 6.0): Lysine, Arginine, Histidine (at pH 6.0).

Another grouping may be those amino acids with phenyl groups: Phenylalanine, Tryptophan, Tyrosine.

Another grouping may be according to molecular weight (i.e., size of R groups): Glycine (75), Alanine (89), Serine (105), Proline (115), Valine (117), Threonine (119), Cysteine (121), Leucine (131), Isoleucine (131), Asparagine (132), Aspartic acid (133), Glutamine (146), Lysine (146), Glutamic acid (147), Methionine (149), Histidine (at pH 6.0) (155), Phenylalanine (165), Arginine (174), Tyrosine (181), Tryptophan (204).

Particularly preferred substitutions are:

Lys for Arg and vice versa such that a positive charge may be maintained;

Glu for Asp and vice versa such that a negative charge may be maintained;

Ser for Thr such that a free—OH can be maintained; and

Gln for Asn such that a free NH$_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces B-turns in the protein's structure. Two amino acid sequences are "substantially homologous" when at least about 70% of the amino acid residues (preferably at least about 80%, and most preferably at least about 90 or 95%) are identical, or represent conservative substitutions.

Likewise, nucleotide sequences utilized in accordance with the invention can also be subjected to substitution, deletion or insertion. Where codons encoding a particular amino acid are degenerate, any codon which codes for a particular amino acid may be used. In addition, where it is desired to substitute one amino acid for another, one can modify the nucleotide sequence according to the known genetic code.

Nucleotides and oligonucleotides may also be modified. U.S. Pat. No. 7,807,816, which is incorporated by reference in its entirety, and particularly for its description of modified nucleotides and oligonucleotides, describes exemplary modifications.

Two nucleotide sequences are "substantially homologous" or "substantially identical" when at least about 70% of the nucleotides (preferably at least about 80%, and most preferably at least about 90 or 95%) are identical.

Two nucleotide sequences are "substantially complementary" when at least about 70% of the nucleotides (preferably at least about 80%, and most preferably at least about 90 or 95%) are able to hydrogen bond to a target sequence.

The term "standard hybridization conditions" refers to salt and temperature conditions substantially equivalent to 5×SSC and 65 C for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20 C below the predicted or determined Tm with washes of higher stringency, if desired.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in a cardiac myocyte feature.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment, as well as a small molecule inhibitor, can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic compositions of the invention are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition of PP2A-mAKAPβ binding desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Because of the necessity for the inhibitor to reach the cytosol, a peptide in accordance with the invention may need to be modified in order to allow its transfer across cell membranes, or may need to be expressed by a vector which encodes the peptide inhibitor. Likewise, a nucleic acid inhibitor (including siRNAs, shRNAs and antisense RNAs) can be expressed by a vector. Any vector capable of entering the cells to be targeted may be used in accordance with the invention. In particular, viral vectors are able to "infect" the cell and express the desired RNA or peptide. Any viral vector capable of "infecting" the cell may be used. A particularly preferred viral vector is adeno-associated virus (AAV).

siRNAs inhibit translation of target mRNAs via a process called RNA interference. When the siRNA is perfectly complementary to the target mRNA, siRNA act by promoting mRNA degradation. shRNAs, as a specialized type of siRNA, have certain advantages over siRNAs that are produced as oligonucleotides. siRNA oligonucleotides are typically synthesized in the laboratory and are delivered to the cell using delivery systems that deliver the siRNA to the cytoplasm. In contrast, shRNAs are expressed as minigenes delivered via vectors to the cell nucleus, where following transcription, the shRNA are processed by cellular enzymes such as Drosha and Dicer into mature siRNA species. siRNAs are usually 99% degraded after 48 hours, while shRNAs can be expressed up to 3 years. Morover, shRNAs can be delivered in much lower copy number than siRNA (5 copies vs. low nM), and are much less likely to produce off-target effects, immune activation, inflammation and toxicity. While siRNAs are suitable for acute disease conditions where high doses are tolerable, shRNAs are suitable for chronic, life threatening diseases or disorders where low doses are desired.

Guidelines for the design of siRNAs and shRNAs can be found in Elbashir (2001) and at various websites including https://www.thermofisher.com/us/en/home/references/ambion-tech-support/rnai-sirna/general-articles/-sirna-design-guidelines.html and http://www.invivogen.com/review-sirna-shrna-design, all of which are hereby incorporated by reference in their entireties. Preferably, the first nucleotide is an A or a G. siRNAs of 25-29 nucleotides may be more effective than shorter ones, but shRNAs with duplex length 19-21 seem to be as effective as longer ones. siRNAs and shRNAs are preferably 19-29 nucleotides. Loop sequences in shRNAs may be 3-9 nucleotides in length, with 5, 7 or 9 nucleotides preferred.

With respect to small molecule inhibitors, any small molecule that inhibits the interaction of PP2A and mAKAPβ may be used. In addition, any small molecules that inhibit the activity of PP2A and/or mAKAPβ may be used.

Small molecules with similar structures and functionalities can likewise be determined by rational and screening approaches.

Likewise, any small molecules that inhibit the expression of PP2A and/or mAKAPβ may be used.

In yet more detail, the present invention is described by the following items which represent preferred embodiments thereof:

1. A method of treating or preventing heart failure with reduced ejection fraction, comprising administering to cardiac cells of a patient a composition that maintains a level of phosphorylation on serum response factor (SRF).
2. The method of Item 1, wherein SRF is phosphorylated on $Ser^{103}$.
3. The method of Item 1, wherein dephosphorylation activity of protein (serine-threonine) phosphatase 2A (PP2A) is inhibited.
4. The method of Item 3, wherein anchoring of PP2A to muscle A-kinase anchoring protein (mAKAPβ) is inhibited.
5. The method of Item 4, wherein the composition comprises a fragment of mAKAPβ.
6. The method of Item 5, wherein the composition comprises an amino acid sequence having at least 90% sequence identity to a fragment of mAKAPβ.
7. The method of Item 5, wherein the composition comprises a fragment of amino acids 2132-2319 of mAKAP.
8. The method of Item 5, wherein the composition comprises amino acids 2132-2319 of mAKAP.
9. The method of Item 4, wherein the composition comprises a fragment of PP2A.
10. The method of Item 4, wherein said composition comprises a vector that encodes a fragment of mAKAP.
11. The method of Item 4, wherein said composition comprises a vector that encodes an amino acid sequence having at least 90% sequence identity to a fragment of mAKAP.
12. The method of Item 10, wherein the vector encodes a fragment of amino acids 2132-2319 of mAKAP.
13. The method of Item 10, wherein the vector encodes amino acids 2132-2319 of mAKAP.
14. The method of Item 10, wherein the vector is adeno-associated virus (AAV).
15. A composition that encodes a molecule that inhibits the anchoring of PP2A to mAKAP.
16. The composition of Item 15, wherein the molecule comprises a fragment of mAKAP.
17. The composition of Item 15, comprising an amino acid sequence having at least 90% sequence identity to a fragment of mAKAP.
18. The composition of Item 16, comprising a fragment of amino acids 2132-2319 of mAKAP.
19. The composition of Item 16, comprising amino acids 2132-2319 of mAKAPβ.
20. The composition of Item 15, comprising a fragment of PP2A.
21. A composition comprising a vector that encodes a molecule that inhibits the anchoring of PP2A to mAKAP.
22. The composition of Item 21, wherein the vector encodes a fragment of mAKAP.
23. The composition of Item 21, wherein the vector encodes an amino acid sequence having at least 90% sequence identity to a fragment of mAKAP.
24. The composition of Item 21, wherein the vector encodes a fragment of amino acids 2132-2319 of mAKAP.
25. The composition of Item 21, wherein the vector encodes amino acids 2132-2319 of mAKAP.
26. The composition of Item 21, wherein the vector encodes a fragment of PP2A.
27. The composition of Item 21, wherein the vector is adeno-associated virus (AAV).

The following examples are provided to aid the understanding of the present invention, the true scope of which is set forth in the appended claims. It is understood that modifications can be made in the procedures set forth without departing from the spirit of the invention.

EXAMPLES

The compositions and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

Example 1

SRF Regulation by mAKAPβ Signalosomes
Materials and Methods

Neonatal Rat Ventricular Myocyte Culture: 1-3 day old Sprague-Dawley rats were decapitated, and the excised hearts placed in 1× ADS Buffer (116 mM NaCl, 20 mM HEPES, 1 mM $NaH_2PO_4$, 5.5 mM glucose, 5.4 mM KCl, 0.8 mM $MgSO_4$, pH 7.35). The atria were carefully removed and the blood washed away. The ventricles were minced and incubated with 15 mL 1× ADS Buffer containing 3.3 mg type II collagenase (Worthington, 230 U/mg) and 9 mg Pancreatin (Sigma) at 37° C. with gentle shaking. After 15 minutes, the dissociated cardiac myocytes were separated by centrifugation at 50 g for 1 minute, resuspended in 4 mL horse serum and incubated at 37° C. with occasional agitation. The steps for enzymatic digestion and isolation of myocytes were repeated 10-12 times to maximize yield. The myocytes were pooled and spun down again at 50 g for 2 minutes and resuspended in Maintenance Medium (DMEM: M199, 4:1) supplemented with 10% horse serum and 5% fetal bovine serum. To remove any contaminating fibroblasts, the cells were pre-plated for 1 hour before plating on gelatin-coated tissue culture plastic ware. This procedure yields >90% pure cardiac myocytes. After 1 day culture, the media was changed to maintenance medium containing 0.1 mM bromodeoxyuridine to suppress fibroblast growth.

Adult rat ventricular myocyte isolation and culture: 2-3 month old rats were anesthetized using Ketamine (80-100 mg/kg) and Xylazine (5-10 mg/kg) IP following 1000 U heparinization for cardiac excision. The heart was transferred immediately into chilled perfusion buffer (NaCl 120 mM, KCl 5.4 mM, $Na_2HPO_4 \cdot 7H_2O$ 1.2 mM, $NaHCO_3$ 20.0 mM, $MgCl_2 \cdot 6H_2O$ 1.6 mM, Taurine 5 mM, Glucose 5.6 mM, 2,3-Butanedione monoxime 10 mM) pre-equilibrated with 95% $O_2$ and 5% $CO_2$. After removal of extraneous tissue, the heart was attached via the aorta to a Harvard Langendorff apparatus cannula. $Ca^{2+}$-free perfusion was used to flush out remaining blood with a constant rate of 8-10 mL/min at 37° C. The heart was then digested through circulatory perfusion with 50 mL perfusion buffer containing 125 mg type II collagenase (Worthington, 245 U/mg), 0.1 mg protease (Sigma type XIV) and 0.1% BSA. After perfusion, the atria were removed and the ventricular myocytes dissociated by slicing and repetitive pipetting. The debris was filtered by a 200 μm nylon mesh, and the myocytes collected by one minute centrifugation at 50 g. $Ca^{2+}$ concentration in the buffer was gradually recovered to 1.8 mM and the myocytes were resuspended in ACCT medium (M199 Medium (Invitrogen 11150-059), Creatine 5 mM, L-carnitine 2 mM, Taurine 5 mM, HEPES 25 mM, 2,3-Butanedione monoxime 10 mM, BSA 0.2% and 1×Insulin-Transferrin-Selenium Supplement) and plated on 10 μg/ml laminin pre-coated dishes. Cells were washed with ACCT medium 1.5 hours after plating and subjected to adenoviral infection or siRNA transfection, in which 100-200 Multiplicity of Infection (MOI) of adenovirus and 100 nmol/L siRNA mixed with Dharmafect1 (Dharmacon) were used, respectively. Adrenergic agonists were added the next day, with biochemical assay and morphological measurement performed after 24 hours of stimulation.

Other Cell Culture: HEK293 and COS-7 cells were maintained in DMEM with 10% FBS and 1% P/S. These cells were transiently transfected with Lipofectamine 2000 (Invitrogen) or infected with adenovirus and Adeno-X Tet-Off virus (Clontech) as suggested by the manufacturers.

Luciferase Assays: 225,000 neonatal rat ventricular myocytes in 24 well dishes were transfected with control or RSK3 specific siRNA oligonucleotides (10 nM) and Dharmafect1 reagent (Thermofisher). The following day, following washing the cells with media, the myocytes were re-transfected with 100 ng SRE-luc (firefly luciferase) and 100 ng −36Prl-rluc (renilla luciferase) reporter plasmids and Transfast reagent for one hour and then cultured in media with 4% horse serum overnight, before washing with media and incubating for one day in the absence or presence of 10 μM PE. Samples were collected in 100 μl PLB and assayed using the Promega Dual Luciferase Kit and a Berthold Centro X luminometer.

Co-Immunoprecipitation: Tissues were homogenized using a Polytron or cells were lysed in IP buffer (50 mM HEPES pH 7.4, 150 mM NaCl, 5 mM EDTA, 10% glycerol, 1% Triton-X 100, 1 mM DTT) with an inhibitor cocktail (1 μg/ml leupeptin, 1 μg/ml pepstatin, 1 mM benzamidine, 1 mM AEBSF, 50 mM NaF, 1 mM sodium orthovanadate). Soluble proteins were separated by centrifugation at 3-10,000 g for 10 minutes. Antibodies and protein-G agarose beads (50% slurry, Upstate) were added to extracts and incubated overnight with rocking at 4° C. Beads were washed four times at 4° C. with IP buffer. Bound proteins were size-fractionated on SDS-PAGE gels and developed by immunoblotting as previously described using a Fujifilm LAS-3000 or GE-A1600 imaging system (46). Protein markers were Precision Plus Protein Standards (Bio-Rad, 1610373).

Immunocytochemistry: Myocytes on coverslips were fixed in 3.7% formaldehyde in PBS for 1 hour, permeabilized with 0.3% Triton X-100, and blocked in PBS containing 0.2% BSA and 1% horse serum. The slides were then sequentially incubated for 1 hour with primary and Alexa fluorescent dye-conjugated specific-secondary antibodies (Invitrogen, 1:1000) diluted in blocking buffer. The slips were washed three times with blocking buffer. 1 μg/mL Hoechst 33258 was included in the last wash stop to label nuclei. Slides were sealed in SlowFade Gold antifade buffer (Invitrogen, S36938) for fluorescent microscopy. Wide-field images were acquired using a Leica DM4000 Microscope.

GST-SRF phosphorylation assays: GST-SRF protein was purified using BL21 *E. coli* and glutathione-sepharose as previously described (Vargas et al. 2012). GST-SRF on beads was incubated with 0.5 μg active recombinant full-length $His_6$-tagged human RSK3 (Millipore 14-462)+/−50 nM BI-D1870 in ATP-containing kinase buffer for 30 minutes. The GST-SRF beads were then either eluted with Laemmlli buffer or washed with PP2A phosphatase buffer and then incubated for an additional 30 minutes in the presence of 50 ng PP2A+/−10 nM okadaic acid before elution with Laemmlli buffer. Equal loading of GST-SRF protein was determined by Ponceau stain and phosphorylation of SRF was detected using a phospho-SRF $S^{103}$-specific antibody.

Plasmid Constructs

SRE-luciferase reporter—SRE-luc was constructed by subcloning two copies of a c-fos SRF response element (TCGAC AGG ATG TCC ATA TTA GGA CAT CTG) (SEQ ID NO:3) (Treisman 1985) in an Xho I site upstream of the −36 bp rat prolactin promoter in a firefly luciferase reporter plasmid as previously described (Kapiloff et al. 1991).

36 Prl-renilla luciferase—An oligonucleotide containing −36-+36 of the rat prolactin promoter with Bgl II and Hind III compatible ends (GATCT CGA AGG TTT ATA AAG TCA ATG TCT GCA GAT GAG AAA GCA GTG GTT CTC TTA GGA CTT CTT GGG GAA GTG TGG TC) (SEQ ID NO:4-) was subcloned into pRL-null (Promega) to provide the control renilla luciferase vector.

mAKAP fragment expression vectors: pS-EGFPC1-mAKAP-1694-1833-mh adenovirus shuttle vector was constructed by subcloning a cDNA encoding a myc, $His_6$, and GFP-tagged mAKAP aa 1694-1833 fragment (RBD) in pEGFPC1 (Clontech) (Li, Kritzer, et al. 2013) into a pTRE shuttle vector previously modified to contain a CMV immediate early promoter. pS-EGFPC1-mh is similarly designed except lacking the mAKAP sequence. pTRE-myc-mAKAP PBD encoding a myc-tagged mAKAP aa 2134-2314 (PBD) fragment was constructed by digesting pTRE-myc-mAKAP containing a full-length, N-terminally myc-tagged mAKAP cDNA with Apa I-Sca I and ligation. pTRE-βgal encoding β-galactosidase control protein was obtained from Clontech. pAcTnTS-EGFP-mAKAP 1694-1833mh plasmid that was used to generate AAV-RBD was constructed by subcloning a NheI-BamHI fragment of pEGFPC1-rmAKAP-1694-1833-mh (Li, Kritzer, et al. 2013) into pAcTnTs provided generously by Dr. Brent French of the University of Virginia (Prasad et al. 2011). pAcTnTs-EGFP-mh plasmid to generate AAV-GFP control virus was generated by digesting pAcTnTS-EGFP-mAKAP 1694-1833mh with Acc65I and BsRGI, blunting, and ligation. Other mAKAP plasmids were as previously described (Pare, Bauman, et al. 2005; Kapiloff, Jackson, and Airhart 2001).

SRF constructs—pFlag-SRF that expressed a Flag-tagged SRF protein was constructed by subcloning a human SRF cDNA from pCGN-SRF (Addgene Plasmid #11977) into the XbaI/EcoRI sites of the pSH160c NFATc1 expression plasmid (Ho et al. 1995). pTRE-Flag-hSRF was constructed by subcloning the Flag-tagged SRF cDNA into pTRE shuttle vector IDC-(Clontech). pTRE-3xHIA-hSRF was constructed by inserting a custom sequence within the SfiI and SanDI sites of pTRE-Flag-hSRF that replaces the Flag tag with 3 tandem HA tags. S103A and S103D mutations were introduced into the pTRE plasmids by site-directed mutagenesis to introduce the sequences ATCGCTGGCAGAG (SEQ I) NO:5-) and GAGCCTGGATGAA (SEQ ID NO:_6) in place of GAGCCTGAGCGAG (SEQ ID NO:7-).pGEX-4T1-FLAG-hSRF for expression of GST-SRF in bacteria was constructed by subcloning a NcoI (blunted)-EcoRI fragment of pTRE-Flag-hSRF into the BamHI (blunted)-EcoRI sites of pGEX-4T1.

RSK3 expression vectors: Plasmids for HA-tagged RSK3 wildtype and S218A mutant and RSK3 fragments are as previously described (Li, Kritzer, et al. 2013). pS-HA-hRSK3 1-42 adenovirus shuttle vector was constructed by subcloning a HA-tagged 1-42 cDNA into the BsaBI and NheI sites of pS-EGFPC1-mh replacing the tagged GFP cDNA.

Adenovirus were prepared using the pTRE shuttle vectors and the Adeno-X Tet-off System (Clontech) via PI-SceI and I-CeuI subcloning and purified after amplification using Vivapure AdenoPACK kits (Sartorius Stedim). These adenovirus conditionally express recombinant protein when co-infected with tetracycline transactivator-expressing virus (adeno-tTA for "tet-off" or reverse tTA for "tet-on"). Some adenovirus were constructed using a modified pTRE shuttle vector (pS) containing a constitutive CMV promoter.

Results

Given the role of RSK3 and mAKAPβ in the determination of concentric myocyte growth, research has focused on the identification of RSK3 cardiac myocyte substrates. The transcription factor serum response factor (SRF) serves important roles in both cardiac development and adult function through the regulation of genes involved in growth and the actin cytoskeleton (Miano 2010). SRF is subject to multiple post-translational modifications (FIG. 19A), including phosphorylation at $Ser^{103}$ (Mack 2011). Because of SRF's prominent role in myocyte regulation and the previously demonstrated phosphorylation of SRF by other RSK family members (Miano 2010; Rivera et al. 1993; Janknecht et al. 1992; Hanlon, Sturgill, and Sealy 2001), SRF was considered to be an effector for RSK3 in cardiac myocytes. Phosphorylation of SRF $Ser^{103}$ by RSK3 was readily confirmed using purified glutathione-S-transferase (GST)-SRF fusion protein (data not shown). SRF contains a conserved MADS (MCM1, agamous, deficiens, SRF) domain that mediates both DNA binding to CArG box [CC(A/T)$_6$GG] serum response elements (SREs) and homo- and hetero-dimerization with other transcription factors (FIG. 19A). Using RSK3 small interfering nucleotides (siRNA) to deplete primary neonatal rat ventricular myocytes cultures (NRVM) of SRF by RNA interference (RNAi), it was determined that loss of RSK3 inhibited SRE-dependent transient reporter activity, including that induced by the α-adrenergic agonist phenylephrine (PE, FIG. 19B). As RSK3 binds the scaffold protein mAKAPβ (Li, Kritzer, et al. 2013), whether SRF might also be associated with mAKAPβ signalosomes, facilitating its phosphorylation was tested. Endogenous mAKAPβ was consistently co-immunoprecipitated with SRF from adult mouse heart extracts using SRF antibodies (FIG. 19C). In addition, SRF and RSK3 can associate in the presence of mAKAPβ when expressed in heterologous cells, forming ternary complexes (FIG. 19D). Accordingly, inhibition of RSK3 and mAKAPβ expression in NRVM inhibited PE-induced SRF $Ser^{103}$ phosphorylation (FIG. 19E). The isoform-specific N-terminal RSK3 domain binds a discrete "RSK3-binding domain" within mAKAPβ at residues 1694-1833 (RBD) (Li, Kritzer, et al. 2013). Expression of a myc-tagged, green fluorescent protein (GFP) RBD-fusion protein that can compete mAKAPβ-RSK3 binding (Li, Kritzer, et al. 2013) inhibited PE-induced SRF $Ser^{103}$ phosphorylation in both NRVM and primary adult rat ventricular myocyte cultures (ARVM, FIG. 19F and data not shown). Similar results were obtained by anchoring disruption using the N-terminal RSK3 peptide (data not shown). These results were corroborated in vivo. SRF $Ser^{103}$ phosphorylation was decreased in hearts obtained from both RSK3 global and mAKAPβ myocyte-specific conditional knock-out mice that were previously described (Kritzer et al. 2014; Li, Kritzer, et al. 2013), as well as in mice expressing RBD in vivo (data not shown). Together these results reveal that SRF is a RSK3 substrate in myocytes whose phosphorylation in response to catecholaminergic stimulation depends upon association with mAKAPβ signalosomes.

mAKAPβ binds two phosphatases, the $Ca^{2+}$/calmodulin-dependent phosphatase calcineurin (PP2B, PPP3) and a protein kinase A (PKA)-activated isoenzyme of PP2A that contains B56δ-subunit (Dodge-Kafka et al. 2010; Li et al. 2010). Treatment of NRVM with the PP1/PP2A inhibitor okadaic acid (OA), but not the calcineurin inhibitor cyclosporin A (CsA) promoted baseline phosphorylation of SRF $Ser^{103}$ (FIG. 19G). Accordingly, purified PP2A readily dephosphorylated SRF $Ser^{103}$ (FIG. 21). Analagous to RSK3, SRF, PP2A, and mAKAPβ form ternary complexes in NRVM, as SRF and PP2A could be co-immunoprecipitated only in the presence of mAKAPβ (FIG. 19H). PP2A binds a C-terminal domain of mAKAPβ (Dodge-Kafka et al. 2010), and expression of the PP2A Binding Domain (myc-PBD, FIG. 4) competed endogenous mAKAPβ-PP2A association in myocytes (FIG. 19I). Consistent with a previously published finding that cAMP activates mAKAPβ-bound PP2A (Dodge-Kafka et al. 2010), PBD expression potentiated the induction of SRF $Ser^{103}$ phosphorylation in ARVM stimulated with the β-adrenergic isoproterenol (Iso, FIG. 19J). In aggregate, these results show that mAKAPβ signalosomes can regulate SRF $Ser^{103}$ phosphorylation in a bidirectional manner in response to different upstream stimuli.

Example 2

SRF $Ser^{03}$ phosphorylation Promotes Concentric Hypertrophy

While both neonatal rat ventricular myocytes (NRVM) and adult rat ventricular myocytes (ARVM) are useful for studying molecular signaling pathways, including α-adrenergic and β-adrenergic induced hypertrophy, the two cellular preparations are significantly different in shape, ultrastructure, and in some circumstances cellular regulation (Peter, Bjerke, and Leinwand 2016). Taking advantage of their roughly cylindrical shape, ARVM was developed as an in vitro model for morphologic hypertrophy more relevant to in vivo cardiac remodeling. Characterization of the RSK3 knock-out mouse suggested that RSK3 was important for concentric hypertrophy (Passariello et al. 2016; Li, Kritzer, et al. 2013). RSK3 overexpression selectively increased the width of cultured ARVM, resulting in a significantly decreased length/width ratio (FIG. 20A,B). This result was similar to that obtained following one day of myocyte culture in the presence of the phenylephrine (PE, FIG. 20C,D). PE induced an increase of 8-10% in width and a decrease of 8-14% in length/width ratio in 24 hours, which compares favorably to the increase of 17-21% in width and the decrease of 14-21% in length/width ratio of mouse myocytes in vivo following two weeks of transverse aortic constriction. Remarkably, expression of a SRF S103D phosphomimetic mutant also increased ARVM width, inducing concentric hypertrophy to the same degree as PE treatment. Conversely, expression of the SRF S103A mutant did not affect basal myocyte size, but inhibited the PE-induced concentric hypertrophy (FIG. 20E,F). This result was phenocopied by expression of the RBD RSK3-anchoring disruptor peptide (FIG. 20G,H) that inhibited SRF Ser$^{103}$ phosphorylation (FIG. 19F). In contrast to PE and RSK3 overexpression, chronic stimulation with the β-adrenergic agonist Iso increased both ARVM length and width, resulting in a more symmetric hypertrophy (FIG. 20I,J), similar to the effect of chronic Iso infusion in vivo (Li, Kritzer, et al. 2013). Like RBD and SRF S103A expression, displacement of PP2A phosphatase from mAKAPβ signalosomes had no effect on basal ARVM morphology. In addition, like SRF S103D expression, PBD anchoring disruptor expression did not enhance nor diminish PE-induced hypertrophy. In contrast, in the presence of Iso, PDB expression promoted ARVM concentric hypertrophy, with the Iso-induced increase in ARVM width and length tending to be greater and lesser, respectively, in the presence of PP2A displacement. This latter result was consistent with the PDB-dependent potentiation of Iso-induced SRF Ser$^{103}$ phosphorylation (FIG. 19J). Taken together, these results support a model in which mAKAPβ-anchored RSK3 and PP2A regulate SRF Ser$^{103}$ phosphorylation that promotes concentric cardiac myocyte hypertrophy.

Example 3

Regulation of PDE4D3 by mAKAPβ-bound PP2A

Antibodies—The following primary antibodies were used for immunoblotting: mouse monoclonal anti-GFP (Santa Cruz; 1:500), mouse monoclonal anti-VSV tag (Sigma: 1:1000), mouse monoclonal anti-mAKAP (Covance, 1:1000), 9E10 mouse anti-myc (Santa Cruz, Inc, 1:500 dilution), polyclonal anti-PP2A-C(Santa Cruz, 1:500), and polyclonal anti-PP1 catalytic subunit (Santa Cruz, Inc, 1:500). A phospho-specific antibody for phospho-PDE4D3 Ser-54 was generated and affinity purified using phosphorylated and non-phosphorylated human PDE4D3 peptides containing residues 70-81 (21st Century Biochemicals) and was used at a dilution of 1:500. Polyclonal B56δ antibodies, both non-phospho-specific and specific for phospho-Ser-566, are as previously described (Ahn et al. 2007).

Expression constructs—Expression vectors for Flag-tagged B56δ, Glutathione-S-transferase (GST) PP2A-A fusion protein, and myc- and green fluorescent protein (GFP)-tagged rat and human mAKAP are as previously described (Ahn et al. 2007; Pare, Bauman, et al. 2005; Kapiloff et al. 1999a; Kapiloff, Jackson, and Airhart 2001). The myc-tagged mAKAP construct deficient in PP2A binding was made by subcloning a cDNA fragment encoding rat mAKAP 1286-2083 generate by PCR into pCMV-Myc (Clontech). mAKAPα and mAKAPβ are two alternatively-spliced isoforms of mAKAP expressed in the heart and brain, respectively (Michel et al. 2005b). mAKAPβ is identical to mAKAPα residues 245-2314; all recombinant mAKAP proteins expressed in this paper are based on mAKAPα. The expression vector used for PDE4D3 throughout this paper was constructed by subcloning a cDNA encoding VSV-tagged PDE4D3 (Dodge et al. 2001) into a GFP-expression vector (Clontech), resulting in a double-tagged PDE4D3 protein.

Immunoprecipitation—HEK293 cells were used in this project as a heterologous system lacking mAKAP in which the various wildtype and mutant proteins could be easily expressed. Cells cultured on 60 mm plates were transfected at 50%-70% confluency by the calcium phosphate method, using 6 μg of each DNA construct per plate. Cells were harvested 24 hours after transfection in 0.5 ml HSE buffer (HEPES, pH 7.4, 150 mM NaCl, 5 mM EDTA, 1% Triton X-100 and protease inhibitors). Supernatants were incubated with 3 μg antibody and 15 μl prewashed protein A- or G-agarose beads. Following overnight incubation at 4° C., the immunoprecipitates were washed three times with the same buffer. Bound proteins were analyzed by immunoblotting.

For immunoprecipitation of endogenous, native mAKAP complexes, adult rat hearts (Pel-Freeze) were homogenized in 10 ml HSE buffer. After centrifugation at 15,000×g for 25 minutes, clarified extracts were immunoprecipitated as above.

PDE assay—PDE activity associated with immunoprecipitated protein complexes was assayed according to the method by Beavo et al. (Beavo, Bechtel, and Krebs 1974). Samples were assayed in 45 μl PDE buffer A (100 mM MOPS, pH 7.5, 4 mM EGTA, 1.0 mg/ml bovine serum albumin) and 50 μl PDE buffer B [100 mM MOPS, pH 7.5, 75 mM MgAc, 1 μM cAMP and 100,000 cpm [$^3$H]cAMP (Dupont, NEN)]. Inhibitors were included as indicated.

Phosphatase Assay—Phosphatase activity was measured according to the method of Ahn et al. using $^{32}$P-labeled histone as substrate (Ahn et al. 2007). Histone was radiolabeled in reactions containing 250 mM MOPS, pH 7.4, 2.5 mM MgAc, 100 mM β-mercaptoethanol, purified PKA catalytic subunit, 1 μM ATP, 20 μM histone, and 1 mCi [γ-$^{32}$P]ATP (6000 Ci/mmol). The reaction was terminated by the addition of 50% TCA, and [$^{32}$P]histone was purified from free radionucleotide by centrifugation. The [$^{32}$P]histone pellet was washed with 1 ml of ether/ethanol/HCL (4:1:0.1) once and 1 ml of ether/ethanol (4:1) three times. The substrate was then suspended in 200 μl PP2A assay buffer (25 mM Tris, pH 7.4, 1 mM DTT, and 10 mM MgCl2) before precipitation with 50% TCA. After repeated washing, the [$^{32}$P]histone was suspended in 200 μl PP2A buffer.

To measure phosphatase activity, immunoprecipitated protein complexes were washed twice in HSE buffer and once in PP2A reaction buffer. The immunoprecipitates were incubated for 30 minutes at 30° C. in 20 μl PP2A assay buffer containing 100,000 cpm [$^{32}$P]histone in the presence and absence of inhibitors. The PP2A inhibitor (Calbiochem) was used at a concentration of 30 nM. Purified I-1 was phosphorylated by PKA before using as a specific PP1 inhibitor. Reactions were terminated by the addition of 100 μl 20% TCA followed by 10 min centrifugation. TCA supernatants containing released $^{32}$PO$_4$ were measured by scintillation counting.

GST-pulldowns—Glutathione resin adsorbed with PP2A-A subunit GST fusion protein or GST control protein were incubated with HEK293 cell extracts. After an overnight incubation, the beads were washed three times. Bound proteins were analyzed by immunoblotting.

Statistics—Each "n" refers to a completely independent experiment performed using separate cultures or heart preparations. All p-values were calculated using a Student's t-test.

Results

Regulation of mAKAP-bound PDE4D3 by an okadaic acid-sensitive phosphatase. A negative feedback loop intrinsic to mAKAP complexes that includes cAMP activation of PKA, PKA phosphorylation and activation of PDE4D3, and PDE4D3-catalyzed cAMP degradation has previously been described (Dodge et al. 2001). PDE4D3 phosphorylation was dependent upon PKA binding to mAKAP. Symmetrically, a mAKAP-bound phosphatase might be responsible for PDE4D3 dephosphorylation. Both PP2A and the $Ca^{2+}$/calmodulin-dependent protein phosphatase calcineurin (PP2B) associate with the mAKAP scaffold in cardiac myocytes (Pare, Bauman, et al. 2005; Kapiloff, Jackson, and Airhart 2001; Li et al. 2009). To begin this study, a heterologous system was used to test whether PP2A or PP2B might dephosphorylate PDE4D3 at Ser-54, the residue within the PDE4D3 Upstream Conserved Region required for PKA activation (Sette and Conti 1996). HEK293 cells over-expressing mAKAP and PDE4D3 were treated with 300 µM okadaic acid (OA) to inhibit PP2A (and protein phosphatase 1 [PP1]) activity or 500 µM cyclosporin A (CsA) to inhibit PP2B activity (FIG. 8A). After immunoprecipitation of protein complexes using a mAKAP-specific antibody, PDE4D3 phosphorylation was assayed by immunoblotting with a phospho-specific antibody to residue Ser-54 had been generated. OA treatment resulted in an increase in the baseline phosphorylation of PDE4D3 Ser-54, while inhibition of PP2B had no effect (FIG. 8A, top panel, lane 2). This increased phosphorylation was further enhanced 1.8 fold when PKA was activated by the addition of the adenylyl cyclase agonist forskolin (Fsk, FIG. 8A, top panel, lane 5). Notably, forskolin alone had no significant effect in the absence of phosphatase inhibition (FIG. 8A, lane 4). Immunoblotting using a non-phospho-specific antibody for PDE4D3 and an antibody for mAKAP demonstrated that two proteins were similarly precipitated under each condition (FIG. 8A, lower panels).

As phosphorylation of PDE4D3 Ser-54 increases phosphodiesterase activity 2 fold (Sette and Conti 1996), whether OA treatment would also increase the activity of mAKAP-bound PDE4D3 was tested. mAKAP complexes were immunoprecipitated from transfected HEK293 cells and assayed for associated phosphodiesterase activity (FIG. 8B). mAKAP-associated phosphodiesterase activity in untreated cells was detected only when mAKAP was co-expressed with PDE4D3 (FIG. 8B, bar 1, and data not shown), consistent with a previous observation that PDE4D3 accounts for all of the phosphodiesterase activity associated with mAKAP in cardiac myocytes (Dodge et al. 2001). In agreement with the results obtained with the phospho-Ser-54 antibody, Fsk treatment alone was unable to significantly stimulate mAKAP-bound PDE4D3 activity in HEK293 cells, while Fsk and OA treatment together synergistically increased PDE4D3 activity (FIG. 8B, bars 3 & 6). CsA had no effect on either basal or stimulated PDE4D3 activity, suggesting that PP2B does not regulate PDE4D3 bound to mAKAP in cells under these conditions. Together, these results show that in this heterologous system, an OA-sensitive phosphatase strongly inhibits both the baseline and Fsk-stimulated phosphorylation and activity of PDE4D3 bound to mAKAP.

The enhancement of phosphodiesterase activity by OA was seen not only with expression of recombinant proteins in HEK293 cells, but also upon isolation of native mAKAP complexes from adult rat heart extracts (FIG. 8C). Both PDE4D3 and PKA are active in purified mAKAP complexes (Dodge et al. 2001). PKA activity present in endogenous mAKAP complexes is responsible for increasing phosphodiesterase activity 2-fold, as was evident upon inhibition of mAKAP-bound PKA with the specific PKA inhibitor PKI (FIG. 8C, bars 2 and 4). Importantly, OA inhibition increased mAKAP-associated phosphodiesterase activity 30% (bars 2 and 3) and 60% when PKA was also inhibited (bars 4 and 5). Taken together, these data demonstrate that an OA-sensitive phosphatase associated with the mAKAP complex is responsible for the dephosphorylation of PDE4D3 and the regulation of phosphodiesterase activity.

Figure 9:
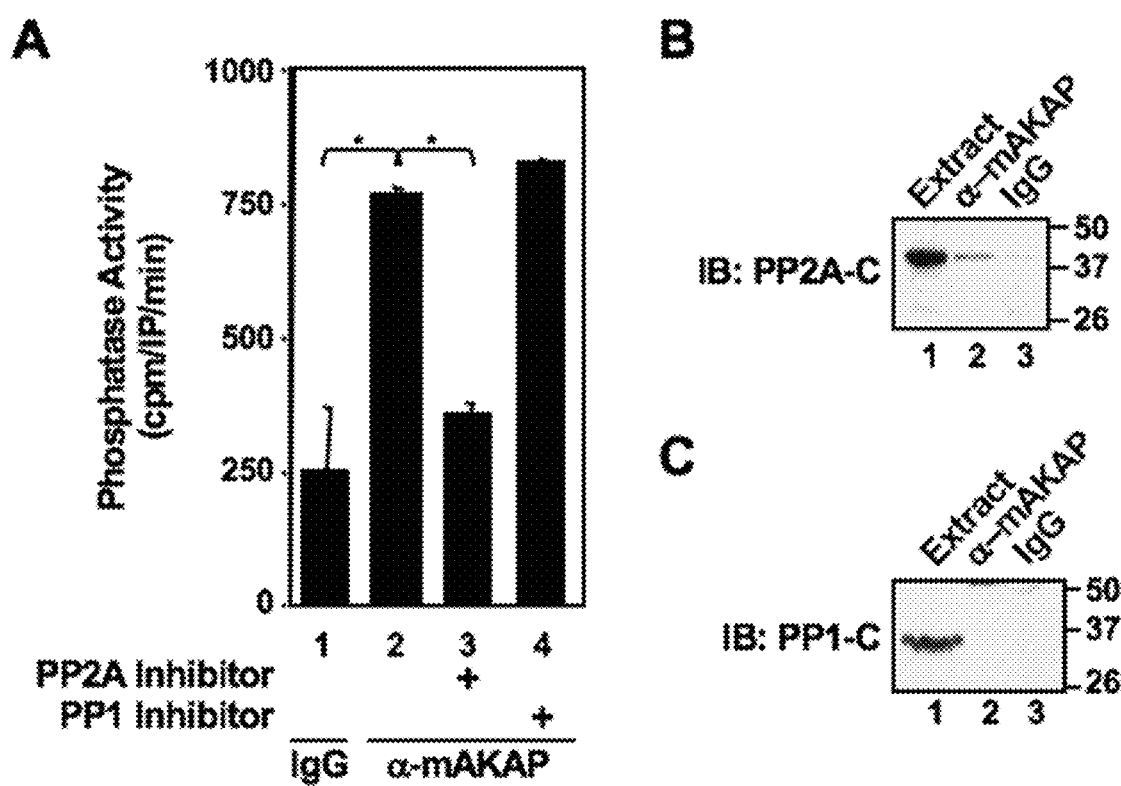
FIG. 9. The protein phosphatase PP2A is associated with the mAKAP scaffold in adult rat heart. A, phosphatase activity associated with protein complexes immunoprecipitated using mAKAP antibody from adult rat heart extracts (500 μg total protein) was assayed using $^{32}$P-labelled histone substrate in the absence or presence of 30 nM PP2A Inhibitor I (Li, Makkinje, and Damuni 1996) and 100 nM PKA-phosphorylated PP1 Inhibitor-1 (Endo et al. 1996). n=3. *p<0.05. B & C, protein complexes were isolated from adult rat heart extracts (2 mg total protein) using control (IgG) or mAKAP-specific antibody. PP2A (panel B) and PP1 (panel C) catalytic subunits in extracts (80 μg) and immunoprecipitates (25% loaded) were detected by immunoblotting. n=3.
Figure 16:
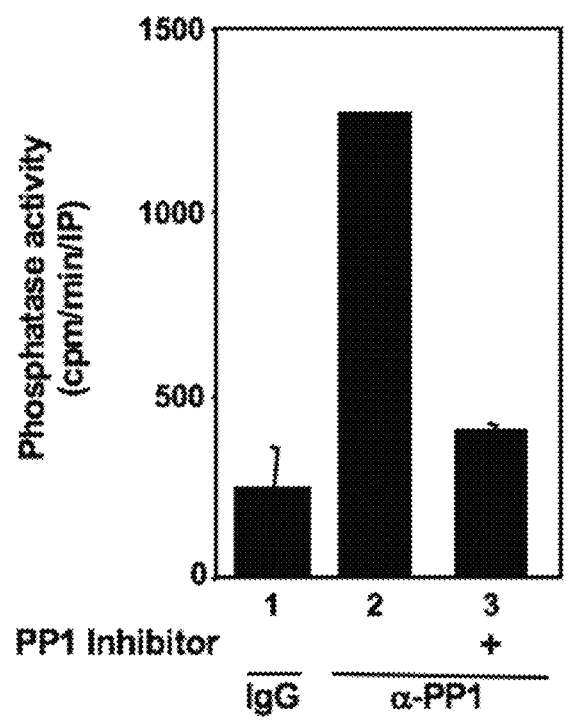
FIG. 16. Confirmation that PKA-phosphorylated I-1 inhibits PP1 activity. Protein complexes were immunoprecipitated from rat heart extracts with PP1 or control IgG antibody, and associated phosphatase activity was assayed using [$^{32}$P]histone substrate in the absence or presence of 100 nM PKA-phosphorylated PP1 Inhibitor-1 (Endo et al. 1996). n=3.

PP2A associates with the mAKAP scaffold in the heart. Having established that an OA-sensitive phosphatase was associated with the mAKAP complex, the phosphatase was identified by co-immunoprecipitation experiments. Phosphatase activity associated with mAKAP complexes isolated from heart cell extracts was measured using [$^{32}$P]histone as a substrate. There was a 3-fold enrichment of phosphatase activity over control IgG immunoprecipitates (FIG. 9A, bars 1 & 2). The mAKAP-associated phosphatase responsible for the immunoprecipitated activity was identified as PP2A, since the phosphatase activity was completely inhibited by 30 nM PP2A Inhibitor I (Li, Makkinje, and Damuni 1996), but not by addition of 100 nM PKA-phosphorylated PP1 Inhibitor-1 (Endo et al. 1996). As a positive control, the PKA-phosphorylated PP1 inhibitor-1 did inhibit PP1 isolated by immunoprecipitation with a PP1 antibody from HEK293 cell extracts (FIG. 16). The mAKAP-associated phosphatase activity was not due to mAKAP-bound PP2B, since no $Ca^{2+}$/calmodulin was included in the phosphatase assay buffer. Confirmation of these results was obtained by immunoblot analysis of mAKAP immunoprecipitates. PP2A-C subunit, but not PP1 catalytic subunit, was detected in mAKAP-specific immunoprecipitates (FIGS. 9B & C).

Figure 12:
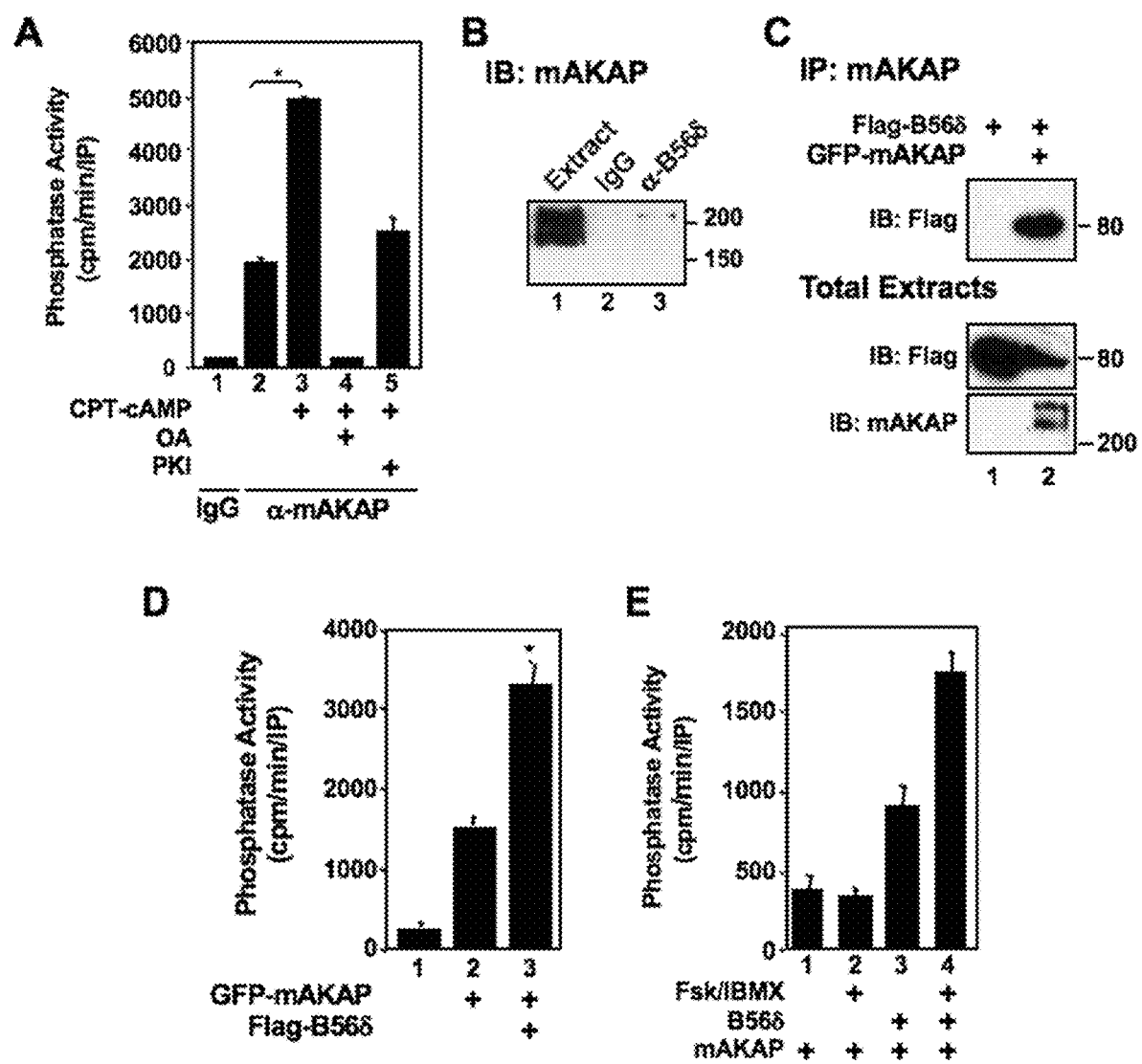
FIG. 12. mAKAP-bound PP2A contains B56δ-subunit and is cAMP-activated. A, protein complexes were immunoprecipitated from adult rat heart extracts (500 μg total protein) using control (IgG) or mAKAP-specific antibody as in FIG. 9B and assayed for associated phosphatase activity. As indicated, the immunoprecipitates were pre-incubated with no addition or with 50 μM CPT-cAMP, 10 nM OA, or 50 nM PKI for 5 minutes before addition of [$^{32}$P]histone substrate. n=3. *p<0.05. B, Endogenous protein complexes were immunoprecipitated from adult heart extract (2 mg total protein) with B56δ and control (IgG) antibodies. mAKAP in 80 μg extract and in the immunoprecipitates (25% loaded) was detected by immunoblot. n=3. C, Flag-tagged B56δ and/or GFP-tagged mAKAP were expressed in HEK293 cells. Protein complexes were immunoprecipitated using a mAKAP antibody. B56δ in the immunoprecipitates (25% loaded) and total extracts (5% loaded) was detected by immunoblotting with a Flag antibody. n=3. D, phosphatase activity associated with mAKAP-antibody immunoprecipitates prepared as in C was assayed using $^{32}$P-labelled histone substrate. n=3. E, HEK293 cells expressing mAKAP and B56δ were treated with 5 μM Fsk and 10 μM IBMX (Fsk/IBMX) for 10 min before immunoprecipitation of protein complexes with mAKAP antibody. Phosphatase activity associated with the immunoprecipitates was assayed using [$^{32}$P]histone substrate. n=3. Note that PP2A B56δ and C-subunit binding to mAKAP was not affected by Fsk/IBMX (see FIG. 13 below).
Figure 17:
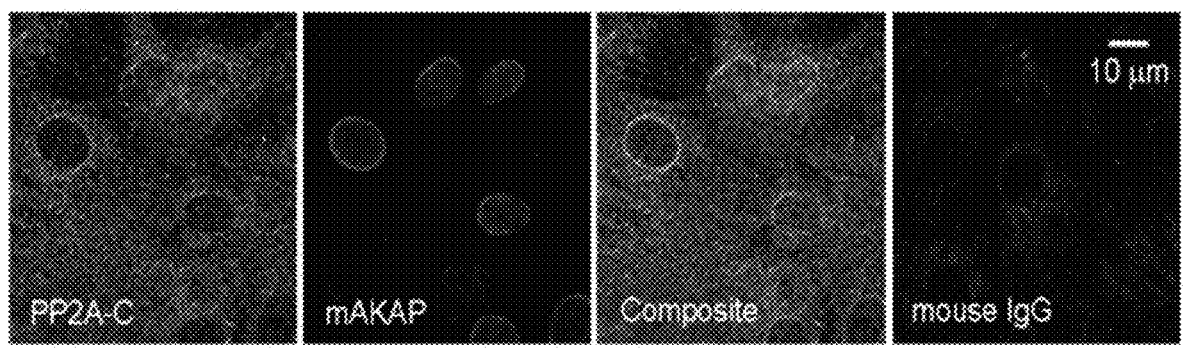
FIG. 17. Distribution of mAKAP and PP2A catalytic subunit in rat neonatal cardiac myocytes. Rat neonatal ventricular myocytes were isolated as previously described (Pare, Easlick, et al. 2005). After treatment with 50 μM phenylephrine for one week to induce myofibrillar organization and mAKAP expression, the cells were fixed and stained with 0.25 μg/ml mouse anti-PP2A-C(green), 0.1 μg/ml OR010 rabbit anti-mAKAP (red) affinity purified antibodies and rhodamine phalloidin (blue in composite image) to show actin myofibrils as previously described (Pare, Easlick, et al. 2005). 4-color Images were acquired on a Zeiss LSM510/UV Confocal Microscope at 400×. Separate PP2A C-subunit and mAKAP images are shown for clarity. PP2A-C subunit was present in a diffuse punctuate pattern in the cytosol, while mAKAP was limited to the location of the nuclear envelope. The presence of PP2A-C subunit staining over the nuclear envelope is consistent with the presence of PP2A-mAKAP complexes (yellow in composite image). Control IgG staining is shown in the right panel. n=3.

Like PKA, PP2A associates with many cellular substrates and is expected to be present in diverse intracellular compartments (Virshup 2000). Confocal fluorescent microscopy of cultured primary neonatal rat cardiomyocytes revealed that PP2A-C subunit is distributed throughout the cytoplasm in a fine punctuate pattern (FIG. 17, green). As found previously, mAKAP was localized primarily to the nuclear envelope (Pare, Easlick, et al. 2005). Consistent with the co-immunoprecipitation of mAKAP and PP2A from adult rat heart extracts, overlap of PP2A and mAKAP staining could be detected at the nuclear envelope (FIG. 17, composite image), supporting the model that a localized signaling complex consisting of discrete pools of PP2A, PKA, and PDE4D3 and the scaffold mAKAP is present in cardiac myocytes.

mAKAP residues 2083-2319 contain the PP2A binding domain. In order to map the PP2A binding site on mAKAP, a bacterially-expressed PP2A-A subunit GST-fusion protein was used to pull down GFP-tagged fragments of mAKAP expressed in HEK293 cells (FIGS. 10A & B). GST-PP2A-A consistently pulled down only fragments of mAKAP containing a domain C-terminal to residue 2085. Both human and rat mAKAP GFP-fusion proteins bound GST-PP2A-A, including rat mAKAP 1835-2312 and human 2085-2319. As a negative control, the GFP-mAKAP fusion proteins did not bind PP1 in HEK293 cells, consistent with the lack of co-immunoprecipitation of PP1 and mAKAP from heart extracts (FIG. 18). To confirm the mapping of the PP2A binding site on mAKAP, myc-tagged mAKAP fragments expressed in HEK293 cells were immunoprecipitated with a myc-tag antibody and assayed for associated PP2A activity (FIG. 10C). mAKAP 1286-2312, but not mAKAP 1286-2083, co-immunoprecipitated with OA-sensitive phosphatase activity. Together, these data show that PP2A binds a C-terminal site within mAKAP that is separate from the binding sites for PKA, PDE4D3, and other known mAKAP-binding proteins (FIG. 10A).

mAKAP-anchored PP2A regulates PDE4D3 phosphorylation in the complex. Data obtained using mAKAP complexes isolated from rat heart extracts implied that mAKAP-bound PP2A regulated PDE4D3 in the complex (FIG. 8C). To test whether PP2A anchoring is required for PDE4D3 dephosphorylation, PDE4D3 was expressed in HEK293 cells and a mAKAP construct containing the binding sites for PDE4D3, PKA and PP2A (myc-mAKAP 1286-2312), or a similar mAKAP construct lacking the PP2A binding site (myc-mAKAP 1286-2083). The cells were stimulated with Fsk and OA, and mAKAP complexes were subsequently isolated by immunoprecipitation. Phosphorylation of mAKAP-bound PDE4D3 was assayed by immunoblotting with the Ser-54 phospho-specific antibody. As was found upon expression of full-length mAKAP (FIG. 8A), phosphorylation of PDE4D3 bound to myc-mAKAP 1286-2312 was detected only when phosphatase activity was suppressed by OA (FIG. 11A, lane 3). Notably, upon expression of myc-mAKAP 1286-2083 which lacked significant PP2A binding (FIG. 11A, lanes 4-6), an increase in the baseline phosphorylation of mAKAP-bound PDE4D3 was detected (0.49±0.19 fold of the level obtained with OA; FIG. 11A, lanes 4 vs. 3). Moreover, upon deletion of the PP2A binding domain, Fsk alone increased phosphorylation of the phosphodiesterase to levels equivalent to that associated with PP2A-containing complexes treated with both Fsk and OA (FIG. 11A, lanes 3, 5, & 6). The changes in PDE4D3 Ser-54 phosphorylation were mirrored by changes in phosphodiesterase activity (FIG. 11B). PDE4D3 activity was 30% higher in myc-mAKAP 1286-2083 immunoprecipitates lacking PP2A than in complexes containing the phosphatase (bar 1 and 4). Importantly, no significant difference in PDE4D3 activity was seen between Fsk stimulation and Fsk stimulation in the presence of OA for the complexes lacking PP2A (bars 5 and 6). These data demonstrate the importance of PP2A anchoring for the regulation of PDE4D3 phosphorylation and activity. Furthermore, they demonstrate that PP2A serves not only to attenuate PKA-activated phosphodiesterase activity, but also to maintain a low basal level of PDE4D3 activity in unstimulated cells.

mAKAP-bound PP2A holoenzyme containing B568subunit is regulated by PKA. PP2A holoenzyme is composed of three subunits, including a core A and C subunit heterodimer and a B subunit that may target the holoenzyme to specific intracellular organelles (Virshup 2000). Three closely related B-subunits have been identified that are expressed in the heart and are localized to the nucleus, B56δ, B56γ1 and B56γ3 (Gigena et al. 2005; McCright et al. 1996). Recent work demonstrated PP2A holoenzyme containing B56δ is regulated by PKA phosphorylation (Ahn et al. 2007). Whether PP2A associated with mAKAP complexes might also be regulated by PKA activity was tested. Native mAKAP complexes were immunoprecipitated from adult rat heart extracts and assayed for associated phosphatase activity (FIG. 12A). mAKAP-associated phosphatase activity was increased 2.5-fold by stimulation of bound PKA with the non-hydrolysable cAMP analog CPT-cAMP (lanes 2 & 3). As controls, all immunoprecipitated phosphatase activity was inhibited by 10 nM OA (lane 4), and the CPT-cAMP-stimulated increase in phosphatase activity was blocked by the addition of the PKA inhibitor PKI (lane 5). Taken together, these data demonstrate that PP2A activity associated with mAKAP complexes in the heart is potentiated by PKA-dependent cAMP signaling.

Because mAKAP-bound PP2A was regulated by PKA activity, whether mAKAP-bound PP2A holoenzyme contained B56δ subunit was tested. Protein complexes were immunoprecipitated from adult rat heart extracts using B56δ and control (IgG) antibody (FIG. 12B). mAKAP was consistently immunoprecipitated with the B56δ antibody. In addition, Flag-tagged B56δ was expressed in HEK293 cells and showed that B56δ was immunoprecipitated with a mAKAP antibody only when co-expressed with (GFP-tagged) mAKAP (FIG. 12C). Finally, the binding of B56δ to mAKAP was shown to recruit PP2A-C subunit to the complex, because mAKAP complexes immunoprecipitated from HEK293 cell extracts were associated with greater phosphatase activity when GFP-mAKAP was co-expressed with Flag-B56δ (FIG. 12D, lanes 2 & 3). Based upon these results, B56δ recruits the PP2A-A/C core heterodimer to mAKAP complexes in the heart, conferring cAMP-dependent phosphatase activity. Accordingly, elevation of intracellular cAMP with Fsk and the phosphodiesterase inhibitor IBMX increased mAKAP-associated phosphatase activity in HEK293 cells, only when mAKAP was co-expressed with B56δ (FIG. 12E).

Figure 11:
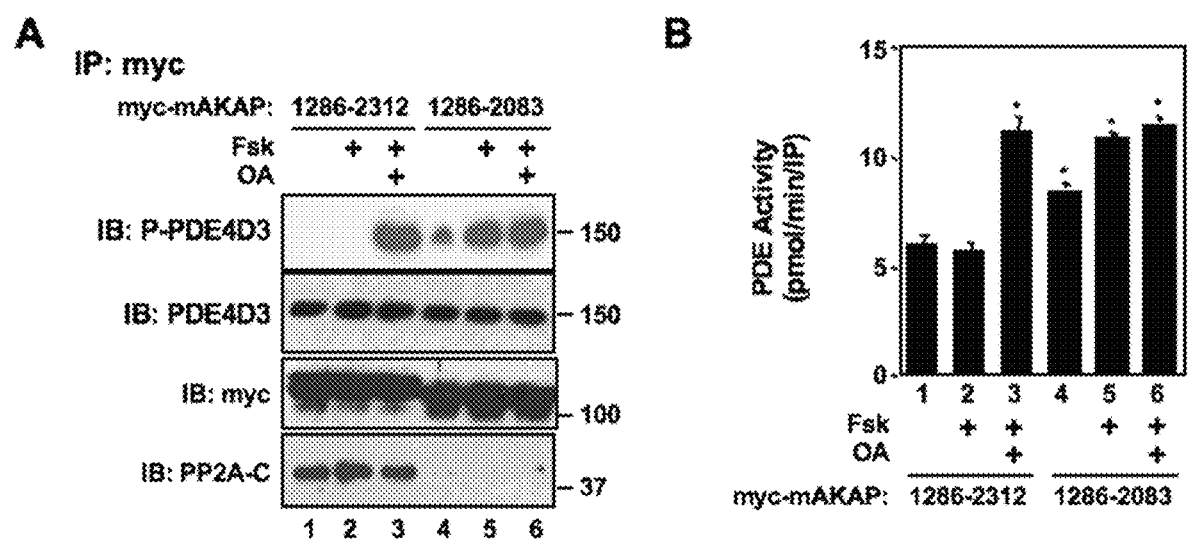
FIG. 11. PP2A association with mAKAP-PDE4D3 complexes is required for inhibition of PDE4D3 phosphorylation. A, HEK293 cells expressing (VSV and GFP-tagged) PDE4D3 and myc-tagged mAKAP 1286-2312 or 1286-2083 lacking the PP2A binding site were treated with 300 μM OA for 30 minutes before stimulation with 5 μM Fsk for 10 minutes. Protein complexes were immunoprecipitated using myc-tag antibody in the presence of phosphatase inhibitors. The phosphorylation state of co-immunoprecipitated PDE4D3 was determined using an antibody specific for phosphorylated PDE4D3 Ser-54 (P-PDE4D3, top panel). Total PDE4D3, myc-mAKAP, and PP2A C-subunit present in the immunoprecipitates were detected using non-phospho-specific antibodies (lower three panels). n=3. B, PDE activity associated with myc-antibody immunoprecipitates isolated from additional cells treated as in A was assayed using [$^3$H]cAMP. n=3.*p<0.05 compared to bar 1.

PKA Binding is required for cAMP-dependent PP2A activity in mAKAP complexes. Previous work found that PKA phosphorylates B56δ on four serine residues (53, 68, 81, 566), and Ser-566 is suggested to account for the induction of PP2A activity (Ahn et al. 2007). Since mAKAP complexes include both PKA and PP2A, association of these molecules into a complex appeared to be important for PP2A phosphorylation, just as PP2A binding to mAKAP was required for PDE4D3 de-phosphorylation (FIG. 11). To test this hypothesis, B56δ was expressed in HEK293 cells with wildtype full-length mAKAP or a full-length mAKAP mutant with an internal deletion of residues 2053-2073 comprising the PKA binding site (ΔPKA, FIG. 13A) (Pare, Bauman, et al. 2005). Following stimulation of the cells with Fsk/IBMX to elevate intracellular cAMP, mAKAP complexes were isolated by immunoprecipitation, and the phosphorylation state of B56δ was determined using a phospho-specific antibody to B56δ Ser-566 (FIG. 13A, top panel) (Ahn et al. 2007). B56δ phosphorylation was detected only after FSK/IBMX treatment and only when B56δ was co-expressed with wildtype mAKAP and not the ΔPKA mutant (FIG. 13A, lanes 2 & 6). As a control, equivalent expression of mutant and wildtype mAKAP and B56δ proteins was demonstrated by immunoblotting with non-phospho-specific antibodies (FIG. 13A, middle and bottom panels). Additionally, wildtype mAKAP was co-expressed with a mutant B56δ form containing alanine residues at each of the four PKA substrate sites (S4A). As expected, Fsk/IBMX stimulation did not induce phosphorylation of B56δ S4A (FIG. 13A lane 4). Since B566 phosphorylation increases PP2A catalytic activity, the mAKAP-antibody immunoprecipitates were assayed for phosphatase activity (FIG. 13B). Consistent with the results obtained using the phospho-specific B56δ antibody, cAMP elevation increased phosphatase activity in mAKAP complexes 1.7 fold (FIG. 13B, lanes 2 & 3). This increase required phosphorylation of B56δ, as complexes containing the S4A mutant showed no augmentation of PP2A activity by increased cAMP (lane 5). Likewise, PKA binding to mAKAP was required to induce PP2A activity, as no increase was obtained when B56δ was co-expressed with the mAKAP ΔPKA mutant scaffold (lane 6). Interestingly, the Fsk/IBMX-induced increase in mAKAP-associated PP2A activity was not due to increased PP2A-C subunit binding to the mAKAP complexes (FIG. 13A, lanes 1 & 2). This result is in accord with an earlier suggestion that B56δ phosphorylation increases PP2A catalytic activity through conformational changes that do not affect holoenzyme formation (Ahn et al. 2007).

Figure 8:
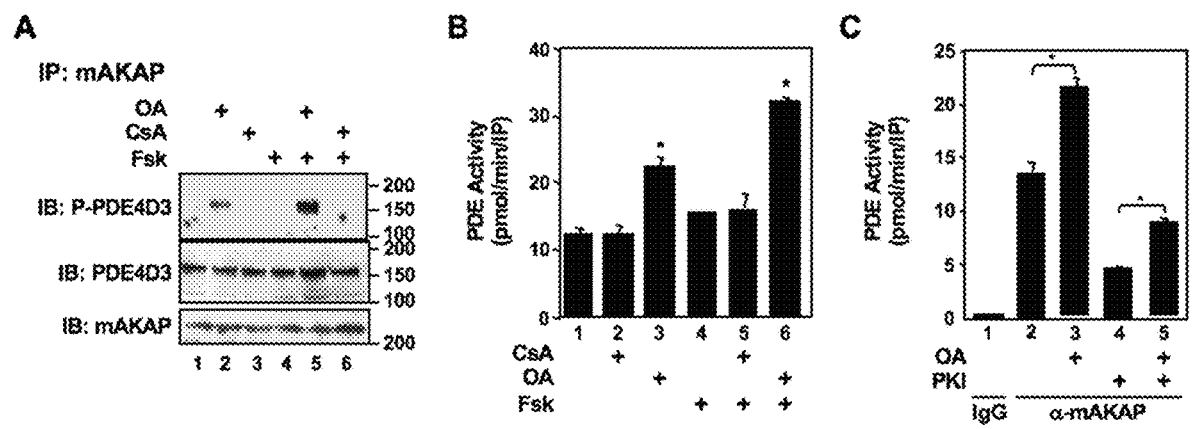
FIG. 8. An okadaic acid-sensitive phosphatase regulates mAKAP-associated PDE4D3. A, transfected HEK293 cells expressing both mAKAP and PDE4D3 were treated with either 300 μM okadaic Acid (OA) or 500 μM cyclosporine A (CsA) for 30 min before stimulation with 5 μM forskolin (Fsk) for 10 min. The phosphorylation state of PDE4D3 present in mAKAP antibody immunoprecipitates was determined using a antibody specific for phosphorylated PDE4D3 Ser-54 (top panel). Total PDE4D3 (middle panel) and mAKAP (bottom panel) present in mAKAP antibody immunoprecipitates were detected using non-phospho-specific antibodies. Note that in these experiments mAKAP was GFP-tagged and PDE4D3 was VSV and GFP-tagged, resulting in increased molecular weights. n=3 B, PDE activity associated with mAKAP antibody immunoprecipitates prepared as in A was assayed using [$^3$H]cAMP substrate. *p<0.05 compared to untreated cells (bar 1). C, endogenous protein complexes were isolated using control (IgG) or mAKAP-specific antibodies from clarified adult rat heart extracts (500 μg total protein). PDE activity associated with the immunoprecipitates was assayed in the presence of 10 nM OA or 50 nM PKI. n=3; *p<0.05.
Figure 13:
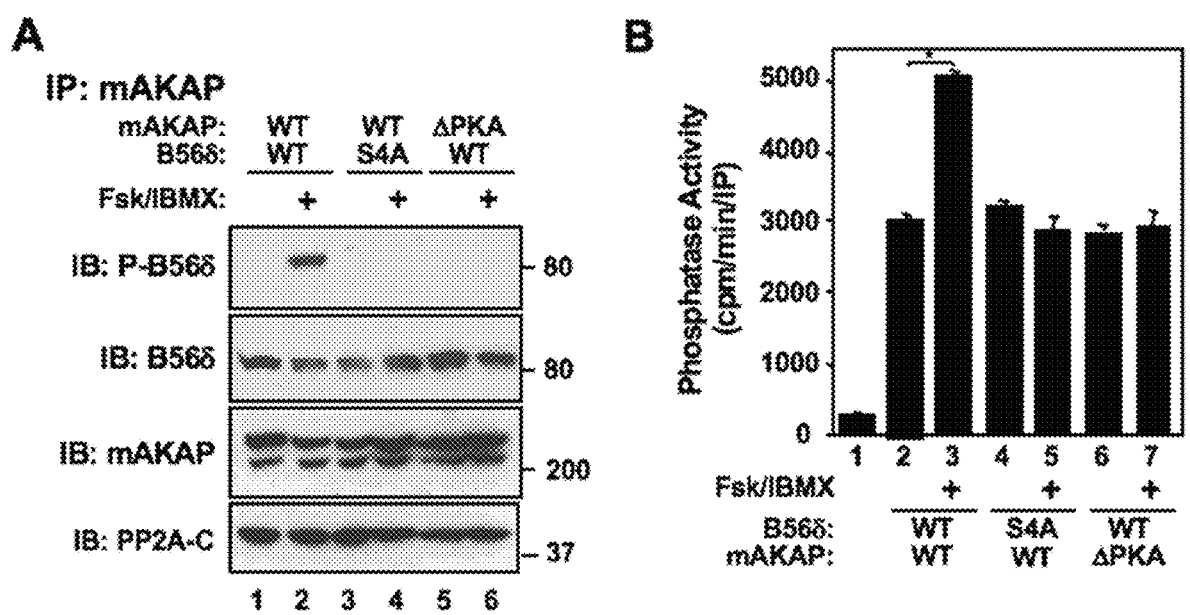
FIG. 13. Phosphorylation of B56δ by PKA increases mAKAP-associated PP2A activity. A, B56δ is phosphorylated on serine residues 53, 68, 81, and 566 by PKA (Ahn et al. 2007). B56δ wildtype or alanine substituted at all four PKA sites (S4A) was co-expressed in HEK293 cells with wildtype mAKAP or a full-length mAKAP mutant lacking the PKA binding site (ΔPKA.
Figure 14:
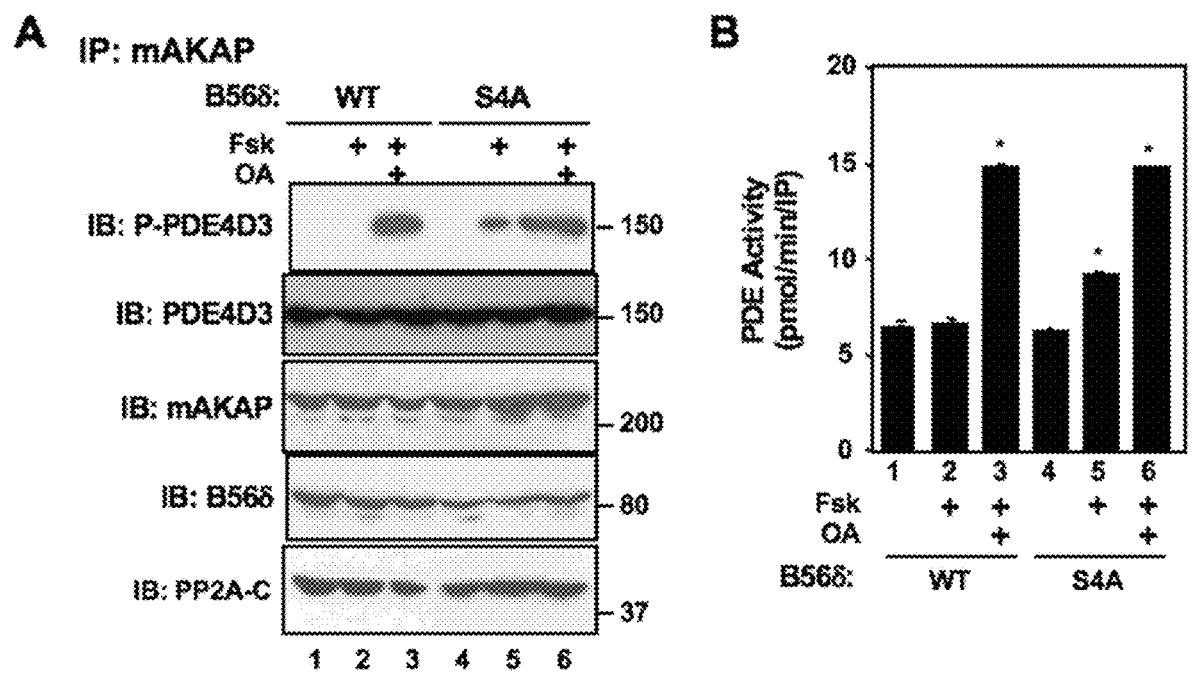
FIG. 14. Phosphorylation of B56δ by PKA enhances the dephosphorylation of mAKAP-associated PDE3D3. A, HEK293 cells expressing (GFP-tagged) mAKAP, (VSV- and GFP-tagged) PDE4D3 and either wild-type B56δ or B56δ S4A mutant at the PKA phosphorylation sites were treated as indicated with 300 μM OA for 30 min before stimulation for 10 min with 5 μM Fsk. Protein complexes were immunoprecipitated with mAKAP antibody in the presence of phosphatase inhibitors. The phosphorylation state of PDE4D3 present in the immunoprecipitates was determined using an antibody specific for phosphorylated PDE4D3 Ser-54 (top panel). Total PDE4D3, mAKAP, B56δ and PP2A-C protein present in the immunoprecipitates were detected using non-phospho-specific antibodies (lower four panels). n=3. B, PDE activity associated with protein complexes isolated from additional cells treated as in A was assayed using [$^3$H]cAMP. n=3. *p<0.05 compared to bar 1.

PP2A regulates PDE4D3 phosphorylation in a PKA-dependent manner. The results described above imply that PP2A dephosphorylation of PDE4D3 in B56δ-mAKAP complexes should be enhanced by PKA-catalyzed phosphorylation of the phosphatase. To address the role of B56δ phosphorylation in the regulation of PDE4D3, PDE4D3 and mAKAP were co-expressed with either wild-type B56δ or the B56δ S4A mutant that is not responsive to PKA. Cells were stimulated with Fsk before isolation of mAKAP complexes. As detected by phospho-specific antibody immunoblot and enzymatic assay, Fsk-stimulation of PDE4D3 Ser-54 phosphorylation and phosphodiesterase activity were only observed for mAKAP complexes containing wildtype B56δ when PP2A was inhibited with OA (FIGS. 14A & B, 1-3), consistent with aforementioned data (FIG. 8). In contrast, expression of B56δ S4A resulted in detectable Fsk-stimulated PDE4D3 phosphorylation (0.39±0.15 fold of Fsk/OA-stimulated cells, FIG. 14A, lane 5) and a concomitant increase in phosphodiesterase activity (FIG. 14B, lane 5), albeit not as strongly as when PP2A activity was directly inhibited by OA (FIGS. 14A & B, lanes 3 & 6). Taken together with the results shown in FIGS. 12 & 13, anchoring of a PKA-stimulated PP2A holoenzyme is responsible for the attenuation of both basal and PKA-stimulated PDE4D3 activity in the mAKAP signaling complex.

Discussion

The results described herein define the biochemical mechanism for the dephosphorylation and inactivation of PKA-phosphorylated PDE4D3 bound by the scaffold protein mAKAP. A PP2A heterotrimer comprised of A-, C-, and B56δ-subunits binds a C-terminal site on mAKAP distinct from the binding sites for other known mAKAP partners (FIG. 10). The association of PP2A with the mAKAP scaffold is of functional significance in two important and novel ways. First, by binding both PP2A and PDE4D3, mAKAP sequesters the phosphatase in close proximity to the phosphodiesterase, allowing for efficient PDE4D3 dephosphorylation and down-regulation (FIG. 11). Second, by binding both PKA and PP2A, mAKAP promotes cAMP-dependent phosphorylation of the PP2A B56δ subunit and induction of PP2A activity (FIG. 13). The relevance of multimolecular signaling complex formation was evident upon expression of mAKAP mutants lacking binding sites for PP2A and PKA.

The concept of phosphatase targeting to generate substrate specificity was first proposed in the mid-1980's with the identification of the glycogen-particle-associated protein as the first PP1-targeting subunit (Bauman and Scott 2002). Since this initial observation, several other phosphatase targeting motifs have been determined (Virshup 2000). AKAPs represent an important mechanism to link phosphatases with their appropriate substrates, and several AKAPs bind protein phosphatases. It has been recently published that mAKAP binds PP2B (calcineurin), and that this interaction is important for PP2B-dependent NFATc3 activation in myocytes (Li et al. 2009). However, PP2B binding to mAKAP does not appear to regulate PDE4D3, as inhibition of PP2B did not affect PDE4D3 Ser-54 phosphorylation or phosphodiesterase activity (FIG. 8). The present data support a unique role for PP2A bound to mAKAP in dephosphorylation of the phosphodiesterase and, as a result, in the control of local cAMP levels.

The overall role of phosphatases in regulating cellular cAMP concentration has yet to be fully explored. In rat adipocytes, PP2A was found to regulate both PDE3B activity and phosphorylation (Resjo et al. 1999). In addition to being phosphorylated by PKA on Ser-54, PDE4D3 is phosphorylated on Ser-579 by MAP kinases, including by ERK5 present in mAKAP complexes (Hoffmann et al. 1999; Dodge-Kafka et al. 2005). Although PP1 does not appear to bind mAKAP (FIG. 9 and FIG. 18), PP1 may dephosphorylate PDE4D3 Ser-579 in other cellular domains, since the addition of purified PP1 to isolated PDE4D3 decreased phosphorylation at this site. Phosphatase(s) are also responsible for the dephosphorylation of mAKAP-bound PDE4D3 at Ser-579, as well as the second PKA site on PDE4D3, Ser-16 (Carlisle Michel et al. 2004).

The anchoring hypothesis suggests that AKAPs function to target the actions of PKA towards specific substrates by localizing both proteins to the same signaling complex. Herein is demonstrated a new target for PKA in the mAKAP complex, the PP2A B56δ-subunit. Previous work found phosphorylation of B56δ stimulated PP2A activity and enhanced de-phosphorylation of DARPP-32 (Ahn et al. 2007). In accordance with these results, stimulation of cardiac myocytes with β-adrenergic receptor agonists increases PP2A activity (De Arcangelis, Soto, and Xiang 2008). The mAKAP scaffold may facilitate this event, as the association of the anchoring protein with both PKA and PP2A is important for the cAMP-enhanced increase in phosphatase activity (FIGS. 11 & 13). Hence, mAKAP has a role in the regulation of phosphatase activity in the heart.

Figure 15:
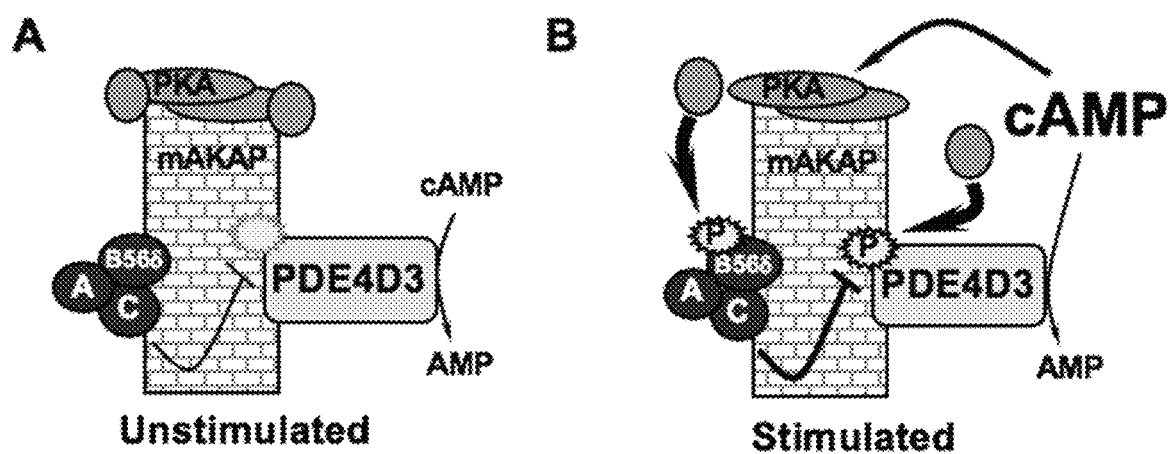
FIG. 15. PKA and PP2A associated with mAKAP complexes coordinately regulate PDE4D3 activity and cAMP degradation. PKA is composed of two regulatory and two catalytic subunits. mAKAP-bound PP2A contains an A, B56δ, and C (catalytic) subunits. A, in unstimulated cells, basal PP2A activity maintains PDE4D3 dephosphorylation, presumably allowing for a more rapid rise in cAMP levels in response to subsequent agonist than if PDE4D3 were phosphorylated and activated. At the same time, basal PDE4D3 activity should maintain low local levels of cAMP, preventing spurious signaling. B, G$_s$-coupled receptor stimulation induces cAMP synthesis, exceeding the rate of cAMP degradation by PDE4D3 and activating mAKAP-bound PKA. PKA phosphorylates and activates both PDE4D3 and PP2A. PDE4D3 activation should limit peak cAMP levels, as well as accelerate the rate of cAMP clearance after GPCR down-regulation. In contrast, PP2A activation opposes PDE4D3 phosphorylation by PKA, attenuating cAMP degradation and contributing to greater, longer lasting cAMP signals.

Based upon these results, a model is proposed in which PP2A serves a dual role in regulating cAMP levels near mAKAP signaling complexes (FIG. 15). First, PP2A in mAKAP complexes should maintain PDE4D3 in a dephosphorylated, minimally active state in the absence of GPCR stimulation (FIG. 15A), presumably allowing for a more rapid rise in cAMP levels in response to agonist. Second, following induction of activating cAMP levels by GPCR stimulation, PKA will phosphorylate both PDE4D3 and PP2A (FIG. 15B). In contrast to the negative feedback on cAMP levels mediated by enhanced PDE4D3 phosphorylation, PKA phosphorylation of PP2A opposes PDE4D3 activation. By inhibiting PDE4D3 phosphorylation, PP2A presumably potentiates and prolongs the actions of local cAMP as part of a positive feedback loop. Thus, in conjunction with the potential inhibition of PDE4D3 by mAKAP-bound ERK5 that has been previously described (not illustrated) (Dodge-Kafka et al. 2005), the mAKAP signaling complex is poised to finely regulate local cAMP levels both by multiple feedback loops intrinsic to the complex, as well as by crosstalk with upstream MAPK signaling pathways. It has been observed that PP2A expression and intracellular localization are altered in heart failure (Reiken et al. 2001; Ai and Pogwizd 2005). Whether PP2A-mediated positive feedback or PDE4D3-mediated negative feedback predominately controls cAMP levels local to mAKAP complexes may ultimately depend both on the stoichiometry of PP2A binding to mAKAP and the relative rates of PDE4D3 phosphorylation and dephosphorylation by PKA and PP2A in disease states.

The present examples demonstrate a novel mechanism by which the scaffold protein mAKAP maintains dynamic regulation of anchored PDE4D3 activity through the association with PDE4D3, PKA and PP2A. Each of the three enzymes plays an important role in the temporal control of cAMP concentration in the vicinity of perinuclear mAKAP complex. This intricate regulation of local cAMP by the mAKAP "signalosome" represents a broader role for AKAPs and phosphatase in the control of cAMP compartmentation.

Example 4

Use of PBD as a Treatment for HFrEF

Heart failure, the common end-stage for cardiac disease, is a syndrome of major public health significance, affecting 6.5 million Americans, including 960,000 new cases each year (Benjamin et al. 2017). Symptomatic heart failure patients can be divided almost evenly into those with reduced (HFrEF) and those with preserved ejection fraction. First-line therapy for heart failure includes angiotensin-converting enzyme (ACE) inhibitors and β-adrenergic receptor blockers (β-blockers) that at least for HFrEF can improve survival and quality of life, as well as reduce mortality (Ponikowski et al. 2016). Despite these and other adjunct therapies, however, 5-year mortality remains about 50% for heart failure (39% in a 2016 post-myocardial infarction study) (Benjamin et al. 2017; Gerber et al. 2016), necessitating the discovery of new therapeutic approaches. Phosphorylation of SRF represents a novel mechanism regulating the transition from compensated hypertrophy to the dilated, failing heart in HFrEF.

As discussed above, expression of SRF S103D both in vitro and in vivo will promote concentric myocyte hypertrophy. In addition, expression of the PP2A anchoring disruptor PBD attenuated the eccentric hypertrophy induced by Iso-treatment of cultured adult myocytes (FIG. 20). These results suggest that SRF $S^{103}$ phosphorylation drives growth in width, while attenuating any elongation of the cardiac myocyte. Given these results and the association of SRF dephosphorylation with systolic dysfunction induced by long term pressure overload (FIG. 33A, E), restoration of normal or increased SRF phosphorylation will prevent the ventricular dilatation resulting in HFrEF in diseases of chronic pressure overload and ischemic heart disease.

Figure 33:
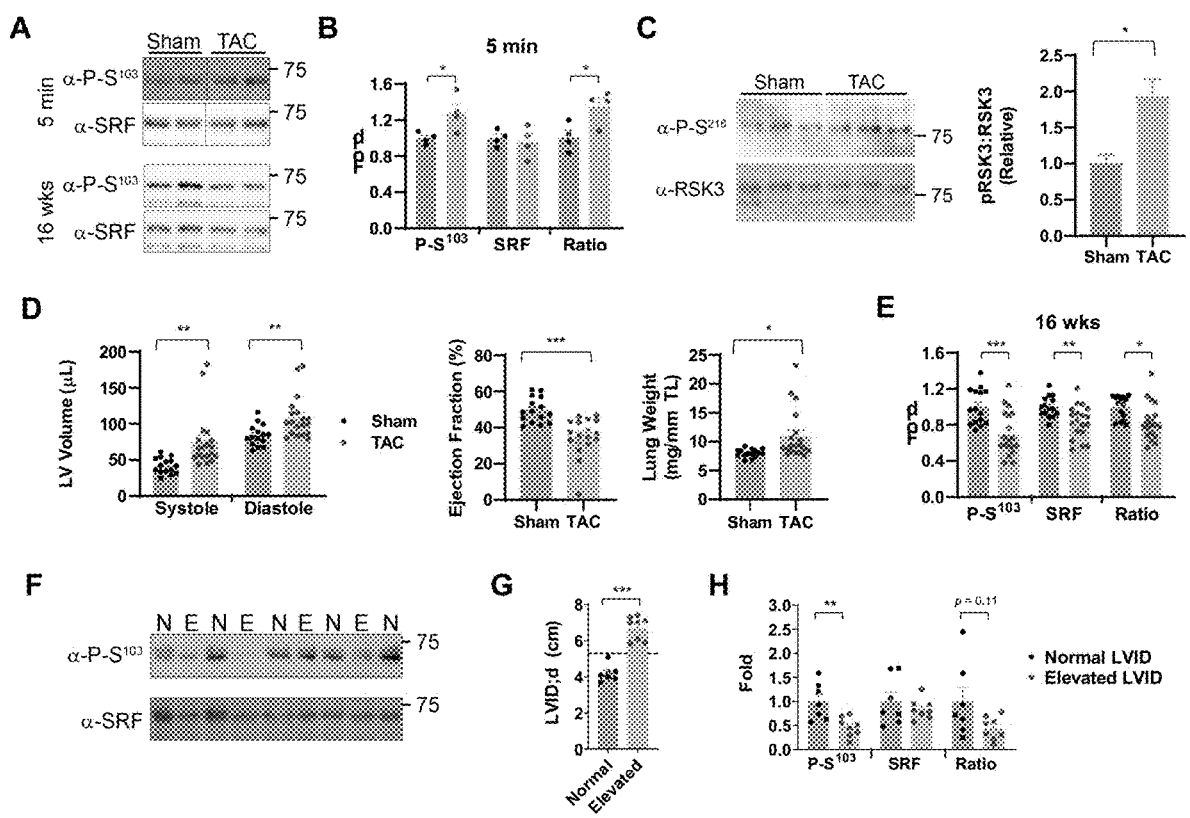
FIG. 33. SRF phosphorylation is decreased in dilated hearts. (A-E) Mouse ventricular protein extracts were assayed for phosphorylated and total SRF 5 min (acute pressure overload, n=4,4) or 16 weeks (heart failure, n=15, 19) following TAC or sham survival surgery. (A) Representative western blots. (B) Densitometry of top panel in A. (C) After 5 min of pressure overload, RSK3 was immunoprecipitated using N-16 RSK3 specific antibody and detected using OR43 RSK3 antibody and a phospho-specific antibody for RSK3 $S^{218}$ that indicates RSK3 activation. The immunoprecipitation-western assay was validated using RSK3$^{-/-}$ mice (not shown). n=3 for each condition. (D) 16 weeks of pressure overload induced heart failure. M-mode echocardiography for left ventricular (LV) volume in diastole and systole and ejection fraction showed that TAC hearts were dilated and had systolic dysfunction. Measurement of wet lung weight (indexed to tibial length) indicating the presence of pulmonary edema showed that TAC mice were in heart failure. (E) Densitometry of bottom panel in A. (F-H) Left ventricular tissue from human patients (including nonischemic and ischemic cardiomyopathies and non-dilated congenital heart disease and controls) were assayed for SRF $S^{103}$ phosphorylation and segregated by normal (<5.3 cm, n=7) or elevated (>5.3 cm, n=8) left ventricular interior diameter in diastole (LVID;d). Equal loading for blots was confirmed using Ponceau S stain for major protein bands (not shown).

Mechanisms that induce "compensatory" concentric hypertrophy early in heart disease predispose the heart to later systolic dysfunction and eventual failure (Schiattarella and Hill 2015). In this regard, targeting of RSK3-mAKAPβ complexes will attenuate cardiac remodeling due to pressure overload and prevent heart failure (Kritzer et al. 2014; Li, Kritzer, et al. 2013). While inhibition of signaling pathways that induce remodeling, including concentric hypertrophy, may be desirable early in disease, the question remains whether efforts to maintain signals promoting concentric and attenuating eccentric myocyte hypertrophy would preserve cardiac volumes and contractility when initiated when the heart is at a stage in the disease process characterized by the eccentric growth and ventricular dilatation leading to HFrEF. Accordingly, maintaining SRF phosphorylation is a strategy to block the eccentric changes in ventricular morphology that typify end-stage disease and HFrEF. The fact that maintaining SRF phosphorylation is a strategy to block the eccentric changes in ventricular morphology that typify end-stage disease and HFrEF is further supported by new observations by the present inventors that SRF phosphorylation is increased in mice subjected to acute pressure overload and reduced in mice and humans undergoing ventricular dilation. Phosphorylated SRF was increased 28% in total left ventricular extracts (which includes about one-third myocytes by cell number) within 5 minutes after induction of pressure overload (FIG. 33 A,B), when RSK3 activation, as detected by $S^{218}$ phosphorylation, was increased 1.9-fold (FIG. 33 C). Remarkably, 16 weeks after transverse aortic constriction surgery, when the hearts were dilated and the mice were in heart failure (FIG. 33 D), phosphorylated SRF was suppressed 30% below that present in sham-operated controls (FIG. 33E). These results are consistent with a phosphatase being responsible for dephosphorylating SRF during the induction of eccentric hypertrophy, opposing RSK3-catalyzed phosphorylation. The relevance of these findings to human disease was assessed using patient tissue samples. When compared to SRF $Ser^{103}$ phosphorylation in left ventricular tissue from patients with normal left ventricular interior diameter, SRF $Ser^{103}$ phosphorylation in patients with dilated hearts was reduced 53% (p=0.005, FIG. 33F-H).

Improved ventricular geometry, i.e., decreased LV internal diameters due to less elongated myocytes and/or increased LV wall thickness due to wider myocytes, will decrease wall stress (Law of LaPlace) and improve systolic function in the heart prone to HFrEF. The prevention of systolic dysfunction has been obtained for a new AAV gene therapy vector based upon expression of the mAKAPβ-derived PBD (FIG. 22).

Treatment of Myocardial Infarction. Coronary heart disease is a leading cause of HFrEF (Writing Group et al. 2016). 8-week old C57BL/6 WT mice were subjected to permanent LAD ligation or sham thoracotomy. Two days post-operatively, heart function was evaluated by echocardiography and the mice were randomized by EF and body weight (FIG. 23B). Two cohorts of mice to be treated with either AAVsc.myc-PBD (n=8) or AAVsc.GFP (n=5) were defined that had average ejection fraction=34% 2-days after LAD ligation (FIG. 23D). Mice were injected via the tail vein 3 days post-operatively with $5\times10^{11}$ vg. While control GFP mice exhibited progressively decreased ejection fraction (EF to 21%), PBD mice exhibited long term restoration of systolic function (EF at 8 weeks post-operatively=43%; p<0.0001). In addition, AAVsc.myc-PBD treated mice had reduced left ventricular volumes consistent with improved cardiac function (systole-69 μl for PBD vs 156 μl for GFP, p<0.001; diastole-118 μl vs.192 μl; p<0.001). At end-point, gravimetrically, ventricular and atrial hypertrophy were reduced (p=0.053 and 0.024, respectively, indexed to tibial length, FIG. 23C), and pulmonary edema, a sign of heart failure, tended to be improved (p=0.078). These results demonstrate that PP2A anchoring disruptor therapy, that displaces PP2A from mAKAPβ where it can dephosphorylate SRF, constitutes a novel therapeutic approach for the prevention of heart failure with reduced ejection fraction in ischemic heart disease.

Methods:

General Method for Ligation of the Left Coronary Artery: The mice were anesthetized with 5% isoflurane for induction and then 2.5-3% for maintenance. Orotracheal intubation was performed using a 16G catheter, and the mouse then ventilated mechanically using a minivent ventilator. The skin over the site of left lateral thoracotomy was prepped and draped in sterile fashion using providone-iodine 10% solution. A heating pad was used to keep mice warm during procedures to prevent heat loss. Surgically sterile non-medicated ophthalmic ointment was applied to the eyes preoperatively to prevent corneal drying. Surgery was performed under microscope view. Once adequate sedation was achieved, the chest was opened via left lateral thoracotomy at the fourth intercostal space. If muscle bleeding was present, hemostasis was achieved by the using a thermal cauterizer (e.g. fine tip Bovie). A 3 mm retractor was used to separate the ribs. Following pericardiotomy, the left coronary artery was ligated with a 7-0 prolene suture to produce an anterior MI. The chest was closed in 3 layers with 5-0 absorbable suture (muscle) and silk 6-0 (for 2 ligatures in the ribs and for the skin). Buprenorphine slow release (Bup-SR-LAB) 0.5-1 mg/kg s.c. was administered in a single dose immediately after surgery to control pain for 72 hr. Fluid replacement was administered immediately after surgery (e.g. Sterile saline solution 0.9%, IP). The mice were allowed to recover until alert and active. Sham-operated mice that experience all but the placement of the coronary artery ligature served as controls.

Echocardiography: Mice minimally anesthetized with 1-2% isoflurane were studied using a Vevo 2100®, High-Resolution Imaging System (VisualSonics). M-mode images were obtained for mice under anesthesia at various time-points. Posterior wall and anterior wall diastolic and systolic thicknesses and left ventricular cavity end-diastolic (LVEDD) and end-systolic diameters (LVESD) were measured, permitting estimation of LV volumes, fractional shortening and ejection fraction.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

REFERENCES

Using siRNA for gene silencing is a rapidly evolving tool in molecular biology, ThermoFisher Scientific, retrieved Jun. 16, 2017 <https://http://www.thermofisher.com/us/en/home/references/ambion-tech-support/rnai-sirna/general-articles/-sirna-design-guidelines.html>.

Abrenica B, AlShaaban M, Czubryt M P. The A-kinase anchor protein AKAP121 is a negative regulator of cardiomyocyte hypertrophy. J Mol Cell Cardiol 46: 674-681, 2009.

Ahn J H, McAvoy T, Rakhilin S V, Nishi A, Greengard P, Nairn A C (2007) Protein kinase A activates protein phosphatase 2A by phosphorylation of the B56delta subunit. Proc Natl Acad Sci USA 104:2979-2984.

Ai X, Pogwizd S M (2005) Connexin 43 downregulation and dephosphorylation in nonischemic heart failure is associated with enhanced colocalized protein phosphatase type 2A. Circ Res 96:54-63.

Andino L M, Conlon T J, Porvasnik S L, Boye S L, Hauswirth W W, Lewin A S (2007) Rapid, widespread transduction of the murine myocardium using self-complementary Adeno-associated virus. Genetic vaccines and therapy 5:13.

Anjum R, Blenis J. The RSK family of kinases: emerging roles in cellular signalling. Nat Rev Mol Cell Biol. 2008; 9(10):747-758.

Appert-Collin A, Cotecchia S, Nenniger-Tosato M, Pedrazzini T, Diviani D. The A-kinase anchoring protein (AKAP)-Lbc-signaling complex mediates alpha1 adrenergic receptor-induced cardiomyocyte hypertrophy. Proc Natl Acad Sci USA 104: 10140-10145, 2007.

Avkiran M, Cook A R, Cuello F. Targeting Na+/H+ exchanger regula-tion for cardiac protection: a RSKy approach? Curr Opin Pharmacol. 2008; 8:133-140.

Bain J, Plater L, Elliott M, Shpiro N, Hastie C J, McLauchlan H, Klevernic I, Arthur J S, Alessi D R, Cohen P. The selectivity of protein kinase inhibitors: a further update. Biochem J. 2007; 408:297-315.

Backs J, Worst B C, Lehmann L H, Patrick D M, Jebessa Z, Kreusser M M, Sun Q, Chen L, Heft C, Katus H A, Olson E N (2011) Selective repression of MEF2 activity by PKA-dependent proteolysis of HDAC4. J Cell Biol 195: 403-415.

Bauman A L, Scott J D (2002) Kinase- and phosphatase-anchoring proteins: harnessing the dynamic duo. Nat Cell Biol 4:E203-206.

Bauman A L, Michel J J, Henson E, Dodge-Kafka K L, Kapiloff M S, "The mAKAP signalosome and cardiac myocyte hypertrophy," IUBMB Life. 2007 March; 59(3): 163-9. Review.

Beavo J A, Bechtel P J, Krebs E G (1974) Preparation of homogeneous cyclic AMP-dependent protein kinase(s) and its subunits from rabbit skeletal muscle. Methods Enzymol 38:299-308.

Beene D L, Scott J D. A-kinase anchoring proteins take shape. Curr Opin Cell Biol 19: 192-198, 2007.

Benjamin E J et al. (2017) Heart Disease and Stroke Statistics-2017 Update: A Report From the American Heart Association. Circulation 135:e146-e603.

Benjamin E J et al. (2019) Heart Disease and Stroke Statistics-2019 Update: A Report From the American Heart Association. Circulation 139: e56-e528.

Bers D M (2006) Cardiac ryanodine-receptor phosphorylation: target sites and functional consequences. Biochem J 396:e1-3.

Bers D M. Calcium cycling and signaling in cardiac myocytes. Annu Rev Physiol 70: 23-49, 2008.

Bione S, Maestrini E, Rivella S, Mancini M, Regis S, Romeo G, Toniolo D (1994) Identification of a novel X-linked gene responsible for Emery-Dreifuss muscular dystrophy. Nat Genet 8:323-327.

Black B L, Olson E N (1998) Transcriptional control of muscle development by myocyte enhancer factor-2 (MEF2) proteins. Annu Rev Cell Dev Biol 14:167-196.

Bonne G, Di Barletta M R, Vamous S, Becane H M, Hammouda E H, Merlini L, Muntoni F, Greenberg C R, Gary F, Urtizberea J A, Duboc D, Fardeau M, Toniolo D, Schwartz K (1999) Mutations in the gene encoding lamin N C cause autosomal dominant Emery-Dreifuss muscular dystrophy. Nat Genet 21:285-288.

Bourajjaj M, Armand A S, da Costa Martins P A, Weijts B, van der Nagel R, Heeneman S, Wehrens X H, De Windt L J (2008) NFATc2 is a necessary mediator of calcineurin-dependent cardiac hypertrophy and heart failure. J Biol Chem 283:22295-22303.

Brown J H, Del Re D P, Sussman M A. The Rac and Rho hall of fame: a decade of hypertrophic signaling hits. Circ Res 98: 730-742, 2006.

Burns-Hamuro L L, Ma Y, Kammerer S, Reineke U, Self C, Cook C, Designing isoform-specific peptide disruptors of protein kinase A localization. Proc Natl Acad Sci USA. 2003 Apr. 1; 100(7):4072-7.

Brunton L L, Hayes J S, Mayer S E (1979) Hormonally specific phosphorylation of cardiac troponin I and activation of glycogen phosphorylase. Nature 280:78-80.

Buck M, Chojkier M. C/EBPbeta-Thr217 phosphorylation signaling contributes to the development of lung injury and fibrosis in mice. PLoS One. 2011; 6(10):e25497.

Bueno O F, Wilkins B J, Tymitz K M, Glascock B J, Kimball T F, Lorenz J N, Molkentin J D (2002) Impaired cardiac hypertrophic response in Calcineurin Abeta-deficient mice. Proc Natl Acad Sci USA 99:4586-4591.

Bueno O F, Lips D J, Kaiser R A Wilkins B J, Dai Y S, Glascock B J, Klevitsky R, Hewett T E, Kimball T R, Aronow B J, Doevendans P A, Molkentin J D (2004) Calcineurin Abeta gene targeting predisposes the myocardium to acute ischemia-induced apoptosis and dysfunction. Circ Res 94:91-99.

Burchfield J S, Xie M, Hill J A (2013) Pathological ventricular remodeling: mechanisms: part 1 of 2. Circulation 128:388-400.

Cappola T P. Molecular remodeling in human heart failure. J Am Coll Cardiol 51: 137-138, 2008.

Cariolato L, Cavin S, Diviani D. A-kinase anchoring protein (AKAP)-Lbc anchors a PKN-based signaling complex involved in alpha1-adrenergic receptor-induced p38 activation. J Biol Chem 286: 7925-7937, 2011.

Carlisle Michel J J, Dodge K L, Wong W, Mayer N C, Langeberg L K, Scott J D (2004) PKA-phosphorylation of PDE4D3 facilitates recruitment of the mAKAP signalling complex. Biochem J 381:587-592.

Carlucci A, Lignitto L, Feliciello A. Control of mitochondria dynamics and oxidative metabolism by cAMP, AKAPs and the proteasome. Trends Cell Biol 18: 604-613, 2008.

Carnegie G K, Smith F D, McConnachie G, Langeberg L K, Scott J D. AKAP-Lbc nucleates a protein kinase D activation scaffold. Mol Cell 15: 889-899, 2004.

Carnegie G K, Soughayer J, Smith F D, Pedroja B S, Zhang F, Diviani D, Bristow M R, Kunkel M T, Newton A C, Langeberg L K, Scott J D. AKAP-Lbc mobilizes a cardiac hypertrophy signaling pathway. Mol Cell 32: 169-179, 2008.

Chaturvedi D, Poppleton H M, Stringfield T, Barbier A, Patel T B. Subcellular localization and biological actions of activated RSK1 are determined by its interactions with subunits of cyclic AMP-dependent protein kinase. Mol Cell Biol. 2006; 26:4586-4600.

Chen L, Kurokawa J, Kass R S. Phosphorylation of the A-kinase anchoring protein Yotiao contributes to protein kinase A regulation of a heart potassium channel. J Biol Chem 280: 31347-31352, 2005.

Chen L, Kurokawa J, Kass R S. Phosphorylation of the A-kinase-anchoring protein Yotiao contributes to protein kinase A regulation of a heart potassium channel. J Biol Chem 280: 31347-31352, 2005.

Chen L, Marquardt M L, Tester D J, Sampson K J, Ackerman M J, Kass R S. Mutation of an A-kinase-anchoring protein causes long-Q T syndrome. Proc Natl Acad Sci USA 104: 20990-20995, 2007.

Chen P P, Patel J R, Rybakova I N, Walker J W, Moss R L. Protein kinase A-induced myofilament desensitization to Ca2+ as a result of phosphorylation of cardiac myosin-binding protein C. J Gen Physiol 136: 615-627, 2010.

Christian F, Szaszak M, Friedl S, Drewianka S, Lorenz D, Goncalves A, Furkert J, Vargas C, Schmieder P, Gotz F, Zuhlke K, Moutty M, Gottert H, Joshi M, Reif B, Haase H, Morano I, Grossmann S, Klukovits A, Verli J, Gaspar R, Noack C, Bergmann M, Kass R, Hampel K, Kashin D, Genieser H G, Herberg F W, Willoughby D, Cooper D M, Baillie G S, Houslay M D, von Kries J P, Zimmermann B, Rosenthal W, Klussmann E. Small molecule AKAP-protein kinase A (PKA) interaction disruptors that activate PKA interfere with compartmentalized cAMP signaling in cardiac myocytes. J Biol Chem 286: 9079-9096, 2011.

Clerk A, Cullingford T E, Fuller S J, Giraldo A, Markou T, Pikkarainen S, Sugden P H (2007) Signaling pathways mediating cardiac myocyte gene expression in physiological and stress responses. J Cell Physiol 212:311-322.

Consensus (1987). "Effects of enalapril on mortality in severe congestive heart failure. Results of the Cooperative North Scandinavian Enalapril Survival Study (CONSENSUS)." N Engl J Med 316(23): 1429-1435.

Cuello F, Snabaitis A K, Cohen M S, Taunton J, Avkiran M. Evidence for direct regulation of myocardial Na+/H+ exchanger isoform 1 phosphorylation and activity by 90-kDa ribosomal S6 kinase (RSK): effects of the novel and specific RSK inhibitor fmk on responses to alpha1-adrenergic stimulation. Mol Pharmacol. 2007; 71:799-806.

De Arcangelis V, Soto D, Xiang Y (2008) Phosphodiesterase 4 and phosphatase 2A differentially regulate cAMP/protein kinase a signaling for cardiac myocyte contraction under stimulation ofbeta1 adrenergicreceptor. Mol Pharmacol 74:1453-1462.

Diviani D, Abuin L, Cotecchia S, Pansier L. Anchoring of both PKA and 14-3-3 inhibits the Rho-GEF activity of the AKAP-Lbc signaling complex. EMBO J 23: 2811-2820, 2004.

Diviani D, Dodge-Kafka K L, Li J, Kapiloff M S. A-kinase anchoring proteins: scaffolding proteins in the heart," Am J Physiol Heart Circ Physiol. 2011 November; 301(5): H1742-53.

Dobrev D, Wehrens X H (2014) Role of RyR2 phosphorylation in heart failure and arrhythmias: Controversies around ryanodine receptor phosphorylation in cardiac disease. Circ Res 114:1311-1319; discussion 1319.

Dodge-Kafka, K. L., M. Gildart, J. Li, H. Thakur, and M. S. Kapiloff. 2018. 'Bidirectional regulation of HDAC5 by mAKAPbeta signalosomes in cardiac myocytes', *Journal of Molecular and Cellular Cardiology*, 118: 13-25.

Dodge-Kafka, K. L., A. Bauman, N. Mayer, E. Henson, L. Heredia, J. Ahn, T. McAvoy, A. C. Nairn and M. S. Kapiloff (2010). "cAMP-stimulated protein phosphatase 2A activity associated with muscle A kinase-anchoring protein (mAKAP) signaling complexes inhibits the phosphorylation and activity of the cAMP-specific phosphodiesterase PDE4D3." J Biol Chem 285(15): 11078-11086.

Dodge-Kafka, K. L. and M. S. Kapiloff (2006). "The mAKAP signaling complex: integration of cAMP, calcium, and MAP kinase signaling pathways." Eur J Cell Biol 85(7): 593-602.

Dodge-Kafka, K. L., J. Soughayer, G. C. Pare, J. J. Carlisle Michel, L. K. Langeberg, M. S. Kapiloff and J. D. Scott (2005). "The protein kinase A anchoring protein mAKAP coordinates two integrated cAMP effector pathways." Nature 437(7058): 574-578.

Dodge, K. L., S. Khouangsathiene, M. S. Kapiloff, R. Mouton, E. V. Hill, M. D. Houslay, L. K. Langeberg and J. D. Scott (2001). "mAKAP assembles a protein kinase A/PDE4 phosphodiesterase cAMP signaling module." EMBO J 20(8): 1921-1930.

Diviani D, Soderling J, Scott J D. AKAP-Lbc anchors protein kinase A and nucleates Galpha 12-selective Rho-mediated stress fiber formation. J Biol Chem 276: 44247-44257, 2001.

Dodge K L, Khouangsathiene S, Kapiloff M S, Mouton R, Hill E V, Houslay M D, Langeberg L K, Scott J D. mAKAP assembles a protein kinase A/PDE4 phosphodiesterase cAMP signaling module. EMBO J 20: 1921-1930, 2001.

Dodge-Kafka K L, Bauman A, Kapiloff M S, A-kinase anchoring proteins as the basis for cAMP signaling," Handb Exp Pharmacol. 2008; (186):3-14.

Dodge-Kafka K L, Bauman A, Mayer N, Henson E, Heredia L, Ahn J, McAvoy T, Nairn A C, Kapiloff M S. cAMP-stimulated protein phosphatase 2A activity associated with muscle A kinase-anchoring protein (mAKAP) signaling complexes inhibits the phosphorylation and activity of the cAMP-specific phosphodiesterase PDE4D3. J Biol Chem. 2010; 285:11078-11086.

Dodge-Kafka K L, Kapiloff M S, "The mAKAP signaling complex: integration of cAMP, calcium, and MAP kinase signaling pathways," Eur J Cell Biol. 2006 July; 85(7): 593-602. Epub 2006 Feb. 7. Review.

Dodge-Kafka K L, Langeberg L, Scott J D (2006) Compartmentation of cyclic nucleotide signaling in the heart: the role of A-kinase anchoring proteins. Circ Res 98:993-1001.

duBell W H, Lederer W J, Rogers T B (1996) Dynamic modulation of excitation-contraction coupling by protein phosphatases in rat ventricular myocytes. J Physiol 493 (Pt 3):793-800.

duBell W H, Gigena M S, Guatimosim S, Long X, Lederer W J, Rogers T B (2002) Effects of PP1/PP2A inhibitor calyculin A on the E-C coupling cascade in murine ventricular myocytes. Am J Physiol Heart Circ Physiol 282:H38-48.

Dulhunty A F, Beard N A, Pouliquin P, Casarotto M G (2007) Agonists and antagonists of the cardiac ryanodine receptor: potential therapeutic agents? Pharmacol Ther 113:247-263.

Dummler B A, Hauge C, Silber J, Yntema H G, Kruse L S, Kofoed B, Hemmings B A, Alessi D R, Frodin M. Functional characterization of human RSK4, a new 90-kDa ribosomal S6 kinase, reveals constitutive activation in most cell types. J Biol Chem. 2005; 280:13304-13314

Edgley A J, Krum H, Kelly D J. Targeting fibrosis for the treatment of heart failure: a role for transforming growth factor-beta. Cardiovasc Ther. 2012; 30(1):e30-40.

Eide T, Coghlan V, Orstavik S, Holsve C, Solberg R, Skalhegg B S, Lamb N J, Langeberg L, Fernandez A, Scott J D, Jahnsen T, Tasken K. Molecular cloning, chromosomal localization, and cell cycle-dependent subcellular distribution of the A-kinase anchoring protein, AKAP95. Exp Cell Res 238: 305-316, 1998.

Elbashir S M, Martinez J, Patkaniowska A, Lendeckel W, Tuschl T, Functional anatomy of SiRNAs for mediating efficient RNAi in Drosophila melanogaster embryo lysate, The EMBO Journal, Vol. 20, No. 23, pp. 6877-6888, 2001.

Endo S, Zhou X, Connor J, Wang B, Shenolikar S (1996) Multiple structural elements define the specificity of recombinant human inhibitor-1 as a protein phosphatase-1 inhibitor. Biochemistry 35:5220-5228.

Escobar M, Cardenas C, Colavita K, Petrenko N B, Franzini-Armstrong C. Structural evidence for perinuclear calcium microdomains in cardiac myocytes. J Mol Cell Cardiol 50: 451-459, 2011.

Fabiato A. Calcium-induced release of calcium from the cardiac sarco-plasmic reticulum. Am J Physiol Cell Physiol 245: C1-C14, 1983.

Farah C S, Reinach F C. The troponin complex and regulation of muscle contraction. FASEB J 9: 755-767, 1995.

Fatkin D, MacRae C, Sasaki T, Wolff M R, Porcu M, Frenneaux M, Atherton J, Vidaillet H J, Jr., Spudich S, De Girolami U, Seidman J G, Seidman C, Muntoni F, Muehle G, Johnson W, McDonough B (1999) Missense mutations in the rod domain of the lamin N C gene as causes of dilated cardiomyopathy and conduction-system disease. N Engl J Med 341:1715-1724.

Faul C, Dhume A, Schecter A D, Mundel P. Protein kinase A, Ca2+/calmodulin-dependent kinase II, and calcineurin regulate the intracellular trafficking of myopodin between the Z-disc and the nucleus of cardiac myocytes. Mol Cell Biol 27: 8215-8227, 2007.

Fink M A, Zakhary D R, Mackey J A, Desnoyer R W, Apperson-Hansen C, Damron D S, Bond M. AKAP-mediated targeting of protein kinase a regulates contractility in cardiac myocytes. Circ Res 88: 291-297, 2001.

Fischmeister R, Castro L R, Abi-Gerges A, Rochais F, Jurevicius J, Leroy J, Vandecasteele G (2006) Compartmentation of cyclic nucleotide signaling in the heart: the role of cyclic nucleotide phosphodiesterases. Circ Res 99:816-828.

Fodstad H, Swan H, Laitinen P, Piippo K, Paavonen K, Viitasalo M, Toivonen L, Kontula K. Four potassium channel mutations account for 73% of the genetic spectrum underlying long-Q T syndrome (LQTS) and provide evidence for a strong founder effect in Finland. Ann Med 36, Suppl 1: 53-63, 2004.

Francis S H, Corbin J D. Structure and function of cyclic nuleotide-dependent protein kinases. Annu Rev Physiol 56: 237-272, 1994.

Fraser I D, Tavalin S J, Lester L B, Langeberg L K, Westphal A M, Dean R A, Marrion N V, Scott J D. A novel lipid-anchored A-kinase anchoring protein facilitates cAMP-responsive membrane events. EMBO J 17: 2261-2272, 1998.

Frey N, Katus H A, Olson E N, Hill J A. Hypertrophy of the heart: a new therapeutic target? Circulation 109: 1580-1589, 2004.

Friday B B, Mitchell P O, Kegley K M, Pavlath G K (2003) Calcineurin initiates skeletal muscle differentiation by activating MEF2 and MyoD. Differentiation 71:217-227.

Fuller M D, Emrick M A, Sadilek M, Scheuer T, Catterall W A. Molecular mechanism of calcium channel regulation in the fight-or-flight response. Sci Signal 3: ra70, 2010.

Gaffin R D, Pena J R, Alves M S, Dias F A, Chowdhury S A, Heinrich L S, Goldspink P H, Kranias E G, Wieczorek D F, Wolska B M. Long-term rescue of a familial hypertrophic cardiomyopathy caused by a mutation in the thin filament protein, tropomyosin, via modulation of a calcium cycling protein. J. Mol. Cell. Cardiol. 2011.

Gao T, Yatani A, Dell'Acqua M L, Sako H, Green S A, Dascal N, Scott J D, Hosey M M. cAMP-dependent regulation of cardiac L-type Ca2+ channels requires membrane targeting of PKA and phosphorylation of channel subunits. Neuron 19: 185-196, 1997.

Gao Y, Dickerson J B, Guo F, Zheng J, Zheng Y. Rational design and characterization of a Rac GTPase-specific small molecule inhibitor. Proc Natl Acad Sci USA 101: 7618-7623, 2004.

Gelb B D, Tartaglia M. RAS signaling pathway mutations and hypertro-phic cardiomyopathy: getting into and out of the thick of it. J Clin Invest. 2011; 121:844-847.

GentilucciL, TolomelliA, SquassabiaF.Peptidesandpeptidomimetics in medicine, surgery and biotechnology. Curr Med Chem 13: 2449-2466, 2006.

Gerber, Y., S. A. Weston, M. Enriquez-Sarano, C. Berardi, A. M. Chamberlain, S. M. Manemann, R. Jiang, S. M. Dunlay and V. L. Roger (2016). "Mortality Associated With Heart Failure After Myocardial Infarction: A Contemporary Community Perspective." Circ Heart Fail 9(1): e002460.

Gigena M S, Ito A, Nojima H, Rogers T B (2005) A B56 regulatory subunit of protein phosphatase 2A localizes to nuclear speckles in cardiomyocytes. Am J Physiol Heart Circ Physiol 289:H285-294.

Go AS et al. (2014) Heart disease and stroke statistics—2014 update: a report from the American Heart Association. Circulation 129:e28-e292.

Gold M G, Lygren B, Dokurno P, Hoshi N, McConnachie G, Tasken K, Carlson C R, Scott J D, Barford D. Molecular basis of AKAP specificity for PKA regulatory subunits. Mol Cell 24: 383-395, 2006.

Goldschmidt-Clermont P J, Seo D M, Wang L, Beecham G W, Liu Z J, Vazquez-Padron R I, Dong C, Hare J M, Kapiloff M S, Bishopric N H, Pericak-Vance M, Vance J M, Velazquez O C, "Inflammation, stem cells and atherosclerosis genetics," Curr Opin Mol Ther. 2010 December; 12(6):712-23. Review.

Good M C, Zalatan J G, Lim W A. Scaffold proteins: hubs for controlling the flow of cellular information. Science. 2011; 332:680-686.

Gould K L, Bretscher A, Esch F S, Hunter T. cDNA cloning and sequencing of the protein-tyrosine kinase substrate, ezrin, reveals homology to band 4.1. EMBO J 8: 4133-4142, 1989. Gray P C, Scott J D, Catterall W A. Regulation of ion channels by cAMP-dependent protein kinase and A-kinase anchoring proteins. Curr Opin Neurobiol 8: 330-334, 1998.

Grossman W, Jones D, McLaurin L P (1975) Wall stress and patterns of hypertrophy in the human left ventricle. J Clin Invest 56:56-64.

Group, Consensus Trial Study. 1987. 'Effects of enalapril on mortality in severe congestive heart failure. Results of the Cooperative North Scandinavian Enalapril Survival Study (CONSENSUS)', *New England Journal of Medicine*, 316: 1429-35.

Guo T, Cornea R L, Huke S, Camors E, Yang Y, Picht E, Fruen B R, Bers D M. Kinetics of FKBP12.6 binding to ryanodine receptors in permeabilized cardiac myocytes and effects on Ca sparks. Circ Res 106: 1743-1752, 2010.

Guo, H., B. Liu, L. Hou, E. The, G. Li, D. Wang, Q. Jie, W. Che and Y. Wei (2015). "The role of mAKAPbeta in the process of cardiomyocyte hypertrophy induced by angiotensin II." Int J Mol Med 35(5): 1159-1168.

Hagemann D, Xiao R P. Dual site phospholamban phosphorylation and its physiological relevance in the heart. Trends Cardiovasc Med 12: 51-56, 2002.

Hanks S K, Quinn A M, Hunter T. The protein kinase family: conserved features and deduced phylogeny of the catalytic domains. Science. 1988; 241:42-52.

Hanlon M, Sturgill T W, Sealy L (2001) ERK2- and p90 (Rsk2)-dependent pathways regulate the CCAAT/enhancer-binding protein-beta interaction with serum response factor. J Biol Chem 276:38449-38456.

Harada H, Becknell B, Wilm M, Mann M, Huang L J, Taylor S S, Scott J D, Korsmeyer S J. Phosphorylation and inactivation of BAD by mitochondria-anchored protein kinase A. Mol Cell 3: 413-422, 1999.

Hayes J S, Brunton L L, Mayer S E (1980) Selective activation of particulate cAMP-dependent protein kinase by isoproterenol and prostaglandin El. J Biol Chem 255: 5113-5119.

Heidenreich, P. A., N. M. Albert, L. A. Allen, D. A. Bluemke, J. Butler, G. C. Fonarow, J. S. Ikonomidis, O. Khavjou, M. A. Konstam, T. M. Maddox, G. Nichol, M. Pham, I. L. Pina, J. G. Trogdon, C. American Heart Association Advocacy Coordinating, T. Council on Arteriosclerosis, B. Vascular, R. Council on Cardiovascular, Intervention, C. Council on Clinical, E. Council on, Prevention and C. Stroke (2013). "Forecasting the impact of heart failure in the United States: a policy statement from the American Heart Association." Circ Heart Fail 6(3): 606-619.

Heineke J, Molkentin J D (2006) Regulation of cardiac hypertrophy by intracellular signaling pathways. Nat Rev Mol Cell Biol 7:589-600.

Hell J W. Beta-adrenergic regulation of the L-type $Ca^{2+}$ channel CaV1.2 by PKA rekindles excitement. Sci Signal 3: pe33, 2010.

Henn V, Edemir B, Stefan E, Wiesner B, Lorenz D, Theilig F, Schmitt R, Vossebein L, Tamma G, Beyermann M, Krause E, Herberg F W, Valenti G, Bachmann S, Rosenthal W, Klussmann E. Identification of a novel A-kinase anchoring protein 18 isoform and evidence for its role in the vasopressin-induced aquaporin-2 shuttle in renal principal cells. J Biol Chem 279: 26654-26665, 2004.

Hill J A, Olson E N. Cardiac plasticity. N Engl J Med 358: 1370-1380, 2008.

Ho S N, Thomas D J, Timmerman L A, Li X, Francke U, Crabtree G R (1995) NFATc3, a lymphoid-specific NFATc family member that is calcium-regulated and exhibits distinct DNA binding specificity. J Biol Chem 270:19898-19907.

Hoffmann R, Baillie G S, MacKenzie S J, Yarwood S J, Houslay M D (1999) The MAP kinase ERK2 inhibits the cyclic AMP-specific phosphodiesterase HSPDE4D3 by phosphorylating it at Ser579. EMBO J 18:893-903.

Houser S R (2014) Role ofRyR2 phosphorylation in heart failure and arrhythmias: protein kinase A-mediated hyperphosphorylation of the ryanodine receptor at serine 2808 does not alter cardiac contractility or cause heart failure and arrhythmias. Circ Res 114:1320-1327; discussion 1327.

Huang L J, Durick K, Weiner J A, Chun J, Taylor S S. D-AKAP2, a novel protein kinase A anchoring protein with a putative RGS domain. Proc Natl Acad Sci USA 94: 11184-11189, 1997.

Huang L J, Durick K, Weiner J A, Chun J, Taylor S S. Identification of a novel dual specificity protein kinase A anchoring protein, D-AKAP1. J Biol Chem 272: 8057-8064, 1997.

Huang L J, Durick K, Weiner J A, Chun J, Taylor S S. Identification of a novel protein kinase A anchoring protein that binds both type I and type II regulatory subunits. J Biol Chem. 1997; 272:8057-8064.

Hulme J T, Ahn M, Hauschka S D, Scheuer T, Catterall W A. A novel leucine zipper targets AKAP15 and cyclic AMP-dependent protein kinase to the C terminus of the skeletal muscle Ca2 channel and modulates its function. J Biol Chem 277: 4079-4087, 2002.

Hulme J T, Lin T W, Westenbroek R E, Scheuer T, Catterall W A. Beta-adrenergic regulation requires direct anchoring of PKA to cardiac CaV1.2 channels via a leucine zipper interaction with A kinase-anchoring protein 15. Proc Natl Acad Sci USA 100: 13093-13098, 2003.

Hulme J T, Westenbroek R E, Scheuer T, Catterall W A. Phosphory-lation of serine 1928 in the distal C-terminal domain of cardiac CaV1.2 channels during beta1-adrenergic regulation. Proc Natl Acad Sci USA 103: 16574-16579, 2006.

Hundsrucker C, Klussmann E. Direct AKAP-mediated protein-protein interactions as potential drug targets. Hand Exp Pharmacol 186: 483-503, 2008.

Hundsrucker C, Krause G, Beyermann M, Prinz A, Zimmermann B, Diekmann O, Lorenz D, Stefan E, Nedvetsky P, Dathe M, Christian F, McSorley T, Krause E, McConnachie G, Herberg F W, Scott J D, Rosenthal W, Klussmann E. High-affinity AKAP7delta-protein kinase A interaction yields novel protein kinase A-anchoring disruptor peptides. Biochem J 396: 297-306, 2006.

Jaakkola P, Mole D R, Tian Y M, Wilson M I, Gielbert J, Gaskell S J, Kriegsheim A, Hebestreit H F, Mukherji M, Schofield C J, Maxwell P H, Pugh C W, Ratcliffe P J. Targeting of HIF-alpha to the von Hippel-Lindau ubiquitylation complex by 02-regulated prolyl hydroxylation. Science 292: 468-472, 2001.

Janknecht R, Hipskind R A, Houthaeve T, Nordheim A, Stunnenberg H G (1992) Identification of multiple SRF N-terminal phosphorylation sites affecting DNA binding properties. EMBO J 11:1045-1054.

Jugdutt B I (2003) Remodeling of the myocardium and potential targets in the collagen degradation and synthesis pathways. Curr Drug Targets Cardiovasc Haematol Disord 3:1-30.

Kamisago M, Sharma S D, DePalma S R, Solomon S, Sharma P, McDonough B, Smoot L, Mullen M P, Woolf P K, Wigle E D, Seidman J G, Seidman C E. Mutations in sarcomere protein genes as a cause of dilated cardiomyopathy. N Engl J Med 343: 1688-1696, 2000.

Kammerer S, Burns-Hamuro L L, Ma Y, Hamon S C, Canaves J M, Shi M M, Nelson M R, Sing C F, Cantor C R, Taylor S S, Braun A. Amino acid variant in the kinase binding domain of dual-specific A kinase-anchoring protein 2: a disease susceptibility polymorphism. Proc Natl Acad Sci USA 100: 4066-4071, 2003.

Kapiloff M S, Chandrasekhar K D, "A-kinase anchoring proteins: temporal and spatial regulation of intracellular signal transduction in the cardiovascular system," Journal Cardiovasc Pharmacol. 2011 October; 58(4):337-8.

Kapiloff M S, Jackson N, Airhart N. mAKAP and the ryanodine receptor are part of a multi-component signaling complex on the cardiomyocyte nuclear envelope. J Cell Sci 114: 3167-3176, 2001.

Kapiloff M S, Piggott L A, Sadana R, Li J, Heredia L A, Henson E, Efendiev R, Dessauer C W, "An adenylyl cyclase-mAKAPbeta signaling complex regulates cAMP levels in cardiac myocytes," J Biol Chem. 2009 Aug. 28; 284(35):23540-6.

Kapiloff M S, Mathis J M, Nelson C A, Lin C R, Rosenfeld M G (1991) Calcium/calmodulin-dependent protein kinase mediates a pathway for transcriptional regulation. Proc Natl Acad Sci US A 88:3710-3714.

Kapiloff M S, Schillace R V, Westphal A M, Scott J D. mAKAP: an A-kinase anchoring protein targeted to the nuclear membrane of differentiated myocytes. J Cell Sci 112: 2725-2736, 1999.

Kato Y, Zhao M, Morikawa A, Sugiyama T, Chakravortty D, Koide N, Yoshida T, Tapping R I, Yang Y, Yokochi T, Lee J D (2000) Big mitogen-activated kinase regulates multiple members of the MEF2 protein family. J Biol Chem 275:18534-18540.

Keely S L (1977) Activation of cAMP-dependent protein kinase without a corresponding increase in phosphorylase activity. Res Commun Chem Pathol Pharmacol 18:283-290.

Keely S L (1979) Prostaglandin El activation of heart cAMP-dependent protein kinase: apparent dissociation of protein kinase activation from increases in phosphorylase activity and contractile force. Mol Pharmacol 15:235-245.

Kehat I, Davis J, Tiburcy M, Accornero F, Saba-El-Leil M K, Maillet M, York A J, Lorenz J N, Zimmermann W H, Meloche S, Molkentin J D. Extracellular signal-regulated kinases 1 and 2 regulate the balance between eccentric and concentric cardiac growth. Circ Res. 2011; 108:176-183.

Kehat I, Molkentin J D. Molecular pathways underlying cardiac re-modeling during pathophysiological stimulation. Circulation. 2010; 122:2727-2735.

Kentish J C, McCloskey D T, Layland J, Palmer S, Leiden J M, Martin A F, Solaro R J. Phosphorylation of troponin I by protein kinase A accelerates relaxation and cross-bridge cycle kinetics in mouse ventric-ular muscle. Circ Res 88: 1059-1065, 2001.

Kido M, Du L, Sullivan C C, Li X, Deutsch R, Jamieson S W, Thistlethwaite P A. Hypoxia-inducible factor 1-alpha reduces infarction and attenuates progression of cardiac dysfunction after myocardial in-farction in the mouse. J Am Coll Cardiol 46: 2116-2124, 2005.

Kim Y, Phan D, van Rooij E, Wang D Z, McAnally J, Qi X, Richardson J A, Hill J A, Bassel-Duby R, Olson E N (2008) The MEF2D transcription factor mediates stress-dependent cardiac remodeling in mice. J Clin Invest 118:124-132.

Kimura T E, Jin J, Zi M, Prehar S, Liu W, Oceandy D, Abe J, Neyses L, Weston A H, Cartwright E J, Wang X. Targeted deletion of the extracel-lular signal-regulated protein kinase 5 attenuates hypertrophic response and promotes pressure overload-induced apoptosis in the heart. Circ Res. 2010; 106:961-970.

Kinderman F S, Kim C, von Daake S, Ma Y, Pham B Q, Spraggon G, Xuong N H, Jennings P A, Taylor S S. A dynamic mechanism for AKAP binding to RII isoforms of cAMP-dependent protein kinase. Mol Cell 24: 397-408, 2006.

Klussmann E, Edemir B, Pepperle B, Tamma G, Henn V, Klauschenz E, Hundsrucker C, Maric K, Rosenthal W. Ht31: the first protein kinase A anchoring protein to integrate protein kinase A and Rho signaling. FEBS Lett 507: 264-268, 2001.

Kodama H, Fukuda K, Pan J, Sano M, Takahashi T, Kato T, Makino S, Manabe T, Murata M, Ogawa S. Significance of ERK cascade compared with JAK/STAT and P13-K pathway in gp130-mediated cardiac hypertrophy. Am J Physiol Heart Circ Physiol. 2000; 279(4):H1635-1644.

Kontaridis M I, Yang W, Bence K K, Cullen D, Wang B, Bodyak N, Ke Q, Hinek A, Kang P M, Liao R, Neel B G. Deletion of Ptpn11 (Shp2) in cardiomyocytes causes dilated cardiomyopathy via effects on the extracellular signal-regulated kinase/mitogen-activated protein kinase and RhoA signaling pathways. Circulation. 2008; 117: 1423-1435.

Kritzer M D, Li J, Dodge-Kafka K, Kapiloff M S, "AKAPs: the architectural underpinnings of local cAMP signaling," J Mol Cell Cardiol. 2012 February; 52(2):351-8.

Kritzer, M. D., J. Li, C. L. Passariello, M. Gayanilo, H. Thakur, J. Dayan, K. Dodge-Kafka and M. S. Kapiloff (2014). "The scaffold protein muscle A-kinase anchoring protein beta orchestrates cardiac myocyte hypertrophic signaling required for the development of heart failure." Circ Heart Fail 7(4): 663-672.

Kumar, D., T. A. Hacker, J. Buck, L. F. Whitesell, E. H. Kaji, P. S. Douglas and T. J. Kamp (2005). "Distinct mouse coronary anatomy and myocardial infarction consequent to ligation." Coron Artery Dis 16(1): 41-44.

Lacana E, Maceyka M, Milstien S, Spiegel S. Cloning and character-ization of a protein kinase A anchoring protein (AKAP)-related protein that interacts with and regulates sphingosine kinase 1 activity. J Biol Chem 277: 32947-32953, 2002.

Layland J, Solaro R J, Shah A M. Regulation of cardiac contractile function by troponin I phosphorylation. Cardiovasc Res 66: 12-21, 2005.

Lechward K, Awotunde O S, Swiatek W, Muszynska G (2001) Protein phosphatase 2A: variety of forms and diversity of functions. Acta Biochim Pol 48:921-933.

Lehnart, S. E., X. H. Wehrens, S. Reiken, S. Warrier, A. E. Belevych, R. D. Harvey, W. Richter, S. L. Jin, M. Conti and A. R. Marks (2005). "Phosphodiesterase 4D deficiency in the ryanodine-receptor complex promotes heart failure and arrhythmias." Cell 123(1): 25-35.

Lester L B, Langeberg L K, Scott J D. Anchoring of protein kinase A facilitates hormone-mediated insulin secretion. Proc Natl Acad Sci USA 94: 14942-14947, 1997.

Li C L, Sathyamurthy A, Oldenborg A, Tank D, Ramanan N (2014) SRF phosphorylation by glycogen synthase kinase-3 promotes axon growth in hippocampal neurons. J Neurosci 34:4027-4042.

Li H, Adamik R, Pacheco-Rodriguez G, Moss J, Vaughan M. Protein kinase A-anchoring (AKAP) domains in brefeldin A-inhibited guanine nucleotide-exchange protein 2 (BIG2). Proc Natl Acad Sci USA 100: 1627-1632, 2003.

Li J, Kritzer M D, Michel J J, Le A, Thakur H, Gayanilo M, Passariello C L, Negro A, Danial J B, Oskouei B, Sanders M, Hare J M, Hanauer A, Dodge-Kafka K, Kapiloff M S, "Anchored p90 ribosomal S6 kinase 3 is required for cardiac myocyte hypertrophy," Circ Res. 2013 Jan. 4; 112(1):128-39.

Li J, Negro A, Lopez J, Bauman A L, Henson E, Dodge-Kafka K, Kapiloff M S. The mAKAPbeta scaffold regulates cardiac myocyte hypertrophy via recruitment of activated calcineurin. J Mol Cell Cardiol 48: 387-394, 2010.

Li J, Negro A, Lopez J, Bauman A L, Henson E, Dodge-Kafka K, Kapiloff M S, "The mAKAPbeta scaffold regulates cardiac myocyte hypertrophy via recruitment of activated calcineurin," J Mol Cell Cardiol. 2010 February; 48(2):387-94.

Li J, Vargas M A, Kapiloff M S, Dodge-Kafka K L, Regulation of MEF2 transcriptional activity by calcineurin/mAKAP complexes," Exp Cell Res. 2013 Feb. 15; 319(4):447-54.

Li, J., S. Aponte Paris, H. Thakur, M. S. Kapiloff, and K. L. Dodge-Kafka. 2019. 'Muscle A-kinase-anchoring protein-beta-bound calcineurin toggles active and repressive transcriptional complexes of myocyte enhancer factor 2D', *Journal of Biological Chemistry*, 294: 2543-54.

Li M, Makkinje A, Damuni Z (1996) Molecular identification of I1PP2A, a novel potent heat-stable inhibitor protein of protein phosphatase 2A. Biochemistry 35:6998-7002.

Liu Q, Hofmann P A (2004) Protein phosphatase 2A-mediated cross-talk between p38 MAPK and ERK in apopfosis of cardiac myocytes. Am J Physiol Heart Circ Physiol 286:H2204-2212.

Lohse M J, Engelhardt S, Eschenhagen T. What is the role of beta-adrenergic signaling in heart failure? Circ Res 93: 896-906, 2003.

Lu J T, Kass R S. Recent progress in congenital long Q T syndrome. Curr Opin Cardiol 25: 216-221, 2010.

Lygren B, Carlson C R, Santamaria K, Lissandron V, McSorley T, Lorenz D, Wiesner B, Rosenthal W, Zaccolo M, Tasken K, Klussmann E. AKAP-complex regulates the $Ca^{2+}$ reuptake into heart sarcoplasmic reticulum. EMBO Rep 8: 1061-1067, 2007.

Lygren B, Tasken K. The potential use of AKAP18delta as a drug target in heart failure patients. Expert Opin Biol Ther 8: 1099-1108, 2008.

Mack C P (2011) Signaling mechanisms that regulate smooth muscle cell differentiation. Arterioscler Thromb Vase Biol 31:1495-1505.

Mackenzie K F, Topping E C, Bugaj-Gaweda B, Deng C, Cheung Y F, Olsen A E, Stockard C R, High Mitchell L, Baillie G S, Grizzle W E, De Vivo M, Houslay M D, Wang D, Bolger G B (2008) Human PDE4A8, a novel brain-expressed PDE4 cAMP-specific phosphodiesterase that has undergone rapid evolutionary change. Biochem J 411:361-369.

MacKenzie S J, Baillie G S, McPhee I, Bolger G B, Houslay M D (2000) ERK2 mitogen-activated protein kinase binding, phosphorylation, and regulation of the PDE4D cAMP-specific phosphodiesterases. The involvement of COOH-terminal docking sites and NH2-terminal UCR regions. J Biol Chem 275:16609-16617.

Maloney D J, Hecht S M. Synthesis of a potent and selective inhibitor of p90 Rsk. Org Lett. 2005; 7:1097-1099.

Maron B J, Maron M S. Hypertrophic cardiomyopathy. Lancet. 2013; 381(9862):242-255.

Maruyama Y, Nishida M, Sugimoto Y, Tanabe S, Turner J H, Kozasa T, Wada T, Nagao T, Kurose H. Galpha(12/13) mediates alpha(1)-adrenergic receptor-induced cardiac hypertrophy. Circ Res 91: 961-969, 2002.

Martinez, E. C., C. L. Passariello, J. Li, C. J. Matheson, K. Dodge-Kafka, P. Reigan and M. S. Kapiloff (2015). "RSK3: A regulator of pathological cardiac remodeling." IUBMB Life 67(5): 331-337.

Marx S O, Kurokawa J, Reiken S, Motoike H, D'Armiento J, Marks A R, Kass R S. Requirement of a macromolecular signaling complex for beta adrenergic receptor modulation of the KCNQ1-KCNE1 potassium channel. Science 295: 496-499, 2002.

Marx S O, Reiken S, Hisamatsu Y, Gaburjakova M, Gaburjakova J, Yang Y M, Rosemblit N, Marks A R. Phosphorylation-dependent regulation of ryanodine receptors: a novel role for leucine/isoleucine zippers. J Cell Biol. 2001; 153:699-708.

Marx S O, Reiken S, Hisamatsu Y, Jayaraman T, Burkhoff D, Rosemblit N, Marks A R. PKA phosphorylation dissociates FKBP12.6 from the calcium release channel (ryanodine receptor): defective regulation in failing hearts. Cell 101: 365-376, 2000.

Maxwell P H, Wiesener M S, Chang G W, Clifford S C, Vaux E C, Cockman M E, Wykoff C C, Pugh C W, Maher E R, Ratcliffe P J. The tumour suppressor protein VHL targets hypoxia-inducible factors for oxygen-dependent proteolysis. Nature 399: 271-275, 1999.

Mayers C M, Wadell J, McLean K, Venere M, Malik M, Shibata T, Driggers P H, Kino T, Guo X C, Koide H, Gorivodsky M, Grinberg A, Mukhopadhyay M, Abu-Asab M, Westphal H, Segars J H. The Rho guanine nucleotide exchange factor AKAP13 (BRX) is essential for cardiac development in mice. J Biol Chem 285: 12344-12354, 2010.

Mccartney S, Little B M, Langeberg L K, Scott J D (1995) Cloning and Characterization of a-Kinase Anchor Protein-100 (AkaplOO)—a Protein That Targets a-Kinase to the Sarcoplasmic-Reticulum. J Biol Chem 270:9327-9333.

McConnell B K, Popovic Z, Mal N, Lee K, Bautista J, Forudi F, Schwartzman R, Jin J P, Penn M, Bond M. Disruption of protein kinase A interaction with A-kinase-anchoring proteins in the heart in vivo: effects on cardiac contractility, protein kinase A phosphorylation, and troponin I proteolysis. J Biol Chem 284: 1583-1592, 2009.

McCright B, Rivers A M, Audlin S, Virshup D M (1996) The B56 family of protein phosphatase 2A (PP2A) regulatory subunits encodes differentiation-induced phosphoproteins that target PP2A to both nucleus and cytoplasm. J Biol Chem 271:22081-22089.

McKinsey T A, Kass D A. Small-molecule therapies for cardiac hypertrophy: moving beneath the cell surface. Nat Rev Drug Discov. 2007; 6:617-635.

Miano J M (2010) Role of serum response factor in the pathogenesis of disease. Lab Invest 90:1274-1284.

Michel J J, Townley I K, Dodge-Kafka K L, Zhang F, Kapiloff M S, Scott J D, "Spatial restriction of PDK1 activation cascades by anchoring to mAKAPalpha," Mol Cell. 2005 Dec. 9; 20(5):661-72.

Michele D E, Gomez C A, Hong K E, Westfall M V, Metzger J M. Cardiac dysfunction in hypertrophic cardiomyopathy mutant tropomyosin mice is transgene-dependent, hypertrophy-independent, and improved by beta-blockade. Circ. Res. 2002; 91(3):255-262.

Monovich L, Vega R B, Meredith E, Miranda K, Rao C, Capparelli M, Lemon D D, Phan D, Koch K A, Chapo J A, Hood D B, McKinsey T A (2010) A novel kinase inhibitor establishes a predominant role for protein kinase D as a cardiac class IIa histone deacetylase kinase. FEBS Lett 584:631-637.

Morissette M R, Sah V P, Glembotski C C, Brown J H. The Rho effector, PKN, regulates ANF gene transcription in cardiomyocytes through a serum response element. Am J Physiol Heart Circ Physiol 278: H1769-H1774, 2000.

Muchir A, Bonne G, van der Kooi A J, van Meegen M, Baas F, Bolhuis P A, de Visser M, Schwartz K (2000) Identification of mutations in the gene encoding lamins A/C in autosomal dominant limb girdle muscular dystrophy with atrioventricular conduction disturbances (LGMD1B). Hum Mol Genet 9:1453-1459.

Naga Prasad S V, Barak L S, Rapacciuolo A, Caron M G, Rockman H A. Agonist-dependent recruitment of phosphoinositide 3-kinase to the membrane by beta-adrenergic receptor kinase 1. A role in receptor sequestration. J Biol Chem 276: 18953-18959, 2001.

Naga Prasad S V, Laporte S A, Chamberlain D, Caron M G, Barak L, Rockman H A. Phosphoinositide 3-kinase regulates beta2-adrenergic receptor endocytosis by AP-2 recruitment to the receptor/beta-arrestin complex. J Cell Biol 158: 563-575, 2002.

Nakagami H, Kikuchi Y, Katsuya T, Morishita R, Akasaka H, Saitoh S, Rakugi H, Kaneda Y, Shimamoto K, Ogihara T. Gene polymor-phism of myospryn (cardiomyopathy-associated 5) is associated with left ventricular wall thickness in patients with hypertension. Hypertens Res 30: 1239-1246, 2007.

Nakamura A, Rokosh D G, Paccanaro M, Yee R R, Simpson P C, Grossman W, Foster E. L V systolic performance improves with development of hypertrophy after transverse aortic constriction in mice. Am J Physiol Heart Circ Physiol. 2001; 281:H1104-1112

Nakayama K, Frew I J, Hagensen M, Skals M, Habelhah H, Bhoumik A, Kadoya T, Erdjument-Bromage H, Tempst P, Frappell P B, Bowtell D D, Ronai Z. Siah2 regulates stability of prolyl-hydroxylases, controls HIF1alpha abundance, and modulates physiological responses to hypoxia. Cell 117: 941-952, 2004.

Nauert J B, Klauck T M, Langeberg L K, Scott J D. Gravin, an autoan-tigen recognized by serum from myasthenia gravis patients, is a kinase scaffold protein. Curr Biol 7: 52-62., 1997.

Naya F J, Olson E (1999) MEF2: a transcriptional target for signaling pathways controlling skeletal muscle growth and differentiation. Curr Opin Cell Biol 11:683-688.

Naya F J, Wu C, Richardson J A, Overbeek P, Olson E N (1999) Transcriptional activity of MEF2 during mouse embryogenesis monitored with a MEF2-dependent transgene. Development 126:2045-2052.

Nerbonne J M, Kass R S. Molecular physiology of cardiac repolariza-tion. Physiol Rev 85: 1205-1253, 2005.

Negro A, Dodge-Kafka K, Kapiloff M S, "Signalosomes as Therapeutic Targets," Prog Pediatr Cardiol. 2008 April; 25(1):51-56.

Nichols C B, Rossow C F, Navedo M F, Westenbroek R E, Catterall W A, Santana L F, McKnight G S. Sympathetic stimulation of adult cardiomyocytes requires association of AKAP5 with a subpopulation of L-type calcium channels. Circ Res 107: 747-756, 2010.

Newlon M G, Roy M, Morikis D, Hausken Z E, Coghlan V, Scott J D, Jennings P A (1999) The molecular basis for protein kinase A anchoring revealed by solution NMR. Nat Struct Biol 6:222-227.

Nicol R L, Frey N, Pearson G, Cobb M, Richardson J, Olson E N. Activated MEK5 induces serial assembly of sarcomeres and eccentric cardiac hypertrophy. EMBO J. 2001; 20:2757-2767.

Niggli E, Lederer W J. Voltage-independent calcium release in heart muscle. Science 250: 565-568, 1990. Papa S, Sardanelli A M, Scacco S, Petruzzella V, Technikova-Dobrova Z, Vergari R, Signorile A. The NADH: ubiquinone oxidoreductase (complex I) of the mammalian respiratory chain and the cAMP cascade. J Bioenerg Biomembr 34: 1-10, 2002.

Ohh M, Park C W, Ivan M, Hoffman M A, Kim T Y, Huang L E, Pavletich N, Chau V, Kaelin W G (2000) Ubiquitination of hypoxia-inducible factor requires direct binding to the beta-domain of the von Hippel-Lindau protein. Nat Cell Biol 2:423-427.

Oka T, Xu J, Kaiser R A, Melendez J, Hambleton M, Sargent M A, Lorts A, Brunskill E W, Dorn G W, 2nd, Conway S J, Aronow B J, Robbins J, Molkentin J D. Genetic manipulation of periostin expression reveals a role in cardiac hypertrophy and ventricular remodeling. Circ. Res. 2007; 101(3):313-321.

Okumura, S., G. Takagi, J. Kawabe, G. Yang, M. C. Lee, C. Hong, J. Liu, D. E. Vatner, J. Sadoshima, S. F. Vatner and Y. Ishikawa (2003). "Disruption of type 5 adenylyl cyclase gene preserves cardiac function against pressure overload." Proc Natl Acad Sci USA 100(17): 9986-9990.

Olson G L, Cantor C R, Braun A, Taylor S S. Designing isoform-specific peptide disruptors of protein kinase A localization. Proc Natl Acad Sci USA 100: 4072-4077, 2003.

Pare G C, Bauman A L, McHenry M, Michel J J, Dodge-Kafka K L, Kapiloff M S. The mAKAP complex participates in the induction of cardiac myocyte hypertrophy by adrenergic receptor signaling. J Cell Sci 118: 5637-5646, 2005.

Pare G C, Easlick J L, Mislow J M, McNally E M, Kapiloff M S. Nesprin-1alpha contributes to the targeting of mAKAP to the cardiac myocyte nuclear envelope. Exp Cell Res 303: 388-399, 2005.

Passariello, C. L., J. Li, K. Dodge-Kafka and M. S. Kapiloff (2015). "mAKAP-a master scaffold for cardiac remodeling." J Cardiovasc Pharmacol 65(3): 218-225.

Passariello C L, Martinez E C, Thakur H, Cesareo M, Li J, Kapiloff M S (2016) RSK3 is required for concentric myocyte hypertrophy in an activated Raf1 model for Noonan syndrome. J Mol Cell Cardiol 93:98-105.

Passariello C L, Gayanilo M, Kritzer M D, Thakur H, Cozacov Z, Rusconi F, Wieczorek D, Sanders M, Li J, Kapiloff M S (2013) p90 ribosomal S6 kinase 3 contributes to cardiac insufficiency in alpha-tropomyosin Glu1 80Gly transgenic mice. Am J Physiol Heart Circ Physiol 305:H1010-1019.

Patel H H, Hamuro L L, Chun B J, Kawaraguchi Y, Quick A, Re-bolledo B, Pennypacker J, Thurston J, Rodriguez-Pinto N, Self C, Olson G, Insel P A, Giles W R, Taylor S S, Roth D M. Disruption of protein kinase A localization using a trans-activator of transcription (TAT)-conjugated A-kinase-anchoring peptide reduces cardiac function. J Biol Chem 285: 27632-27640, 2010.

Pawson C T, Scott J D. Signal integration through blending, bolstering and bifurcating of intracellular information. Nat Struct Mol Biol 17: 653-658, 2010.

Pawson T, Nash P (2003) Assembly of cell regulatory systems through protein interaction domains. Science 300:445-452.

Perino A, Ghigo A, Ferrero E, Morello F, Santulli G, Baillie G S, Damilano F, Dunlop A J, Pawson C, Walser R, Levi R, Altruda F, Silengo L, Langeberg L K, Neubauer G, S H, Lembo G, Wymann M P, Wetzker R, Houslay M D, Iaccarino G, Scott J D, Hirsch E. Integrating cardiac PIP3 and cAMP signaling through a PKA anchoring function of p110gamma. Mol Cell 42: 84-95, 2011.

Perrino C, Feliciello A, Schiattarella G G, Esposito G, Guerriero R, Zaccaro L, Del Gatto A, Saviano M, Garbi C, Carangi R, Di Lorenzo E, Donato G, Indolfi C, Avvedimento V E, Chiariello M. AKAP121 downregulation impairs protective cAMP signals, promotes mitochon-drial dysfunction, and increases oxidative stress. Cardiovasc Res 88: 101-110, 2010.

Perrino C, Naga Prasad S V, Mao L, Noma T, Yan Z, Kim H S, Smithies O, Rockman H A. Intermittent pressure overload triggers hypertrophy-independent cardiac dysfunction and vascular rarefaction. J Clin Invest. 2006; 116:1547-1560.

Peter A K, Bjerke M A, Leinwand L A (2016) Biology of the cardiac myocyte in heart disease. Mol Biol Cell 27:2149-2160.

Ponikowski, P., A. A. Voors, S. D. Anker, H. Bueno, J. G. Cleland, A. J. Coats, V. Falk, J. R. Gonzalez-Juanatey, V. P. Harjola, E. A. Jankowska, M. Jessup, C. Linde, P. Nihoyannopoulos, J. T. Parissis, B. Pieske, J. P. Riley, G. M. Rosano, L. M. Ruilope, F. Ruschitzka, F. H. Rutten, P. van der Meer and M. Authors/Task Force (2016). "2016 ESC Guidelines for the diagnosis and treatment of acute and chronic heart failure: The Task Force for the diagnosis and treatment of acute and chronic heart failure of the European Society of Cardiology (ESC) Developed with the special contribution of the Heart Failure Association (HFA) of the ESC." Eur Heart J 37(27): 2129-2200.

Potthoff M J, Olson E N (2007) MEF2: a central regulator of diverse developmental programs. Development 134: 4131-4140.

Prabhakar R, Boivin G P, Grupp I L, Hoit B, Arteaga G, Solaro J R, Wieczorek D F. A familial hypertrophic cardiomyopathy alpha-tropomyosin mutation causes severe cardiac hypertrophy and death in mice. J. Mol. Cell. Cardiol. 2001; 33(10):1815-1828.

Prasad, K. M., Y. Xu, Z. Yang, S. T. Acton and B. A. French (2011). "Robust cardiomyocyte-specific gene expression following systemic injection of AAV: in vivo gene delivery follows a Poisson distribution." Gene Ther 18(1): 43-52.

Rababa'h A, Craft J W, Jr., Wijaya C S, Atrooz F, Fan Q, Singh S, Guillory A N, Katsonis P, Lichtarge O, McConnell B K (2013) Protein kinase A and phosphodiesterase-4D3 binding to coding polymorphisms of cardiac muscle anchoring protein (mAKAP). J Mol Biol 425:3277-3288, Ranganathan A, Pearson G W, Chrestensen C A, Sturgill T W, Cobb M H (2006) The MAP kinase ERK5 binds to and phosphorylates p90 RSK. Arch Biochem Biophys 449:8-16.

Reiken S, Gaburjakova M, Gaburjakova J, He Ki K L, Prieto A, Becker E, Yi Gh G H, Wang J, Burkhoff D, Marks A R (2001) beta-adrenergic receptor blockers restore cardiac calcium release channel (ryanodine receptor) structure and function in heart failure. Circulation 104:2843-2848.

Resjo S, Oknianska A, Zolnierowicz S, Manganiello V, Degerman E (1999) Phosphorylation and activation of phosphodiesterase type 3B (PDE3B) in adipocytes in response to serine/threonine phosphatase inhibitors: deactivation of PDE3B in vitro by protein phosphatase type 2A. Biochem J 341 (Pt 3):839-845.

Reynolds J G, McCalmon S A, Tomczyk T, Naya F J. Identification and mapping of protein kinase A binding sites in the costameric protein myospryn. Biochim Biophys Acta 1773: 891-902, 2007.

Richards S A, Dreisbach V C, Murphy L O, Blenis J. Characterization of regulatory events associated with membrane targeting of p90 ribosomal S6 kinase 1. Mol Cell Biol. 2001; 21:7470-7480.

Rivera V M, Miranti C K, Misr; i R P, Ginty D D, Chen R H, Blenis J, Greenberg M E (1993) A growth factor-induced kinase phosphorylates the serum response factor at a site that regulates its DNA-binding activity. Mol Cell Biol 13:6260-6273.

Rockman H A, Koch W J, Lefkowitz R J. Seven-transmembrane-span-ning receptors and heart function. Nature 415: 206-212, 2002.

Rockman H A, Ross R S, Harris A N, Knowlton K U, Steinhelper M E, Field L J, Ross J Jr, Chien K R. Segregation of atrial-specific and in-ducible expression of an atrial natriuretic factor transgene in an in vivo murine model of cardiac hypertrophy. Proc Natl Acad Sci USA. 1991; 88:8277-8281.

Roger V L, Go A S, Lloyd-Jones D M, Adams R J, Berry J D, Brown T M, Carnethon M R, Dai S, de Simone G, Ford E S, Fox C S, Fullerton H J, Gillespie C, Greenlund K J, Hailpern S M, Heit J A, Ho P M, Howard V J, Kissela B M, Kittner S J, Lackland D T, Lichtman J H, Lisabeth L D, Makuc D M, Marcus G M, Marelli A, Matchar D B, McDermott M M, Meigs J B, Moy C S, Mozaffarian D, Mussolino M E, Nichol G, Paynter N P, Rosamond W D, Sorlie P D, Stafford R S, Turan T N, Turner M B, Wong N D, Wylie-Rosett J; American Heart Association Statistics Committee and Stroke Statistics Subcommittee. Heart disease and stroke statistics-2011 update: a report from the American Heart Association. Circulation 123: e18-e209, 2011.

Rose B A, Force T, Wang Y. Mitogen-activated protein kinase signaling in the heart: angels versus demons in a heart-breaking tale. Physiol Rev. 2010; 90:1507-1546.

Russell M A, Lund L M, Haber R, McKeegan K, Cianciola N, Bond M. The intermediate filament protein, synemin, is an AKAP in the heart. Arch Biochem Biophys 456: 204-215, 2006.

Sadoshima J, Qiu Z, Morgan J P, Izumo S. Angiotensin II and other hypertrophic stimuli mediated by G protein-coupled receptors activate tyrosine kinase, mitogen-activated protein kinase, and 90-kD S6 kinase in cardiac myocytes. The critical role of Ca(2+)-dependent signaling. Circ. Res. 1995; 76(1):1-15.

Sapkota G P, Cummings L, Newell F S, Armstrong C, Bain J, Frodin M, Grauert M, Hoffmann M, Schnapp G, Steegmaier M, Cohen P, Alessi D R. BI-D1870 is a specific inhibitor of the p90 RSK (ribosomal S6 kinase) isoforms in vitro and in vivo. Biochem J. 2007; 401:29-38.

Schiattarella G G, Hill J A (2015) Inhibition of hypertrophy is a good therapeutic strategy in ventricular pressure overload. Circulation 131:1435-1447.

Scholten A, Poh M K, van Veen T A, van Breukelen B, Vos M A, Heck A J. Analysis of the cGMP/cAMP interactome using a chemical proteom-ics approach in mammalian heart tissue validates sphingosine kinase type 1-interacting protein as a genuine and highly abundant AKAP. J Proteome Res 5: 1435-1447, 2006.

Scholten A, van Veen T A, Vos M A, Heck A J. Diversity of cAMP-dependent protein kinase isoforms and their anchoring proteins in mouse ventricular tissue. J Proteome Res 6: 1705-1717, 2007.

Schulze D H, Mughal M, Lederer W J, Ruknudin A M. Sodium/calcium exchanger (NCX1) macromolecular complex. J Biol Chem 278: 28849-28855, 2003.

Scott J D, Dessauer C W, Tasken K (2013) Creating order from chaos: cellular regulation by kinase anchoring. Annu Rev Pharmacol Toxicol 53:187-210.

Scott, J. D. and T. Pawson (2009). "Cell signaling in space and time: where proteins come together and when they're apart." Science 326(5957): 1220-1224.

Semenza G L. Hypoxia-inducible factor 1 (HIF-1) pathway. Sci STKE 2007: cm8, 2007.

Semenza G L. Regulation of oxygen homeostasis by hypoxia-inducible factor 1. Physiology 24: 97-106, 2009.

Sette C, Conti M (1996) Phosphorylation and activation of a cAMP-specific phosphodiesterase by the cAMP-dependent protein kinase. Involvement of serine 54 in the enzyme activation. J Biol Chem 271:16526-16534.

Sfichi-Duke L, Garcia-Cazarin M L, Sumandea C A, Sievert G A, Balke C W, Zhan D Y, Morimoto S, Sumandea M P. Cardiomyopathy-causing deletion K210 in cardiac troponin T alters phosphorylation propensity of sarcomeric proteins. J Mol Cell Cardiol 48: 934-942, 2010.

Shan J, Betzenhauser M J, Kushnir A, Reiken S, Meli A C, Wronska A, Dura M, Chen B X, Marks A R. Role of chronic ryanodine receptor phosphorylation in heart failure and beta-adrenergic receptor blockade in mice. J Clin Invest 120: 4375-4387, 2010.

Shan J, Kushnir A, Betzenhauser M J, Reiken S, Li J, Lehnart S E, Lindegger N, Mongillo M, Mohler P J, Marks A R. Phosphorylation of the ryanodine receptor mediates the cardiac fight or flight response in mice. J Clin Invest 120: 4388-4398, 2010.

Sharma K, Kass D A (2014) Heart failure with preserved ejection fraction: mechanisms, clinical features, and therapies. Circ Res 115:79-96.

Shyu K G, Wang M T, Wang B W, Chang C C, Leu J G, Kuan P, Chang H. Intramyocardial injection of naked DNA encoding HIF-1alpha/VP16 hybrid to enhance angiogenesis in an acute myocardial infarction model in the rat. Cardiovasc Res 54: 576-583, 2002.

Silva, J. M., M. Z. Li, K. Chang, W. Ge, M. C. Golding, R. J. Rickles, D. Siolas, G. Hu, P. J. Paddison, M. R. Schlabach, N. Sheth, J. Bradshaw, J. Burchard, A. Kulkarni, G. Cavet, R. Sachidanandam, W. R. McCombie, M. A. Cleary, S. J. Elledge and G. J. Hannon (2005). "Second-generation shRNA libraries covering the mouse and human genomes." Nat Genet 37(11): 1281-1288.

Singh A, Redden J M, Kapiloff M S, Dodge-Kafka K L, "The large isoforms of A-kinase anchoring protein 18 mediate the phosphorylation of inhibitor-1 by protein kinase A and the inhibition of protein phosphatase 1 activity," Mol Pharmacol. 2011 March; 79(3):533-40.

Skroblin P, Grossmann S, Schafer G, Rosenthal W, Klussmann E. Mechanisms of protein kinase A anchoring. Int Rev Cell Mol Biol 283: 235-330, 2010.

Smith F D, Langeberg L K, Cellurale C, Pawson T, Morrison D K, Davis R J, Scott J D. AKAP-Lbc enhances cyclic AMP control of the ERK1/2 cascade. Nat Cell Biol 12: 1242-1249, 2010.

Smith J A, Poteet-Smith C E, Xu Y, Errington T M, Hecht S M, Lannigan D A. Identification of the first specific inhibitor of p90 ribosomal S6 ki-nase (RSK) reveals an unexpected role for RSK in cancer cell prolifera-tion. Cancer Res. 2005; 65:1027-1034.

Spinale F G, Janicki J S, Zile M R. Membrane-associated matrix proteolysis and heart failure. Circ. Res. 2013; 112(1):195-208.

Steinberg S F, Brunton L L (2001) Cornpartrnentation of G protein-coupled signaling pathways in cardiac myocytes. Annu Rev Pharmacol Toxicol 41:751-773.

Stelzer J E, Patel J R, Walker J W, Moss R L. Differential roles of cardiac myosin-binding protein C and cardiac troponin I in the myofi-brillar force responses to protein kinase A phosphorylation. Circ Res 101: 503-511, 2007.

Sumandea C A, Garcia-Cazarin M L, Bozio C H, Sievert G A, Balke C W, Sumandea M P. Cardiac troponin T, a sarcomeric AKAP, tethers protein kinase A at the myofilaments. J Biol Chem 286: 530-541, 2011

Takeishi Y, Huang Q, Abe J, Che W, Lee J D, Kawakatsu H, Hoit B D, Berk B C, Walsh R A. Activation of mitogen-activated protein kinases and p90 ribosomal S6 kinase in failing human hearts with dilated cardiomy-opathy. Cardiovasc Res. 2002; 53:131-137.

Terrenoire C, Houslay M D, Baillie G S, Kass R S. The cardiac IKs potassium channel macromolecular complex includes the phosphodies terase PDE4D3. J Biol Chem 284: 9140-9146, 2009.

Thomas G M, Rumbaugh G R, Harrar D B, Huganir R L. Ribosomal S6 kinase 2 interacts with and phosphorylates PDZ domain-containing proteins and regulates AMPA receptor transmission. Proc Natl Acad Sci USA. 2005; 102:15006-15011.

Tingley W G, Pawlikowska L, Zaroff J G, Kim T, Nguyen T, Young S G, Vranizan K, Kwok P Y, Whooley M A, Conklin B R. Gene-trapped mouse embryonic stem cell-derived cardiac myocytes and human genet-ics implicate AKAP10 in heart rhythm regulation. Proc Natl Acad Sci USA 104: 8461-8466, 2007.

Treisrnan R (1985) Transient accumulation of c-fos RNA following serum stimulation requires a conserved 5' element and c-fos 3' sequences. Cell 42:889-902.

Uys G M, Ramburan A, Loos B, Kinnear C J, Korkie L J, Mouton J, Riedemann J, Moolman-Smook J. Myomegalin is a novel A-kinase anchoring protein involved in the phosphorylation of cardiac myosin binding protein C. BMC Cell Biol 12: 18, 2011.

Valdivia H H, Kaplan J H, Ellis-Davies G C, Lederer W J (1995) Rapid adaptation of cardiac ryanodine receptors: modulation by Mg2+ and phosphorylation. Science 267: 1997-2000.

Vargas M A, Tirnauer J S, Glidden N, Kapiloff M S, Dodge-Kafka K L, "Myocyte enhancer factor 2 (MEF2) tethering to muscle selective A-kinase anchoring protein (mAKAP) is necessary for myogenic differentiation," Cell Signal. 2012 August; 24(8):1496-503.

Virshup D M (2000) Protein phosphatase 2A: a panoply of enzymes. Curr Opin Cell Biol 12:180-185.

Wang X, Tang X, Li M, Marshall J, Mao Z (2005) Regulation of neuroprotective activity of myocyte-enhancer factor 2 by cAMP-protein kinase A signaling pathway in neuronal survival. J Biol Chem 280:16705-16713.

Wang, Y., E. G. Cameron, J. Li, T. L. Stiles, M. D. Kritzer, R. Lodhavia, J. Hertz, T. Nguyen, M. S. Kapiloff and J. L. Goldberg (2015). "Muscle A-Kinase Anchoring Protein-alpha is an Injury-Specific Signaling Scaffold Required for Neurotrophic- and Cyclic Adenosine Monophosphate-Mediated Survival." EBioMedicine 2(12): 1880-1887.

Wang, Z., H. I. Ma, J. Li, L. Sun, J. Zhang and X. Xiao (2003). "Rapid and highly efficient transduction by double-stranded adeno-associated virus vectors in vitro and in vivo." Gene Ther 10(26): 2105-2111.

Wera S, Hemmings B A (1995) Serine/threonine protein phosphatases. Biochem J 311 (Pt 1):17-29.

Wilkins B J, De Windt L J, Bueno O F, Braz J C, Glascock B J, Kimball T F, Molkentin J D (2002) Targeted disruption of NFATc3, but not NFATc4, reveals an intrinsic defect m calcineurin-mediated cardiac hypertrophic growth. Mol Cell Biol 22:7603-7613.

Wilkins B J, Dai Y S, Bueno O F, Parsons S A, Xu J, Plank D M, Jones F, Kimball T R, Molkentin J D (2004) Calcineurin/NFAT coupling participates in pathological, but not physiological, cardiac hypertrophy. Circ Res 94:110-118.

Wong W, Goehring A S, Kapiloff M S, Langeberg L K, Scott J D, "mAKAP compartmentalizes oxygen-dependent control of HIF-1alpha," Sci Signal. 2008 Dec. 23; 1(51).

Welch E J, Jones B W, Scott J D. Networking with AKAPs: context-dependent regulation of anchored enzymes. Mol Interv 10: 86-97, 2010. 114. Wu X, Simpson J, Hong J H, Kim K H, Thavarajah N K, Backx P H, Neel B G, Araki T. MEK-ERK pathway modulation ameliorates disease phe-notypes in a mouse model of Noonan syndrome associated with the Raf1(L613V) mutation. J Clin Invest. 2011; 121:1009-1025.

Wollert K C, Taga T, Saito M, Narazaki M, Kishimoto T, Glembotski C C, Vernallis A B, Heath J K, Pennica D, Wood W I, Chien K R. Cardiotrophin-1 activates a distinct form of cardiac muscle cell hypertrophy. Assembly of sarcomeric units in series VIA gp130/leukemia inhibitory factor receptor-dependent pathways. J Biol Chem. 1996; 271:9535-9545.

Writing Group, M., D. Mozaffarian, E. J. Benjamin, A. S. Go, D. K. Arnett, M. J. Blaha, M. Cushman, S. R. Das, S. de Ferranti, J. P. Despres, H. J. Fullerton, V. J. Howard, M. D. Huffman, C. R. Isasi, M. C. Jimenez, S. E. Judd, B. M. Kissela, J. H. Lichtman, L. D. Lisabeth, S. Liu, R. H. Mackey, D. J. Magid, D. K. McGuire, E. R. Mohler, 3rd, C. S. Moy, P. Muntner, M. E. Mussolino, K. Nasir, R. W. Neumar, G. Nichol, L. Palaniappan, D. K. Pandey, M. J. Reeves, C. J. Rodriguez, W. Rosamond, P. D. Sorlie, J. Stein, A. Towfighi, T. N. Turan, S. S. Virani, D. Woo, R. W. Yeh, M. B. Turner, C. American Heart Association Statistics and S. Stroke Statistics (2016). "Heart Disease and Stroke Statistics-2016 Update: A Report From the American Heart Association." Circulation 133(4): e38-360.

Wu H, Rothermel B, Kanatous S, Rosenberg P, Naya F J, Shelton J M, Hutcheson K A, DiMaio J M, Olson E N, Bassel-Duby R, Williams R S (2001) Activation of MEF2 by muscle activity is mediated through a calcineurin-dependent pathway. EMBO J 20:6414-6423.

Xie M, Hill J A (2013) HDAC-dependent ventricular remodeling. Trends Cardiovasc Med 23:229-235.

Xu J, Ismat F A, Wang T, Lu M M, Antonucci N, Epstein J A. Cardiomyocyte-specific loss of neurofibromin promotes cardiac hypertrophy and dysfunction. Circ Res. 2009; 105:304-311.

Yang J, Drazba J A, Ferguson D G, Bond M (1998) A-kinase anchoring protein 100 (AKAPlOO) is localized in multiple subcellular compartments in the adult rat heart. J Cell Biol 142:511-522.

Yang K C, Jay P Y, McMullen J R, Nerbonne J M. Enhanced car-diac PI3Ka signalling mitigates arrhythmogenic electrical remodel-ling in pathological hypertrophy and heart failure. Cardiovasc Res. 2012; 93:252-262.

Zakhary D R, Fink M A, Ruehr M L, Bond M (2000) Selectivity and regulation of A-kinase anchoring proteins in the heart. The role of autophosphorylation of the type II regulatory subunit of cAMP-dependent protein kinase. J Biol Chem 275:41389-41395.

Zhang L, Malik S, Kelley G G, Kapiloff M S, Smrcka A V, "Phospholipase Cepsilon scaffolds to muscle-specific A kinase anchoring protein (mAKAPbeta) and integrates multiple hypertrophic stimuli in cardiac myocytes," J Biol Chem. 2011 Jul. 1; 286(26):23012-21.

Zhang, L., S. Malik, J. Pang, H. Wang, K. M. Park, D. I. Yule, B. C. Blaxall and A. V. Smrcka (2013). "Phospholipase Cepsilon hydrolyzes perinuclear phosphatidylinositol 4-phosphate to regulate cardiac hypertrophy." Cell 153(1): 216-227.

Zhang Q, Bethmann C, Worth N F, Davies J D, Wasner C, Feuer A, Ragnauth C D, Yi Q, Mellad J A, Warren D T, Wheeler M A, Ellis J A, Skepper J N, Vorgerd M, Schlotter-Weigel B, Weissberg P L, Roberts R G, Wehnert M, Shanahan C M (2007) Nesprin-1 and -2 are involved in the pathogenesis of Emery Dreifuss muscular dystrophy and are critical for nuclear envelope integrity. Hum Mol Genet 16:2816-2833.

Zhao Y, Bjorbaek C, Moller D E. Regulation and interaction of pp90(rsk) isoforms with mitogen-activated protein kinases. J Biol Chem. 1996; 271:29773-29779.

Zhao Y, Bjorbaek C, Weremowicz S, Morton C C, Moller D E. RSK3 encodes a novel pp90rsk isoform with a unique N-terminal sequence: growth factor-stimulated kinase function and nuclear translocation. Mol Cell Biol. 1995 August; 15(8): 4353-436.

What is claimed is:

1. A composition comprising a nucleic acid that encodes a molecule consisting of amino acids 2132-2319 of human mAKAP, wherein said molecule inhibits the-dephosphorylation activity of protein (serine-threonine) phosphatase 2A (PP2A) resulting in a maintained level of phosphorylation on serum response factor (SRF).

2. The composition of claim 1, wherein the nucleic acid is in a vector.

3. The composition of claim 2, wherein the vector is adeno-associated virus (AAV).

4. The composition of claim 2, wherein SRF is phosphorylated on Ser$^{103}$.

5. The composition of claim 1, wherein SRF is phosphorylated on Ser$^{103}$.

6. A method of treating heart failure with reduced ejection fraction, comprising administering to cardiac cells of a patient in need thereof, a therapeutically effective amount of a composition comprising a nucleic acid that encodes a molecule consisting of amino acids 2132-2319 of human mAKAP, wherein said molecule inhibits the dephosphorylation activity of protein (serine-threonine) phosphatase 2A (PP2A) resulting in a maintained level of phosphorylation on serum response factor (SRF).

7. The method of claim 6, wherein SRF is phosphorylated on Ser$^{103}$.

8. The method of claim 6, wherein said nucleic acid is in a vector.

9. The method of claim 8, wherein the vector is adeno-associated virus (AAV).

10. The method of claim 6, wherein said composition inhibits the expression of PP2A B566 (PPP2R5D).

* * * * *

UNITED STATES PATENT AND TRADEMARK OFFICE
CERTIFICATE OF CORRECTION

| | | |
|---|---|---|
| PATENT NO. | : 11,938,198 B2 | Page 1 of 1 |
| APPLICATION NO. | : 16/818771 | |
| DATED | : March 26, 2024 | |
| INVENTOR(S) | : Michael S. Kapiloff and Jinliang Li | |

It is certified that error appears in the above-identified patent and that said Letters Patent is hereby corrected as shown below:

In the Claims

Column 172, Line 38-39:
Please change Claim 10 from "The method of claim 6, wherein said composition inhibits the expression of PP2A B566 (PPP2R5D)" to "The method of claim 6, wherein said composition inhibits the phosphorylation of PP2A B566 (PPP2R5D)".

Signed and Sealed this
Thirtieth Day of July, 2024

Katherine Kelly Vidal
*Director of the United States Patent and Trademark Office*

SEQUENCE LISTING

<160> NUMBER OF SEQ ID NOS: 23

<210> SEQ ID NO 1
<211> LENGTH: 733
<212> TYPE: PRT
<213> ORGANISM: Homo sapiens

<400> SEQUENCE: 1

Met Asp Leu Ser Met Lys Lys Phe Ala Val Arg Arg Phe Phe Ser Val
1               5                   10                  15

Tyr Leu Arg Arg Lys Ser Arg Ser Lys Ser Ser Ser Leu Ser Arg Leu
            20                  25                  30

Glu Glu Glu Gly Val Val Lys Glu Ile Asp Ile Ser His His Val Lys
        35                  40                  45

Glu Gly Phe Glu Lys Ala Asp Pro Ser Gln Phe Glu Leu Leu Lys Val
    50                  55                  60

Leu Gly Gln Gly Ser Tyr Gly Lys Val Phe Leu Val Arg Lys Val Lys
65                  70                  75                  80

Gly Ser Asp Ala Gly Gln Leu Tyr Ala Met Lys Val Leu Lys Lys Ala
                85                  90                  95

Thr Leu Lys Val Arg Asp Arg Val Arg Ser Lys Met Glu Arg Asp Ile
            100                 105                 110

Leu Ala Glu Val Asn His Pro Phe Ile Val Lys Leu His Tyr Ala Phe
        115                 120                 125

Gln Thr Glu Gly Lys Leu Tyr Leu Ile Leu Asp Phe Leu Arg Gly Gly
    130                 135                 140

Asp Leu Phe Thr Arg Leu Ser Lys Glu Val Met Phe Thr Glu Glu Asp
145                 150                 155                 160

Val Lys Phe Tyr Leu Ala Glu Leu Ala Leu Ala Leu Asp His Leu His
                165                 170                 175

Ser Leu Gly Ile Ile Tyr Arg Asp Leu Lys Pro Glu Asn Ile Leu Leu
            180                 185                 190

Asp Glu Glu Gly His Ile Lys Ile Thr Asp Phe Gly Leu Ser Lys Glu
        195                 200                 205

Ala Ile Asp His Asp Lys Arg Ala Tyr Ser Phe Cys Gly Thr Ile Glu
    210                 215                 220

Tyr Met Ala Pro Glu Val Val Asn Arg Arg Gly His Thr Gln Ser Ala
225                 230                 235                 240

Asp Trp Trp Ser Phe Gly Val Leu Met Phe Glu Met Leu Thr Gly Ser
                245                 250                 255

Leu Pro Phe Gln Gly Lys Asp Arg Lys Glu Thr Met Ala Leu Ile Leu
            260                 265                 270

Lys Ala Lys Leu Gly Met Pro Gln Phe Leu Ser Gly Glu Ala Gln Ser
        275                 280                 285

Leu Leu Arg Ala Leu Phe Lys Arg Asn Pro Cys Asn Arg Leu Gly Ala
    290                 295                 300

Gly Ile Asp Gly Val Glu Glu Ile Lys Arg His Pro Phe Phe Val Thr
305                 310                 315                 320

Ile Asp Trp Asn Thr Leu Tyr Arg Lys Glu Ile Lys Pro Pro Phe Lys
                325                 330                 335

Pro Ala Val Gly Arg Pro Glu Asp Thr Phe His Phe Asp Pro Glu Phe
            340                 345                 350

Thr Ala Arg Thr Pro Thr Asp Ser Pro Gly Val Pro Pro Ser Ala Asn
        355                 360                 365

```
Ala His His Leu Phe Arg Gly Phe Ser Phe Val Ala Ser Ser Leu Ile
370                 375                 380

Gln Glu Pro Ser Gln Gln Asp Leu His Lys Val Pro Val His Pro Ile
385                 390                 395                 400

Val Gln Gln Leu His Gly Asn Asn Ile His Phe Thr Asp Gly Tyr Glu
            405                 410                 415

Ile Lys Glu Asp Ile Gly Val Gly Ser Tyr Ser Val Cys Lys Arg Cys
            420                 425                 430

Val His Lys Ala Thr Asp Thr Glu Tyr Ala Val Lys Ile Ile Asp Lys
            435                 440                 445

Ser Lys Arg Asp Pro Ser Glu Glu Ile Glu Ile Leu Leu Arg Tyr Gly
450                 455                 460

Gln His Pro Asn Ile Ile Thr Leu Lys Asp Val Tyr Asp Asp Gly Lys
465                 470                 475                 480

Phe Val Tyr Leu Val Met Glu Leu Met Arg Gly Gly Glu Leu Leu Asp
                485                 490                 495

Arg Ile Leu Arg Gln Arg Tyr Phe Ser Glu Arg Glu Ala Ser Asp Val
            500                 505                 510

Leu Cys Thr Ile Thr Lys Thr Met Asp Tyr Leu His Ser Gln Gly Val
            515                 520                 525

Val His Arg Asp Leu Lys Pro Ser Asn Ile Leu Tyr Arg Asp Glu Ser
530                 535                 540

Gly Ser Pro Glu Ser Ile Arg Val Cys Asp Phe Gly Phe Ala Lys Gln
545                 550                 555                 560

Leu Arg Ala Gly Asn Gly Leu Leu Met Thr Pro Cys Tyr Thr Ala Asn
                565                 570                 575

Phe Val Ala Pro Glu Val Leu Lys Arg Gln Gly Tyr Asp Ala Ala Cys
            580                 585                 590

Asp Ile Trp Ser Leu Gly Ile Leu Leu Tyr Thr Met Leu Ala Gly Phe
            595                 600                 605

Thr Pro Phe Ala Asn Gly Pro Asp Asp Thr Pro Glu Glu Ile Leu Ala
            610                 615                 620

Arg Ile Gly Ser Gly Lys Tyr Ala Leu Ser Gly Gly Asn Trp Asp Ser
625                 630                 635                 640

Ile Ser Asp Ala Ala Lys Asp Val Val Ser Lys Met Leu His Val Asp
                645                 650                 655

Pro His Gln Arg Leu Thr Ala Met Gln Val Leu Lys His Pro Trp Val
            660                 665                 670

Val Asn Arg Glu Tyr Leu Ser Pro Asn Gln Leu Ser Arg Gln Asp Val
            675                 680                 685

His Leu Val Lys Gly Ala Met Ala Ala Thr Tyr Phe Ala Leu Asn Arg
690                 695                 700

Thr Pro Gln Ala Pro Arg Leu Glu Pro Val Leu Ser Ser Asn Leu Ala
705                 710                 715                 720

Gln Arg Arg Gly Met Lys Arg Leu Thr Ser Thr Arg Leu
                725                 730

<210> SEQ ID NO 2
<211> LENGTH: 2314
<212> TYPE: PRT
<213> ORGANISM: Rattus rattus

<400> SEQUENCE: 2

Met Leu Thr Met Ser Val Thr Leu Ser Pro Leu Arg Ser Gln Gly Pro
1               5                   10                  15
```

```
Asp Pro Met Ala Thr Asp Ala Ser Pro Met Ala Ile Asn Met Thr Pro
             20                  25                  30

Thr Val Glu Gln Glu Gly Glu Gly Glu Ala Val Lys Ala Ile
         35                  40                  45

Asp Ala Glu Gln Gln Tyr Gly Lys Pro Pro Leu His Thr Ala Ala
         50                  55                  60

Asp Trp Lys Ile Val Leu His Leu Pro Glu Ile Glu Thr Trp Leu Arg
 65                  70                  75                  80

Met Thr Ser Glu Arg Val Arg Asp Leu Thr Tyr Ser Val Gln Gln Asp
                 85                  90                  95

Ala Asp Ser Lys His Val Asp Val His Leu Val Gln Leu Lys Asp Ile
                100                 105                 110

Cys Glu Asp Ile Ser Asp His Val Glu Gln Ile His Ala Leu Leu Glu
                115                 120                 125

Thr Glu Phe Ser Leu Lys Leu Leu Ser Tyr Ser Val Asn Val Ile Val
130                 135                 140

Asp Ile His Ala Val Gln Leu Leu Trp His Gln Leu Arg Val Ser Val
145                 150                 155                 160

Leu Val Leu Arg Glu Arg Ile Leu Gln Gly Leu Gln Asp Ala Asn Gly
                165                 170                 175

Asn Tyr Thr Arg Gln Thr Asp Ile Leu Gln Ala Phe Ser Glu Glu Thr
                180                 185                 190

Thr Glu Gly Arg Leu Asp Ser Leu Thr Glu Val Asp Asp Ser Gly Gln
                195                 200                 205

Leu Thr Ile Lys Cys Ser Gln Asp Tyr Leu Ser Leu Asp Cys Gly Ile
                210                 215                 220

Thr Ala Phe Glu Leu Ser Asp Tyr Ser Pro Ser Glu Asp Leu Leu Gly
225                 230                 235                 240

Gly Leu Gly Asp Met Thr Thr Ser Gln Ala Lys Thr Lys Ser Phe Asp
                245                 250                 255

Ser Trp Ser Tyr Ser Glu Met Glu Lys Glu Phe Pro Glu Leu Ile Arg
                260                 265                 270

Ser Val Gly Leu Leu Thr Val Ala Thr Glu Pro Val Pro Ser Ser Cys
                275                 280                 285

Gly Glu Ala Asn Glu Asp Ser Ser Gln Ala Ser Leu Ser Asp Asp His
                290                 295                 300

Lys Gly Glu His Gly Glu Asp Gly Ala Pro Val Pro Gly Gln Gln Leu
305                 310                 315                 320

Asp Ser Thr Val Gly Met Ser Ser Leu Asp Gly Thr Leu Ala Asn Ala
                325                 330                 335

Ala Glu His Pro Ser Glu Thr Ala Lys Gln Asp Ser Thr Ser Ser Pro
                340                 345                 350

Gln Leu Gly Ala Lys Lys Thr Gln Pro Gly Pro Cys Glu Ile Thr Thr
                355                 360                 365

Pro Lys Arg Ser Ile Arg Asp Cys Phe Asn Tyr Asn Glu Asp Ser Pro
                370                 375                 380

Thr Gln Pro Thr Leu Pro Lys Arg Gly Leu Phe Leu Lys Glu Thr Gln
385                 390                 395                 400

Lys Asn Glu Arg Lys Gly Ser Asp Arg Lys Gly Gln Val Val Asp Leu
                405                 410                 415

Lys Pro Glu Leu Ser Arg Ser Thr Pro Ser Leu Val Asp Pro Pro Asp
                420                 425                 430
```

Arg Ser Lys Leu Cys Leu Val Leu Gln Ser Ser Tyr Pro Ser Ser Pro
            435                 440                 445

Ser Ala Ala Ser Gln Ser Tyr Glu Cys Leu His Lys Val Gly Leu Gly
        450                 455                 460

Asn Leu Glu Asn Ile Val Arg Ser His Ile Lys Glu Ile Ser Ser Ser
465                 470                 475                 480

Leu Gly Arg Leu Thr Asp Cys His Lys Glu Lys Leu Arg Leu Lys Lys
                485                 490                 495

Pro His Lys Thr Leu Ala Glu Val Ser Leu Cys Arg Ile Pro Lys Gln
                500                 505                 510

Gly Gly Gly Ser Gly Lys Arg Ser Glu Ser Thr Gly Ser Ser Ala Gly
            515                 520                 525

Pro Ser Met Val Ser Pro Gly Ala Pro Lys Ala Thr Met Arg Pro Glu
        530                 535                 540

Thr Asp Ser Ala Ser Thr Ala Ser Gly Gly Leu Cys His Gln Arg Asn
545                 550                 555                 560

Arg Ser Gly Gln Leu Pro Val Gln Ser Lys Ala Ser Ser Pro Pro
                565                 570                 575

Cys Ser His Ser Ser Glu Ser Ser Leu Gly Ser Asp Ser Ile Lys Ser
                580                 585                 590

Pro Val Pro Leu Leu Ser Lys Asn Lys Ser Gln Lys Ser Ser Pro Pro
        595                 600                 605

Ala Pro Cys His Ala Thr Gln Asn Gly Gln Val Val Glu Ala Trp Tyr
        610                 615                 620

Gly Ser Asp Glu Tyr Leu Ala Leu Pro Ser His Leu Lys Gln Thr Glu
625                 630                 635                 640

Val Leu Ala Leu Lys Leu Glu Ser Leu Thr Lys Leu Leu Pro Gln Lys
                645                 650                 655

Pro Arg Gly Glu Thr Ile Gln Asp Ile Asp Asp Trp Glu Leu Ser Glu
                660                 665                 670

Met Asn Ser Asp Ser Glu Ile Tyr Pro Thr Tyr His Ile Lys Lys Lys
            675                 680                 685

His Thr Arg Leu Gly Thr Val Ser Pro Ser Ser Ser Ser Asp Ile Ala
        690                 695                 700

Ser Ser Leu Gly Glu Ser Ile Glu Ser Gly Pro Leu Ser Asp Ile Leu
705                 710                 715                 720

Ser Asp Glu Asp Leu Cys Leu Pro Leu Ser Ser Val Lys Lys Phe Thr
                725                 730                 735

Asp Glu Lys Ser Glu Arg Pro Ser Ser Ser Glu Lys Asn Glu Ser His
            740                 745                 750

Ser Ala Thr Arg Ser Ala Leu Ile Gln Lys Leu Met His Asp Ile Gln
        755                 760                 765

His Gln Glu Asn Tyr Glu Ala Ile Trp Glu Arg Ile Glu Gly Phe Val
        770                 775                 780

Asn Lys Leu Asp Glu Phe Ile Gln Trp Leu Asn Glu Ala Met Glu Thr
785                 790                 795                 800

Thr Glu Asn Trp Thr Pro Pro Lys Ala Glu Thr Asp Ser Leu Arg Leu
                805                 810                 815

Tyr Leu Glu Thr His Leu Ser Phe Lys Leu Asn Val Asp Ser His Cys
                820                 825                 830

Ala Leu Lys Glu Ala Val Glu Glu Gly His Gln Leu Leu Glu Leu
            835                 840                 845

Val Val Ser His Lys Ala Gly Leu Lys Asp Thr Leu Arg Met Ile Ala

```
            850             855             860
Ser Gln Trp Lys Glu Leu Gln Arg Gln Ile Lys Arg Gln His Ser Trp
865                 870                 875                 880

Ile Leu Arg Ala Leu Asp Thr Ile Lys Ala Glu Ile Leu Ala Thr Asp
                885                 890                 895

Val Ser Val Glu Asp Glu Glu Gly Thr Gly Ser Pro Lys Ala Glu Val
            900                 905                 910

Gln Leu Cys His Leu Glu Thr Gln Arg Asp Ala Val Glu Gln Met Ser
        915                 920                 925

Leu Lys Leu Tyr Ser Glu Gln Tyr Thr Ser Gly Ser Lys Arg Lys Glu
    930                 935                 940

Glu Phe Ala Asn Met Ser Lys Ala His Ala Glu Gly Ser Asn Gly Leu
945                 950                 955                 960

Leu Asp Phe Asp Ser Glu Tyr Gln Glu Leu Trp Asp Trp Leu Ile Asp
                965                 970                 975

Met Glu Ser Leu Val Met Asp Ser His Asp Leu Met Met Ser Glu Glu
            980                 985                 990

Gln Gln Gln His Leu Tyr Lys Arg Tyr Ser Val Glu Met Ser Ile Arg
        995                 1000                1005

His Leu Lys Lys Ser Glu Leu Leu Ser Lys Val Glu Ala Leu Lys
    1010                1015                1020

Lys Gly Gly Leu Ser Leu Pro Asp Asp Ile Leu Glu Lys Val Asp
    1025                1030                1035

Ser Ile Asn Glu Lys Trp Glu Leu Leu Gly Lys Thr Leu Arg Glu
    1040                1045                1050

Lys Ile Gln Asp Thr Ile Ala Gly His Ser Gly Ser Gly Pro Arg
    1055                1060                1065

Asp Leu Leu Ser Pro Glu Ser Gly Ser Leu Val Arg Gln Leu Glu
    1070                1075                1080

Val Arg Ile Lys Glu Leu Lys Arg Trp Leu Arg Asp Thr Glu Leu
    1085                1090                1095

Phe Ile Phe Asn Ser Cys Leu Arg Gln Glu Lys Glu Gly Thr Ser
    1100                1105                1110

Ala Glu Lys Gln Leu Gln Tyr Phe Lys Ser Leu Cys Arg Glu Ile
    1115                1120                1125

Lys Gln Arg Arg Arg Gly Val Ala Ser Ile Leu Arg Leu Cys Gln
    1130                1135                1140

His Leu Leu Asp Asp Arg Asp Thr Cys Asn Leu Asn Ala Asp His
    1145                1150                1155

Gln Pro Met Gln Leu Ile Ile Val Asn Leu Glu Arg Arg Trp Glu
    1160                1165                1170

Ala Ile Val Met Gln Ala Val Gln Trp Gln Thr Arg Leu Gln Lys
    1175                1180                1185

Lys Met Gly Lys Glu Ser Glu Thr Leu Asn Val Ile Asp Pro Gly
    1190                1195                1200

Leu Met Asp Leu Asn Gly Met Ser Glu Asp Ala Leu Glu Trp Asp
    1205                1210                1215

Glu Thr Asp Ile Ser Asn Lys Leu Ile Ser Val His Glu Glu Ser
    1220                1225                1230

Asn Asp Leu Asp Gln Asp Pro Glu Pro Met Leu Pro Ala Val Lys
    1235                1240                1245

Leu Glu Glu Thr His His Lys Asp Ser Gly Tyr Glu Glu Glu Ala
    1250                1255                1260
```

-continued

```
Gly Asp Cys Gly Gly Ser Pro Tyr Thr Ser Asn Ile Thr Ala Pro
1265                1270                1275

Ser Ser Pro His Ile Tyr Gln Val Tyr Ser Leu His Asn Val Glu
1280                1285                1290

Leu His Glu Asp Ser His Thr Pro Phe Leu Lys Ser Ser Pro Lys
1295                1300                1305

Phe Thr Gly Thr Thr Gln Pro Thr Val Leu Thr Lys Ser Leu Ser
1310                1315                1320

Lys Asp Ser Ser Phe Ser Ser Thr Lys Ser Leu Pro Asp Leu Leu
1325                1330                1335

Gly Gly Ser Gly Leu Val Arg Pro Tyr Ser Cys His Ser Gly Asp
1340                1345                1350

Leu Ser Gln Asn Ser Gly Ser Glu Ser Gly Ile Val Ser Glu Gly
1355                1360                1365

Asp Asn Glu Met Pro Thr Asn Ser Asp Met Ser Leu Phe Ser Met
1370                1375                1380

Val Asp Gly Ser Pro Ser Asn Pro Glu Thr Glu His Pro Asp Pro
1385                1390                1395

Gln Met Gly Asp Ala Ala Asn Val Leu Glu Gln Lys Phe Lys Asp
1400                1405                1410

Asn Gly Glu Ser Ile Lys Leu Ser Ser Val Ser Arg Ala Ser Val
1415                1420                1425

Ser Pro Val Gly Cys Val Asn Gly Lys Ala Gly Asp Leu Asn Ser
1430                1435                1440

Val Thr Lys His Thr Ala Asp Cys Leu Gly Glu Glu Leu Gln Gly
1445                1450                1455

Lys His Asp Val Phe Thr Phe Tyr Asp Tyr Ser Tyr Leu Gln Gly
1460                1465                1470

Ser Lys Leu Lys Leu Pro Met Ile Met Lys Gln Pro Gln Ser Glu
1475                1480                1485

Lys Ala His Val Glu Asp Pro Leu Leu Gly Gly Phe Tyr Phe Asp
1490                1495                1500

Lys Lys Ser Cys Lys Ala Lys His Gln Ala Ser Glu Ser Gln Pro
1505                1510                1515

Asp Ala Pro Pro His Glu Arg Ile Leu Ala Ser Ala Pro His Glu
1520                1525                1530

Met Gly Arg Ser Ala Tyr Lys Ser Ser Asp Ile Glu Lys Thr Phe
1535                1540                1545

Thr Gly Ile Gln Ser Ala Arg Gln Leu Ser Leu Leu Ser Arg Ser
1550                1555                1560

Ser Ser Val Glu Ser Leu Ser Pro Gly Gly Asp Leu Phe Gly Leu
1565                1570                1575

Gly Ile Phe Lys Asn Gly Ser Asp Ser Leu Gln Arg Ser Thr Ser
1580                1585                1590

Leu Glu Ser Trp Leu Thr Ser Tyr Lys Ser Asn Glu Asp Leu Phe
1595                1600                1605

Ser Cys His Ser Ser Gly Asp Ile Ser Val Ser Ser Gly Ser Val
1610                1615                1620

Gly Glu Leu Ser Lys Arg Thr Leu Asp Leu Leu Asn Arg Leu Glu
1625                1630                1635

Asn Ile Gln Ser Pro Ser Glu Gln Lys Ile Lys Arg Ser Val Ser
1640                1645                1650
```

```
Asp Met Thr Leu Gln Ser Ser Ser Gln Lys Met Pro Phe Ala Gly
    1655                1660                1665

Gln Met Ser Leu Asp Val Ala Ser Ser Ile Asn Glu Asp Ser Pro
    1670                1675                1680

Ala Ser Leu Thr Glu Leu Ser Ser Ser Asp Glu Leu Ser Leu Cys
    1685                1690                1695

Ser Glu Asp Ile Val Leu His Lys Asn Lys Ile Pro Glu Ser Asn
    1700                1705                1710

Ala Ser Phe Arg Lys Arg Leu Asn Arg Ser Val Ala Asp Glu Ser
    1715                1720                1725

Asp Val Asn Val Ser Met Ile Val Asn Val Ser Cys Thr Ser Ala
    1730                1735                1740

Cys Thr Asp Asp Glu Asp Ser Asp Leu Leu Ser Ser Ser Thr
    1745                1750                1755

Leu Thr Leu Thr Glu Glu Glu Leu Cys Leu Lys Asp Glu Asp Asp
    1760                1765                1770

Asp Ser Ser Ile Ala Thr Asp Asp Glu Ile Tyr Glu Glu Ser Asn
    1775                1780                1785

Leu Met Ser Gly Leu Asp Tyr Ile Lys Asn Glu Leu Gln Thr Trp
    1790                1795                1800

Ile Arg Pro Lys Leu Ser Leu Thr Arg Glu Lys Lys Arg Ser Gly
    1805                1810                1815

Val Thr Asp Glu Ile Lys Val Asn Lys Asp Gly Gly Gly Asn Glu
    1820                1825                1830

Lys Ala Asn Pro Ser Asp Thr Leu Asp Ile Glu Ala Leu Leu Asn
    1835                1840                1845

Gly Ser Ile Arg Cys Leu Ser Glu Asn Asn Gly Asn Gly Lys Thr
    1850                1855                1860

Pro Pro Arg Thr His Gly Ser Gly Thr Lys Gly Glu Asn Lys Lys
    1865                1870                1875

Ser Thr Tyr Asp Val Ser Lys Asp Pro His Val Ala Asp Met Glu
    1880                1885                1890

Asn Gly Asn Ile Glu Ser Thr Pro Glu Arg Glu Arg Glu Lys Pro
    1895                1900                1905

Gln Gly Leu Pro Glu Val Ser Glu Asn Leu Ala Ser Asn Val Lys
    1910                1915                1920

Thr Ile Ser Glu Ser Glu Leu Ser Glu Tyr Glu Ala Val Met Asp
    1925                1930                1935

Gly Ser Glu Asp Ser Ser Val Ala Arg Lys Glu Phe Cys Pro Pro
    1940                1945                1950

Asn Asp Arg His Pro Pro Gln Met Gly Pro Lys Leu Gln His Pro
    1955                1960                1965

Glu Asn Gln Ser Gly Asp Cys Lys Pro Val Gln Asn Pro Cys Pro
    1970                1975                1980

Gly Leu Leu Ser Glu Ala Gly Val Gly Ser Arg Gln Asp Ser Asn
    1985                1990                1995

Gly Leu Lys Ser Leu Pro Asn Asp Ala Pro Ser Gly Ala Arg Lys
    2000                2005                2010

Pro Ala Gly Cys Cys Leu Leu Glu Gln Asn Glu Thr Glu Glu Ser
    2015                2020                2025

Ala Ser Ile Ser Ser Asn Ala Ser Cys Cys Asn Cys Lys Pro Asp
    2030                2035                2040

Val Phe His Gln Lys Asp Asp Glu Asp Cys Ser Val His Asp Phe
```

|   |   |   |   |   | 2045 |   |   |   | 2050 |   |   |   | 2055 |   |
|---|---|---|---|---|------|---|---|---|------|---|---|---|------|---|

Val Lys Glu Ile Ile Asp Met Ala Ser Thr Ala Leu Lys Ser Lys
2060                2065                2070

Ser Gln Pro Glu Ser Glu Val Ala Ala Pro Thr Ser Leu Thr Gln
2075                2080                2085

Ile Lys Glu Lys Val Leu Glu His Ser His Arg Pro Ile His Leu
2090                2095                2100

Arg Lys Gly Asp Phe Tyr Ser Tyr Leu Ser Leu Ser Ser His Asp
2105                2110                2115

Ser Asp Cys Gly Glu Val Thr Asn Tyr Ile Asp Glu Lys Ser Ser
2120                2125                2130

Thr Pro Leu Pro Pro Asp Ala Val Asp Ser Gly Leu Asp Asp Lys
2135                2140                2145

Glu Asp Met Asp Cys Phe Phe Glu Ala Cys Val Glu Asp Glu Pro
2150                2155                2160

Val Asn Glu Glu Ala Gly Leu Pro Gly Ala Leu Pro Asn Glu Ser
2165                2170                2175

Ala Ile Glu Asp Gly Ala Glu Gln Lys Ser Glu Gln Lys Thr Ala
2180                2185                2190

Ser Ser Pro Val Leu Ser Asp Lys Thr Asp Leu Val Pro Leu Ser
2195                2200                2205

Gly Leu Ser Pro Gln Lys Gly Ala Asp Asp Ala Lys Glu Gly Asp
2210                2215                2220

Asp Val Ser His Thr Ser Gln Gly Cys Ala Glu Ser Thr Glu Pro
2225                2230                2235

Thr Thr Pro Ser Gly Lys Ala Asn Ala Glu Gly Arg Ser Arg Met
2240                2245                2250

Gln Gly Val Ser Ala Thr Pro Glu Glu Asn Ala Ala Ser Ala Lys
2255                2260                2265

Pro Lys Ile Gln Ala Phe Ser Leu Asn Ala Lys Gln Pro Lys Gly
2270                2275                2280

Lys Val Ala Met Arg Tyr Pro Ser Pro Gln Thr Leu Thr Cys Lys
2285                2290                2295

Glu Lys Leu Val Asn Phe His Glu Asp Arg His Ser Asn Met His
2300                2305                2310

Arg

<210> SEQ ID NO 3
<211> LENGTH: 29
<212> TYPE: DNA
<213> ORGANISM: Artificial Sequence
<220> FEATURE:
<223> OTHER INFORMATION: chemically synthesized

<400> SEQUENCE: 3
tcgacaggat gtccatatta ggacatctg                              29

<210> SEQ ID NO 4
<211> LENGTH: 79
<212> TYPE: DNA
<213> ORGANISM: Artificial Sequence
<220> FEATURE:
<223> OTHER INFORMATION: chemically synthesized

<400> SEQUENCE: 4
gatctcgaag gtttataaag tcaatgtctg cagatgagaa agcagtggtt ctcttaggac    60

-continued

```
ttcttgggga agtgtggtc                                              79
```

<210> SEQ ID NO 5
<211> LENGTH: 13
<212> TYPE: DNA
<213> ORGANISM: Artificial Sequence
<220> FEATURE:
<223> OTHER INFORMATION: chemically synthesized

<400> SEQUENCE: 5

```
atcgctggca gag                                                    13
```

<210> SEQ ID NO 6
<211> LENGTH: 13
<212> TYPE: DNA
<213> ORGANISM: Artificial Sequence
<220> FEATURE:
<223> OTHER INFORMATION: chemically synthesized

<400> SEQUENCE: 6

```
gagcctggat gaa                                                    13
```

<210> SEQ ID NO 7
<211> LENGTH: 13
<212> TYPE: DNA
<213> ORGANISM: Artificial Sequence
<220> FEATURE:
<223> OTHER INFORMATION: chemically synthesized

<400> SEQUENCE: 7

```
gagcctgagc gag                                                    13
```

<210> SEQ ID NO 8
<211> LENGTH: 2319
<212> TYPE: PRT
<213> ORGANISM: Homo sapiens

<400> SEQUENCE: 8

```
Met Leu Thr Met Ser Val Thr Leu Ser Pro Leu Arg Ser Gln Asp Leu
1               5                   10                  15

Asp Pro Met Ala Thr Asp Ala Ser Pro Met Ala Ile Asn Met Thr Pro
            20                  25                  30

Thr Val Glu Gln Gly Glu Gly Glu Ala Met Lys Asp Met Asp Ser
        35                  40                  45

Asp Gln Gln Tyr Glu Lys Pro Pro Leu His Thr Gly Ala Asp Trp
    50                  55                  60

Lys Ile Val Leu His Leu Pro Glu Ile Glu Thr Trp Leu Arg Met Thr
65                  70                  75                  80

Ser Glu Arg Val Arg Asp Leu Thr Tyr Ser Val Gln Gln Asp Ser Asp
                85                  90                  95

Ser Lys His Val Asp Val His Leu Val Gln Leu Lys Asp Ile Cys Glu
            100                 105                 110

Asp Ile Ser Asp His Val Glu Gln Ile His Ala Leu Leu Glu Thr Glu
        115                 120                 125

Phe Ser Leu Lys Leu Leu Ser Tyr Ser Val Asn Val Ile Val Asp Ile
    130                 135                 140

His Ala Val Gln Leu Leu Trp His Gln Leu Arg Val Ser Val Leu Val
145                 150                 155                 160

Leu Arg Glu Arg Ile Leu Gln Gly Leu Gln Asp Ala Asn Gly Asn Tyr
                165                 170                 175
```

-continued

```
Thr Arg Gln Thr Asp Ile Leu Gln Ala Phe Ser Glu Glu Thr Lys Glu
            180                 185                 190

Gly Arg Leu Asp Ser Leu Thr Glu Val Asp Asp Ser Gly Gln Leu Thr
        195                 200                 205

Ile Lys Cys Ser Gln Asn Tyr Leu Ser Leu Asp Cys Gly Ile Thr Ala
    210                 215                 220

Phe Glu Leu Ser Asp Tyr Ser Pro Ser Glu Asp Leu Leu Ser Gly Leu
225                 230                 235                 240

Gly Asp Met Thr Ser Gln Val Lys Thr Lys Pro Phe Asp Ser Trp
            245                 250                 255

Ser Tyr Ser Glu Met Glu Lys Glu Phe Pro Glu Leu Ile Arg Ser Val
        260                 265                 270

Gly Leu Leu Thr Val Ala Ala Asp Ser Ile Ser Thr Asn Gly Ser Glu
    275                 280                 285

Ala Val Thr Glu Glu Val Ser Gln Val Ser Leu Ser Val Asp Asp Lys
        290                 295                 300

Gly Gly Cys Glu Glu Asp Asn Ala Ser Ala Val Glu Glu Gln Pro Gly
305                 310                 315                 320

Leu Thr Leu Gly Val Ser Ser Ser Gly Glu Ala Leu Thr Asn Ala
            325                 330                 335

Ala Gln Pro Ser Ser Glu Thr Val Gln Gln Glu Ser Ser Ser Ser Ser
            340                 345                 350

His His Asp Ala Lys Asn Gln Pro Val Pro Cys Glu Asn Ala Thr
            355                 360                 365

Pro Lys Arg Thr Ile Arg Asp Cys Phe Asn Tyr Asn Glu Asp Ser Pro
    370                 375                 380

Thr Gln Pro Thr Leu Pro Lys Arg Gly Leu Phe Leu Lys Glu Glu Thr
385                 390                 395                 400

Phe Lys Asn Asp Leu Lys Gly Asn Gly Gly Lys Arg Gln Met Val Asp
                405                 410                 415

Leu Lys Pro Glu Met Ser Arg Ser Thr Pro Ser Leu Val Asp Pro Pro
            420                 425                 430

Asp Arg Ser Lys Leu Cys Leu Val Leu Gln Ser Ser Tyr Pro Asn Ser
        435                 440                 445

Pro Ser Ala Ala Ser Gln Ser Tyr Glu Cys Leu His Lys Val Gly Asn
    450                 455                 460

Gly Asn Leu Glu Asn Thr Val Lys Phe His Ile Lys Glu Ile Ser Ser
465                 470                 475                 480

Ser Leu Gly Arg Leu Asn Asp Cys Tyr Lys Glu Lys Ser Arg Leu Lys
                485                 490                 495

Lys Pro His Lys Thr Ser Glu Glu Val Pro Pro Cys Arg Thr Pro Lys
            500                 505                 510

Arg Gly Thr Gly Ser Gly Lys Gln Ala Lys Asn Thr Lys Ser Ser Ala
        515                 520                 525

Val Pro Asn Gly Glu Leu Ser Tyr Thr Ser Lys Ala Ile Glu Gly Pro
    530                 535                 540

Gln Thr Asn Ser Ala Ser Thr Ser Ser Leu Glu Pro Cys Asn Gln Arg
545                 550                 555                 560

Ser Trp Asn Ala Lys Leu Gln Leu Gln Ser Glu Thr Ser Ser Ser Pro
                565                 570                 575

Ala Phe Thr Gln Ser Ser Glu Ser Ser Val Gly Ser Asp Asn Ile Met
            580                 585                 590

Ser Pro Val Pro Leu Leu Ser Lys His Lys Ser Lys Lys Gly Gln Ala
```

```
            595                 600                 605
Ser Ser Pro Ser His Val Thr Arg Asn Gly Glu Val Glu Ala Trp
610                 615                 620

Tyr Gly Ser Asp Glu Tyr Leu Ala Leu Pro Ser His Leu Lys Gln Thr
625                 630                 635                 640

Glu Val Leu Ala Leu Lys Leu Glu Asn Leu Thr Lys Leu Leu Pro Gln
                645                 650                 655

Lys Pro Arg Gly Glu Thr Ile Gln Asn Ile Asp Asp Trp Glu Leu Ser
                660                 665                 670

Glu Met Asn Ser Asp Ser Glu Ile Tyr Pro Thr Tyr His Val Lys Lys
                675                 680                 685

Lys His Thr Arg Leu Gly Arg Val Ser Pro Ser Ser Ser Asp Ile
690                 695                 700

Ala Ser Ser Leu Gly Glu Ser Ile Glu Ser Gly Pro Leu Ser Asp Ile
705                 710                 715                 720

Leu Ser Asp Glu Glu Ser Ser Met Pro Leu Ala Gly Met Lys Lys Tyr
                725                 730                 735

Ala Asp Glu Lys Ser Glu Arg Ala Ser Ser Glu Lys Asn Glu Ser
                740                 745                 750

His Ser Ala Thr Lys Ser Ala Leu Ile Gln Lys Leu Met Gln Asp Ile
                755                 760                 765

Gln His Gln Asp Asn Tyr Glu Ala Ile Trp Glu Lys Ile Glu Gly Phe
770                 775                 780

Val Asn Lys Leu Asp Glu Phe Ile Gln Trp Leu Asn Glu Ala Met Glu
785                 790                 795                 800

Thr Thr Glu Asn Trp Thr Pro Pro Lys Ala Glu Met Asp Asp Leu Lys
                805                 810                 815

Leu Tyr Leu Glu Thr His Leu Ser Phe Lys Leu Asn Val Asp Ser His
                820                 825                 830

Cys Ala Leu Lys Glu Ala Val Glu Glu Gly His Gln Leu Leu Glu
                835                 840                 845

Leu Ile Ala Ser His Lys Ala Gly Leu Lys Asp Met Leu Arg Met Ile
850                 855                 860

Ala Ser Gln Trp Lys Glu Leu Gln Arg Gln Ile Lys Arg Gln His Ser
865                 870                 875                 880

Trp Ile Leu Arg Ala Leu Asp Thr Ile Lys Ala Glu Ile Leu Ala Thr
                885                 890                 895

Asp Val Ser Val Glu Asp Glu Glu Gly Thr Gly Ser Pro Lys Ala Glu
                900                 905                 910

Val Gln Leu Cys Tyr Leu Glu Ala Gln Arg Asp Ala Val Glu Gln Met
                915                 920                 925

Ser Leu Lys Leu Tyr Ser Glu Gln Tyr Thr Ser Ser Lys Arg Lys
930                 935                 940

Glu Glu Phe Ala Asp Met Ser Lys Val His Ser Val Gly Ser Asn Gly
945                 950                 955                 960

Leu Leu Asp Phe Asp Ser Glu Tyr Gln Glu Leu Trp Asp Cys Leu Ile
                965                 970                 975

Asp Met Glu Ser Leu Val Met Asp Ser His Asp Leu Met Ser Glu
                980                 985                 990

Glu Gln Gln Gln His Leu Tyr Lys Arg Tyr Ser Val Glu Met Ser Ile
                995                 1000                1005

Arg His Leu Lys Lys Thr Glu Leu Leu Ser Lys Val Glu Ala Leu
    1010                1015                1020
```

```
Lys Lys Gly Gly Val Leu Leu Pro Asn Asp Leu Leu Glu Lys Val
1025                1030                1035

Asp Ser Ile Asn Glu Lys Trp Glu Leu Leu Gly Lys Thr Leu Gly
1040                1045                1050

Glu Lys Ile Gln Asp Thr Met Ala Gly His Ser Gly Ser Ser Pro
1055                1060                1065

Arg Asp Leu Leu Ser Pro Glu Ser Gly Ser Leu Val Arg Gln Leu
1070                1075                1080

Glu Val Arg Ile Lys Glu Leu Lys Gly Trp Leu Arg Asp Thr Glu
1085                1090                1095

Leu Phe Ile Phe Asn Ser Cys Leu Arg Gln Glu Lys Glu Gly Thr
1100                1105                1110

Met Asn Thr Glu Lys Gln Leu Gln Tyr Phe Lys Ser Leu Cys Arg
1115                1120                1125

Glu Ile Lys Gln Arg Arg Arg Gly Val Ala Ser Ile Leu Arg Leu
1130                1135                1140

Cys Gln His Leu Leu Asp Asp Arg Glu Thr Cys Asn Leu Asn Ala
1145                1150                1155

Asp His Gln Pro Met Gln Leu Ile Ile Val Asn Leu Glu Arg Arg
1160                1165                1170

Trp Glu Ala Ile Val Met Gln Ala Val Gln Trp Gln Thr Arg Leu
1175                1180                1185

Gln Lys Lys Met Gly Lys Glu Ser Glu Thr Leu Asn Val Ile Asp
1190                1195                1200

Pro Gly Leu Met Asp Leu Asn Gly Met Ser Glu Asp Ala Leu Glu
1205                1210                1215

Trp Asp Glu Met Asp Ile Ser Asn Lys Leu Ile Ser Leu Asn Glu
1220                1225                1230

Glu Ser Asn Asp Leu Asp Gln Glu Leu Gln Pro Val Ile Pro Ser
1235                1240                1245

Leu Lys Leu Gly Glu Thr Ser Asn Glu Asp Pro Gly Tyr Asp Glu
1250                1255                1260

Glu Ala Asp Asn His Gly Gly Ser Gln Tyr Ala Ser Asn Ile Thr
1265                1270                1275

Ala Pro Ser Ser Pro His Ile Tyr Gln Val Tyr Ser Leu His Asn
1280                1285                1290

Val Glu Leu Tyr Glu Asp Asn His Met Pro Phe Leu Lys Asn Asn
1295                1300                1305

Pro Lys Val Thr Gly Met Thr Gln Pro Asn Val Leu Thr Lys Ser
1310                1315                1320

Leu Ser Lys Asp Ser Ser Phe Ser Ser Thr Lys Ser Leu Pro Asp
1325                1330                1335

Leu Leu Gly Gly Ser Asn Leu Val Lys Pro Cys Ala Cys His Gly
1340                1345                1350

Gly Asp Met Ser Gln Asn Ser Gly Ser Glu Ser Gly Ile Val Ser
1355                1360                1365

Glu Gly Asp Thr Glu Thr Thr Thr Asn Ser Glu Met Cys Leu Leu
1370                1375                1380

Asn Ala Val Asp Gly Ser Pro Ser Asn Leu Glu Thr Glu His Leu
1385                1390                1395

Asp Pro Gln Met Gly Asp Ala Val Asn Val Leu Lys Gln Lys Phe
1400                1405                1410
```

```
Thr Asp Glu Gly Glu Ser Ile Lys Leu Pro Asn Ser Ser Gln Ser
1415                1420                1425

Ser Ile Ser Pro Val Gly Cys Val Asn Gly Lys Val Gly Asp Leu
1430                1435                1440

Asn Ser Ile Thr Lys His Thr Pro Asp Cys Leu Gly Glu Glu Leu
1445                1450                1455

Gln Gly Lys His Asp Val Phe Thr Phe Tyr Asp Tyr Ser Tyr Leu
1460                1465                1470

Gln Gly Ser Lys Leu Lys Leu Pro Met Ile Met Lys Gln Ser Gln
1475                1480                1485

Ser Glu Lys Val His Val Glu Asp Pro Leu Leu Arg Gly Phe Tyr
1490                1495                1500

Phe Asp Lys Lys Ser Cys Lys Ser Lys His Gln Thr Thr Glu Leu
1505                1510                1515

Gln Pro Asp Val Pro Pro His Glu Arg Ile Leu Ala Ser Ala Ser
1520                1525                1530

His Glu Met Asp Arg Ile Ser Tyr Lys Ser Gly Asn Ile Glu Lys
1535                1540                1545

Thr Phe Thr Gly Met Gln Asn Ala Lys Gln Leu Ser Leu Leu Ser
1550                1555                1560

His Ser Ser Ser Ile Glu Ser Leu Ser Pro Gly Gly Asp Leu Phe
1565                1570                1575

Gly Leu Gly Ile Phe Lys Asn Gly Ser Asp Ser Leu Gln Arg Ser
1580                1585                1590

Thr Ser Leu Glu Ser Trp Leu Thr Ser Tyr Lys Ser Asn Glu Asp
1595                1600                1605

Leu Phe Ser Cys His Ser Ser Gly Asp Ile Ser Val Ser Ser Gly
1610                1615                1620

Ser Val Gly Glu Leu Ser Lys Arg Thr Leu Asp Leu Leu Asn Arg
1625                1630                1635

Leu Glu Asn Ile Gln Ser Pro Ser Glu Gln Lys Ile Lys Arg Ser
1640                1645                1650

Val Ser Asp Ile Thr Leu Gln Ser Ser Ser Gln Lys Met Ser Phe
1655                1660                1665

Thr Gly Gln Met Ser Leu Asp Ile Ala Ser Ser Ile Asn Glu Asp
1670                1675                1680

Ser Ala Ala Ser Leu Thr Glu Leu Ser Ser Ser Asp Glu Leu Ser
1685                1690                1695

Leu Cys Ser Glu Asp Ile Val Leu His Lys Asn Lys Ile Pro Glu
1700                1705                1710

Ser Asn Ala Ser Phe Arg Lys Arg Leu Thr Arg Ser Val Ala Asp
1715                1720                1725

Glu Ser Asp Val Asn Val Ser Met Ile Val Asn Val Ser Cys Thr
1730                1735                1740

Ser Ala Cys Thr Asp Asp Glu Asp Asp Ser Asp Leu Leu Ser Ser
1745                1750                1755

Ser Thr Leu Thr Leu Thr Glu Glu Leu Cys Ile Lys Asp Glu
1760                1765                1770

Asp Asp Asp Ser Ser Ile Ala Thr Asp Asp Glu Ile Tyr Glu Asp
1775                1780                1785

Cys Thr Leu Met Ser Gly Leu Asp Tyr Ile Lys Asn Glu Leu Gln
1790                1795                1800

Thr Trp Ile Arg Pro Lys Leu Ser Leu Thr Arg Asp Lys Lys Arg
```

```
            1805                1810                1815

Cys Asn Val Ser Asp Glu Met Lys Gly Ser Lys Asp Ile Ser Ser
            1820                1825                1830

Ser Glu Met Thr Asn Pro Ser Asp Thr Leu Asn Ile Glu Thr Leu
            1835                1840                1845

Leu Asn Gly Ser Val Lys Arg Val Ser Glu Asn Asn Gly Asn Gly
            1850                1855                1860

Lys Asn Ser Ser His Thr His Glu Leu Gly Thr Lys Arg Glu Asn
            1865                1870                1875

Lys Lys Thr Ile Phe Lys Val Asn Lys Asp Pro Tyr Val Ala Asp
            1880                1885                1890

Met Glu Asn Gly Asn Ile Glu Gly Ile Pro Glu Arg Gln Lys Gly
            1895                1900                1905

Lys Pro Asn Val Thr Ser Lys Val Ser Glu Asn Leu Gly Ser His
            1910                1915                1920

Gly Lys Glu Ile Ser Glu Ser Glu His Cys Lys Cys Lys Ala Leu
            1925                1930                1935

Met Asp Ser Leu Asp Asp Ser Asn Thr Ala Gly Lys Glu Phe Val
            1940                1945                1950

Ser Gln Asp Val Arg His Leu Pro Lys Lys Cys Pro Asn His His
            1955                1960                1965

His Phe Glu Asn Gln Ser Thr Ala Ser Thr Pro Thr Glu Lys Ser
            1970                1975                1980

Phe Ser Glu Leu Ala Leu Glu Thr Arg Phe Asn Asn Arg Gln Asp
            1985                1990                1995

Ser Asp Ala Leu Lys Ser Ser Asp Ala Pro Ser Met Ala Gly
            2000                2005                2010

Lys Ser Ala Gly Cys Cys Leu Ala Leu Glu Gln Asn Gly Thr Glu
            2015                2020                2025

Glu Asn Ala Ser Ile Ser Asn Ile Ser Cys Cys Asn Cys Glu Pro
            2030                2035                2040

Asp Val Phe His Gln Lys Asp Ala Glu Asp Cys Ser Val His Asn
            2045                2050                2055

Phe Val Lys Glu Ile Ile Asp Met Ala Ser Thr Ala Leu Lys Ser
            2060                2065                2070

Lys Ser Gln Pro Glu Asn Glu Val Ala Ala Pro Thr Ser Leu Thr
            2075                2080                2085

Gln Ile Lys Glu Lys Val Leu Glu His Ser His Arg Pro Ile Gln
            2090                2095                2100

Leu Arg Lys Gly Asp Phe Tyr Ser Tyr Leu Ser Leu Ser Ser His
            2105                2110                2115

Asp Ser Asp Cys Gly Glu Val Thr Asn Tyr Ile Glu Glu Lys Ser
            2120                2125                2130

Ser Thr Pro Leu Pro Leu Asp Thr Thr Asp Ser Gly Leu Asp Asp
            2135                2140                2145

Lys Glu Asp Ile Glu Cys Phe Phe Glu Ala Cys Val Glu Gly Asp
            2150                2155                2160

Ser Asp Gly Glu Glu Pro Cys Phe Ser Ser Ala Pro Pro Asn Glu
            2165                2170                2175

Ser Ala Val Pro Ser Glu Ala Ala Met Pro Leu Gln Ala Thr Ala
            2180                2185                2190

Cys Ser Ser Glu Phe Ser Asp Ser Ser Leu Ser Ala Asp Asp Ala
            2195                2200                2205
```

```
Asp Thr Val Ala Leu Ser Ser Pro Ser Ser Gln Glu Arg Ala Glu
    2210                2215                2220

Val Gly Lys Glu Val Asn Gly Leu Pro Gln Thr Ser Ser Gly Cys
    2225                2230                2235

Ala Glu Asn Leu Glu Phe Thr Pro Ser Lys Leu Asp Ser Glu Lys
    2240                2245                2250

Glu Ser Ser Gly Lys Pro Gly Glu Ser Gly Met Pro Glu Glu His
    2255                2260                2265

Asn Ala Ala Ser Ala Lys Ser Lys Val Gln Asp Leu Ser Leu Lys
    2270                2275                2280

Ala Asn Gln Pro Thr Asp Lys Ala Ala Leu His Pro Ser Pro Lys
    2285                2290                2295

Thr Leu Thr Cys Glu Glu Asn Leu Leu Asn Leu His Glu Lys Arg
    2300                2305                2310

His Arg Asn Met His Arg
    2315
```

<210> SEQ ID NO 9
<211> LENGTH: 190
<212> TYPE: PRT
<213> ORGANISM: Homo sapiens

<400> SEQUENCE: 9

```
Met Gly Lys Ser Ser Thr Pro Leu Pro Leu Asp Thr Asp Ser Gly
1               5                   10                  15

Leu Asp Asp Lys Glu Asp Ile Glu Cys Phe Phe Glu Ala Cys Val Glu
                20                  25                  30

Gly Asp Ser Asp Gly Glu Glu Pro Cys Phe Ser Ser Ala Pro Pro Asn
            35                  40                  45

Glu Ser Ala Val Pro Ser Glu Ala Ala Met Pro Leu Gln Ala Thr Ala
        50                  55                  60

Cys Ser Ser Glu Phe Ser Asp Ser Ser Leu Ser Ala Asp Asp Ala Asp
65                  70                  75                  80

Thr Val Ala Leu Ser Ser Pro Ser Ser Gln Glu Arg Ala Glu Val Gly
                85                  90                  95

Lys Glu Val Asn Gly Leu Pro Gln Thr Ser Ser Gly Cys Ala Glu Asn
                100                 105                 110

Leu Glu Phe Thr Pro Ser Lys Leu Asp Ser Glu Lys Glu Ser Ser Gly
            115                 120                 125

Lys Pro Gly Glu Ser Gly Met Pro Glu Glu His Asn Ala Ala Ser Ala
130                 135                 140

Lys Ser Lys Val Gln Asp Leu Ser Leu Lys Ala Asn Gln Pro Thr Asp
145                 150                 155                 160

Lys Ala Ala Leu His Pro Ser Pro Lys Thr Leu Thr Cys Glu Glu Asn
                165                 170                 175

Leu Leu Asn Leu His Glu Lys Arg His Arg Asn Met His Arg
            180                 185                 190
```

<210> SEQ ID NO 10
<211> LENGTH: 5887
<212> TYPE: DNA
<213> ORGANISM: Artificial Sequence
<220> FEATURE:
<223> OTHER INFORMATION: chemically synthesized

<400> SEQUENCE: 10

-continued

```
accgagttgc tctcacccgg cgtcaatacg ggataatacc gcgccacata gcagaacttt    60
aaaagtgctc atcattggaa aacgttcttc ggggcgaaaa ctctcaagga tcttaccgct   120
gttgagatcc agttcgatgt aacccactcg tgcacccaac tgatcttcag catcttttac   180
tttcaccagc gtttctgggt gagcaaaaac aggaaggcaa aatgccgcaa aaagggaat    240 aagggcgaca cggaaatgtt caattcaact actcttcctt tttcaatatt attgaagcat   300
ttatcagggt tattgtctca tgagcggata catatttgaa tgtatttaga aaataaaca    360 aatagggggtt ccgcgcacat ttccccgaaa agtgccacct gacgtctaag aaaccattat   420
tatcatgaca ttaacctata aaataggcg tatcacgagg cccttctcgtc tcgcgcgttt   480 cggtgatgac ggtgaaaacc tctgacacat gcagctcccg gagacggtca cagcttgtct   540
gtaagcggat gccgggagca gacaagcccg tcagggcgcg tcagcgggtg ttggcgggtg   600
tcggggctgg cttaactatg cggcatcaga gcagattgta ctgagagtgc accatatggc   660
cgtcccgtca gtcagcgta atgctctgcc agtgttacaa ccaattaacc aattctgatt   720
agaaaaactc atcgagcatc aaatgaaact gcaatttatt catatcagga ttatcaatac   780
catatttttg aaaaagccgt ttctgtaatg aaggagaaaa ctcaccgagg cagttccata   840
ggatggcaag atcctggtat cggtctgcga ttccgactcg tccaacatca atacaaccta   900
ttaatttccc ctcgtcaaaa ataaggttat caagtgagaa atcaccatga gtgacgactg   960
aatccggtga gaatggcaaa agcttatgca tttctttcca gacttgttca acaggccagc  1020
cattacgctc gtcatcaaaa tcactcgcat caaccaaacc gttattcatt cgtgattgcg  1080
cctgagcgag acgaaatacg cgatcgctgt taaaaggaca attacaaaca ggaatcgaat  1140
gcaaccggcg caggaacact gccagcgcat caacaatatt ttcacctgaa tcaggatatt  1200
cttctaatac ctggaatgct gttttcccgg ggatcgcagt ggtgagtaac catgcatcat  1260
caggagtacg gataaaatgc ttgatggtcg gaagaggcat aaattccgtc agccagttta  1320
gtctgaccat ctcatctgta acatcattgg caacgctacc tttgccatgt ttcagaaaca  1380
actctggcgc atcgggcttc ccatacaatc gatagattgt cgcacctgat tgcccgacat  1440
tatcgcgagc ccatttatac ccatataaat cagcatccat gttggaattt aatcgcggcc  1500
tcgagcaaga cgtttcccgt tgaatatggc tcataacacc ccttgtatta ctgtttatgt  1560
aagcagacag ttttattgtt catgatgata tattttatc ttgtgcaatg taacatcaga  1620
gattttgaga cacaacgtgg ctttgttgaa taaatcgaac ttttgctgag ttgaaggatc  1680
agatcacgca tcttcccgac aacgcagacc gttccgtggc aaagcaaaag ttcaaaatca  1740
ccaactggtc cacctacaac aaagctctca tcaaccgtgg ctccctcact ttctggctgg  1800 atgatgggc gattcaggcc tggtatgagt cagcaacacc ttcttcacga ggcagacctc   1860
agcgctactc gagcctgcgc gctcgctcgc tcactgaggc cgcccgggca agcccgggc    1920 gtcgggcgac ctttggtcgc ccggcctcag tgagcgagcg agcgcgcaga gagggagtgg  1980
ccaactccat cactagggggt tccttgtagt taatgattaa cccgccatgc tacttatcta  2040
cgtagccatg cagtagaaaa acagccaagc tagggaggct gggaggccaa gccccagata  2100
ccttacatag ctctgctcag cctctgtctc attaggaact ccattttag gatgcagttg  2160 tttcaggcta aaaataaatc atgcaatgaa taaaaaagtt agatacgaca ctgtagaggg  2220
attcgctgat acagtctgtc cgatctagag cagtctgggc tttcacaaga cagcatctgg  2280
ggctgcggca gagggtcggg tccgaagcgc tgccttatca gcgtcccag ccctgggagg   2340 tgacagctgg ctggcttgtg tcagcccctc gggcactcac gtatctccgt ccgacgggtt  2400
```

```
taaaatagca aaactctgag gccacacaat agcttgggct tatatgggct cctgtggggg   2460 aaggggagc acggaggggg ccggggccgc tgctgccaaa atagcagctc acaagtgttg    2520
cattcctctc tgggcgccgg gcacattcct gctggctctg cccgcccggg ggtgggcgcc   2580 gggggacct taaagcctct gccccccaag gagcccttcc cagacagccg ccggcaccca    2640
ccgctccgtg ggacctaagc ttgctagcgc taccggtcgc caccatgggt aaaagcagca   2700
ctccattgcc actagacacc actgactcgg gcttagatga caaggaagat attgaatgct   2760
tttttgaggc ctgtgttgag ggtgactctg atggagagga gccttgtttc tctagtgctc   2820
ctccaaatga atctgcagtt cccagcgaag ctgcaatgcc actacaagca acagcatgtt   2880
cttctgagtt cagtgatagt tctctttcag ctgatgatgc agatacagtg gctctttcaa   2940
gtccttcctc tcaggaaaga gctgaggttg aaaggaagt gaatggtttg ccccaaactt    3000
ccagtggctg tgcagaaaac ttagagttta ctccttcaaa gcttgacagt gaaaaggaaa   3060
gttccggaaa accaggtgaa tctggaatgc cagaagaaca taatgctgct tcagccaaat   3120
ctaaagttca agacctctcc ttgaaggcaa atcagccaac agacaaggcc gcattgcatc   3180
ccagccccaa aactttaacc tgtgaagaaa atcttctaaa ccttcatgaa aaacgacata   3240
gaaatatgca taggtagagt gtaatgcccc cacgcatgga aatcatctca ttgaaagata   3300
gcctggctga agctcagggc tagttaagtt tgatccgcgg ccgcaatcaa cctctggatt   3360
acaaaatttg tgaaagattg actgatattc ttaactatgt tgctccttt acgctgtgtg     3420 gatatgctgc tttaatacct ctgtatcgtg ctattgcttc ccgtacggct ttcgttttct   3480
cctccttgta taaatcctgg ttgctgtctc tttataagga gttgtggccc gttgtccgtc   3540
aacgtggcgt ggtgtgctct gtgtttgctg acgcaacccc cactggctgg ggcattgcca   3600
ccacctgtca actccttct gggactttcg ctttccccct cccgatcgcc acggcagaac     3660
tcatcgccgc ctgccttgcc cgctgctgga caggggctag gttgctgggc actgataatt   3720
ccgtggtgtt gtcggggaaa tcatcgtcct ttccttggct gctcgcctgt gttgccaact   3780
ggatcctgcg cggggacgtcc ttctgctacg tcccttcggc tctcaatcca gcggacctcc   3840
cttcccgcgg ccttctgccg gttctgcggc ctctcccgcg tcttcgcttt cggcctccga   3900
cgagtcggat ctccctttgg gccgcctccc cgcctgtagg cctcacctgc gatctcgatg   3960
ctttatttgt gaaatttgtg atgctattgc tttatttgta accattataa gctgcaataa   4020
acaagttaac aacaacaatt gcattcattt tatgtttcag gttcagggg aggtgtggga    4080 ggttttttaa agcaagtaaa acctctacaa atgtggtatg gctgattacc actccctctc   4140
tgcgcgctcg ctcgctcact gaggccgggc gaccaaaggt cgcccgacgc ccgggctttg   4200
cccgggcggc ctcagtgagc gagcgagcgc gcagctgaa gctatcagat ctgccggtct    4260
ccctatagtg agtcgtatta atttcgataa gccaggttaa cctgcattaa tgaatcggcc   4320
aacgcgcggg gagaggcggt ttgcgtattg ggcgctcttc cgcttcctcg ctcactgact   4380
cgctgcgctc ggtcgttcgg ctgcggcgag cggtatcagc tcactcaaag gcggtaatac   4440
ggttatccac agaatcaggg gataacgcag gaaagaacat gtgagcaaaa ggccagcaaa   4500
aggccaggaa ccgtaaaaag gccgcgttgc tggcgttttt ccataggctc cgcccccctg   4560
acgagcatca caaaaatcga cgctcaagtc agaggtggcg aaacccgaca ggactataaa   4620
gataccaggc gtttccccct ggaagctccc tcgtgcgctc tcctgttccg accctgccgc   4680
ttaccggata cctgtccgcc tttctccctt cgggaagcgt ggcgctttct catagctcac   4740
```

```
gctgtaggta tctcagttcg gtgtaggtcg ttcgctccaa gctgggctgt gtgcacgaac   4800
cccccgttca gcccgaccgc tgcgccttat ccggtaacta tcgtcttgag tccaacccgg   4860
taagacacga cttatcgcca ctggcagcag ccactggtaa caggattagc agagcgaggt   4920
atgtaggcgg tgctacagag ttcttgaagt ggtggcctaa ctacggctac actagaagaa   4980
cagtatttgg tatctgcgct ctgctgaagc cagttacctt cggaaaaaga gttggtagct   5040
cttgatccgg caaacaaacc accgctggta gcggtggttt ttttgtttgc aagcagcaga   5100
ttacgcgcag aaaaaaagga tctcaagaag atcctttgat cttttctacg ggtctgacg   5160 ctcagtggaa cgaaaactca cgttaaggga ttttggtcat gagattatca aaaaggatct   5220
tcacctagat ccttttaaat taaaaatgaa gttttaaatc aatctaaagt atatatgagt   5280
aaacttggtc tgacagttac caatgcttaa tcagtgaggc acctatctca gcgatctgtc   5340
tatttcgttc atccatagtt gcctgactcc ccgtcgtgta gataactacg atacgggagg   5400
gcttaccatc tggccccagt gctgcaatga taccgcgaga cccacgctca ccggctccag   5460
atttatcagc aataaatcag ccagccggaa gggccgagcg cagaagtggt cctgcaactt   5520
tatccgcctc catccagtct attcattgtt gccgggaagc tagagtaagt agttcgccag   5580
ttaatagttt tcacaacgtt gttgccattg ctacaggcat cgtggtgtca cgctcgtcgt   5640
ttggtatggc ttcattcagc tccggttccc aacgatcaag gcgagttaca tgtcaccca   5700 tgttgtgcaa aaaagcggtt agctccttcg gtcctccgat cgttgtcaga gtaagttgg   5760 ccgcagtgtt atcactcatg gttatggcag cactgcataa ttctcttact gtcatgccat   5820
ccgtaagatg cttttctgtg actggtgagt actcaaccaa gtcattctga aatagtgta   5880 tgcggcg                                                              5887
```

<210> SEQ ID NO 11
<211> LENGTH: 190
<212> TYPE: PRT
<213> ORGANISM: Artificial Sequence
<220> FEATURE:
<223> OTHER INFORMATION: chemically synthesized

<400> SEQUENCE: 11

```
Met Gly Lys Ser Ser Thr Pro Leu Pro Leu Asp Thr Thr Asp Ser Gly
1               5                   10                  15

Leu Asp Asp Lys Glu Asp Ile Glu Cys Phe Phe Glu Ala Cys Val Glu
            20                  25                  30

Gly Asp Ser Asp Gly Glu Glu Pro Cys Phe Ser Ser Ala Pro Pro Asn
        35                  40                  45

Glu Ser Ala Val Pro Ser Glu Ala Ala Met Pro Leu Gln Ala Thr Ala
    50                  55                  60

Cys Ser Ser Glu Phe Ser Asp Ser Ser Leu Ala Asp Asp Ala Asp
65                  70                  75                  80

Thr Val Ala Leu Ser Ser Pro Ser Ser Gln Glu Arg Ala Glu Val Gly
                85                  90                  95

Lys Glu Val Asn Gly Leu Pro Gln Thr Ser Ser Gly Cys Ala Glu Asn
            100                 105                 110

Leu Glu Phe Thr Pro Ser Lys Leu Asp Ser Glu Lys Glu Ser Ser Gly
        115                 120                 125

Lys Pro Gly Glu Ser Gly Met Pro Glu Glu His Asn Ala Ala Ser Ala
    130                 135                 140

Lys Ser Lys Val Gln Asp Leu Ser Leu Lys Ala Asn Gln Pro Thr Asp
145                 150                 155                 160
```

Lys Ala Ala Leu His Pro Ser Pro Lys Thr Leu Thr Cys Glu Glu Asn
            165                 170                 175

Leu Leu Asn Leu His Glu Lys Arg His Arg Asn Met His Arg
        180                 185                 190

<210> SEQ ID NO 12
<211> LENGTH: 209
<212> TYPE: PRT
<213> ORGANISM: Artificial Sequence
<220> FEATURE:
<223> OTHER INFORMATION: myc-tagged rat mAKAP PBD

<400> SEQUENCE: 12

Met Glu Gln Lys Leu Ile Ser Glu Glu Asp Leu Ser Pro Gly Met Leu
1               5                   10                  15

Thr Met Ser Val Thr Leu Ser Pro Leu Arg Ser Gln Thr Pro Leu Pro
            20                  25                  30

Pro Asp Ala Val Asp Ser Gly Leu Asp Asp Lys Glu Asp Met Asp Cys
        35                  40                  45

Phe Phe Glu Ala Cys Val Glu Asp Glu Pro Val Asn Glu Glu Ala Gly
    50                  55                  60

Leu Pro Gly Ala Leu Pro Asn Glu Ser Ala Ile Glu Asp Gly Ala Glu
65                  70                  75                  80

Gln Lys Ser Glu Gln Lys Thr Ala Ser Ser Pro Val Leu Ser Asp Lys
                85                  90                  95

Thr Asp Leu Val Pro Leu Ser Gly Leu Ser Pro Gln Lys Gly Ala Asp
            100                 105                 110

Asp Ala Lys Glu Gly Asp Asp Val Ser His Thr Ser Gln Gly Cys Ala
        115                 120                 125

Glu Ser Thr Glu Pro Thr Thr Pro Ser Gly Lys Ala Asn Ala Glu Gly
    130                 135                 140

Arg Ser Arg Met Gln Gly Val Ser Ala Thr Pro Glu Glu Asn Ala Ala
145                 150                 155                 160

Ser Ala Lys Pro Lys Ile Gln Ala Phe Ser Leu Asn Ala Lys Gln Pro
                165                 170                 175

Lys Gly Lys Val Ala Met Arg Tyr Pro Ser Pro Gln Thr Leu Thr Cys
            180                 185                 190

Lys Glu Lys Leu Val Asn Phe His Glu Asp Arg His Ser Asn Met His
        195                 200                 205

Arg

<210> SEQ ID NO 13
<211> LENGTH: 4064
<212> TYPE: DNA
<213> ORGANISM: Artificial Sequence
<220> FEATURE:
<223> OTHER INFORMATION: pscA-TnT-myc-rat mAKAP PBD plasmid

<400> SEQUENCE: 13
actcaaccaa gtcattctga gaatagtgta tgcggcgacc gagttgctct tgcccggcgt     60
caatacggga taataccgcg ccacatagca gaactttaaa agtgctcatc attggaaaac    120
gttcttcggg gcgaaaactc tcaaggatct taccgctgtt gagatccagt tcgatgtaac    180
ccactcgtgc acccaactga tcttcagcat cttttacttt caccagcgtt tctgggtgag    240
caaaaacagg aaggcaaaat gccgcaaaaa agggaataag ggcgacacgg aaatgttgaa    300
tactcatact cttcctttt caatattatt gaagcattta tcagggttat gtctcatga    360

```
gcggatacat atttgaatgt atttagaaaa ataaacaaat aggggttccg cgcacatttc    420
cccgaaaagt gccacctgac gtctaagaaa ccattattat catgacatta acctataaaa    480
ataggcgtat cacgaggccc tttcgtctcg cgcgtttcgg tgatgacggt gaaaacctct    540
gacacatgca gctcccggag acggtcacag cttgtctgta agcggatgcc gggagcagac    600
aagcccgtca gggcgcgtca gcgggtgttg gcgggtgtcg gggctggctt aactatgcgg    660
catcagagca gattgtactg agagtgcacc atatggacat attgtcgtta gaacgcggct    720
acaattaata cataaccttg tgtatcatac acatacgatt taggtgacac tatagaactc    780
gagcctgcgc gctcgctcgc tcactgaggc cgcccgggca aagcccgggc gtcgggcgac    840 cttggtcgc ccggcctcag tgagcgagcg agcgcgcaga gagggagtgg ccaactccat    900 cactagggt tccttgtagt taatgattaa cccgccatgc tacttatcta cgtagccatg    960
ctctagagca gtctgggctt tcacaagaca gcatctgggg ctgcggcaga gggtcgggtc   1020
cgaagcgctg ccttatcagc gtccccagcc ctgggaggtg acagctggct ggcttgtgtc   1080 agccctcgg gcactcacgt atctccgtcc gacgggttta aaatagcaaa actctgaggc   1140
cacacaatag cttgggctta tatgggctcc tgtgggggaa gggggagcac ggaggggcc   1200 ggggccgctg ctgccaaaat agcagctcac aagtgttgca ttcctctctg ggcgccgggc   1260
acattcctgc tggctctgcc cgccccgggg tgggcgccgg ggggacctta agcctctgc   1320 cccccaagga gcccttccca gacagccgcc ggcacccacc gctccgtggg acctaagctt   1380
gctagcgcta ccggtcgcca ccatggagca gaaactcatc tctgaagagg atctgagccc   1440
ggggatgtta accatgagcg tgacactttc cccactgagg tcacagactc cattgccacc   1500
ggacgctgtg gactctggct tagatgacaa ggaagacatg gactgcttct ttgaagcttg   1560
tgttgaggat gagcctgtca atgaggaagc tggtctcccc ggtgcccttc ccaatgaatc   1620
agccatcgag gatggagcag agcaaaagtc agaacaaaag acagccagct ctcctgtgct   1680
cagtgacaag acagacctgg tgcctctttc aggactttcc cctcagaagg gagctgatga   1740
tgcaaaggaa ggagatgatg tgtctcacac ttcccagggc tgtgcagaga cacagagcc   1800 taccaccccc tcaggaaagg ccaatgcaga ggggaggtca agaatgcaag gtgtatcagc   1860
aacgccagaa gaaacgctgc cttcggccaa accgaaaatt caagctttct cttttgaatgc   1920 aaaacagcca aaaggcaagg ttgccatgag gtatcccagc ccccaaactc taacctgtaa   1980
agagaagctc gtaaactttc atgaagatcg acacagtaac atgcataggt agagtgtaat   2040 gccccccacgc atggaaatca tctcattgaa agatagcctg gctgaagctc agggctagtt   2100
aagtttgatc cagacatgat aagatacatt gatgagtttg gacaaaccac aactagaatg   2160
cagtgaaaaa aatgctttat ttgtgaaatt tgtgatgcta ttgctttatt tgtaaccatt   2220
ataagctgca ataaacaagt taacaacaac aattgcattc attttatgtt tcaggttcag   2280
ggggaggtgt gggaggtttt ttaaagcaag taaaacctct acaaatgtgg tatgctgat    2340 taccactccc tctctgcgcg ctcgctcgct cactgaggcc gggcgaccaa aggtcgcccg   2400
acgcccggga tttgcccggg cggcctcagt gagcgagcga gcgcgccagc tgaagctatc   2460
agatctgccg gtctccctat agtgagtcgt attaatttcg ataagccagg ttaacctgca   2520
ttaatgaatc ggccaacgcg cggggagagg cggtttgcgt attgggcgct cttccgcttc   2580
ctcgctcact gactcgctgc gctcggtcgt tcggctgcgg cgagcggtat cagctcactc   2640
aaaggcggta atacggttat ccacagaatc aggggataac gcaggaaaga acatgtgagc   2700
```

-continued

```
aaaaggccag caaaaggcca ggaaccgtaa aaaggccgcg ttgctggcgt ttttccatag    2760
gctccgcccc cctgacgagc atcacaaaaa tcgacgctca agtcagaggt ggcgaaaccc    2820
gacaggacta taaagatacc aggcgtttcc ccctggaagc tccctcgtgc gctctcctgt    2880
tccgacccug ccgcttaccg gatacctgtc cgcctttctc ccttcgggaa gcgtggcgct    2940
ttctcatagc tcacgctgta ggtatctcag ttcggtgtag gtcgttcgct ccaagctggg    3000
ctgtgtgcac gaaccccccg ttcagcccga ccgctgcgcc ttatccggta actatcgtct    3060
tgagtccaac ccggtaagac acgacttatc gccactggca gcagccactg gtaacaggat    3120
tagcagagcg aggtatgtag gcggtgctac agagttcttg aagtggtggc ctaactacgg    3180
ctacactaga agaacagtat ttggtatctg cgctctgctg aagccagtta ccttcggaaa    3240
aagagttggt agctcttgat ccggcaaaca aaccaccgct ggtagcggtg gtttttttgt    3300
ttgcaagcag cagattacgc gcagaaaaaa aggatctcaa gaagatcctt tgatcttttc    3360
tacggggtct gacgctcagt ggaacgaaaa ctcacgttaa gggattttgg tcatgagatt    3420
atcaaaaagg atcttcacct agatcctttt aaattaaaaa tgaagtttta atcaatcta    3480
aagtatatat gagtaaactt ggtctgacag ttaccaatgc ttaatcagtg aggcacctat    3540
ctcagcgatc tgtctatttc gttcatccat agttgcctga ctccccgtcg tgtagataac    3600
tacgatacgg gagggcttac catctggccc cagtgctgca atgataccgc gagacccacg    3660
ctcaccggct ccagatttat cagcaataaa ccagccagcc ggaagggccg agcgcagaag    3720
tggtcctgca actttatccg cctccatcca gtctattaat tgttgccggg aagctagagt    3780
aagtagttcg ccagttaata gtttgcgcaa cgttgttgcc attgctacag gcatcgtggt    3840
gtcacgctcg tcgtttggta tggcttcatt cagctccggt tcccaacgat caaggcgagt    3900
tacatgatcc cccatgttgt gcaaaaaagc ggttagctcc ttcggtcctc cgatcgttgt    3960
cagaagtaag ttggccgcag tgttatcact catggttatg gcagcactgc ataattctct    4020
tactgtcatg ccatccgtaa gatgcttttc tgtgactggt gagt                    4064
```

<210> SEQ ID NO 14
<211> LENGTH: 209
<212> TYPE: PRT
<213> ORGANISM: Artificial Sequence
<220> FEATURE:
<223> OTHER INFORMATION: pscA-TnT-myc-rat mAKAP PBD

<400> SEQUENCE: 14

```
Met Glu Gln Lys Leu Ile Ser Glu Glu Asp Leu Ser Pro Gly Met Leu
1               5                   10                  15

Thr Met Ser Val Thr Leu Ser Pro Leu Arg Ser Gln Thr Pro Leu Pro
            20                  25                  30

Pro Asp Ala Val Asp Ser Gly Leu Asp Lys Glu Asp Met Asp Cys
        35                  40                  45

Phe Phe Glu Ala Cys Val Glu Asp Glu Pro Val Asn Glu Glu Ala Gly
    50                  55                  60

Leu Pro Gly Ala Leu Pro Asn Glu Ser Ala Ile Glu Asp Gly Ala Glu
65                  70                  75                  80

Gln Lys Ser Glu Gln Lys Thr Ala Ser Ser Pro Val Leu Ser Asp Lys
                85                  90                  95

Thr Asp Leu Val Pro Leu Ser Gly Leu Ser Pro Gln Lys Gly Ala Asp
            100                 105                 110

Asp Ala Lys Glu Gly Asp Asp Val Ser His Thr Ser Gln Gly Cys Ala
        115                 120                 125
```

```
        Glu Ser Thr Glu Pro Thr Thr Pro Ser Gly Lys Ala Asn Ala Glu Gly
            130                 135                 140

Arg Ser Arg Met Gln Gly Val Ser Ala Thr Pro Glu Glu Asn Ala Ala
        145                 150                 155                 160

Ser Ala Lys Pro Lys Ile Gln Ala Phe Ser Leu Asn Ala Lys Gln Pro
                        165                 170                 175

Lys Gly Lys Val Ala Met Arg Tyr Pro Ser Pro Gln Thr Leu Thr Cys
                        180                 185                 190

Lys Glu Lys Leu Val Asn Phe His Glu Asp Arg His Ser Asn Met His
                        195                 200                 205

Arg

<210> SEQ ID NO 15
        <211> LENGTH: 5817
        <212> TYPE: DNA
        <213> ORGANISM: Homo sapiens

<400> SEQUENCE: 15
gcggagaagg aggcggaggg agcgattgtg gccccggccg cggtggccgg cgcggcctgc         60
cctttgtgac cgcagctcgc gccccacgcc ccgcgcccat ggccgccgtg ccgggctccc        120
tggccacgcg tgcccgcccg cggacctgag ccccgcgcct gggatgccgg ggatgcgcgt        180
cccccggccc tgcggctgct ccgggctggg cgcggggcga tggacctgag catgaagaag        240
ttcgccgtgc gcaggttctt ctctgtgtac ctgcgcagga agtcgcgctc caagagctcc        300
agcctgagcc ggctcgagga agaaggcgtc gtgaaggaga tagacatcag ccatcatgtg        360
aaggagggct ttgagaaggc agatccttcc cagtttgagc tgctgaaggt tttaggacaa        420
ggatcctatg gaaaggtgtt cctggtgagg aaggtgaagg ggtccgacgc tgggcagctc        480
tacgccatga aggtccttaa gaaagccacc ctaaaagttc gggaccgagt gagatcgaag        540
atggagagag acatcttggc agaagtgaat caccccttca ttgtgaagct tcattatgcc        600
tttcagacgg aaggaaagct ctacctgatc ctggacttcc tgcggggagg ggacctcttc        660
acccggctct ccaaagaggt catgttcacg gaggaggatg tcaagttcta cctggctgag        720
ctggccttgg ctttagacca tctccacagc ctggggatca tctacagaga tctgaagcct        780
gagaacatcc tcctggatga agaggggcac attaagatca cagatttcgg cctgagtaag        840
gaggccattg accacgacaa gagagcgtac tccttctgcg gacgatcga gtacatggcg        900 cccgaggtgg tgaaccggcg aggacacacg cagagtgccg actggtggtc cttcggcgtg        960
ctcatgtttg agatgctcac ggggtccctg ccgttccagg ggaaggacag gaaggagacc       1020
atggctctca tcctcaaagc caagctgggg atgccgcagt tcctcagtgg ggaggcacag       1080
agtttgctgc gagctctctt caaacggaac ccctgcaacc ggctgggtgc tggcattgac       1140
ggagtggagg aaattaagcg ccatcccttc tttgtgacca tagactggaa cacgctgtac       1200
cggaaggaga tcaagccacc gttcaaacca gcagtgggca ggcctgagga caccttccac       1260
tttgaccccg agttcacagc gcggacgccc acagactctc ctggcgtccc cccgagtgca       1320
aacgctcatc acctgtttag aggattcagc tttgtggcct caagcctgat ccaggagccc       1380
tcacagcaag atctgcacaa agtcccagtt cacccaatcg tgcagcagtt acacgggaac       1440
aacatccact tcaccgatgg ctacgagatc aaggaggaca tcggggtggg ctcctactca       1500
gtgtgcaagc gatgtgtgca taagccaca gacaccgagt atgccgtgaa gatcattgat       1560
aagagcaaga gagacccctc ggaagagatt gagatcctcc tgcggtacgg ccagcacccg       1620
```

```
aacatcatca ccctcaagga tgtctatgat gatggcaagt ttgtgtacct ggtaatggag   1680
ctgatgcgtg gtggggagct cctggaccgc atcctccggc agagatactt ctcggagcgc   1740
gaagccagtg acgtcctgtg caccatcacc aagaccatgg actacctcca ttcccagggg   1800
gttgttcatc gagacctgaa gccgagtaac atcctgtaca gggatgagtc ggggagccca   1860
gaatccatcc gagtctgcga cttcggcttt gccaagcagc tgcgcgcggg gaacgggctg   1920
ctcatgacac cctgctacac ggccaatttc gtggccccgg aggtcctgaa gcgtcaaggc   1980
tatgatgcgg cgtgtgacat ctggagtttg gggatcctgt tgtacaccat gctggcagga   2040
tttacccctt ttgcaaatgg gccagacgat acccctgagg agattctggc gcggatcggc   2100
agtgggaagt atgccctttc tgggggaaac tgggactcga tatctgacgc agctaaagac   2160
gtcgtgtcca agatgctcca cgtggaccct catcagcgcc tgacggcgat gcaagtgctc   2220
aaacacccgt gggtggtcaa cagagagtac ctgtccccaa accagctcag ccgacaggac   2280
gtgcacctgg tgaagggcgc gatggccgcc acctactttg ctctaaacag aacacctcag   2340
gccccgcggc tggagcccgt gctgtcatcc aacctggctc agcgcagagg catgaagaga   2400
ctcacgtcca cgcggctgta gcgggtggga ccctggcccc agcgtcccct gccagcatcc   2460
tcgtgggctc acagaccccg gcctcggagc ccgtctggca cccagagtga ccacaagtcc   2520
agcagggagg cggcgcccgc cctcgccgtg tccgtgtttt cttttcagc cccgagagg    2580
gtcctgacct gggggcttct ccaagcctca ctgcgccagc ctccccgccc gctctctttt   2640
ctcccaagcg aaaccaaatg cgccccttca cctcgcgtgc ccgtgcgagg ccggggcttt   2700
cttttcagagc ccgcgggtcc tctcatacat ggcttctgtt tctgccgaga gatctgtttt  2760
ccaattatga agccggtcgg tttggtcaga ctcccgacac ccacgtccca ggtaccgggt   2820
gggaaagtgg cagtgcgagg gcgcagccat ggtggttgc agggccccag agggctgggg   2880
tgacctggca tcccggggct ccccacgggc tggatgacgg ggttggcact gtggcgtcca   2940
ggaggagatg cctggttctg cccaaaataa tccaaagagc cgtttcctcc tcgcccttca   3000
gttttttgcct gaggtgctgg gtagcccatc ctttcctctg tcccagattc aaatgaggag   3060
taagagccca gacgagagga aggcaggctg gatctttgcc ttgagagctc cgtgtcacca   3120
ggatggaagg gggtgcctct cggaggagcc tgtgtccacc tccagtctcg gctttccccg   3180
gggggccaag cgcactgggc tgccgtctgt ccccagctcc cgtggccaca cagctatctg   3240
gaggctttgc agggagtcgt gggttctcgc acctgctcag ccctgtgtcg gcttcctgtg   3300
tgctcaccta aagctgtggt tttgctgtgt tcacttcgat ttttctggtc tgtggagaaa   3360
ctgtgaattg gagaaatgga gctctgtggc ttcccaccca aaccttctca gtccagctgg   3420
aggctggagg gagacacagg ccccacccag cagactgagg ggcagaggca caggtgggag   3480
ggcagcggag atcagcgtgg acaggagcga tgcactttgt agatgctgtg ctttgtgtt   3540
gcgtttgtgt tctctgttgc acagatctgt ttttttcacac tgatccgtat tccctgggt   3600
gtgcacacag ggcgggtgtg gggcatttag gccatgctgt gctctacttc attgagtaaa   3660
atcgagtgag aggttccggg cagcaggatc gacgcccagt ccagccggca gagggaacac   3720
acgggtcctt cattgtcctg taagggtgtt gaagatgctc cctggcggcc cccaagcaga   3780
ctagatggga ggaggcgccg ctcagcccct caccctgcat cactgaagag cggcgcctct   3840
gcagcaagca gggcttcagg aggtgcccgc tggccacagc caggttttcc ctaagaagat   3900
gttatttttgt tgggttttgt tccccctcca tctcgattct cgtacccaac taaaaaaaaa   3960
```

```
aaaataaaga aaaaatgtgc tgcgttctga aaaataactc cttagcttgg tctgattgtt    4020
ttcagacctt aaaatataaa cttgtttcac aagctttaat ccatgtggat ttttttttc     4080 ttagagaacc acaaaacata aaaggagcaa gtcggactga atacctgttt ccatagtgcc    4140
cacagggtat tcctcacatt ttctccatag aagatgcttt ttcccaaggc tagaacgact    4200
tccaccatga tgaatttgct ttttaggtct taattatttc acttcttttt agaaacttag    4260
gaagaagtgg ataatcctga ggtcacacaa tctgtcctcc cagaaatgaa caaaagtcat    4320 cacctttct gcttgctaca caggcaacga ttcccccatc agctgcccgg acccctttggc   4380 ctggcttggt gtgcaggcct gtctgtttgc ttaaagtcag tgggttctgg tgcagggagt    4440
gagaagtggg ggaagtgaaa gggaaagcat ccgtgagaaa gcggccacgg tttttccctcc   4500 ttgtgtgccc atggggcacc agctcatggt cttttttcagt catcccagtt tgtacagact   4560
tagcttctga actctaagaa tgccaaaggg accgacgaga ctccccatca cagcgagctc    4620
tgtccttaca tgtatttgat gtgcatcagc ggaggagaac actggcttgg ccctgctccg    4680
ctgagtgtct gtgaaatacc tctactttcc ctcccatatc cagaacaaaa tgatacttga    4740
catccttcca caaagtcag cctaaagaag ttatggtatc atatgttaaa ctaagctttc     4800 aaaaaccta gtgaaatagc aagtgactgc tttcaagcag cagtcgacat gtaaatgaag    4860
gtgttcttag aattcgcatt ttgccagctc agcgcacctc cacaacgaat gaaatgctcc    4920
gtatgatttg cacaaatgac atagacctcc ccaaaagtta actggctctc cttcctcaca    4980
cagttcatca taacccaacc cccaccccc gggtcatgaa atcacagaa cttataaaca      5040 cattgaaccc tagatctcag gcttcctgac ctaccgccag tggccccttg ctggccaccc    5100
tatagggtcc tccttccctg gcagccccc atgtgggaga aatacctgat tctcccaatc     5160
tgcagtggga gagctttgct gaattccatc ccaaagtcaa acatgggcaa gaggtgagga    5220
tttcactttt accctcaagt ccgatttgtc tgtgatttta aactaactgt gtatgtattg    5280
atgtttggaa gattgtttga atttttaaagt gataatagta cttaatgtta tccagtattg   5340
ttcattaaat ggtgttatcc taaagctgca cttgggatttt ttacctaacg ctttactgat   5400
tctctcaagc acatggcaaa gtttgatttg cactccgttc atttctgaca cgttttgctg    5460
cctcctacct ttctaagcgt catgcaaatt cgagaatgga aaggacgct gccggtccct     5520 gagcggtgtg gagagggcgg aaggtggact ccagcgcagc ttgaggggct gaggacggag    5580
gctgcagcat ctgtgtcgtt ctactgagca cgcttctctg cctcgctcct gactcagcac    5640
tttgttcact ggctcagcag ttatgtttac acatcatttt tatgttcctg ctttgtaatt    5700
catgtttgag atgggtggcc actgtacaga tatttattac gctttccaga ctttctgaat    5760 agatttttt gaataaacat ggttttatga agtgtaatct ttttctagcc taacaat       5817
```

<210> SEQ ID NO 16
<211> LENGTH: 8841
<212> TYPE: DNA
<213> ORGANISM: Artificial Sequence
<220> FEATURE:
<223> OTHER INFORMATION: rat mAKAPalpha mRNA

<400> SEQUENCE: 16

```
gcatcatgca gcaggtcaaa caaggcatct cctagtattg catcctccag atgtgctgta      60
aacatcaaaa ggagacgctg ggagcaggag atgctgtttt ggaaagaagt aaggcttaga    120
tttctccatg ttaaccatga gcgtgacact ttccccactg aggtcacagg gcccagatcc    180
catggcgacg gatgcttcac ccatggccat caacatgaca cccactgtgg agcaggagga    240
```

```
aggagaggga gaggaagccg tgaaggccat agacgctgag cagcagtatg gaaagccacc    300
tccgctccac acagcagccg actggaagat tgtcctgcac ttacctgaga ttgagacctg    360
gctccggatg acctcagaga gggtccgtga cctgacctac tcagtccagc aggatgcaga    420
cagcaagcat gtggatgtgc atctagttca gctgaaggac atttgtgagg atatttctga    480
ccatgtggag cagatccatg ccctccttga gacggagttt tccctaaagc tgctgtccta    540
ctcggtcaac gtcatcgtag acatccacgc agtacagctg ctctggcacc agctccgcgt    600
atccgtgctg gtcctccggg agcgcatcct acaaggtctg caggacgcca atggcaacta    660
caccaggcag actgacattc tgcaagcgtt ctctgaagaa caacggagg gccggcttga    720 ttcccttaca gaagtggacg actcagggca gttaactatc aaatgttcac aggattactt    780
gtctctggat tgtggcatta ccgcatttga actctccgac tacagtccaa gtgaggatct    840
gcttggtggc ctgggcgaca tgaccaccag ccaggccaaa actaaatctt ttgactcttg    900
gagctacagt gagatggaga aagagttccc tgagcttatc cgaagcgttg gctgcttac    960 agtggccacc gagcctgtcc cttccagctg tggagaagcc aatgaggatt catctcaagc   1020 gtcccttttca gatgatcaca aaggtgaaca cggggaagac ggtgctcccg tacctggaca   1080
gcagctggac tcaacggtgg gaatgtcttc cttagacggc acgctggcaa atgctgccga   1140
acacccttcg gagacagcaa aacaagactc tacttcctcc ccacagcttg gtgcgaagaa   1200
aacccagcct ggtccttgtg aaattacgac tcccaagaga tccatccgcg attgctttaa   1260
ttataacgag gactccccca cacagcccac attacccaaa agagggcttt ttctaaaaga   1320
aactcaaaag aatgagcgca aaggcagtga caggaagggg caggtggttg atttaaagcc   1380
tgaactgagc agaagcaccc cttcccctggt ggaccccct gacagatcga agctctgcct   1440
agtgttgcag tcctcctacc ccagcagccc ttctgctgcc agccagtcct atgaatgttt   1500
gcacaaggtg gggctcggca atcttgaaaa catagtcaga agtcacatta agaaatttc   1560 ttccagtctg gaaggcttaa ctgactgcca taaagagaaa ttgcgactga aaaagccaca   1620
caagaccttg gccgaagtgt ctctgtgcag aatccctaaa cagggaggcg gttcaggaaa   1680
gcgatctgag agcaccggga gctcagcagg gcccagcatg gtatcacctg gagctcccaa   1740
agccacgatg agaccagaaa cagattctgc gtctacagcc tcaggtggcc tgtgccacca   1800
gagaaatcgc agtggacaat tgccagtgca gtcgaaggcc tccagttcac ccccttgcag   1860
tcacagcagt gaatcttctc ttggctcaga tagcatcaaa tccccggttc ctcttctttc   1920
aaaaaacaaa agccaaaaaa gctccccacc tgctccatgt cacgccacac agaacggtca   1980
ggtggtggag gcctggtacg gctctgatga gtacctagcg ctgccctctc acctgaagca   2040
gacggaggtg ttagctctca agctggagag cctaaccaag ctcctacccc agaaacccag   2100
aggagagacc atccaggata ttgatgactg ggaactgtct gaaatgaatt cagattccga   2160
aatctatcca acataccaca tcaagaaaaa acacacgaga ctgggcacag tgtctccaag   2220
ctcatccagc gacatagcct catctctcgg ggagagcatt gaatccgggc ccctgagtga   2280
cattctttct gacgaggact tatgtctgcc cctctccagc gtgaaaaagt tcactgacga   2340
gaaatcagag agaccttcat cctccgagaa gaacgagagc cattctgcaa caagatcagc   2400
tttgattcag aaactaatgc acgatattca gcaccaagag aactatgaag ccatctggga   2460
aagaattgag gggtttgtga acaagctgga tgaattcatt cagtggctaa acgaagccat   2520
ggagaccacc gagaactgga ctcctcctaa agccgagacc gacagcctcc ggctgtacct   2580
```

-continued

```
ggagacacac ttgagtttta agttgaacgt agacagccac tgtgccctca aggaagccgt   2640
ggaggaagaa ggacaccaac ttcttgagct cgttgtatct cacaaagcag gactgaagga   2700
cacgctgagg atgattgcga gtcaatggaa ggagctgcag aggcaaatca acggcaaca   2760 cagctggatt ctcagagccc tggacaccat caaagccgag atactggcta ctgatgtgtc   2820
tgtggaggac gaggagggga cgggaagccc caaggccgag gttcagctct gccacctgga   2880
aacacagaga gacgccgtgg aacagatgtc cctgaagctg tacagcgagc agtacaccag   2940
cgggagcaag aggaaggaag agtttgccaa catgtcgaaa gcgcacgcgg agggaagcaa   3000
tgggcttctg gactttgatt cagaatatca ggagctctgg gattggctga ttgacatgga   3060
gtccctcgtg atggacagcc acgacctgat gatgtcagag gagcagcagc agcatcttta   3120
caagaggtac agtgtggaaa tgtccatcag gcatctgaaa aagtcagagc tactcagcaa   3180
ggttgaagct ttgaagaaag gtggcctttc actaccagac gatatcctgg aaaaagtgga   3240
ttcaattaat gaaaaatggg agctgcttgg gaaaaccta agagagaaga tacaggacac   3300
aatagcgggg cacagtgggt cgggcccacg tgacctgcta tctcctgaaa gcggaagcct   3360
ggtaaggcag ctggaggtca ggatcaaaga gctgaaaagg tggctaagag atacagagct   3420
tttcatcttc aattcctgtc tgagacaaga gaaggaagga acaagcgccg agaaacagct   3480
ccaatacttt aagtcgctct gtcgtgagat caagcagcgg cgtcgaggag tggcctccat   3540
tctgaggttg tgccagcacc ttctggatga ccggacacg tgcaacctga cgcagatca   3600 ccagcccatg cagctgatca ttgtaaacct cgagaggcgg tgggaggcca tcgtcatgca   3660
agctgtccag tggcaaacac ggttacaaaa gaagatgggg aaggaatccg agactttgaa   3720
tgtgattgat cctggcttga tggacctgaa tggaatgagt gaggatgccc tggaatggga   3780
tgaaacagac ataagtaaca aactcattag tgtgcatgaa gaatcaaacg accttgatca   3840
agacccagag cctatgctac ccgcagtgaa gcttgaagag acacaccaca aggactctgg   3900
ttatgaagag gaggcaggtg actgtggagg gtctccgtat acctcaaata tcactgcacc   3960
ttccagccca cacatttacc aagtgtacag tcttcacaat gtggagctcc acgaggacag   4020
ccacactcca tttctgaaaa gcagccctaa gttcacaggc acaacacagc ctactgtttt   4080
aactaagagc ctcagcaagg actcttcctt ttcatctaca aaatcgttac cagaccttct   4140 aggggggttcc ggtttggtga ggccttactc gtgtcacagt ggagacttga gccagaattc   4200
aggcagtgag agtggaattg tcagcgaagg agacaacgag atgccgacca actctgacat   4260
gagcttgttc agtatggtag acgggtcccc aagtaaccct gaaacggagc atccggaccc   4320
acaaatggga gatgcagcca atgtgctaga gcaaaagttt aaagacaacg gggaaagcat   4380
taagctttca agtgtctctc gggcatccgt ctcaccagtg ggttgtgtaa atggaaaagc   4440
aggggattta acagtgtta ccaaacacac tgctgattgt ttgggagaag aactacaagg   4500
aaaacatgac gtgtttacat tttatgatta ctcgtacctc caaggctcaa aactcaaatt   4560
accaatgata atgaaacagc cacagagtga aaaggcacac gtggaggatc cccttcttgg   4620 tggttttttat tttgataaaa agtcctgcaa agctaaacat caggcttcag agtcacaacc   4680
agatgcgcct cccacgaaa ggattctggc aagcgcgccc cacgagatgg gacgcagcgc   4740 atacaaagt agcgacatag agaagacatt cacgggcatt cagagtgcca gacagctctc   4800
ccttctatct cgtagctcat ctgtagagtc ccttttctcca ggggtgatt tgtttggatt   4860 gggaatcttt aaaaatggca gtgacagcct ccagcggagc acttctttag aaagttggtt   4920
gacatcctat aagagcaatg aggatctctt tagctgtcac agctctgggg acataagtgt   4980
```

```
gagcagtggc tcagttggtg agctgagtaa gaggacgtta gaccttctga atcgcctgga    5040
gaatatacag agcccctcgg agcaaaagat caagcggagt gtttctgaca tgactctaca    5100
aagcagttcc caaaagatgc ccttcgctgg ccagatgtca ctggatgtcg catcctccat    5160
caatgaagac tctccggcat ctcttacaga actgagtagt agcgatgagc tctctctttg    5220
ctcggaggac attgtgttac acaaaaacaa gatcccagaa tccaacgcat cattcaggaa    5280
gcgcctgaat cgctcagtgg ctgatgagag cgacgtcaat gttagcatga ttgtcaatgt    5340
gtcctgcacc tctgcttgca ctgatgatga agatgacagc gacctcctct ccagctccac    5400
tctcacctta actgaagaag agctgtgcct caaagatgag gatgacgact ccagtattgc    5460
aacagatgat gaaatttatg aagagagcaa cctgatgtct gggctggact acataaagaa    5520
tgaactgcag acttggataa gaccaaaact ttccttgacg agagaaaaga aacggtccgg    5580
tgtcactgat gaaataaagg tcaataaaga tgggggaggc aatgagaagg ccaatccctc    5640
ggacaccctg gacatcgagg cccttctcaa tggctccata agatgtcttt ccgaaaacaa    5700
cgggaatggt aagactccgc ccagaactca tggctcagga accaaaggtg aaaataagaa    5760
aagtacgtat gacgttagta aggatccgca cgtggctgac atggaaaatg gcaatattga    5820
aagtacccca gaaagagaaa gggagaagcc acaagggctt ccagaggtgt cagagaacct    5880
tgcttcaaat gtgaaaacga tttctgaatc tgagctcagc gagtatgaag cagtaatgga    5940
tggttctgag gattcaagtg ttgccagaaa ggaattttgt cccccaaatg acagacatcc    6000
tccacagatg ggtcccaaac tccagcatcc cgaaaatcaa agtggcgact gcaagccagt    6060
ccagaaccct tgcccggggc tactgtcgga agctggcgtt ggaagcaggc aagacagcaa    6120
tggactaaaa tctttgccta acgatgcacc aagtgggget agaaaacctg ccggttgctg    6180
cctgctggag cagaatgaga cagaggaaag tgcttctatc agcagcaacg cttcctgttg    6240
caactgcaag ccagatgttt tccatcaaaa agatgatgaa gattgttcag tacatgactt    6300
tgttaaggaa atcattgaca tggcatcaac agccctaaaa agtaagtcac agcctgaaag    6360
tgaggtggcc gcacccacat cactaaccca aattaaggag aaggtgttag agcattcgca    6420
ccggcccata cacctgagaa agggggactt ttactcctac ttatcacttt cgtcccacga    6480
cagtgactgt ggggaggtca ccaattacat agatgagaag agcagtactc cattgccacc    6540
ggacgctgtg gactctggct tagatgacaa ggaagacatg gactgcttct ttgaagcttg    6600
tgttgaggat gagcctgtca atgaggaagc tggtctcccc ggtgcccttc ccaatgaatc    6660
agccatcgag gatggagcag agcaaaagtc agaacaaaag acagccagct ctcctgtgct    6720
cagtgacaag acagacctgg tgcctctttc aggactttcc cctcagaagg gagctgatga    6780
tgcaaaggaa ggagatgatg tgtctcacac ttcccagggc gtgtgcagaga gcacagagcc    6840 taccaccccc tcaggaaagg ccaatgcaga ggggaggtca agaatgcaag gtgtatcagc    6900
aacgccagaa gaaacgctg cttcggccaa accgaaaatt caagctttct ctttgaatgc    6960
aaaacagcca aaaggcaagg ttgccatgag gtatcccagc ccccaaactc taacctgtaa    7020
agagaagctc gtaaactttc atgaagatcg acacagtaac atgcataggt agagtgtaat    7080
gcccccacgc atgaaaatca tctcattgaa agatagcctg gctgaagctc agggctagcc    7140
caatccaccc tgggccggtc ttgggctcca tcctgttatc actgccgcct gtcacattga    7200
ctttctgaag acgaaccttc cttccgaatg cagtctgtcc acgtgggcct ctcgacctgg    7260
atgtgtgcat tgcttctctt aggtgatcat cctagttcca caaagctgct tgttctcccg    7320
```

```
tggattcctg tcccaagcta cctctggcaa ccctgtctct ccagcaagac ttcggttttc    7380
cctcccctc ctcccccccc ttaaagttcc gcggctcacc aaattgatgg tccatcaaac    7440
ccactgtctg gaatgatacc cctcccatca gtacttgacc aatgttatgt tttgctctga   7500
aaactttcgc tgtattagac caatgtttat tgaaagagat ttacctaaaa agcccgccct   7560
tgatttggtt gcagtataga ggagacacat tgatccttct aacaaaatta agtgatgtct   7620
gaaagcgcca ttttaattat ttcttttttaa ataatgatct atgcagcact tcaagaaaca  7680
actataacag tgttgtatct tataaactgg tacattctac tattaagttt gttttttggtt 7740
tctatgcttc ttgaggtggt gatgagaaaa atggttttttt tttaaaacg gtgtgccttg   7800
ctgtattact tatagcattt attaaaaagc tgctttcatg gtaagattac actggtttga   7860
aaggaggaaa tagcaaggtt aagatgcgtg cataatttct gtatatatgt ataagctagt   7920
gcaaacactg atgtatgaca gtataaaatg cttcatgtt tgtgatgtcc agtggtgtgg    7980
aatataagcc ttaaacccgt tcgattgcat ggtaattaaa attggcataa taaaaatagc   8040
ttattggggg aaaggaaaat taatgatctc ttctacctgt gttaccaat ttcttttcatg   8100
tggttctggg aaagaaaaag aaacaaaccc catatattag cttccaaaat atccatattg   8160
cacagaaggc ttaagttgct tagactacag actgggcctg aagacttcat gattttccaa   8220
atttttctgt ttcactataa acatccgaaa tagcaaagat ttcttcccc tccatcaaca    8280
gcatttatt ctgaatgttt ttatttctac ttgttaatgg tttaaagttg tatttggaga    8340
tctcttacat gccctaattt attttaaata tttgaatggg tttggtggat ggtatagaaa   8400
attaattat tattttattt aaactacaga tttcaggtgt atttattttg ttaaatattc    8460
catttggtct tttggtcttt ttatgacttg aaagtttcag cttttaattt atatcataac   8520
tcctactaaa gtgcctgaca cacagtaggt atttcataga gtttcctgaa ttagagtatt   8580
gggtggttta tatatatata tatatatatg agattcctgc attaaaacta gaaaaagatg   8640
tgcaaagtga accagacaca gcatattatc agatttcaaa aaggaaagag aacatagcca   8700
cagaaatgac aatcattcat tcagtagatt agcatctttt gcctgcaagt caccattcta   8760
gattcaggga gagcagctat gaccgatgca ctgccttttgg aggcttctgt gttagagaca  8820
gagtgacctc gtgccgaatt c                                             8841

<210> SEQ ID NO 17
<211> LENGTH: 10227
<212> TYPE: DNA
<213> ORGANISM: Artificial Sequence
<220> FEATURE:
<223> OTHER INFORMATION: human mAKAPbeta

<400> SEQUENCE: 17
gagtctggga gctgagtgac tgaggatttg aaaccttgct atagttacag ttcataacaa    60
gcgtctaggc agttagacct taagtgttca ggtatggaaa gaaagtcata tgttatgttt   120
tagattctgt ttgtaaagct ggttaactag agacagctga tgaaaaacca aatcgacttg   180
agttacaaga tctgggcttt ctctgctctg ctttcaacct gttggttggt ggtggagtag   240
ctgacagaag cgaatggctt ggctgaggga catgaagtga cagcagcctg tttaggacca   300
caccacattt tggacctctt gctgtgcagt tcaggacatt tgtgaagata tttctgatca   360
tgttgagcaa atccatgccc tccttgaaac agagttctcc ctaaagctgc tgtcttactc   420
tgtcaacgtg atagtggaca tccacgcagt gcagctcctc tggcaccagc ttcgagtctc   480
agtgctggtt ctgcgggagc gcattctgca aggtctgcag gacgccaatg gcaactacac   540
```

```
taggcagacg gacattctgc aagctttctc tgaagagaca aaagagggcc ggcttgattc    600
tctaacagaa gtggatgact caggacaatt aaccatcaaa tgttctcaaa attacttgtc    660
tctggattgt ggcattactg cattcgaact gtctgactac agtccaagtg aggatttgct    720
cagtgggcta ggtgacatga cctctagcca agtcaaaacc aaacccttg actcttggag     780 ctacagtgag atggaaaagg agtttcctga gcttatccga agtgttggtt tacttacggt    840
agctgctgac tctatctcta ccaatggcag tgaagcagtt actgaggagg tatctcaagt    900
atctctctca gtagacgaca aaggtggatg tgaggaagac aatgcttctg cagtcgaaga    960
gcaaccaggc ttaacactgg gggtgtcatc atcttcagga gaagctctga caaatgctgc   1020
tcaaccctcc tctgagactg tgcagcaaga atccagttcc tcctcccatc atgatgcaaa   1080
gaatcagcag cctgttcctt gtgaaaatgc aaccccaaa cgaaccatca gagattgctt    1140
taattataac gaggactctc ccacgcagcc tacattgcca aaaagaggac ttttcttaa    1200 agaggaaact tttaagaatg atctgaaagg caatggtgga agaggcaaa tggttgatct    1260 aaagcctgag atgagcagaa gcacccctc gctagtagat cctcctgaca gatccaaact   1320
ttgcctggta ttgcagtctt cttaccccaa cagcccttct gctgccagcc agtcttatga   1380
gtgtttacac aaggtgggga tgggaacct tgaaaacaca gtcaaatttc acattaaaga    1440
aatttcttcc agcctgggaa ggcttaacga ctgctataaa gagaaatctc gacttaaaaa   1500
gccacacaag acctcagaag aggtgcctcc atgccgaaca cctaaacggg ggactggttc   1560
aggcaaacaa gctaaaaata caaagagctc agcagtgcca aatggagagc tttcttatac   1620
ttccaaggcc atagagggc cacaaacaaa ttctgcttcc acatcctcac ttgagccttg    1680
taatcagaga agttggaatg ccaaattgca attgcagtca gaaacatcca gttcaccagc   1740
ttttactcag agcagtgaat cctctgttgg ctcagacaac atcatgtctc cggtgccact   1800
tctttcaaaa cacaaaagca aaaaaggtca agcctcctct ccaagtcacg tcactaggaa   1860
tggtgaggtt gtggaggcct ggtatggctc tgatgaatac ctagcactgc cctctcacct   1920
taagcagaca gaagtattgg ctttgaagtt ggaaaaccta acaaagcttc tgcctcagaa   1980
acccagagga gaaaccatcc agaatattga tgactgggaa ctgtctgaaa tgaattcaga   2040
ttctgaaatc tatccaacct atcatgtcaa aaagaagcat acaaggctag caggtgtc     2100 tccaagctca tctagtgaca tagcctcttc actaggggag agcattgaat ctgggcccct   2160
gagtgacatt ctttctgatg aggagtccag tatgcctctc gctggcatga aaaagtatgc   2220
tgatgagaag tcagaaagag cttcatcctc tgagaaaaat gagagccatt ctgccactaa   2280 atcagctta attcagaaac tgatgcaaga tattcagcac caagacaact atgaagccat    2340
atgggaaaaa atagagggt ttgtaaacaa actggatgaa ttcattcaat ggttaaatga    2400
agccatggaa actacagaga attggactcc ccctaaagca gagatggatg accttaaact   2460
gtatctggag acacacttga gttttaagtt gaatgtagac agtcattgtg ctctcaagga   2520
agctgtggag gaggaaggac accaacttct tgagcttatt gcatctcaca aagcaggact   2580
gaaggacatg ctgcggatga ttgcaagtca atggaaggag ctgcagaggc aaatcaaacg   2640
gcagcacagc tggattctca gggctctgga taccatcaaa gccgagatac tggctactga   2700
tgtgtctgtg gaggatgagg aagggactgg aagccccaag gctgaggttc aactatgcta   2760
cctggaagca caaagagatg ctgttgagca gatgtccctc aagctgtaca gcgagcagta   2820
taccagcagc agcaagcgaa aggaagagtt tgctgatatg tcaaaagttc attcagtggg   2880
```

```
aagcaatggg cttctggact ttgattcaga atatcaggag ctctgggatt gcttgattga    2940
catggagtcc cttgtgatgg acagccacga cctgatgatg tcagaggagc agcagcagca    3000
tctttacaag cgatacagtg tggaaatgtc catcagacac ctgaaaaaga cggagctgct    3060
tagtaaggtt gaagctttga agaaaggtgg cgtttttacta ccaaatgatc tccttgaaaa    3120
agtggattca attaatgaaa aatgggaact gcttgggaaa accctaggag agaagatcca    3180
ggacacaatg gcagggcaca gtgggtcgag tccacgtgac ctgctctctc ctgaaagtgg    3240
aagcctggta aggcagctgg aggtcaggat caaagaactg aaaggatggc taagagatac    3300
agagcttttc atcttcaatt cctgtctgag acaagaaaag gaaggaacaa tgaatactga    3360
gaaacaactg caatacttta gtccctctg tcgtgaaatc aagcaacgac gtcgaggagt    3420
tgcctccatt ctgcgactat gccagcatct tttggatgac cgggagcttg caatctgaa    3480 tgcagaccac cagcccatgc agctgatcat tgtaaatctt gaaagaaggt gggaagccat    3540
tgtcatgcaa gccgtccagt ggcaaacacg tctacaaaag aagatgggaa aggaatctga    3600
gactttgaat gtgattgatc ctggcttgat ggacctaaat gggatgagtg aggatgccct    3660
ggaatgggat gaaatggaca taagtaacaa gttaattagt ttgaatgagg aatcaaatga    3720
ccttgatcaa gaactccaac ctgttatccc ttccttgaag cttggagaga caagtaatga    3780
ggaccctggt tatgacgagg aggctgataa ccatggggga tctcagtatg cctcaaatat    3840
tactgccccc tctagtccac acatttacca ggtgtacagc ctccacaatg ttgaactcta    3900
tgaggacaac cacatgccat ttctgaaaaa caatccaaag gtcactggca tgacacagcc    3960
taatgtttta actaagagtc tcagtaaaga ctcttcattt tcatctacca aatctttgcc    4020
agatcttcta ggtggttcca atttggtaaa gccctgcgca tgtcatggag gagacatgag    4080
ccagaattca ggcagtgaga gtggaattgt cagtgaagga gacacagaaa ccactaccaa    4140
ctctgaaatg tgcttgctca atgcagtgga tgggtcccca agtaaccttg aaactgaaca    4200
tctggaccca caaatgggag atgcagttaa cgtgttaaag caaaaatttta cagatgaggg    4260 ggaaagcatt aagcttccaa atagctctca gtcgtccatt tcaccagtgg gttgtgtaaa    4320
tggaaaagtt ggagatttaa acagtattac caaacatacc cctgactgtt gggagaaga    4380 attacaagga aaacatgatg tgtttacatt ttatgattac tcatacctcc aaggctcaaa    4440
actcaaatta ccaatgataa tgaaacagtc acaaagcgaa aaagtgcatg tggaggatcc    4500
cctgcttcgt ggttttatt ttgataaaaa atcatgcaaa tctaaacatc agactacaga    4560
gttacaacca gatgtacctc cccatgaaag gattttggca agtgcatctc atgaaatgga    4620
tcgcatttca tataaaagtg gcaatataga aaagacattc actggcatgc agaatgccaa    4680
acagctctcc cttttatctc atagttcatc tattgagtcc cttttctcag ggggtgattt    4740
atttggattg ggcatcttta aaaatggcag tgacagcctc cagcgaagca cttctttaga    4800 aagtggttg acttcctata aaagcaatga agatctcttt agctgtcaca gctctgggga    4860
tataagcgtg agcagtggct cagttggtga actaagtaaa agaacattag atctcctgaa    4920
tcgtttggag aatatccaga gcccctcaga gcaaaagata aaacgaagtg tttctgatat    4980
cactcttcaa agcagttccc aaaagatgtc ctttactggc cagatgtcat ggacatagc    5040 atcttctatc aatgaagact cagcggcatc tctaacagaa cttagcagca gtgacgagct    5100
ctctctttgc tcagaggata ttgtgttaca caagaacaag atcccggaat cgaatgcatc    5160
gttcaggaag cgtctgactc gttcagtggc tgatgaaagc gatgtcaatg tcagcatgat    5220
tgttaatgtc tcttgcacct ctgcttgcac tgatgatgaa gatgacagcg acctgctctc    5280
```

```
cagctctacc cttaccttga ctgaagaaga gctgtgcatc aaagatgagg atgacgactc    5340
cagtattgca acagatgatg aaatttatga agactgcacc ttgatgtcag ggctagacta    5400
cataaagaat gaattacaga cctggattag gccaaaattg tctttgacaa gagataagaa    5460
aaggtgcaat gtcagtgatg agatgaaggg cagtaaagat ataagtagca gtgagatgac    5520
caatccctct gatactctga atattgagac ccttctaaat ggctctgtaa acgtgtctc     5580 tgaaaataat ggaaatggta agaattcatc tcatacccat gagttaggga caaagcgtga    5640
aaataagaaa actattttca aagttaataa agatccatat gtggctgaca tggaaaatgg    5700
caatattgaa ggtattccag aaaggcaaaa gggcaaaccg aatgtgactt caaaggtatc    5760
agaaaatctt ggttcacatg ggaaagagat ttcagagagt gagcattgta agtgtaaagc    5820
acttatggat agtttagatg attcaaatac tgctggcaag gaatttgttt cccaagatgt    5880
tagacatctt ccaaagaaat gtccaaatca ccaccatttt gaaaatcaaa gcactgcctc    5940
tactcccact gagaagtctt tctcagaact ggctttagaa accaggttta acaacagaca    6000
agactctgat gcactgaaat catctgatga tgcaccgagt atggctggaa aatctgctgg    6060
ttgttgccta gcacttgaac aaaacggaac agaggaaaat gcttctatca gcaacatttc    6120
ctgttgcaac tgtgagccag atgttttcca tcaaaaagat gccgaagatt gttcagtaca    6180
caactttgtt aaggaaatca ttgacatggc ttcgacagcc ctaaaaagta aatctcaacc    6240
tgaaaacgag gtggctgctc ctacttcatt aactcaaatc aaggagaaag tgttggagca    6300
ttctcaccgg cccatccagc tgagaaaagg ggacttttat tcgtacttat ctctctcatc    6360
tcatgacagt gattgtgggg aggtcaccaa ttacatagaa gagaaaagca gcactccatt    6420
gccactagac accactgact cgggcttaga tgacaaggaa gatattgaat gcttttttga    6480
ggcctgtgtt gagggtgact ctgatggaga ggagccttgt ttctctagtg ctcctccaaa    6540
tgaatctgca gttcccagcg aagctgcaat gccactacaa gcaacagcat gttcttctga    6600
gttcagtgat agttctcttt cagctgatga tgcagataca gtggctcttt caagtccttc    6660
ctctcaggaa agagctgagg ttggaaagga agtgaatggt ttgccccaaa cttccagtgg    6720
ctgtgcagaa aacttagagt ttactccttc aaagcttgac agtgaaaagg aaagttccgg    6780
aaaaccaggt gaatctggaa tgccagaaga acataatgct gcttcagcca aatctaaagt    6840
tcaagacctc tccttgaagg caaatcagcc aacagacaag gccgcattgc atcccagccc    6900 caaaactta acctgtgaag aaaatcttct aaaccttcat gaaaaacgac atagaaatat     6960
gcataggtag aatgtacccc ctccccaagc atgaaaatca tctcactgaa agatacgcct    7020
ggctgcaact caggggtggc ctcatcctcc cgccctgggc tggcctctgg ttccatcacg    7080
tttgtcactg ccgttattta cattgacttc tcccaagatg aatcttcctt ccaaatgtgt    7140
tttctccaca caagccttgt gatctgaatg tgtgcgctgg ttctctttag gtgatcgtct    7200
ttgaagttca gcaaagctgc ttgttctccc atggattcct gtcccaagct acctctacca    7260
accctctctc tccagctaga ctttttctctt tgcctcctcc cttcccttcc actctttaaa    7320
gttctgcagt tcaccaactg gtagtccatt aaattctcct gtctagaatg accccccac     7380 cagtacttga ccaatttcat gtatcaatct ggatttttt tttaacggta taatgactgt     7440
gcttattgaa agagttttac ctaaaaagcc aacatttgaa ttggttgcag catagagaag    7500
aaacactggt ccttctttca aaattaagca actattaaaa gcgccatttt atttatttca    7560
tttaaaaaat aatctatgca gcatttcaag aaacaaccat atggtgttgt atattataaa    7620
```

```
ctggtgacat tctactattg aattatgtac aacattttca ttttttatgc ttcttgaggt    7680
ggtaatgaga aaaagttttt ttaaaaaagt gtgccttgct gtatttctta taccatttat    7740
taaaaagctg ctttcacggt aaaattatgt tggtttgaaa ggaggaaata gcaaggttaa    7800
gatgtgtgaa taatttctgt atatatgtat aaccaagtac aaacattgat gtataatgac    7860
agtataaaat gctttcatgt ttgtgatgtc tagtgatgtg gaaaatataa gccttaaatc    7920
cattagattg catggtaatt aaaattggca taataaacac agattattgg gggaaaagga    7980
aaattagtga tctcttctac tatgttcttt accaaattgt tgcatctggt tctgaaaaag    8040
tatagcatgt agcagcttcc aaacatattc atattgctta agaggcttaa cattacctaa    8100
actagagact agacgtaaag ccttcagttt tcaaaatctt tctggtcact ataaagatct    8160
tggaacagca aatgattaaa tgtcagttcc cctaaaccaa taaacattta tactagattt    8220
tttatttcca cttatcatta atgatttaat gttggatttc aggtaccttg tatgtcttaa    8280
tttattttaa atatttattt tgaatgagtt tgatagaaag ctagtagaaa agtacagaaa    8340
atttgactat tatttataga tttcaggtat atttatatgt gtaaagaaaa ttgacaaaga    8400
aatatttcat ctggccttta ctgactcctg ttaaatgcag ttttaaattt atatcgtaac    8460
acctacttaa gtgcctgaca cagtaggtat tcaataaaaa tttactgaat taaggattaa    8520
aattaggtga catggtgaca tctatcccctt tattttgaca ctaaaacatg gacacaacta    8580
gaaagaggta caatgcaata taagtcaca atagataata tatatcaaat ttctaaaagg    8640
taaagaatgt tgtgggttca tgcagtcaca ggaatgacaa tcattcaaca gatagttcag    8700
aaacactttt tatctgcaag gcactattct agatccagaa gatgcaatgt tgaacaaaca    8760
gacaaagccc tgccctcaga aggctgtcct gcattaggaa caagtgaaca cgcaaatgac    8820
atgaagtatt tgttgcagag ctgaggaaca gagcaaatgt agtgatagaa gcgcaatgag    8880
agaagcagca gtgggtacaa ggaggaagaa aaagggcttg cagagagtgg aaagttagtg    8940
gaatattcat gaaacttcat tgcaggggta atagaagaaa aagtaaattg ggaggactta    9000
atggaaggtc ttttaaaaag ttaacttgga gcttctgtat gtaaaatgct aggtaataag    9060
gacactttgt acaggctgtt ttgcacctga ttttatttat cattagtgcc acgccaagat    9120
catttagacg atgcttatct gtaattctac cactttaata actatttgta tttttatgcc    9180
ccttctgatc ttttccatat gtatttctaa atggataaat tattctaggc ttcttaatag    9240
gtagtaattt gttcaaaagc ggttttagcc agacatctag ttgcagtgtt caagaggatt    9300
atggggaaa gagattagag ataattgtct agttagggg cagctggaga aaataagcta    9360
agtttgcaat aacagagtac acaagtatag tggcccagga tgtagtgaaa gaacaaatcc    9420
tagagtcttt gaaatttcta agggcattct agacctctgt tgggatatgg tattatttta    9480
catactgaca caacctaaat tttctttggg tagtaactaa tgtcaagtct acatcgactg    9540
gtaaaacatt caaagaacaa actgacaatg atgttctacc tacttgttac atgctcatgg    9600
aagaccgtgc agtattgaaa gtatttgtta attatctgct tagtattaac actaaatttg    9660
tagaatgact ttcaggtttg ttgaacaatg ccttttcagg ttggaagaag aaaaatagcc    9720
tcaatctccc accccatgta ggcactacct ccccaattac ccttagaaaa tgatcacacc    9780
aactctgcct acacacttcc agtgatagtg gctcattgtc tgttaaggca aactgttcca    9840
ctgttgggca tatctctttg ttagaaagtt ctttcttagg ttgctaaaat ctgcctagta    9900
ccccgctacc ctgttctgtc ttatggagca gcccagatta tctttactcc ctcttctctca   9960
tggcaaccct gaagataatc aaggccagtt actcatcatc tcccaaccac tgtttcctca   10020
```

```
actgcccttc atatgtcatg gttttcagat ccattccaac ctgactgaat gttaacagac    10080
agaattcttc acattaagga actgtcttca tcatcataca tgtagaaaag aatctgaaca    10140
tttaagtgcg aagttttctc tagaaatata ttcaagatat gtttattcta ttattgtaaa    10200
tttcaaacaa taaataaata agaatcc                                       10227

<210> SEQ ID NO 18
<211> LENGTH: 2077
<212> TYPE: PRT
<213> ORGANISM: Artificial Sequence
<220> FEATURE:
<223> OTHER INFORMATION: human mAKAPbeta

<400> SEQUENCE: 18
```

Met Thr Ser Ser Gln Val Lys Thr Lys Pro Phe Asp Ser Trp Ser Tyr
1               5                   10                  15

Ser Glu Met Glu Lys Glu Phe Pro Glu Leu Ile Arg Ser Val Gly Leu
            20                  25                  30

Leu Thr Val Ala Ala Asp Ser Ile Ser Thr Asn Gly Ser Glu Ala Val
        35                  40                  45

Thr Glu Glu Val Ser Gln Val Ser Leu Ser Val Asp Asp Lys Gly Gly
    50                  55                  60

Cys Glu Glu Asp Asn Ala Ser Ala Val Glu Glu Gln Pro Gly Leu Thr
65                  70                  75                  80

Leu Gly Val Ser Ser Ser Gly Glu Ala Leu Thr Asn Ala Ala Gln
            85                  90                  95

Pro Ser Ser Glu Thr Val Gln Gln Glu Ser Ser Ser Ser His His
            100                 105                 110

Asp Ala Lys Asn Gln Gln Pro Val Pro Cys Glu Asn Ala Thr Pro Lys
        115                 120                 125

Arg Thr Ile Arg Asp Cys Phe Asn Tyr Asn Glu Asp Ser Pro Thr Gln
    130                 135                 140

Pro Thr Leu Pro Lys Arg Gly Leu Phe Leu Lys Glu Glu Thr Phe Lys
145                 150                 155                 160

Asn Asp Leu Lys Gly Asn Gly Gly Lys Arg Gln Met Val Asp Leu Lys
                165                 170                 175

Pro Glu Met Ser Arg Ser Thr Pro Ser Leu Val Asp Pro Pro Asp Arg
            180                 185                 190

Ser Lys Leu Cys Leu Val Leu Gln Ser Ser Tyr Pro Asn Ser Pro Ser
        195                 200                 205

Ala Ala Ser Gln Ser Tyr Glu Cys Leu His Lys Val Gly Asn Gly Asn
    210                 215                 220

Leu Glu Asn Thr Val Lys Phe His Ile Lys Glu Ile Ser Ser Ser Leu
225                 230                 235                 240

Gly Arg Leu Asn Asp Cys Tyr Lys Glu Lys Ser Arg Leu Lys Lys Pro
                245                 250                 255

His Lys Thr Ser Glu Glu Val Pro Pro Cys Arg Thr Pro Lys Arg Gly
            260                 265                 270

Thr Gly Ser Gly Lys Gln Ala Lys Asn Thr Lys Ser Ser Ala Val Pro
        275                 280                 285

Asn Gly Glu Leu Ser Tyr Thr Ser Lys Ala Ile Glu Gly Pro Gln Thr
    290                 295                 300

Asn Ser Ala Ser Thr Ser Ser Leu Glu Pro Cys Asn Gln Arg Ser Trp
305                 310                 315                 320

-continued

```
Asn Ala Lys Leu Gln Leu Gln Ser Glu Thr Ser Ser Pro Ala Phe
            325                 330                 335
Thr Gln Ser Ser Glu Ser Ser Val Gly Ser Asp Asn Ile Met Ser Pro
        340                 345                 350
Val Pro Leu Leu Ser Lys His Lys Ser Lys Lys Gly Gln Ala Ser Ser
        355                 360                 365
Pro Ser His Val Thr Arg Asn Gly Glu Val Val Glu Ala Trp Tyr Gly
370                 375                 380
Ser Asp Glu Tyr Leu Ala Leu Pro Ser His Leu Lys Gln Thr Glu Val
385                 390                 395                 400
Leu Ala Leu Lys Leu Glu Asn Leu Thr Lys Leu Leu Pro Gln Lys Pro
                405                 410                 415
Arg Gly Glu Thr Ile Gln Asn Ile Asp Asp Trp Glu Leu Ser Glu Met
            420                 425                 430
Asn Ser Asp Ser Glu Ile Tyr Pro Thr Tyr His Val Lys Lys His
        435                 440                 445
Thr Arg Leu Gly Arg Val Ser Pro Ser Ser Ser Asp Ile Ala Ser
    450                 455                 460
Ser Leu Gly Glu Ser Ile Glu Ser Gly Pro Leu Ser Asp Ile Leu Ser
465                 470                 475                 480
Asp Glu Glu Ser Ser Met Pro Leu Ala Gly Met Lys Lys Tyr Ala Asp
                485                 490                 495
Glu Lys Ser Glu Arg Ala Ser Ser Glu Lys Asn Glu Ser His Ser
            500                 505                 510
Ala Thr Lys Ser Ala Leu Ile Gln Lys Leu Met Gln Asp Ile Gln His
            515                 520                 525
Gln Asp Asn Tyr Glu Ala Ile Trp Glu Lys Ile Glu Gly Phe Val Asn
530                 535                 540
Lys Leu Asp Glu Phe Ile Gln Trp Leu Asn Glu Ala Met Glu Thr Thr
545                 550                 555                 560
Glu Asn Trp Thr Pro Pro Lys Ala Glu Met Asp Asp Leu Lys Leu Tyr
                565                 570                 575
Leu Glu Thr His Leu Ser Phe Lys Leu Asn Val Asp Ser His Cys Ala
            580                 585                 590
Leu Lys Glu Ala Val Glu Glu Gly His Gln Leu Leu Glu Leu Ile
    595                 600                 605
Ala Ser His Lys Ala Gly Leu Lys Asp Met Leu Arg Met Ile Ala Ser
    610                 615                 620
Gln Trp Lys Glu Leu Gln Arg Gln Ile Lys Arg Gln His Ser Trp Ile
625                 630                 635                 640
Leu Arg Ala Leu Asp Thr Ile Lys Ala Glu Ile Leu Ala Thr Asp Val
                645                 650                 655
Ser Val Glu Asp Glu Glu Gly Thr Gly Ser Pro Lys Ala Glu Val Gln
            660                 665                 670
Leu Cys Tyr Leu Glu Ala Gln Arg Asp Ala Val Glu Gln Met Ser Leu
            675                 680                 685
Lys Leu Tyr Ser Glu Gln Tyr Thr Ser Ser Lys Arg Lys Glu Glu
    690                 695                 700
Phe Ala Asp Met Ser Lys Val His Ser Val Gly Ser Asn Gly Leu Leu
705                 710                 715                 720
Asp Phe Asp Ser Glu Tyr Gln Glu Leu Trp Asp Cys Leu Ile Asp Met
                725                 730                 735
Glu Ser Leu Val Met Asp Ser His Asp Leu Met Met Ser Glu Glu Gln
```

```
                    740                 745                 750
        Gln Gln His Leu Tyr Lys Arg Tyr Ser Val Glu Met Ser Ile Arg His
                    755                 760                 765
        Leu Lys Lys Thr Glu Leu Leu Ser Lys Val Glu Ala Leu Lys Lys Gly
                    770                 775                 780
        Gly Val Leu Leu Pro Asn Asp Leu Leu Glu Lys Val Asp Ser Ile Asn
        785                 790                 795                 800
        Glu Lys Trp Glu Leu Leu Gly Lys Thr Leu Gly Glu Lys Ile Gln Asp
                        805                 810                 815
        Thr Met Ala Gly His Ser Gly Ser Ser Pro Arg Asp Leu Leu Ser Pro
                        820                 825                 830
        Glu Ser Gly Ser Leu Val Arg Gln Leu Glu Val Arg Ile Lys Glu Leu
                        835                 840                 845
        Lys Gly Trp Leu Arg Asp Thr Glu Leu Phe Ile Phe Asn Ser Cys Leu
                        850                 855                 860
        Arg Gln Glu Lys Glu Gly Thr Met Asn Thr Glu Lys Gln Leu Gln Tyr
        865                 870                 875                 880
        Phe Lys Ser Leu Cys Arg Glu Ile Lys Gln Arg Arg Arg Gly Val Ala
                        885                 890                 895
        Ser Ile Leu Arg Leu Cys Gln His Leu Leu Asp Asp Arg Glu Thr Cys
                        900                 905                 910
        Asn Leu Asn Ala Asp His Gln Pro Met Gln Leu Ile Ile Val Asn Leu
                        915                 920                 925
        Glu Arg Arg Trp Glu Ala Ile Val Met Gln Ala Val Gln Trp Gln Thr
                        930                 935                 940
        Arg Leu Gln Lys Lys Met Gly Lys Glu Ser Glu Thr Leu Asn Val Ile
        945                 950                 955                 960
        Asp Pro Gly Leu Met Asp Leu Asn Gly Met Ser Glu Asp Ala Leu Glu
                        965                 970                 975
        Trp Asp Glu Met Asp Ile Ser Asn Lys Leu Ile Ser Leu Asn Glu Glu
                        980                 985                 990
        Ser Asn Asp Leu Asp Gln Glu Leu  Gln Pro Val Ile Pro  Ser Leu Lys
                        995                 1000                1005
        Leu Gly  Glu Thr Ser Asn Glu  Asp Pro Gly Tyr Asp  Glu Glu Ala
                 1010                1015                1020
        Asp Asn His Gly Gly Ser Gln  Tyr Ala Ser Asn Ile  Thr Ala Pro
                 1025                1030                1035
        Ser Ser  Pro His Ile Tyr Gln  Val Tyr Ser Leu His  Asn Val Glu
                 1040                1045                1050
        Leu Tyr  Glu Asp Asn His Met  Pro Phe Leu Lys Asn  Asn Pro Lys
                 1055                1060                1065
        Val Thr  Gly Met Thr Gln Pro  Asn Val Leu Thr Lys  Ser Leu Ser
                 1070                1075                1080
        Lys Asp  Ser Ser Phe Ser Ser  Thr Lys Ser Leu Pro  Asp Leu Leu
                 1085                1090                1095
        Gly Gly  Ser Asn Leu Val Lys  Pro Cys Ala Cys His  Gly Gly Asp
                 1100                1105                1110
        Met Ser  Gln Asn Ser Gly Ser  Glu Ser Gly Ile Val  Ser Glu Gly
                 1115                1120                1125
        Asp Thr  Glu Thr Thr Thr Asn  Ser Glu Met Cys Leu  Leu Asn Ala
                 1130                1135                1140
        Val Asp  Gly Ser Pro Ser Asn  Leu Glu Thr Glu His  Leu Asp Pro
                 1145                1150                1155
```

-continued

```
Gln Met Gly Asp Ala Val Asn Val Leu Lys Gln Lys Phe Thr Asp
    1160                1165                1170

Glu Gly Glu Ser Ile Lys Leu Pro Asn Ser Ser Gln Ser Ser Ile
    1175                1180                1185

Ser Pro Val Gly Cys Val Asn Gly Lys Val Gly Asp Leu Asn Ser
    1190                1195                1200

Ile Thr Lys His Thr Pro Asp Cys Leu Gly Glu Leu Gln Gly
    1205                1210                1215

Lys His Asp Val Phe Thr Phe Tyr Asp Tyr Ser Tyr Leu Gln Gly
    1220                1225                1230

Ser Lys Leu Lys Leu Pro Met Ile Met Lys Gln Ser Gln Ser Glu
    1235                1240                1245

Lys Val His Val Glu Asp Pro Leu Leu Arg Gly Phe Tyr Phe Asp
    1250                1255                1260

Lys Lys Ser Cys Lys Ser Lys His Gln Thr Thr Glu Leu Gln Pro
    1265                1270                1275

Asp Val Pro His Glu Arg Ile Leu Ala Ser Ala Ser His Glu
    1280                1285                1290

Met Asp Arg Ile Ser Tyr Lys Ser Gly Asn Ile Glu Lys Thr Phe
    1295                1300                1305

Thr Gly Met Gln Asn Ala Lys Gln Leu Ser Leu Ser His Ser
    1310                1315                1320

Ser Ser Ile Glu Ser Leu Ser Pro Gly Gly Asp Leu Phe Gly Leu
    1325                1330                1335

Gly Ile Phe Lys Asn Gly Ser Asp Ser Leu Gln Arg Ser Thr Ser
    1340                1345                1350

Leu Glu Ser Trp Leu Thr Ser Tyr Lys Ser Asn Glu Asp Leu Phe
    1355                1360                1365

Ser Cys His Ser Ser Gly Asp Ile Ser Val Ser Ser Gly Ser Val
    1370                1375                1380

Gly Glu Leu Ser Lys Arg Thr Leu Asp Leu Leu Asn Arg Leu Glu
    1385                1390                1395

Asn Ile Gln Ser Pro Ser Glu Gln Lys Ile Lys Arg Ser Val Ser
    1400                1405                1410

Asp Ile Thr Leu Gln Ser Ser Gln Lys Met Ser Phe Thr Gly
    1415                1420                1425

Gln Met Ser Leu Asp Ile Ala Ser Ser Ile Asn Glu Asp Ser Ala
    1430                1435                1440

Ala Ser Leu Thr Glu Leu Ser Ser Ser Asp Glu Leu Ser Leu Cys
    1445                1450                1455

Ser Glu Asp Ile Val Leu His Lys Asn Lys Ile Pro Glu Ser Asn
    1460                1465                1470

Ala Ser Phe Arg Lys Arg Leu Thr Arg Ser Val Ala Asp Glu Ser
    1475                1480                1485

Asp Val Asn Val Ser Met Ile Val Asn Val Ser Cys Thr Ser Ala
    1490                1495                1500

Cys Thr Asp Asp Glu Asp Asp Ser Asp Leu Leu Ser Ser Ser Thr
    1505                1510                1515

Leu Thr Leu Thr Glu Glu Glu Leu Cys Ile Lys Asp Glu Asp Asp
    1520                1525                1530

Asp Ser Ser Ile Ala Thr Asp Asp Glu Ile Tyr Glu Asp Cys Thr
    1535                1540                1545
```

```
Leu Met Ser Gly Leu Asp Tyr Ile Lys Asn Glu Leu Gln Thr Trp
    1550                1555                1560

Ile Arg Pro Lys Leu Ser Leu Thr Arg Asp Lys Lys Arg Cys Asn
    1565                1570                1575

Val Ser Asp Glu Met Lys Gly Ser Lys Asp Ile Ser Ser Ser Glu
    1580                1585                1590

Met Thr Asn Pro Ser Asp Thr Leu Asn Ile Glu Thr Leu Leu Asn
    1595                1600                1605

Gly Ser Val Lys Arg Val Ser Glu Asn Gly Asn Gly Lys Asn
    1610                1615                1620

Ser Ser His Thr His Glu Leu Gly Thr Lys Arg Glu Asn Lys Lys
    1625                1630                1635

Thr Ile Phe Lys Val Asn Lys Asp Pro Tyr Val Ala Asp Met Glu
    1640                1645                1650

Asn Gly Asn Ile Glu Gly Ile Pro Glu Arg Gln Lys Gly Lys Pro
    1655                1660                1665

Asn Val Thr Ser Lys Val Ser Glu Asn Leu Gly Ser His Gly Lys
    1670                1675                1680

Glu Ile Ser Glu Ser Glu His Cys Lys Cys Lys Ala Leu Met Asp
    1685                1690                1695

Ser Leu Asp Asp Ser Asn Thr Ala Gly Lys Glu Phe Val Ser Gln
    1700                1705                1710

Asp Val Arg His Leu Pro Lys Lys Cys Pro Asn His His His Phe
    1715                1720                1725

Glu Asn Gln Ser Thr Ala Ser Thr Pro Thr Glu Lys Ser Phe Ser
    1730                1735                1740

Glu Leu Ala Leu Glu Thr Arg Phe Asn Asn Arg Gln Asp Ser Asp
    1745                1750                1755

Ala Leu Lys Ser Ser Asp Asp Ala Pro Ser Met Ala Gly Lys Ser
    1760                1765                1770

Ala Gly Cys Cys Leu Ala Leu Glu Gln Asn Gly Thr Glu Glu Asn
    1775                1780                1785

Ala Ser Ile Ser Asn Ile Ser Cys Cys Asn Cys Glu Pro Asp Val
    1790                1795                1800

Phe His Gln Lys Asp Ala Glu Asp Cys Ser Val His Asn Phe Val
    1805                1810                1815

Lys Glu Ile Ile Asp Met Ala Ser Thr Ala Leu Lys Ser Lys Ser
    1820                1825                1830

Gln Pro Glu Asn Glu Val Ala Ala Pro Thr Ser Leu Thr Gln Ile
    1835                1840                1845

Lys Glu Lys Val Leu Glu His Ser His Arg Pro Ile Gln Leu Arg
    1850                1855                1860

Lys Gly Asp Phe Tyr Ser Tyr Leu Ser Leu Ser Ser His Asp Ser
    1865                1870                1875

Asp Cys Gly Glu Val Thr Asn Tyr Ile Glu Glu Lys Ser Ser Thr
    1880                1885                1890

Pro Leu Pro Leu Asp Thr Thr Asp Ser Gly Leu Asp Asp Lys Glu
    1895                1900                1905

Asp Ile Glu Cys Phe Phe Glu Ala Cys Val Glu Gly Asp Ser Asp
    1910                1915                1920

Gly Glu Glu Pro Cys Phe Ser Ser Ala Pro Pro Asn Glu Ser Ala
    1925                1930                1935

Val Pro Ser Glu Ala Ala Met Pro Leu Gln Ala Thr Ala Cys Ser
```

| | | | | | | | | | | | |
|---|---|---|---|---|---|---|---|---|---|---|---|
| | | 1940 | | | | 1945 | | | | 1950 | |
| Ser | Glu | Phe | Ser | Asp | Ser | Ser | Leu | Ser | Ala | Asp | Asp | Ala | Asp | Thr |
| | 1955 | | | | 1960 | | | | 1965 | | |

Val Ala Leu Ser Ser Pro Ser Ser Gln Glu Arg Ala Glu Val Gly
    1970                1975                    1980

Lys Glu Val Asn Gly Leu Pro Gln Thr Ser Ser Gly Cys Ala Glu
    1985                1990                    1995

Asn Leu Glu Phe Thr Pro Ser Lys Leu Asp Ser Glu Lys Glu Ser
    2000                2005                    2010

Ser Gly Lys Pro Gly Glu Ser Gly Met Pro Glu Glu His Asn Ala
    2015                2020                    2025

Ala Ser Ala Lys Ser Lys Val Gln Asp Leu Ser Leu Lys Ala Asn
    2030                2035                    2040

Gln Pro Thr Asp Lys Ala Ala Leu His Pro Ser Pro Lys Thr Leu
    2045                2050                    2055

Thr Cys Glu Glu Asn Leu Leu Asn Leu His Glu Lys Arg His Arg
    2060                2065                    2070

Asn Met His Arg
    2075

```
<210> SEQ ID NO 19
<211> LENGTH: 10343
<212> TYPE: DNA
<213> ORGANISM: Artificial Sequence
<220> FEATURE:
<223> OTHER INFORMATION: human mAKAPalpha

<400> SEQUENCE: 19
catcatgcag caggtcaaac aaggcatctc ctagtattgc atcctacaga tgtgctgtaa      60
acatcaaaag aagacggtgg gatcaggaga tgctgttttg gaaagaagtg aggtttagac     120
ttctccatgt taaccatgag cgtgacactt tccccccctga ggtcacagga cctggatccc     180
atggctactg atgcttcacc catggccatc aacatgacac ccactgtgga gcagggtgag     240
ggagaagagg caatgaagga catggactct gaccagcagt atgaaaagcc acccccacta     300
cacacagggg ctgactggaa gattgtcctc cacttacctg aaattgagac ctggctccgg     360
atgacctcag agagggtccg agacctaacc tattcagtcc agcaggattc ggacagcaag     420
catgtggatg tacatctagt tcaactaaag gacatttgtg aagatatttc tgatcatgtt     480
gagcaaatcc atgccctcct tgaaacagag ttctccctaa agctgctgtc ttactctgtc     540
aacgtgatag tggacatcca cgcagtgcag ctcctctggc accagcttcg agtctcagtg     600
ctggttctgc gggagcgcat tctgcaaggt ctgcaggacg ccaatggcaa ctacactagg     660
cagacggaca ttctgcaagc tttctctgaa gagacaaaag agggccggct tgattctcta     720
acagaagtgg atgactcagg acaattaacc atcaaatgtt ctcaaaatta cttgtctctg     780
gattgtggca ttactgcatt cgaactgtct gactacagtc caagtgagga tttgctcagt     840
gggctaggtg acatgaccct agccaagtc aaaaccaaac cctttgactc ttggagctac     900
agtgagatgg aaaaggagtt tcctgagctt atccgaagtg ttggtttact tacggtagct     960
gctgactcta tctctaccaa tggcagtgaa gcagttactg aggaggtatc tcaagtatct    1020
ctctcagtag acgacaaagg tggatgtgag gaagacaatg cttctgcagt cgaagagcaa    1080
ccaggcttaa cactgggggt gtcatcatct tcaggagaag ctctgacaaa tgctgctcaa    1140
ccctcctctg agactgtgca gcaagaatcc agttcctcct cccatcatga tgcaaagaat    1200
```

```
cagcagcctg ttccttgtga aaatgcaacc cccaaacgaa ccatcagaga ttgctttaat    1260
tataacgagg actctcccac gcagcctaca ttgccaaaaa gaggacttttt tcttaaagag   1320 gaaactttta agaatgatct gaaaggcaat ggtggaaaga ggcaaatggt tgatctaaag   1380
cctgagatga gcagaagcac cccttcgcta gtagatcctc ctgacagatc caaactttgc   1440
ctggtattgc agtcttctta ccccaacagc ccttctgctg ccagccagtc ttatgagtgt   1500
ttacacaagg tggggaatgg gaaccttgaa aacacagtca aatttcacat taagaaaatt   1560
tcttccagcc tgggaaggct taacgactgc tataaagaga atctcgact taaaaagcca    1620 cacaagacct cagaagaggt gcctccatgc cgaacaccta acgggggac tggttcaggc    1680 aaacaagcta aaatacaaa gagctcagca gtgccaaatg gagagctttc ttatacttcc    1740
aaggccatag gggggccaca aacaaattct gcttccacat cctcacttga gccttgtaat   1800
cagagaagtt ggaatgccaa attgcaattg cagtcagaaa catccagttc accagctttt   1860
actcagagca gtgaatcctc tgttggctca gacaacatca tgtctccggt gccacttctt   1920
tcaaaacaca aaagcaaaaa aggtcaagcc tcctctccaa gtcacgtcac taggaatggt   1980
gaggttgtgg aggcctggta tggctctgat gaatacctag cactgccctc tcaccttaag   2040
cagacagaag tattggcttt gaagttggaa aacctaacaa agcttctgcc tcagaaaccc   2100
agaggagaaa ccatccagaa tattgatgac tgggaactgt ctgaaatgaa ttcagattct   2160
gaaatctatc caacctatca tgtcaaaaag aagcatacaa ggctaggcag ggtgtctcca   2220
agctcatcta gtgacatagc ctcttcacta ggggagagca ttgaatctgg gcccctgagt   2280
gacattcttt ctgatgagga gtccagtatg cctctcgctg gcatgaaaaa gtatgctgat   2340
gagaagtcag aaagagcttc atcctctgag aaaaatgaga gccattctgc cactaaatca   2400
gctttaattc agaaactgat gcaagatatt cagcaccaag acaactatga agccatatgg   2460
gaaaaaatag aggggtttgt aaacaaactg gatgaattca ttcaatggtt aaatgaagcc   2520
atggaaacta cagagaattg gactcccccct aaagcagaga tggatgacct taaactgtat   2580
ctggagacac acttgagttt taagttgaat gtagacagtc attgtgctct caaggaagct   2640
gtggaggagg aaggacacca acttcttgag cttattgcat ctcacaaagc aggactgaag   2700
gacatgctgc ggatgattgc aagtcaatgg aaggagctgc agaggcaaat caaacggcag   2760
cacagctgga ttctcagggc tctggatacc atcaaagccg agatactggc tactgatgtg   2820
tctgtggagg atgaggaagg gactggaagc cccaaggctg aggttcaact atgctacctg   2880
gaagcacaaa gagatgctgt tgagcagatg tccctcaagc tgtacagcga gcagtatacc   2940
agcagcagca agcgaaagga agagtttgct gatatgtcaa aagttcattc agtgggaagc   3000
aatgggcttc tggactttga ttcagaatat caggagctct gggattgctt gattgacatg   3060
gagtcccttg tgatggacag ccacgacctg atgatgtcag aggagcagca gcagcatctt   3120
tacaagcgat acagtgtgga aatgtccatc agacacctga aaaagacgga gctgcttagt   3180
aaggttgaag ctttgaagaa aggtggcgtt ttactaccaa atgatctcct tgaaaaagtg   3240
gattcaatta atgaaaaatg ggaactgctt gggaaaaccc taggagagaa gatccaggac   3300
acaatggcag ggcacagtgg gtcgagtcca cgtgacctgc tctctcctga agtggaagc    3360 ctggtaaggc agctggaggt caggatcaaa gaactgaaag gatggctaag agatacagag   3420
cttttcatct tcaattcctg tctgagacaa gaaaaggaag gaacaatgaa tactgagaaa   3480
caactgcaat actttaagtc cctctgtcgt gaaatcaagc aacgacgtcg aggagttgcc   3540
tccattctgc gactatgcca gcatcttttg gatgaccggg agacttgcaa tctgaatgca   3600
```

```
gaccaccagc ccatgcagct gatcattgta aatcttgaaa gaaggtggga agccattgtc    3660
atgcaagccg tccagtggca aacacgtcta caaaagaaga tgggaaagga atctgagact    3720
ttgaatgtga ttgatcctgg cttgatggac ctaaatggga tgagtgagga tgccctggaa    3780
tgggatgaaa tggacataag taacaagtta attagtttga atgaggaatc aaatgacctt    3840
gatcaagaac tccaacctgt tatcccttcc ttgaagcttg gagagacaag taatgaggac    3900
cctggttatg acgaggaggc tgataaccat gggggatctc agtatgcctc aaatattact    3960
gccccctcta gtccacacat ttaccaggtg tacagcctcc acaatgttga actctatgag    4020
gacaaccaca tgccatttct gaaaaacaat ccaaaggtca ctggcatgac acagcctaat    4080
gttttaacta gagtctcag taaagactct tcattttcat ctaccaaatc tttgccagat    4140
cttctaggtg gttccaattt ggtaaagccc tgcgcatgtc atggaggaga catgagccag    4200
aattcaggca gtgagagtgg aattgtcagt gaaggagaca cagaaaccac taccaactct    4260
gaaatgtgct tgctcaatgc agtggatggg tccccaagta accttgaaac tgaacatctg    4320
gacccacaaa tgggagatgc agttaacgtg ttaaagcaaa aatttacaga tgaggggaa    4380 agcattaagc ttccaaatag ctctcagtcg tccatttcac cagtgggttg tgtaaatgga    4440
aaagttggag atttaaacag tattaccaaa catacccctg actgtttggg agaagaatta    4500
caaggaaaac atgatgtgtt tacatttat gattactcat acctccaagg ctcaaaactc    4560
aaattaccaa tgataatgaa acagtcacaa agcgaaaaag tgcatgtgga ggatcccctg    4620
cttcgtggtt tttatttga taaaaaatca tgcaaatcta aacatcagac tacagagtta    4680
caaccagatg tacctcccca tgaaaggatt ttggcaagtg catctcatga aatggatcgc    4740
atttcatata aaagtggcaa tatagaaaag acattcactg gcatgcagaa tgccaaacag    4800
ctctcccttt tatctcatag ttcatctatt gagtcccttt ctccagggg tgatttattt    4860 ggattgggca tctttaaaaa tggcagtgac agcctccagc gaagcacttc tttagaaagt    4920
tggttgactt cctataaaag caatgaagat ctctttagct gtcacagctc tggggatata    4980
agcgtgagca gtggctcagt tggtgaacta agtaaaagaa cattagatct cctgaatcgt    5040
ttggagaata tccagagccc ctcagagcaa aagataaaac gaagtgtttc tgatatcact    5100
cttcaaagca gttcccaaaa gatgtccttt actggccaga tgtcattgga catagcatct    5160
tctatcaatg aagactcagc ggcatctcta acagaactta gcagcagtga cgagctctct    5220
ctttgctcag aggatattgt gttacacaag aacaagatcc cggaatcgaa tgcatcgttc    5280
aggaagcgtc tgactcgttc agtggctgat gaaagcgatg tcaatgtcag catgattgtt    5340
aatgtctctt gcacctctgc ttgcactgat gatgaagatg acagcgacct gctctccagc    5400 tctacccctta ccttgactga agaagagctg tgcatcaaag atgaggatga cgactccagt    5460
attgcaacag atgatgaaat ttatgaagac tgcaccttga tgtcagggct agactacata    5520
aagaatgaat tacagacctg gattaggcca aaattgtctt tgacaagaga taagaaaagg    5580
tgcaatgtca gtgatgagat gaagggcagt aaagatataa gtagcagtga gatgaccaat    5640
ccctctgata ctctgaatat tgagacccct ctaaatggct ctgtaaaacg tgtctctgaa    5700
aataatggaa atggtaagaa ttcatctcat acccatgagt tagggacaaa gcgtgaaaat    5760
aagaaaacta ttttcaaagt taataaagat ccatatgtgg ctgacatgga aaatggcaat    5820
attgaaggta ttccagaaag gcaaaagggc aaaccgaatg tgacttcaaa ggtatcagaa    5880
aatcttggtt cacatgggaa agagatttca gagagtgagc attgtaagtg taaagcactt    5940
```

```
atggatagtt tagatgattc aaatactgct ggcaaggaat ttgtttccca agatgttaga    6000
catcttccaa agaaatgtcc aaatcaccac cattttgaaa atcaaagcac tgcctctact    6060
cccactgaga agtctttctc agaactggct ttagaaacca ggtttaacaa cagacaagac    6120
tctgatgcac tgaaatcatc tgatgatgca ccgagtatgg ctggaaaatc tgctggttgt    6180
tgcctagcac ttgaacaaaa cggaacagag gaaaatgctt ctatcagcaa catttcctgt    6240
tgcaactgtg agccagatgt tttccatcaa aaagatgccg aagattgttc agtacacaac    6300
tttgttaagg aaatcattga catggcttcg acagccctaa aaagtaaatc tcaacctgaa    6360
aacgaggtgg ctgctcctac ttcattaact caaatcaagg agaaagtgtt ggagcattct    6420
caccggccca tccagctgag aaaagggggac ttttattcgt acttatctct ctcatctcat    6480
gacagtgatt gtggggaggt caccaattac atagaagaga aaagcagcac tccattgcca    6540
ctagacacca ctgactcggg cttagatgac aaggaagata ttgaatgctt ttttgaggcc    6600
tgtgttgagg gtgactctga tggagaggag ccttgtttct ctagtgctcc tccaaatgaa    6660
tctgcagttc ccagcgaagc tgcaatgcca ctacaagcaa cagcatgttc ttctgagttc    6720
agtgatagtt ctcttttcagc tgatgatgca gatacagtgg ctcttttcaag tccttcctct    6780 caggaaagag ctgaggttgg aaaggaagtg aatggtttgc cccaaacttc cagtggctgt    6840
gcagaaaact tagagtttac tccttcaaag cttgacagtg aaaaggaaag ttccggaaaa    6900
ccaggtgaat ctggaatgcc agaagaacat aatgctgctt cagccaaatc taaagttcaa    6960
gacctctcct tgaaggcaaa tcagccaaca gacaaggccg cattgcatcc cagccccaaa    7020
actttaacct gtgaagaaaa tcttctaaac cttcatgaaa aacgacatag aaatatgcat    7080
aggtagaatg taccccctcc ccaagcatga aaatcatctc actgaaagat acgcctggct    7140
gcaactcagg ggtggcctca tcctcccgcc ctgggctggc ctctggttcc atcacgtttg    7200
tcactgccgt ttattacatt gacttctccc aagatgaatc ttccttccaa atgtgttttc    7260
tccacacaag ccttgtgatc tgaatgtgtg cgctggttct ctttaggtga tcgtctttga    7320
agttcagcaa agctgcttgt tctcccatgg attcctgtcc caagctacct ctaccaaccc    7380
tctctctcca gctagacttt tctctttgcc tcctcccttc ccttccactc tttaaagttc    7440
tgcagttcac caactggtag tccattaaat tctcctgtct agaatgaccc ccccaccagt    7500
acttgaccaa tttcatgtat caatctggat ttttttttta acggtataat gactgtgctt    7560
attgaaagag ttttacctaa aaagccaaca tttgaattgg ttgcagcata gagaagaaac    7620
actggtcctt ctttcaaaat taagcaacta ttaaaagcgc cattttattt atttcattta    7680
aaaaataatc tatgcagcat ttcaagaaac aaccatatgg tgttgtatat tataaactgg    7740
tgacattcta ctattgaatt atgtacaaca ttttcatttt ttatgcttct tgaggtggta    7800
atgagaaaaa agttttttaa aaaagtgtgc cttgctgtat ttcttatacc atttattaaa    7860
aagctgcttt cacggtaaaa ttatgttggt ttgaaaggag gaaatagcaa ggttaagatg    7920
tgtgaataat ttctgtatat atgtataacc aagtacaaac attgatgtat aatgacagta    7980
taaaatgctt tcatgtttgt gatgtctagt gatgtggaaa atataagcct taaatccatt    8040
agattgcatg gtaattaaaa ttggcataat aaacacagat tattggggga aaaggaaaat    8100
tagtgatctc ttctactatg ttcttttacca aattgttgca tctggttctg aaaaagtata    8160
gcatgtagca gcttccaaac atattcatat tgcttaagag gcttaacatt acctaaacta    8220
gagactagac gtaaagcctt cagttttcaa aatcttctg gtcactataa agatcttgga    8280
acagcaaatg attaaatgtc agttccccta aaccaataaa catttatact agatttttta    8340
```

```
tttccactta tcattaatga tttaatgttg gatttcaggt accttgtatg tcttaattta    8400
ttttaaatat ttattttgaa tgagtttgat agaaagctag tagaaaagta cagaaaattt    8460
gactattatt tatagatttc aggtatattt atatgtgtaa aagaaattga caaagaaata    8520
tttcatctgg cctttactga ctcctgttaa atgcagtttt aaatttatat cgtaacacct    8580
acttaagtgc ctgacacagt aggtattcaa taaaaattta ctgaattaaa ggattaaatt    8640
aggtgacatg tgacatcta tccctttatt ttgacactaa acatggaca caactagaaa     8700 gaggtacaat gcaatataaa gtcacaatag ataatatata tcaaatttct aaaaggtaaa    8760
gaatgttgtg ggttcatgca gtcacaggaa tgacaatcat tcaacagata gttcagaaac    8820 acttttatc tgcaaggcac tattctagat ccagaagatg caatgttgaa caaacagaca     8880
aagccctgcc ctcagaaggc tgtcctgcat taggaacaag tgaacacgca aatgacatga    8940
agtatttgtt gcagagctga ggaacagagc aaatgtagtg atagaagcgc aatgagagaa    9000
gcagcagtgg gtacaaggag gaagaaaaag ggcttgcaga gagtgaaaag ttagtggaat    9060
attcatgaaa cttcattgca ggggtaatag aagaaaaagt aaattgggag gacttaatgg    9120
aaggtctttt aaaaagttaa cttggagctt ctgtatgtaa aatgctaggt aataaggaca    9180 cttttgtacag gctgttttgc acctgattt atttatcatt agtgccacgc caagatcatt    9240
tagacgatgc ttatctgtaa ttctaccact ttaataacta tttgtatttt tatgcccctt    9300
ctgatctttt ccatatgtat ttctaaatgg ataaattatt ctaggcttct taataggtag    9360
taatttgttc aaaagcggtt ttagccagac atctagttgc agtgttcaag aggattatgg    9420
gggaaagaga ttagagataa ttgtctagtt aggggcagc tggagaaaat aagctaagtt     9480
tgcaataaca gagtacacaa gtatagtggc ccaggatgta gtgaaagaac aaatcctaga    9540
gtctttgaaa tttctaaggg cattctagac ctctgttggg atatggtatt attttacata    9600
ctgacacaac ctaaattttc tttgggtagt aactaatgtc aagtctacat cgactggtaa    9660
aacattcaaa gaacaaactg acaatgatgt tctacctact tgttacatgc tcatggaaga    9720
ccgtgcagta ttgaaagtat ttgttaatta tctgcttagt attaacacta aatttgtaga    9780
atgactttca ggtttgttga acaatgcctt ttcaggttgg aagaagaaaa atagcctcaa    9840
tctcccaccc catgtaggca ctacctcccc aattacccctt agaaaatgat cacaccaact    9900
ctgcctacac acttccagtg atagtggctc attgtctgtt aaggcaaact gttccactgt    9960
tgggcatatc tctttgttag aaagttcttt cttaggttgc taaaatctgc ctagtaccccc   10020 gctaccctgt tctgtcttat ggagcagccc agattatctt tactccctct ttctcatggc    10080
aaccctgaag ataatcaagg ccagttactc atcatctccc aaccactgtt tcctcaactg    10140
cccttcatat gtcatggttt tcagatccat tccaacctga ctgaatgtta acagacagaa    10200
ttcttcacat taaggaactg tcttcatcat catacatgta gaaaagaatc tgaacattta    10260
agtgcgaagt tttctctaga aatatattca agatatgttt attctattat tgtaaatttc    10320
aaacaataaa taaataagaa tcc                                             10343
```

<210> SEQ ID NO 20
<211> LENGTH: 2319
<212> TYPE: PRT
<213> ORGANISM: Artificial Sequence
<220> FEATURE:
<223> OTHER INFORMATION: human mAKAPalpha

<400> SEQUENCE: 20

-continued

```
Met Leu Thr Met Ser Val Thr Leu Ser Pro Leu Arg Ser Gln Asp Leu
1               5                   10                  15

Asp Pro Met Ala Thr Asp Ala Ser Pro Met Ala Ile Asn Met Thr Pro
            20                  25                  30

Thr Val Glu Gln Gly Glu Gly Glu Ala Met Lys Asp Met Asp Ser
        35                  40                  45

Asp Gln Gln Tyr Glu Lys Pro Pro Leu His Thr Gly Ala Asp Trp
    50                  55                  60

Lys Ile Val Leu His Leu Pro Glu Ile Glu Thr Trp Leu Arg Met Thr
65                  70                  75                  80

Ser Glu Arg Val Arg Asp Leu Thr Tyr Ser Val Gln Gln Asp Ser Asp
                85                  90                  95

Ser Lys His Val Asp Val His Leu Val Gln Leu Lys Asp Ile Cys Glu
                100                 105                 110

Asp Ile Ser Asp His Val Glu Gln Ile His Ala Leu Leu Glu Thr Glu
                115                 120                 125

Phe Ser Leu Lys Leu Leu Ser Tyr Ser Val Asn Val Ile Val Asp Ile
            130                 135                 140

His Ala Val Gln Leu Leu Trp His Gln Leu Arg Val Ser Val Leu Val
145                 150                 155                 160

Leu Arg Glu Arg Ile Leu Gln Gly Leu Gln Asp Ala Asn Gly Asn Tyr
                165                 170                 175

Thr Arg Gln Thr Asp Ile Leu Gln Ala Phe Ser Glu Glu Thr Lys Glu
            180                 185                 190

Gly Arg Leu Asp Ser Leu Thr Glu Val Asp Asp Ser Gly Gln Leu Thr
        195                 200                 205

Ile Lys Cys Ser Gln Asn Tyr Leu Ser Leu Asp Cys Gly Ile Thr Ala
210                 215                 220

Phe Glu Leu Ser Asp Tyr Ser Pro Ser Glu Asp Leu Leu Ser Gly Leu
225                 230                 235                 240

Gly Asp Met Thr Ser Ser Gln Val Lys Thr Lys Pro Phe Asp Ser Trp
                245                 250                 255

Ser Tyr Ser Glu Met Glu Lys Glu Phe Pro Glu Leu Ile Arg Ser Val
                260                 265                 270

Gly Leu Leu Thr Val Ala Ala Asp Ser Ile Ser Thr Asn Gly Ser Glu
            275                 280                 285

Ala Val Thr Glu Glu Val Ser Gln Val Ser Leu Ser Val Asp Asp Lys
        290                 295                 300

Gly Gly Cys Glu Glu Asp Asn Ala Ser Ala Val Glu Glu Gln Pro Gly
305                 310                 315                 320

Leu Thr Leu Gly Val Ser Ser Ser Gly Glu Ala Leu Thr Asn Ala
                325                 330                 335

Ala Gln Pro Ser Ser Glu Thr Val Gln Gln Glu Ser Ser Ser Ser Ser
            340                 345                 350

His His Asp Ala Lys Asn Gln Gln Pro Val Pro Cys Glu Asn Ala Thr
            355                 360                 365

Pro Lys Arg Thr Ile Arg Asp Cys Phe Asn Tyr Asn Glu Asp Ser Pro
        370                 375                 380

Thr Gln Pro Thr Leu Pro Lys Arg Gly Leu Phe Leu Lys Glu Glu Thr
385                 390                 395                 400

Phe Lys Asn Asp Leu Lys Gly Asn Gly Gly Lys Arg Gln Met Val Asp
                405                 410                 415

Leu Lys Pro Glu Met Ser Arg Ser Thr Pro Ser Leu Val Asp Pro Pro
```

```
                420                 425                 430
Asp Arg Ser Lys Leu Cys Leu Val Leu Gln Ser Ser Tyr Pro Asn Ser
            435                 440                 445

Pro Ser Ala Ala Ser Gln Ser Tyr Glu Cys Leu His Lys Val Gly Asn
450                 455                 460

Gly Asn Leu Glu Asn Thr Val Lys Phe His Ile Lys Glu Ile Ser Ser
465                 470                 475                 480

Ser Leu Gly Arg Leu Asn Asp Cys Tyr Lys Glu Lys Ser Arg Leu Lys
            485                 490                 495

Lys Pro His Lys Thr Ser Glu Glu Val Pro Pro Cys Arg Thr Pro Lys
            500                 505                 510

Arg Gly Thr Gly Ser Gly Lys Gln Ala Lys Asn Thr Lys Ser Ser Ala
            515                 520                 525

Val Pro Asn Gly Glu Leu Ser Tyr Thr Ser Lys Ala Ile Glu Gly Pro
            530                 535                 540

Gln Thr Asn Ser Ala Ser Thr Ser Ser Leu Glu Pro Cys Asn Gln Arg
545                 550                 555                 560

Ser Trp Asn Ala Lys Leu Gln Leu Gln Ser Glu Thr Ser Ser Ser Pro
            565                 570                 575

Ala Phe Thr Gln Ser Ser Glu Ser Ser Val Gly Ser Asp Asn Ile Met
            580                 585                 590

Ser Pro Val Pro Leu Leu Ser Lys His Lys Ser Lys Lys Gly Gln Ala
            595                 600                 605

Ser Ser Pro Ser His Val Thr Arg Asn Gly Glu Val Val Glu Ala Trp
            610                 615                 620

Tyr Gly Ser Asp Glu Tyr Leu Ala Leu Pro Ser His Leu Lys Gln Thr
625                 630                 635                 640

Glu Val Leu Ala Leu Lys Leu Glu Asn Leu Thr Lys Leu Leu Pro Gln
            645                 650                 655

Lys Pro Arg Gly Glu Thr Ile Gln Asn Ile Asp Asp Trp Glu Leu Ser
            660                 665                 670

Glu Met Asn Ser Asp Ser Glu Ile Tyr Pro Thr Tyr His Val Lys Lys
            675                 680                 685

Lys His Thr Arg Leu Gly Arg Val Ser Pro Ser Ser Ser Ser Asp Ile
            690                 695                 700

Ala Ser Ser Leu Gly Glu Ser Ile Glu Ser Gly Pro Leu Ser Asp Ile
705                 710                 715                 720

Leu Ser Asp Glu Glu Ser Ser Met Pro Leu Ala Gly Met Lys Lys Tyr
            725                 730                 735

Ala Asp Glu Lys Ser Glu Arg Ala Ser Ser Ser Glu Lys Asn Glu Ser
            740                 745                 750

His Ser Ala Thr Lys Ser Ala Leu Ile Gln Lys Leu Met Gln Asp Ile
            755                 760                 765

Gln His Gln Asp Asn Tyr Glu Ala Ile Trp Glu Lys Ile Glu Gly Phe
            770                 775                 780

Val Asn Lys Leu Asp Glu Phe Ile Gln Trp Leu Asn Glu Ala Met Glu
785                 790                 795                 800

Thr Thr Glu Asn Trp Thr Pro Pro Lys Ala Glu Met Asp Asp Leu Lys
            805                 810                 815

Leu Tyr Leu Glu Thr His Leu Ser Phe Lys Leu Asn Val Asp Ser His
            820                 825                 830

Cys Ala Leu Lys Glu Ala Val Glu Glu Glu Gly His Gln Leu Leu Glu
            835                 840                 845
```

-continued

```
Leu Ile Ala Ser His Lys Ala Gly Leu Lys Asp Met Leu Arg Met Ile
850                 855                 860

Ala Ser Gln Trp Lys Glu Leu Gln Arg Gln Ile Lys Arg Gln His Ser
865                 870                 875                 880

Trp Ile Leu Arg Ala Leu Asp Thr Ile Lys Ala Glu Ile Leu Ala Thr
                885                 890                 895

Asp Val Ser Val Glu Asp Glu Glu Gly Thr Gly Ser Pro Lys Ala Glu
                900                 905                 910

Val Gln Leu Cys Tyr Leu Glu Ala Gln Arg Asp Ala Val Glu Gln Met
                915                 920                 925

Ser Leu Lys Leu Tyr Ser Glu Gln Tyr Thr Ser Ser Lys Arg Lys
930                 935                 940

Glu Glu Phe Ala Asp Met Ser Lys Val His Ser Val Gly Ser Asn Gly
945                 950                 955                 960

Leu Leu Asp Phe Asp Ser Glu Tyr Gln Glu Leu Trp Asp Cys Leu Ile
                965                 970                 975

Asp Met Glu Ser Leu Val Met Asp Ser His Asp Leu Met Met Ser Glu
                980                 985                 990

Glu Gln Gln Gln His Leu Tyr Lys Arg Tyr Ser Val Glu Met Ser Ile
                995                 1000                1005

Arg His Leu Lys Lys Thr Glu Leu Leu Ser Lys Val Glu Ala Leu
    1010                1015                1020

Lys Lys Gly Gly Val Leu Leu Pro Asn Asp Leu Leu Glu Lys Val
    1025                1030                1035

Asp Ser Ile Asn Glu Lys Trp Glu Leu Leu Gly Lys Thr Leu Gly
    1040                1045                1050

Glu Lys Ile Gln Asp Thr Met Ala Gly His Ser Gly Ser Ser Pro
    1055                1060                1065

Arg Asp Leu Leu Ser Pro Glu Ser Gly Ser Leu Val Arg Gln Leu
    1070                1075                1080

Glu Val Arg Ile Lys Glu Leu Lys Gly Trp Leu Arg Asp Thr Glu
    1085                1090                1095

Leu Phe Ile Phe Asn Ser Cys Leu Arg Gln Glu Lys Glu Gly Thr
    1100                1105                1110

Met Asn Thr Glu Lys Gln Leu Gln Tyr Phe Lys Ser Leu Cys Arg
    1115                1120                1125

Glu Ile Lys Gln Arg Arg Arg Gly Val Ala Ser Ile Leu Arg Leu
    1130                1135                1140

Cys Gln His Leu Leu Asp Asp Arg Glu Thr Cys Asn Leu Asn Ala
    1145                1150                1155

Asp His Gln Pro Met Gln Leu Ile Ile Val Asn Leu Glu Arg Arg
    1160                1165                1170

Trp Glu Ala Ile Val Met Gln Ala Val Gln Trp Gln Thr Arg Leu
    1175                1180                1185

Gln Lys Lys Met Gly Lys Glu Ser Glu Thr Leu Asn Val Ile Asp
    1190                1195                1200

Pro Gly Leu Met Asp Leu Asn Gly Met Ser Glu Asp Ala Leu Glu
    1205                1210                1215

Trp Asp Glu Met Asp Ile Ser Asn Lys Leu Ile Ser Leu Asn Glu
    1220                1225                1230

Glu Ser Asn Asp Leu Asp Gln Glu Leu Gln Pro Val Ile Pro Ser
    1235                1240                1245
```

-continued

```
Leu Lys Leu Gly Glu Thr Ser Asn Glu Asp Pro Gly Tyr Asp Glu
    1250                1255                1260

Glu Ala Asp Asn His Gly Gly Ser Gln Tyr Ala Ser Asn Ile Thr
    1265                1270                1275

Ala Pro Ser Ser Pro His Ile Tyr Gln Val Tyr Ser Leu His Asn
    1280                1285                1290

Val Glu Leu Tyr Glu Asp Asn His Met Pro Phe Leu Lys Asn Asn
    1295                1300                1305

Pro Lys Val Thr Gly Met Thr Gln Pro Asn Val Leu Thr Lys Ser
    1310                1315                1320

Leu Ser Lys Asp Ser Ser Phe Ser Ser Thr Lys Ser Leu Pro Asp
    1325                1330                1335

Leu Leu Gly Gly Ser Asn Leu Val Lys Pro Cys Ala Cys His Gly
    1340                1345                1350

Gly Asp Met Ser Gln Asn Ser Gly Ser Glu Ser Gly Ile Val Ser
    1355                1360                1365

Glu Gly Asp Thr Glu Thr Thr Thr Asn Ser Glu Met Cys Leu Leu
    1370                1375                1380

Asn Ala Val Asp Gly Ser Pro Ser Asn Leu Glu Thr Glu His Leu
    1385                1390                1395

Asp Pro Gln Met Gly Asp Ala Val Asn Val Leu Lys Gln Lys Phe
    1400                1405                1410

Thr Asp Glu Gly Glu Ser Ile Lys Leu Pro Asn Ser Ser Gln Ser
    1415                1420                1425

Ser Ile Ser Pro Val Gly Cys Val Asn Gly Lys Val Gly Asp Leu
    1430                1435                1440

Asn Ser Ile Thr Lys His Thr Pro Asp Cys Leu Gly Glu Glu Leu
    1445                1450                1455

Gln Gly Lys His Asp Val Phe Thr Phe Tyr Asp Tyr Ser Tyr Leu
    1460                1465                1470

Gln Gly Ser Lys Leu Lys Leu Pro Met Ile Met Lys Gln Ser Gln
    1475                1480                1485

Ser Glu Lys Val His Val Glu Asp Pro Leu Leu Arg Gly Phe Tyr
    1490                1495                1500

Phe Asp Lys Lys Ser Cys Lys Ser Lys His Gln Thr Thr Glu Leu
    1505                1510                1515

Gln Pro Asp Val Pro Pro His Glu Arg Ile Leu Ala Ser Ala Ser
    1520                1525                1530

His Glu Met Asp Arg Ile Ser Tyr Lys Ser Gly Asn Ile Glu Lys
    1535                1540                1545

Thr Phe Thr Gly Met Gln Asn Ala Lys Gln Leu Ser Leu Leu Ser
    1550                1555                1560

His Ser Ser Ser Ile Glu Ser Leu Ser Pro Gly Gly Asp Leu Phe
    1565                1570                1575

Gly Leu Gly Ile Phe Lys Asn Gly Ser Asp Ser Leu Gln Arg Ser
    1580                1585                1590

Thr Ser Leu Glu Ser Trp Leu Thr Ser Tyr Lys Ser Asn Glu Asp
    1595                1600                1605

Leu Phe Ser Cys His Ser Ser Gly Asp Ile Ser Val Ser Ser Gly
    1610                1615                1620

Ser Val Gly Glu Leu Ser Lys Arg Thr Leu Asp Leu Leu Asn Arg
    1625                1630                1635

Leu Glu Asn Ile Gln Ser Pro Ser Glu Gln Lys Ile Lys Arg Ser
```

```
                1640                1645                1650
Val Ser Asp Ile Thr Leu Gln Ser Ser Ser Gln Lys Met Ser Phe
    1655                1660                1665

Thr Gly Gln Met Ser Leu Asp Ile Ala Ser Ser Ile Asn Glu Asp
    1670                1675                1680

Ser Ala Ala Ser Leu Thr Glu Leu Ser Ser Ser Asp Glu Leu Ser
    1685                1690                1695

Leu Cys Ser Glu Asp Ile Val Leu His Lys Asn Lys Ile Pro Glu
    1700                1705                1710

Ser Asn Ala Ser Phe Arg Lys Arg Leu Thr Arg Ser Val Ala Asp
    1715                1720                1725

Glu Ser Asp Val Asn Val Ser Met Ile Val Asn Val Ser Cys Thr
    1730                1735                1740

Ser Ala Cys Thr Asp Asp Glu Asp Asp Ser Asp Leu Leu Ser Ser
    1745                1750                1755

Ser Thr Leu Thr Leu Thr Glu Glu Glu Leu Cys Ile Lys Asp Glu
    1760                1765                1770

Asp Asp Asp Ser Ser Ile Ala Thr Asp Asp Glu Ile Tyr Glu Asp
    1775                1780                1785

Cys Thr Leu Met Ser Gly Leu Asp Tyr Ile Lys Asn Glu Leu Gln
    1790                1795                1800

Thr Trp Ile Arg Pro Lys Leu Ser Leu Thr Arg Asp Lys Lys Arg
    1805                1810                1815

Cys Asn Val Ser Asp Glu Met Lys Gly Ser Lys Asp Ile Ser Ser
    1820                1825                1830

Ser Glu Met Thr Asn Pro Ser Asp Thr Leu Asn Ile Glu Thr Leu
    1835                1840                1845

Leu Asn Gly Ser Val Lys Arg Val Ser Glu Asn Asn Gly Asn Gly
    1850                1855                1860

Lys Asn Ser Ser His Thr His Glu Leu Gly Thr Lys Arg Glu Asn
    1865                1870                1875

Lys Lys Thr Ile Phe Lys Val Asn Lys Asp Pro Tyr Val Ala Asp
    1880                1885                1890

Met Glu Asn Gly Asn Ile Glu Gly Ile Pro Glu Arg Gln Lys Gly
    1895                1900                1905

Lys Pro Asn Val Thr Ser Lys Val Ser Glu Asn Leu Gly Ser His
    1910                1915                1920

Gly Lys Glu Ile Ser Glu Ser Glu His Cys Lys Cys Lys Ala Leu
    1925                1930                1935

Met Asp Ser Leu Asp Asp Ser Asn Thr Ala Gly Lys Glu Phe Val
    1940                1945                1950

Ser Gln Asp Val Arg His Leu Pro Lys Lys Cys Pro Asn His His
    1955                1960                1965

His Phe Glu Asn Gln Ser Thr Ala Ser Thr Pro Thr Glu Lys Ser
    1970                1975                1980

Phe Ser Glu Leu Ala Leu Glu Thr Arg Phe Asn Asn Arg Gln Asp
    1985                1990                1995

Ser Asp Ala Leu Lys Ser Ser Asp Asp Ala Pro Ser Met Ala Gly
    2000                2005                2010

Lys Ser Ala Gly Cys Cys Leu Ala Leu Glu Gln Asn Gly Thr Glu
    2015                2020                2025

Glu Asn Ala Ser Ile Ser Asn Ile Ser Cys Cys Asn Cys Glu Pro
    2030                2035                2040
```

```
Asp Val Phe His Gln Lys Asp Ala Glu Asp Cys Ser Val His Asn
2045                2050                2055

Phe Val Lys Glu Ile Ile Asp Met Ala Ser Thr Ala Leu Lys Ser
2060                2065                2070

Lys Ser Gln Pro Glu Asn Glu Val Ala Ala Pro Thr Ser Leu Thr
2075                2080                2085

Gln Ile Lys Glu Lys Val Leu Glu His Ser His Arg Pro Ile Gln
2090                2095                2100

Leu Arg Lys Gly Asp Phe Tyr Ser Tyr Leu Ser Leu Ser Ser His
2105                2110                2115

Asp Ser Asp Cys Gly Glu Val Thr Asn Tyr Ile Glu Glu Lys Ser
2120                2125                2130

Ser Thr Pro Leu Pro Leu Asp Thr Thr Asp Ser Gly Leu Asp Asp
2135                2140                2145

Lys Glu Asp Ile Glu Cys Phe Phe Glu Ala Cys Val Glu Gly Asp
2150                2155                2160

Ser Asp Gly Glu Glu Pro Cys Phe Ser Ser Ala Pro Pro Asn Glu
2165                2170                2175

Ser Ala Val Pro Ser Glu Ala Ala Met Pro Leu Gln Ala Thr Ala
2180                2185                2190

Cys Ser Ser Glu Phe Ser Asp Ser Ser Leu Ser Ala Asp Asp Ala
2195                2200                2205

Asp Thr Val Ala Leu Ser Ser Pro Ser Ser Gln Glu Arg Ala Glu
2210                2215                2220

Val Gly Lys Glu Val Asn Gly Leu Pro Gln Thr Ser Ser Gly Cys
2225                2230                2235

Ala Glu Asn Leu Glu Phe Thr Pro Ser Lys Leu Asp Ser Glu Lys
2240                2245                2250

Glu Ser Ser Gly Lys Pro Gly Glu Ser Gly Met Pro Glu Glu His
2255                2260                2265

Asn Ala Ala Ser Ala Lys Ser Lys Val Gln Asp Leu Ser Leu Lys
2270                2275                2280

Ala Asn Gln Pro Thr Asp Lys Ala Ala Leu His Pro Ser Pro Lys
2285                2290                2295

Thr Leu Thr Cys Glu Glu Asn Leu Leu Asn Leu His Glu Lys Arg
2300                2305                2310

His Arg Asn Met His Arg
2315

<210> SEQ ID NO 21
<211> LENGTH: 10
<212> TYPE: PRT
<213> ORGANISM: Artificial Sequence
<220> FEATURE:
<223> OTHER INFORMATION: Myc-tag

<400> SEQUENCE: 21

Glu Gln Lys Leu Ile Ser Glu Glu Asp Leu
1               5                   10

<210> SEQ ID NO 22
<211> LENGTH: 189
<212> TYPE: PRT
<213> ORGANISM: Artificial Sequence
<220> FEATURE:
<223> OTHER INFORMATION: mAKAP PBD
<220> FEATURE:
```

```
<221> NAME/KEY: MISC_FEATURE
<222> LOCATION: (1)..(1)
<223> OTHER INFORMATION: Xaa is Lys or Arg
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any naturally occurring amino acid
<220> FEATURE:
<221> NAME/KEY: MISC_FEATURE
<222> LOCATION: (21)..(21)
<223> OTHER INFORMATION: Xaa is Ile or Met
<220> FEATURE:
<221> NAME/KEY: MISC_FEATURE
<222> LOCATION: (22)..(22)
<223> OTHER INFORMATION: Xaa is Glu or Asp
<220> FEATURE:
<221> NAME/KEY: MISC_FEATURE
<222> LOCATION: (31)..(31)
<223> OTHER INFORMATION: Xaa can be any naturally occurring amino acid
<220> FEATURE:
<221> NAME/KEY: MISC_FEATURE
<222> LOCATION: (32)..(32)
<223> OTHER INFORMATION: Xaa is Asp or Glu
<220> FEATURE:
<221> NAME/KEY: MISC_FEATURE
<222> LOCATION: (33)..(35)
<223> OTHER INFORMATION: Xaa can be any naturally occurring amino acid
<220> FEATURE:
<221> NAME/KEY: MISC_FEATURE
<222> LOCATION: (38)..(42)
<223> OTHER INFORMATION: Xaa can be any naturally occurring amino acid
<220> FEATURE:
<221> NAME/KEY: MISC_FEATURE
<222> LOCATION: (44)..(44)
<223> OTHER INFORMATION: Xaa can be any naturally occurring amino acid
<220> FEATURE:
<221> NAME/KEY: MISC_FEATURE
<222> LOCATION: (50)..(50)
<223> OTHER INFORMATION: Xaa is Val or Ile
<220> FEATURE:
<221> NAME/KEY: MISC_FEATURE
<222> LOCATION: (51)..(53)
<223> OTHER INFORMATION: Xaa can be any naturally occurring amino acid
<220> FEATURE:
<221> NAME/KEY: MISC_FEATURE
<222> LOCATION: (55)..(56)
<223> OTHER INFORMATION: Xaa can be any naturally occurring amino acid
<220> FEATURE:
<221> NAME/KEY: MISC_FEATURE
<222> LOCATION: (57)..(58)
<223> OTHER INFORMATION: Xaa can be any naturally occurring amino acid
      or absent
<220> FEATURE:
<221> NAME/KEY: MISC_FEATURE
<222> LOCATION: (59)..(59)
<223> OTHER INFORMATION: Xaa can be any naturally occurring amino acid
<220> FEATURE:
<221> NAME/KEY: MISC_FEATURE
<222> LOCATION: (60)..(60)
<223> OTHER INFORMATION: Xaa is Ala or Ser
<220> FEATURE:
<221> NAME/KEY: MISC_FEATURE
<222> LOCATION: (61)..(63)
<223> OTHER INFORMATION: Xaa can be any naturally occurring amino acid
      or absent
<220> FEATURE:
<221> NAME/KEY: MISC_FEATURE
<222> LOCATION: (64)..(67)
<223> OTHER INFORMATION: Xaa can be any naturally occurring amino acid
<220> FEATURE:
<221> NAME/KEY: MISC_FEATURE
```

```
<222> LOCATION: (68)..(68)
<223> OTHER INFORMATION: Xaa is Ser or Ala
<220> FEATURE:
<221> NAME/KEY: MISC_FEATURE
<222> LOCATION: (69)..(69)
<223> OTHER INFORMATION: Xaa can be any naturally occurring amino acid
<220> FEATURE:
<221> NAME/KEY: MISC_FEATURE
<222> LOCATION: (71)..(71)
<223> OTHER INFORMATION: Xaa can be any naturally occurring amino acid
<220> FEATURE:
<221> NAME/KEY: MISC_FEATURE
<222> LOCATION: (72)..(72)
<223> OTHER INFORMATION: Xaa is Leu or Val
<220> FEATURE:
<221> NAME/KEY: MISC_FEATURE
<222> LOCATION: (73)..(73)
<223> OTHER INFORMATION: Xaa can be any naturally occurring amino acid
<220> FEATURE:
<221> NAME/KEY: MISC_FEATURE
<222> LOCATION: (74)..(74)
<223> OTHER INFORMATION: Xaa is Ala or Ser
<220> FEATURE:
<221> NAME/KEY: MISC_FEATURE
<222> LOCATION: (76)..(77)
<223> OTHER INFORMATION: Xaa can be any naturally occurring amino acid
<220> FEATURE:
<221> NAME/KEY: MISC_FEATURE
<222> LOCATION: (79)..(79)
<223> OTHER INFORMATION: Xaa can be any naturally occurring amino acid
<220> FEATURE:
<221> NAME/KEY: MISC_FEATURE
<222> LOCATION: (81)..(81)
<223> OTHER INFORMATION: Xaa can be any naturally occurring amino acid
<220> FEATURE:
<221> NAME/KEY: MISC_FEATURE
<222> LOCATION: (84)..(85)
<223> OTHER INFORMATION: Xaa can be any naturally occurring amino acid
<220> FEATURE:
<221> NAME/KEY: MISC_FEATURE
<222> LOCATION: (87)..(87)
<223> OTHER INFORMATION: Xaa can be any naturally occurring amino acid
<220> FEATURE:
<221> NAME/KEY: MISC_FEATURE
<222> LOCATION: (89)..(90)
<223> OTHER INFORMATION: Xaa can be any naturally occurring amino acid
<220> FEATURE:
<221> NAME/KEY: MISC_FEATURE
<222> LOCATION: (92)..(92)
<223> OTHER INFORMATION: Xaa is Glu or Asp
<220> FEATURE:
<221> NAME/KEY: MISC_FEATURE
<222> LOCATION: (93)..(93)
<223> OTHER INFORMATION: Xaa can be any naturally occurring amino acid
<220> FEATURE:
<221> NAME/KEY: MISC_FEATURE
<222> LOCATION: (94)..(94)
<223> OTHER INFORMATION: Xaa is Gly or Ala
<220> FEATURE:
<221> NAME/KEY: MISC_FEATURE
<222> LOCATION: (97)..(99)
<223> OTHER INFORMATION: Xaa can be any naturally occurring amino acid
<220> FEATURE:
<221> NAME/KEY: MISC_FEATURE
<222> LOCATION: (100)..(100)
<223> OTHER INFORMATION: Xaa is Leu of Val
<220> FEATURE:
<221> NAME/KEY: MISC_FEATURE
<222> LOCATION: (101)..(102)
<223> OTHER INFORMATION: Xaa can be any naturally occurring amino acid
<220> FEATURE:
<221> NAME/KEY: MISC_FEATURE
<222> LOCATION: (105)..(105)
<223> OTHER INFORMATION: Xaa can be any naturally occurring amino acid
<220> FEATURE:
<221> NAME/KEY: MISC_FEATURE
<222> LOCATION: (110)..(111)
<223> OTHER INFORMATION: Xaa can be any naturally occurring amino acid
<220> FEATURE:
```

```
<221> NAME/KEY: MISC_FEATURE
<222> LOCATION: (113)..(113)
<223> OTHER INFORMATION: Xaa can be any naturally occurring amino acid
<220> FEATURE:
<221> NAME/KEY: MISC_FEATURE
<222> LOCATION: (115)..(119)
<223> OTHER INFORMATION: Xaa can be any naturally occurring amino acid
<220> FEATURE:
<221> NAME/KEY: MISC_FEATURE
<222> LOCATION: (120)..(120)
<223> OTHER INFORMATION: Xaa is Ser or Ala
<220> FEATURE:
<221> NAME/KEY: MISC_FEATURE
<222> LOCATION: (121)..(122)
<223> OTHER INFORMATION: Xaa can be any naturally occurring amino acid
<220> FEATURE:
<221> NAME/KEY: MISC_FEATURE
<222> LOCATION: (124)..(126)
<223> OTHER INFORMATION: Xaa can be any naturally occurring amino acid
<220> FEATURE:
<221> NAME/KEY: MISC_FEATURE
<222> LOCATION: (127)..(127)
<223> OTHER INFORMATION: Xaa is Lys or Arg
<220> FEATURE:
<221> NAME/KEY: MISC_FEATURE
<222> LOCATION: (128)..(135)
<223> OTHER INFORMATION: Xaa can be any naturally occurring amino acid
<220> FEATURE:
<221> NAME/KEY: MISC_FEATURE
<222> LOCATION: (137)..(137)
<223> OTHER INFORMATION: Xaa can be any naturally occurring amino acid
<220> FEATURE:
<221> NAME/KEY: MISC_FEATURE
<222> LOCATION: (144)..(144)
<223> OTHER INFORMATION: Xaa can be any naturally occurring amino acid
<220> FEATURE:
<221> NAME/KEY: MISC_FEATURE
<222> LOCATION: (146)..(146)
<223> OTHER INFORMATION: Xaa is Val or Ile
<220> FEATURE:
<221> NAME/KEY: MISC_FEATURE
<222> LOCATION: (148)..(149)
<223> OTHER INFORMATION: Xaa can be any naturally occurring amino acid
<220> FEATURE:
<221> NAME/KEY: MISC_FEATURE
<222> LOCATION: (152)..(152)
<223> OTHER INFORMATION: Xaa can be any naturally occurring amino acid
<220> FEATURE:
<221> NAME/KEY: MISC_FEATURE
<222> LOCATION: (154)..(154)
<223> OTHER INFORMATION: Xaa can be any naturally occurring amino acid
<220> FEATURE:
<221> NAME/KEY: MISC_FEATURE
<222> LOCATION: (157)..(158)
<223> OTHER INFORMATION: Xaa can be any naturally occurring amino acid
<220> FEATURE:
<221> NAME/KEY: MISC_FEATURE
<222> LOCATION: (160)..(160)
<223> OTHER INFORMATION: Xaa can be any naturally occurring amino acid
<220> FEATURE:
<221> NAME/KEY: MISC_FEATURE
<222> LOCATION: (162)..(162)
<223> OTHER INFORMATION: Xaa is Leu or Met
<220> FEATURE:
<221> NAME/KEY: MISC_FEATURE
<222> LOCATION: (163)..(164)
<223> OTHER INFORMATION: Xaa can be any naturally occurring amino acid
<220> FEATURE:
<221> NAME/KEY: MISC_FEATURE
<222> LOCATION: (165)..(165)
<223> OTHER INFORMATION: Xaa can be any naturally occurring amino acid
      absent
<220> FEATURE:
<221> NAME/KEY: MISC_FEATURE
<222> LOCATION: (168)..(168)
<223> OTHER INFORMATION: Xaa can be any naturally occurring amino acid
<220> FEATURE:
<221> NAME/KEY: MISC_FEATURE
<222> LOCATION: (173)..(173)
```

-continued

```
<223> OTHER INFORMATION: Xaa can be any naturally occurring amino acid
<220> FEATURE:
<221> NAME/KEY: MISC_FEATURE
<222> LOCATION: (175)..(175)
<223> OTHER INFORMATION: Xaa can be any naturally occurring amino acid
<220> FEATURE:
<221> NAME/KEY: MISC_FEATURE
<222> LOCATION: (177)..(177)
<223> OTHER INFORMATION: Xaa is Leu or Val
<220> FEATURE:
<221> NAME/KEY: MISC_FEATURE
<222> LOCATION: (179)..(179)
<223> OTHER INFORMATION: Xaa can be any naturally occurring amino acid
<220> FEATURE:
<221> NAME/KEY: MISC_FEATURE
<222> LOCATION: (182)..(182)
<223> OTHER INFORMATION: Xaa can be any naturally occurring amino acid
<220> FEATURE:
<221> NAME/KEY: MISC_FEATURE
<222> LOCATION: (185)..(185)
<223> OTHER INFORMATION: Xaa can be any naturally occurring amino acid

<400> SEQUENCE: 22

Xaa Ser Xaa Thr Pro Leu Pro Xaa Asp Xaa Xaa Asp Ser Gly Leu Asp
1               5                   10                  15

Asp Lys Glu Asp Xaa Xaa Cys Phe Phe Glu Ala Cys Val Glu Xaa Xaa
            20                  25                  30

Xaa Xaa Xaa Glu Glu Xaa Xaa Xaa Xaa Xaa Ala Xaa Pro Asn Glu Ser
        35                  40                  45

Ala Xaa Xaa Xaa Xaa Ala Xaa Xaa Xaa Xaa Xaa Xaa Xaa Xaa Xaa Xaa
    50                  55                  60

Xaa Xaa Xaa Xaa Xaa Ser Xaa Xaa Xaa Xaa Asp Xaa Xaa Asp Xaa Val
65                  70                  75                  80

Xaa Leu Ser Xaa Xaa Ser Xaa Gln Xaa Xaa Ala Xaa Xaa Xaa Lys Glu
            85                  90                  95

Xaa Xaa Xaa Xaa Xaa Xaa Thr Ser Xaa Gly Cys Ala Glu Xaa Xaa Glu
        100                 105                 110

Xaa Thr Xaa Xaa Xaa Xaa Xaa Xaa Xaa Glu Xaa Xaa Xaa Xaa Xaa Xaa
    115                 120                 125

Xaa Xaa Xaa Xaa Xaa Xaa Xaa Glu Xaa Asn Ala Ala Ser Ala Lys Xaa
130                 135                 140

Lys Xaa Gln Xaa Xaa Ser Leu Xaa Ala Xaa Gln Pro Xaa Xaa Lys Xaa
145                 150                 155                 160

Ala Xaa Xaa Xaa Xaa Ser Pro Xaa Thr Leu Thr Cys Xaa Glu Xaa Leu
            165                 170                 175

Xaa Asn Xaa His Glu Xaa Arg His Xaa Asn Met His Arg
            180                 185

<210> SEQ ID NO 23
<211> LENGTH: 188
<212> TYPE: PRT
<213> ORGANISM: Artificial Sequence
<220> FEATURE:
<223> OTHER INFORMATION: Protein
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
```

```
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (30)..(34)
<223> OTHER INFORMATION: Xaa can be any naturally occurring amino acid
<220> FEATURE:
<221> NAME/KEY: misc_feature
<222> LOCATION: (37)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (49)..(52)
<223> OTHER INFORMATION: Xaa can be any naturally occurring amino acid
<220> FEATURE:
<221> NAME/KEY: misc_feature
<222> LOCATION: (54)..(68)
<223> OTHER INFORMATION: Xaa can be any naturally occurring amino acid
<220> FEATURE:
<221> NAME/KEY: misc_feature
<222> LOCATION: (70)..(73)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (83)..(84)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (88)..(89)
<223> OTHER INFORMATION: Xaa can be any naturally occurring amino acid
<220> FEATURE:
<221> NAME/KEY: misc_feature
<222> LOCATION: (91)..(93)
<223> OTHER INFORMATION: Xaa can be any naturally occurring amino acid
<220> FEATURE:
<221> NAME/KEY: misc_feature
<222> LOCATION: (96)..(101)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (114)..(121)
<223> OTHER INFORMATION: Xaa can be any naturally occurring amino acid
<220> FEATURE:
<221> NAME/KEY: misc_feature
<222> LOCATION: (123)..(134)
```

```
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (147)..(148)
<223> OTHER INFORMATION: Xaa can be any naturally occurring amino acid
<220> FEATURE:
<221> NAME/KEY: misc_feature
<222> LOCATION: (151)..(151)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (161)..(164)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (176)..(176)
<223> OTHER INFORMATION: Xaa can be any naturally occurring amino acid
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid

<400> SEQUENCE: 23

Ser Xaa Thr Pro Leu Pro Xaa Asp Xaa Xaa Asp Ser Gly Leu Asp Asp
1               5                   10                  15

Lys Glu Asp Xaa Xaa Cys Phe Phe Glu Ala Cys Val Glu Xaa Xaa Xaa
                20                  25                  30

Xaa Xaa Glu Glu Xaa Xaa Xaa Xaa Ala Xaa Pro Asn Glu Ser Ala
        35                  40                  45

Xaa Xaa Xaa Xaa Ala Xaa Xaa Xaa Xaa Xaa Xaa Xaa Xaa Xaa Xaa Xaa
    50                  55                  60
```

```
Xaa Xaa Xaa Xaa Ser Xaa Xaa Xaa Asp Xaa Xaa Asp Xaa Val Xaa
 65              70              75             80

Leu Ser Xaa Xaa Ser Xaa Gln Xaa Xaa Ala Xaa Xaa Xaa Lys Glu Xaa
             85              90                  95

Xaa Xaa Xaa Xaa Xaa Thr Ser Xaa Gly Cys Ala Glu Xaa Xaa Glu Xaa
           100             105             110

Thr Xaa Xaa Xaa Xaa Xaa Xaa Xaa Glu Xaa Xaa Xaa Xaa Xaa Xaa
       115             120             125

Xaa Xaa Xaa Xaa Xaa Xaa Glu Xaa Asn Ala Ala Ser Ala Lys Xaa Lys
       130             135             140

Xaa Gln Xaa Xaa Ser Leu Xaa Ala Xaa Gln Pro Xaa Xaa Lys Xaa Ala
145             150             155             160

Xaa Xaa Xaa Xaa Ser Pro Xaa Thr Leu Thr Cys Xaa Glu Xaa Leu Xaa
               165             170             175

Asn Xaa His Glu Xaa Arg His Xaa Asn Met His Arg
           180             185
```